(12) United States Patent
Delorme et al.

(10) Patent No.: US 7,288,567 B2
(45) Date of Patent: Oct. 30, 2007

(54) INHIBITORS OF HISTONE DEACETYLASE

(75) Inventors: Daniel Delorme, St. Lazare (CA); Soon Hyung Woo, Beaconsfield (CA); Arkadii Vaisburg, Kirkland (CA)

(73) Assignee: Methylgene Inc. (CA)

( * ) Notice: Subject to any disclaimer, the term of this patent is extended or adjusted under 35 U.S.C. 154(b) by 84 days.

(21) Appl. No.: 09/817,374

(22) Filed: Mar. 26, 2001

(65) Prior Publication Data

US 2002/0115826 A1     Aug. 22, 2002

Related U.S. Application Data

(60) Provisional application No. 60/192,151, filed on Mar. 24, 2000.

(51) Int. Cl.
| | |
|---|---|
| C07D 307/40 | (2006.01) |
| C07D 307/80 | (2006.01) |
| C07D 333/10 | (2006.01) |
| C07D 333/52 | (2006.01) |
| A61K 31/341 | (2006.01) |
| A61K 31/38 | (2006.01) |
| A61K 31/343 | (2006.01) |

(52) U.S. Cl. ............... 514/438; 514/461; 514/465; 514/342; 514/362; 514/363; 514/365; 546/279.7; 546/281.1; 546/281.7; 546/282.7; 548/125; 548/146

(58) Field of Classification Search ............ 549/29, 549/49, 59, 429, 462; 514/438, 443, 461, 514/464, 436, 469, 462, 342, 362, 363, 365; 546/462, 279.1, 281.1, 281.7, 282.7
See application file for complete search history.

(56) References Cited

U.S. PATENT DOCUMENTS 5,344,843 A * 9/1994 Guthrie et al. ............ 514/473
6,423,729 B1 * 7/2002 Kurihara et al. ............ 514/364

FOREIGN PATENT DOCUMENTS

WO     WO 9904780 A1 *  2/1999
WO     WO 9942443 A1 *  8/1999

OTHER PUBLICATIONS

Cohen et al. Tetrahedron Letters, 22(35): 3377-3380, 1981.*
See Rosato et al., Expert Opin. Investig. Drugs 13(1), 21-38, 2004.*
Manfred Jung et al., Journal of Medicinal Chemistry, American Chemical Society, "Amide Analogues of Trichostatin A as Inhibitors of Histone Deacertylase and Inducers of Terminal Cell Differentiation", 42:4669-4679, 1999.
Jung et al., Bioorganic & Medicinal Chemistry Letters, "Analogues of Trichostatin A and Trapoxin B as Histone Deacetylase Inhibitors", 7:1655-1658.
Suzuki et al, Journal of Medicinal Chemistry, American Chemical Society, "Synthesis and Histone Deacetylase Inhibitory Activity of New Benzamide Derivatives", 42:3001-3003, 1999.

* cited by examiner

*Primary Examiner*—Venkataraman Balasubramanian
(74) *Attorney, Agent, or Firm*—Keown & Zucchero, LLP; Wayne A. Keown; Joseph C. Zucchero

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions.

54 Claims, No Drawings

INHIBITORS OF HISTONE DEACETYLASE

CROSS-REFERENCE TO RELATED APPLICATIONS

This application claims priority from U.S. Provisional Patent Application Ser. No. 60/192,151, filed on Mar. 24, 2000.

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.,* 286:23-38 (1990) teaches that histones are subject to posttranslational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science,* 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA,* 96: 4868-4873 (1999), teaches that HDACs may be divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.,* 14: 55-66 (2000), discloses HDAC7, a new member of the second class of HDACs. Van den Wyngaert, *FEBS,* 478: 77-83 (2000) discloses HDAC8, a new member of the first class of HDACs.

Richon et al., *Proc. Natl. Acad. Sci. USA,* 95: 3003-3007 (1998), discloses that HDAC activity is inhibited by trichostatin A (TSA), a natural product isolated from *Streptomyces hygroscopicus*, and by a synthetic compound, suberoylanilide hydroxamic acid (SAHA). Yoshida and Beppu, *Exper. Cell Res.,* 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature,* 401: 188-193 (1999), teaches that TSA and SAHA inhibit cell growth, induce terminal differentiation, and prevent the formation of tumors in mice.

These findings suggest that inhibition of HDAC activity represents a novel approach for intervening in cell cycle regulation and that HDAC inhibitors have great therapeutic potential in the treatment of cell proliferative diseases or conditions. To date, only a few inhibitors of histone deacetylase are known in the art. There is thus a need to identify additional HDAC inhibitors and to identify the structural features required for potent HDAC inhibitory activity.

BRIEF SUMMARY OF THE INVENTION

The invention provides compounds and methods for treating cell proliferative diseases. The invention provides new inhibitors of histone deacetylase enzymatic activity.

In a first aspect, therefore, the invention provides novel inhibitors of histone deacetylase. In one embodiment, the novel inhibitors of histone deacetylase are represented by formula (1):

$$\text{Cy-X—Y}^1\text{—W} \qquad (1)$$

wherein

Cy is cycloalkyl, aryl, or a radical of a heterocyclic moiety, any of which may be optionally substituted;

X is selected from the group consisting of C=O, C=CH$_2$, CH(OH), CH(OR$^1$), C=N(OH), and C=N(OR$^1$), where R$^1$ is alkyl, aryl, aralkyl, or acyl;

Y$^1$ is a C$_3$-C$_7$ alkylene, wherein said alkylene may be optionally substituted, and wherein one or two carbon atoms in the linear chain connecting X and W may be replaced with O, NR$^3$, or S(O)$_n$, where R$^3$ is hydrogen, alkyl, aryl, aralkyl, sulfonyl, acyl, alkoxycarbonyl, or carbamoyl, and n is 0, 1, or 2, provided that the atoms in Y$^1$ that are attached to X and to W are carbon atoms, and further provided that Y$^1$ does not comprise an ester or amide linkage in the linear chain connecting X and W; and W is selected from the group consisting of —C(O)—CH$_2$—SR$^2$, —C(O)—NH—OM, —NH—C(O)—NH-Z, and —C(O)—NH-Z, where R$^2$ is alkyl, aryl, aralkyl, or acyl, wherein the aryl portion of any such groups may be optionally substituted;

M is hydrogen or a pharmaceutically acceptable cation;

Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, C$_1$-C$_4$ alkyl, or C$_1$-C$_4$ alkoxy;

provided that X is C=CH$_2$, CH(OR$^1$), C=N(OH), or C=N (OR$^1$) when W is —C(O)—NH—OM and Cy is unsubstituted phenyl, dimethylaminophenyl, or methoxyphenyl; and further provided that when W is —C(O)—CH$_2$—SR$^2$, the carbon atom in Y$^1$ that is attached to W is unsubstituted or is substituted with other than amino, acylamino, alkoxycarbonyl, or carbamoyl.

In another embodiment, the novel inhibitors of histone deacetylase are represented by formula (2):

$$\text{Cy-Y}^2\text{—W} \qquad (2)$$

wherein

Cy is cycloalkyl, aryl, or a radical of a heterocyclic moiety, any of which may be optionally substituted;

Y$^2$ is C$_5$-C$_7$ alkylene, wherein said alkylene may be optionally substituted, and wherein one or two carbon atoms in the linear chain connecting Cy and W may be replaced with O, NR$^3$, or S(O)$_n$, where R$^3$ is hydrogen, alkyl, aryl, aralkyl, sulfonyl, acyl, alkoxycarbonyl, or carbamoyl, and n is 0, 1, or 2, provided that Y$^2$ does not comprise an ester or amide linkage in the linear chain connecting Cy and W; and W is selected from the group consisting of —C(O)—CH$_2$—SR$^2$, —NH—C(O)—NH-Z, and —C(O)—NH-Z, where R$^2$ is alkyl, aryl, aralkyl, or acyl, wherein the aryl portion of any such groups may be optionally substituted; and Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, C$_1$-C$_4$alkyl, or C$_1$-C$_4$ alkoxy;

provided that when W is —C(O)—CH$_2$—SR$_2$, the carbon atom in y$^2$ that is attached to W is unsubstituted or is substituted with other than amino, acylamino, alkoxycarbonyl, or carbamoyl.

In yet another embodiment, the novel inhibitor of histone deacetylase is represented by formula (3):

wherein

Cy is cycloalkyl, aryl, or a radical of a heterocyclic moiety, any of which may be optionally substituted, provided that Cy is other than dimethylaminonaphthyl when Y$^3$ is —(CH$_2$)$_3$—;

Y$^3$ is C$_2$-C$_6$ alkylene, wherein said alkylene may be optionally substituted with one or more substituents independently selected from the group consisting of halo, hydroxy, oxo, nitro, haloalkyl, alkyl, aralkyl, alkoxy, aryloxy, carboxy, hydroxyalkyl, acyl, acyloxy, and cyano; and W is selected from the group consisting of —C(O)—CH$_2$—SR$^2$, —C(O)—NH—OM, —NH—C(O)—NH-Z, and —C(O)—NH-Z, where R$^2$ is alkyl, aryl, aralkyl, or acyl, wherein the aryl portion of any such groups may be optionally substituted;

M is hydrogen or a pharmaceutically acceptable cation; and

Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, C$_1$-C$_4$alkyl, or C$_1$-C$_4$ alkoxy;

provided that Z does not have the formula —(C$_5$H$_3$N)—NHC(O)—Y$^3$—NH—S(O)$_2$-Cy.

In still yet another embodiment, the novel inhibitor of histone deacetylase is represented by one of formulae (4)-(7):

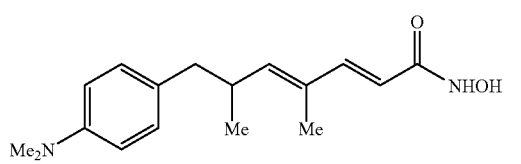

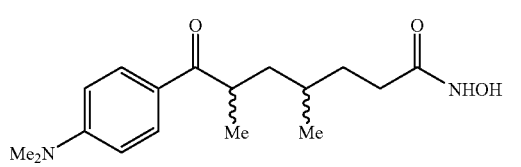

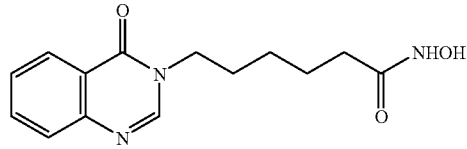

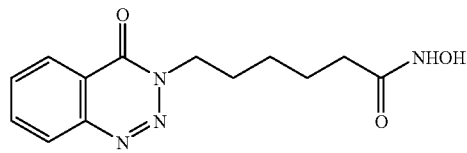

In a second aspect, the invention provides a pharmaceutical composition comprising an inhibitor of histone deacetylase represented by any one of formulae (1)-(7) and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase represented by any one of formulae (1)-(7).

DETAILED DESCRIPTION OF THE PREFERRED EMBODIMENTS

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:

As used herein, the terms "histone deacetylase"0 and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, and HDAC-8. In some other preferred embodiments, the histone deacetylase is derived from a protozoal or fungal source.

The term "histone deacetylase inhibitor" or "inhibitor of histone deacetylase" is used to identify a compound having a structure as defined herein, which is capable of interacting with a histone deacetylase and inhibiting its enzymatic activity. Inhibiting histone deacetylase enzymatic activity means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

The term "alkyl" as employed herein refers to straight and branched chain aliphatic groups having from 1 to 12 carbon atoms, preferably 1-8 carbon atoms, and more preferably 1-6 carbon atoms, which may be optionally substituted with one, two or three substituents. Unless otherwise explicitly stated, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated alkyl" will be used. Preferred saturated alkyl groups include, without limitation, methyl, ethyl, propyl, isopropyl, butyl, isobutyl, sec-butyl, tert-butyl, pentyl, and hexyl.

An "alkylene" group is an alkyl group, as defined hereinabove, that is positioned between and serves to connect two other chemical groups. The term "alkylene" includes saturated, unsaturated and partially unsaturated alkyl groups. Where the term "alkylene" includes a descriptor indicating the number of carbon atoms or a range in the number of carbon atoms, e.g., $C_6$ alkylene, the number of carbon atoms refers to the length of the linear chain connecting the two chemical groups between which the alkylene group is positioned. Any of the carbon atoms of the alkylene group may be optionally substituted, as described below, and the substituents may contain additional carbon atoms.

The term "cycloalkyl" as employed herein includes saturated and partially unsaturated cyclic hydrocarbon groups having from 3 to about 12 carbons, preferably from 3 to about 8 carbons, and more preferably from 3 to about 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$-$C_{14}$ aromatic moiety comprising one to three aromatic rings, which may be optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$-$C_6$)alk-($C_6$-$C_{10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

A "heterocyclic moiety" or "heterocyclyl" is a ring structure having from about 3 to about 8 atoms, wherein one or more atoms are selected from the group consisting of N, O, and S. In some embodiments, the heterocyclic group is saturated or partially saturated. In these embodiments, the heterocyclic group may be optionally substituted on carbon at one or more positions, and may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred saturated heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl or heteroaryl group. Examples of such fused heterocycles include, without limitation, tetrahydroquinoline and dihydrobenzofuran.

In some other embodiments, the heterocyclic moiety is a heteroaryl group. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, from one to about three heteroatoms selected from the group consisting of N, O, and S. Preferred heteroaryl groups include, without limitation, thienyl, benzothienyl, furanyl, benzofuranyl, dibenzofuranyl, pyrrolyl, imidazolyl, pyrazolyl, pyridyl, pyrazinyl, pyrimidinyl, indolyl, quinolinyl, isoquinolinyl, quinoxalinyl, tetrazolyl, oxazolyl, thiazolyl, and isoxazolyl.

As employed herein, a "substituted" alkyl, cycloalkyl, aryl, heteroaryl, or heterocyclic group is one having from one to about four, preferably from one to about three, more preferably one or two, non-hydrogen substituents. Suitable substituents include, without limitation, halo, hydroxy, oxo, oximino, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, acyl, acyloxy, cyano, and ureido groups.

The term "halogen" or "halo" as employed herein refers to chlorine, bromine, fluorine, or iodine.

As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. Unless otherwise explicitly limited, the term "amino" is meant to include $NH_2$, alkylamino, dialkylamino, arylamino, aralkylamino, and cyclic amino groups.

The term "oximino" refers to a =N(OH) or =N(OR) group, wherein R is alkyl, aryl, aralkyl, sulfonyl, or acyl. Unless otherwise explicitly limited, the term "oximino" is meant to include oximes of either E- or Z-configuration, or mixtures thereof.

The term "ureido" as employed herein refers to a substituted or unsubstituted urea moiety.

Compounds

In a first aspect, the invention provides novel inhibitors of histone deacetylase. In a first embodiment, the novel inhibitors of histone deacetylase are represented by formula (1):

Cy-X—Y$^1$—W (1)

wherein

Cy is cycloalkyl, aryl, or a radical of a heterocyclic moiety, any of which may be optionally substituted;

X is selected from the group consisting of C=O, C=CH$_2$, CH(OH), CH(OR$^1$), C=N(OH), and C=N(OR$^1$), where R$^1$ is alkyl, aryl, aralkyl, or acyl;

Y$^1$ is a C$_3$-C$_7$ alkylene, wherein said alkylene may be optionally substituted, and wherein one or two carbon atoms in the linear chain connecting X and W may be replaced with O, NR$^3$, or S(O)$_n$, where R$^3$ is hydrogen, alkyl, aryl, aralkyl, sulfonyl, acyl, alkoxycarbonyl, or carbamoyl, and n is 0, 1, or 2, provided that the atoms in Y$^1$ that are attached to X and to W are carbon atoms, and further provided that Y$^1$ does not comprise an ester or amide linkage in the linear chain connecting X and W; and W is selected from the group consisting of —C(O)—CH$_2$—SR$^2$, —C(O)—NH—OM, —NH—C(O)—NH-Z, and —C(O)—NH-Z, where R$^2$ is alkyl, aryl, aralkyl, or acyl, wherein the aryl portion of any such groups may be optionally substituted;

M is hydrogen or a pharmaceutically acceptable cation;

Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, C$_1$-C$_4$ alkyl, or C$_1$-C$_4$ alkoxy;

provided that X is C=CH$_2$, CH(OR$^1$), C=N(OH), or C=N(OR$^1$) when W is —C(O)—NH—OM and Cy is unsubstituted phenyl, dimethylaminophenyl, or methoxyphenyl; and further provided that when W is —C(O)—CH$_2$—SR$^2$, the carbon atom in Y$^1$ that is attached to W is unsubstituted or is substituted with other than amino, acylamino, alkoxycarbonyl, or carbamoyl.

In certain preferred embodiments according to this aspect of the invention, Cy is C$_3$-C$_{12}$ cycloalkyl, more preferably C$_3$-C$_8$ cycloalkyl, most preferably C$_3$-C$_6$ cycloalkyl, any of which may be optionally substituted. In certain other preferred embodiments, Cy is C$_6$-C$_{14}$ aryl, more preferably C$_6$-C$_{10}$ aryl, and most preferably phenyl or naphthyl, any of which may be optionally substituted.

In still yet other preferred embodiments, Cy is a radical of a heterocyclic moiety. In some preferred embodiments, the heterocycle is selected from the group consisting of thiophene, benzothiophene, furan, benzofuran, pyridine, quinoline, indole, isoquinoline, thiazole, morpholine, piperidine, and piperazine, any of which may be optionally substituted.

Unless otherwise stated, substituted alkyl, aryl, or heterocyclic groups preferably have from one to about four, preferably from one to about three, more preferably one or two substituents, which are preferably selected from the group consisting of C$_1$-C$_6$ alkyl, preferably C$_1$-C$_4$ alkyl; halo, preferably Cl, Br, or F; haloalkyl, preferably (halo)$_{1-5}$(C$_1$-C$_6$)alkyl, more preferably (halo)$_{1-5}$(C$_1$-C$_3$)alkyl, and most preferably CF$_3$; C$_1$-C$_6$ alkoxy, preferably methoxy, ethoxy, or benzyloxy; C$_6$-C$_{10}$ aryloxy, preferably phenoxy; heteroaryloxy; C$_1$-C$_6$ alkoxycarbonyl, preferably C$_1$-C$_3$ alkoxycarbonyl, most preferably carbomethoxy or carboethoxy; C$_6$-C$_{10}$ aryloxycarbonyl, preferably carbophenoxy; heteroaryloxycarbonyl; C$_6$-C$_{10}$ aryl, preferably phenyl; (C$_6$-C$_{10}$)ar(C$_1$-C$_6$)alkyl, preferably (C$_6$-C$_{10}$)ar(C$_1$-C$_3$)alkyl, more preferably benzyl, naphthylmethyl or phenylethyl; hydroxy(C$_1$-C$_6$)alkyl, preferably hydroxy(C$_1$-C$_3$)alkyl, more preferably hydroxymethyl; amino(C$_1$-C$_6$)alkyl, preferably amino(C$_1$-C$_3$)alkyl, more preferably aminomethyl; (C$_1$-C$_6$)alkylamino, preferably methylamino, ethylamino, or propylamino; di-(C$_1$-C$_6$)alkylamino, preferably dimethylamino or diethylamino; (C$_1$-C$_6$)alkylcarbamoyl, preferably methylcarbamoyl, dimethylcarbamoyl, or benzylcarbamoyl; (C$_6$-C$_{10}$)arylcarbamoyl, preferably phenylcarbamoyl; (C$_1$-C$_6$)alkaneacylamino, preferably acetylamino; (C$_6$-C$_{10}$)areneacylamino, preferably benzoylamino; (C$_1$-C$_6$)alkanesulfonyl, preferably methanesulfonyl; (C$_1$-C$_6$)alkanesulfonamido, preferably methanesulfonamido; (C$_6$-C$_{10}$)arenesulfonyl, preferably benzenesulfonyl or toluenesulfonyl; (C$_6$-C$_{10}$)arenesulfonamido, preferably benzenesulfonyl or toluenesulfonyl; (C$_6$-C$_{10}$)ar(C$_1$-C$_6$)alkylsulfonamido, preferably benzylsulfonamido; C$_1$-C$_6$ alkylcarbonyl, preferably C$_1$-C$_3$ alkylcarbonyl, more preferably acetyl; (C$_1$-C$_6$)acyloxy, preferably acetoxy; cyano; amino; carboxy; hydroxy; ureido; and nitro. One or more carbon atoms of an alkyl, cycloalkyl, or heterocyclyl group may also be optionally substituted with an oxo or oximino group.

In some preferred embodiments, Cy is substituted by one or two substituents independently selected from the group consisting of C$_1$-C$_4$ alkyl, C$_1$-C$_4$ haloalkyl, C$_6$-C$_{10}$ aryl, (C$_6$-C$_{10}$)ar(C$_1$-C$_6$)alkyl, halo, nitro, hydroxy, C$_1$-C$_6$ alkoxy, C$_6$-C$_{10}$ aryloxy, heteroaryloxy, C$_1$-C$_6$ alkoxycarbonyl, C$_6$-C$_{10}$ aryloxycarbonyl, heteroaryloxycarbonyl, carboxy, and amino. Preferably, the amino group is selected from the group consisting of NH$_2$, (C$_1$-C$_6$)alkylamino, di(C$_1$-C$_6$)alkylamino, (C$_6$-C$_{10}$)arylamino, and (C$_6$-C$_{10}$)ar(C$_1$-C$_6$)alkylamino.

In certain particularly preferred embodiments, Cy has the formula -Cy$^1$-Cy$^2$ or -Cy$^1$-G-Cy$^2$, wherein Cy$^1$ $^{and\ Cy2}$ are independently C$_3$-C$_6$ cycloalkyl, C$_6$-C$_{10}$ aryl, or a radical of a heterocyclic moiety, which groups optionally may be substituted, and G is O, NR$^3$, or S(O)$_n$, where R$^3$ is hydrogen, alkyl, aryl, aralkyl, sulfonyl, acyl, alkoxycarbonyl, or carbamoyl, and n is 0, 1, or 2. Preferably, Cy$^1$ and Cy$^2$ are independently selected from the group consisting of phenyl, pyridinyl, morpholinyl, piperidinyl, piperazinyl, which groups optionally may be substituted.

In some preferred embodiments, X is C=O, C=CH$_2$, C=N(OH), and C=N(OR$^1$), where R$^1$ is C$_1$-C$_6$ alkyl, C$_6$-C$_{10}$ aryl, or (C$_6$-C$_{10}$)ar(C$_1$-C$_6$)alkyl. More preferably, R$^1$ is C$_1$-C$_4$ alkyl, and still more preferably R$^1$ is methyl. When X is C=N(OH) or C=N(OR$^1$), it may be in either the (E)- or (Z)-configuration, or it may be a mixture of the two. In some preferred embodiments, the C=N(OH) or C=N(OR$^1$) group is in the (E)-configuration. Most preferably, X is C=O or C=N(OH), provided, however, that X is not C=O when W is —C(O)—NH—OM and Cy is unsubstituted phenyl, dimethylaminophenyl, or methoxyphenyl.

In some other preferred embodiments, X is CH(OH) or CH(OR$^1$), where R$^1$ is C$_1$-C$_6$ alkyl, C$_6$-C$_{10}$ aryl, or (C$_6$-C$_{10}$)ar(C$_1$-C$_6$)alkyl. The CH(OH) or CH(OR$^1$) group may be of either (R)- or (S)-stereochemistry, or it may be a mixture of the two. Preferably, X is CH(OH) or CH(OR$^1$), where R$^1$ is C$_1$-C$_4$ alkyl, provided, however, that X is not CH(OH) when W is —C(O)—NH—OM and Cy is unsubstituted phenyl, dimethylaminophenyl, or methoxyphenyl. In certain particularly preferred embodiments, X is CH(OMe).

Y$^1$ is a C$_3$-C$_7$ alkylene, wherein said alkylene may be optionally substituted. Preferably Y$^1$ is a C$_4$-C$_7$ alkylene, more preferably a C$_5$-C$_7$ alkylene, and most preferably a C$_5$ or C$_6$ alkylene. The alkylene may be saturated, unsaturated, or partially unsaturated. In certain preferred embodiments, Y$^1$ comprises an all-carbon linear chain connecting X and W. In certain other preferred embodiments, one or two carbon atoms in the linear chain connecting X and W are replaced with O, NR$^3$, or S(O)$_n$, where R$^3$ is hydrogen, alkyl, aryl, aralkyl, sulfonyl, acyl, alkoxycarbonyl, or carbamoyl, and n is 0, 1, or 2, provided that the atoms in Y$^1$ that are attached to X and to W are carbon atoms, and further provided that Y$^1$ does not comprise an ester or amide linkage in the linear chain connecting X and W. In certain particularly preferred embodiments, $Y^1$ is —$(CH_2)$—$S(O)_n$—$(CH_2)_p$, where n is 0, 1, or 2, and p is 3, 4, or 5.

In some preferred embodiments, $Y^1$ comprises a dienyl moiety, wherein the dienyl moiety is attached to W. Preferably, the dienyl moiety is of the E,E-configuration. In certain particularly preferred embodiments, $Y^1$ has one of the following structures:

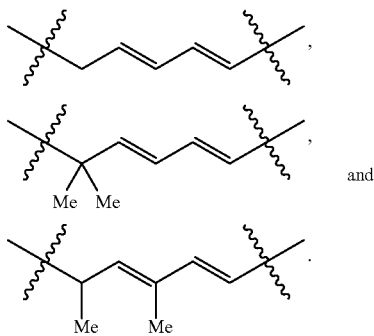

In some other preferred embodiments, $Y^1$ is fully saturated and has the formula —$(CH_2)_m$, where m is 5, 6, or 7.

In some preferred embodiments, W is —C(O)—NH—OM, M being hydrogen or any pharmaceutically acceptable cation. Examples of pharmaceutically acceptable cations include, without limitation, sodium, potassium, magnesium, and calcium.

In some other preferred embodiments, W is —C(O)—$CH_2$—$SR^2$. $R^2$ is preferably selected from the group consisting of alkyl, preferably $C_1$-$C_6$ alkyl, more preferably $C_1$-$C_4$ alkyl, most preferably methyl; aryl, preferably $C_6$-$C_{10}$ aryl, more preferably phenyl or naphthyl; aralkyl, preferably $(C_6$-$C_{10})$ar$(C_1$-$C_6)$alkyl, more preferably $(C_6$-$C_{10})$ar$(C_1$-$C_4)$ alkyl, most preferably benzyl or naphthylmethyl; alkylcarbonyl, preferably $(C_1$-$C_6$ alkyl)carbonyl, more preferably $(C_1$-$C_4$ alkyl)carbonyl, still more preferably acetyl; arylcarbonyl, more preferably $(C_6$-$C_{10}$ aryl)carbonyl, still more preferably benzoyl; and aralkylcarbonyl, preferably $(C_6$-$C_{10})$ar$(C_1$-$C_6)$alkylcarbonyl, more preferably $(C_6$-$C_{10})$ar$(C_1$-$C_4)$alkylcarbonyl, still more preferably benzylcarbonyl. The aryl portion of any such groups may be optionally substituted.

In some other preferred embodiments, W is —C(O)—NH-Z or —NH—C(O)—NH-Z. Z is preferably selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, $C_1$-$C_4$ alkyl, or $C_1$-$C_4$ alkoxy. More preferably, Z is selected from the group consisting of 2-anilinyl, 2-pyridyl, 2-hydroxyphenyl, 1,3,4-thiadiazol-2-yl, 2-anilinylmethyl, and 2-pyridylmethyl. In certain particularly preferred embodiments, Z is unsubstituted 2-anilinyl or unsubstituted 2-pyridyl.

In a second embodiment, the novel inhibitors of histone deacetylase are represented by formula (2):

$$Cy-Y^2—W \quad (2)$$

wherein

Cy is cycloalkyl, aryl, or a radical of a heterocyclic moiety, any of which may be optionally substituted;

$Y^2$ is $C_5$-$C_7$ alkylene, wherein said alkylene may be optionally substituted, and wherein one or two carbon atoms in the linear chain connecting Cy and W may be replaced with O, $NR^3$, or $S(O)_n$, where $R^3$ is hydrogen, alkyl, aryl, aralkyl, sulfonyl, acyl, alkoxycarbonyl, or carbamoyl, and n is 0, 1, or 2, provided that $Y^2$ does not comprise an ester or amide linkage in the linear chain connecting Cy and W; and W is selected from the group consisting of —C(O)—$CH_2$—$SR^2$, —NH—C(O)—NH-Z, and —C(O)—NH-Z, where $R^2$ is alkyl, aryl, aralkyl, or acyl, wherein the aryl portion of any such groups may be optionally substituted; and Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, $C_1$-$C_4$ alkyl, or $C_1$-$C_4$ alkoxy;

provided that when W is —C(O)—$CH_2$—$SR^2$, the carbon atom in $Y^2$ that is attached to W is unsubstituted or is substituted with other than amino, acylamino, alkoxycarbonyl, or carbamoyl.

In certain preferred embodiments according to this aspect of the invention, Cy is $C_3$-$C_{12}$ cycloalkyl, more preferably $C_3$-$C_8$ cycloalkyl, most preferably $C_3$-$C_6$ cycloalkyl, any of which may be optionally substituted. In certain other preferred embodiments, Cy is $C_6$-$C_{14}$ aryl, more preferably $C_6$-$C_{10}$ aryl, and most preferably phenyl or naphthyl, any of which may be optionally substituted.

In still yet other preferred embodiments, Cy is a radical of a heterocyclic moiety. In some preferred embodiments, the heterocycle is selected from the group consisting of thiophene, benzothiophene, furan, benzofuran, pyridine, quinoline, indole, isoquinoline, thiazole, morpholine, piperidine, piperazine, quinazolinone, benzotriazinone, phthalimide, and dioxobenzoisoquinoline, any of which may be optionally substituted. Preferred substituents are as described above for the inhibitors of formula (1).

In certain particularly preferred embodiments, Cy has the formula -$Cy^1$-$Cy^2$ or -$Cy^1$-G-$Cy^2$, wherein $Cy^1$ and $Cy^2$ are independently $C_3$-$C_6$ cycloalkyl, $C_6$-$C_{10}$ aryl, or a radical of a heterocyclic moiety, which groups optionally may be substituted, and G is O, $NR^3$, or $S(O)_n$, where $R^3$ is hydrogen, alkyl, aryl, aralkyl, sulfonyl, acyl, alkoxycarbonyl, or carbamoyl, and n is 0, 1, or 2. Preferably, $Cy^1$ and $Cy^2$ are independently selected from the group consisting of phenyl, pyridinyl, morpholinyl, piperidinyl, piperazinyl, which groups optionally may be substituted.

Preferred values for W, $R^2$, and Z are as defined above for the inhibitors of formula (1).

$Y^2$ is $C_5$-$C_7$ alkylene, wherein said alkylene may be optionally substituted and may be saturated, unsaturated, or partially unsaturated. In certain preferred embodiments, $Y^2$ comprises an all-carbon linear chain connecting Cy and W. In some preferred embodiments, $Y^2$ comprises a dienyl moiety, wherein the dienyl moiety is attached to W. Preferably, the dienyl moiety is of the E,E-configuration. In certain particularly preferred embodiments, $Y^2$ has one of the following structures:

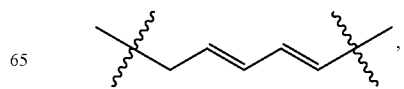

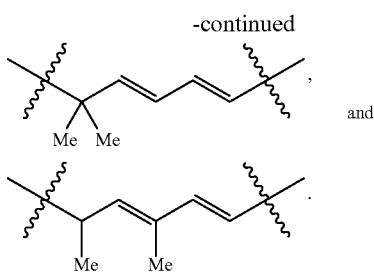

In some other particularly preferred embodiments, $Y^1$ is fully saturated and has the formula —$(CH_2)_m$—, where m is 5, 6, or 7.

In certain other preferred embodiments, one or two carbon atoms in the linear chain connecting Cy and W are replaced with O, $NR^3$, or $S(O)_n$, where $R^3$ is hydrogen, alkyl, aryl, aralkyl, sulfonyl, acyl, alkoxycarbonyl, or carbamoyl, and n is 0, 1, or 2, provided that $Y^2$ does not comprise an ester or amide linkage in the linear chain connecting Cy and W. In some preferred embodiments, one or two carbon atoms in the linear chain connecting Cy and W are replaced by O.

In some other preferred embodiments, one carbon atom in the linear chain connecting Cy and W is replaced with $NR^3$, where $R^3$ is preferably selected from the group consisting of $C_1$-$C_6$ alkyl, more preferably $C_1$-$C_4$ alkyl, most preferably methyl; $C_6$-$C_{10}$ aryl, preferably phenyl or naphthyl; $(C_6$-$C_{10})$ar$(C_1$-$C_6)$alkyl, more preferably $(C_6$-$C_{10})$ar$(C_1$-$C_4)$alkyl, most preferably benzyl or naphthylmethyl; $(C_1$-$C_6$ alkyl)oxycarbonyl, more preferably $(C_1$-$C_4$ alkyl)oxycarbonyl, most preferably tert-butyloxycarbonyl; $(C_6$-$C_{10}$ aryl)oxycarbonyl, preferably phenyloxycarbonyl; and $((C_6$-$C_{10})$ar$(C_1$-$C_6)$alkyl)oxycarbonyl, preferably $((C_6$-$C_{10})$ar$(C_1$-$C_4)$alkyl) oxycarbonyl, more preferably benzyloxycarbonyl; and acyl, preferably $C_1$-$C_6$ alkylcarbonyl or $C_6$-$C_{10}$ arylcarbonyl, more preferably $C_1$-$C_3$ alkylcarbonyl or $C_6$-$C_{10}$ arylcarbonyl, more preferably acetyl or benzoyl.

In yet another embodiment, the novel inhibitor of histone deacetylase is represented by formula (3):

wherein

Cy is cycloalkyl, aryl, or a radical of a heterocyclic moiety, any of which may be optionally substituted, provided that Cy is other than dimethylaminonaphthyl when $Y^3$ is —$(CH_2)_3$—;

$Y^3$ is $C_2$-$C_6$ alkylene, wherein said alkylene may be optionally substituted with one or more substituents independently selected from the group consisting of halo, hydroxy, oxo, nitro, haloalkyl, alkyl, aralkyl, alkoxy, aryloxy, carboxy, hydroxyalkyl, acyl, acyloxy, and cyano; and W is selected from the group consisting of —C(O)—$CH_2$—$SR^2$, —C(O)—NH—OM, —NH—C(O)—NH—Z, and —C(O)—NH—Z, where $R^2$ is alkyl, aryl, aralkyl, or acyl, wherein the aryl portion of any such groups may be optionally substituted;

M is hydrogen or a pharmaceutically acceptable cation; and

Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxy, amino, nitro, $C_1$-$C_4$ alkyl, or $C_1$-$C_4$ alkoxy;

provided that Z does not have the formula —$(C_5H_3N)$—NHC(O)—$Y^3$—NH—$S(O)_2$—Cy.

Preferred substituents Cy and W for the histone deacetylase inhibitors of formula (3) are as defined above for the inhibitors of formula (1).

$Y^3$ is a $C_2$-$C_6$ alkylene, more preferably a $C_4$-$C_5$ alkylene, which may be saturated, unsaturated, or partially unsaturated. The $C_2$-$C_6$ alkylene optionally may be substituted with from one to about four, preferably from one to about three, and more preferably one or two, non-hydrogen substituents independently selected from the group consisting of halo, preferably Cl, Br, or F; hydroxy, oxo, nitro, haloalkyl, preferably (halo)$_{1-5}$($C_1$-$C_6$)alkyl, more preferably (halo)$_{1-5}$($C_1$-$C_3$)alkyl, and most preferably $CF_3$; alkyl, preferably $C_1$-$C_6$ alkyl, more preferably $C_1$-$C_4$ alkyl; aralkyl, preferably $(C_6$-$C_{10})$ar$(C_1$-$C_6)$alkyl, more preferably $(C_6$-$C_{10})$ar$(C_1$-$C_3)$ alkyl, and still more preferably benzyl, naphthylmethyl or phenethyl; alkoxy, preferably $C_1$-$C_6$ alkoxy, more preferably methoxy, ethoxy, or benzyloxy; aryloxy, preferably $C_6$-$C_{10}$ aryloxy, more preferably phenoxy; alkoxycarbonyl, preferably $C_1$-$C_6$ alkoxycarbonyl, more preferably $C_1$-$C_3$ alkoxycarbonyl, and still more preferably carbomethoxy or carboethoxy; carboxy, hydroxyalkyl, preferably hydroxy($C_1$-$C_6$)alkyl, more preferably hydroxy($C_1$-$C_3$)alkyl, and still more preferably hydroxymethyl; acyl, preferably $C_1$-$C_6$ alkylcarbonyl or $C_6$-$C_{10}$ arylcarbonyl, more preferably $C_1$-$C_3$ alkylcarbonyl or $C_6$-$C_{10}$ arylcarbonyl, more preferably acetyl or benzoyl; acyloxy, preferably $C_1$-$C_6$ alkylcarbonyloxy or $C_6$-$C_{10}$ arylcarbonyloxy, more preferably $C_1$-$C_3$ alkylcarbonyloxy or $C_6$-$C_{10}$ arylcarbonyloxy, and still more preferably acetoxy or benzoyloxy; and cyano.

In a still yet another embodiment, the novel histone deacetylase inhibitor is represented by one of formulae (4)-(7):

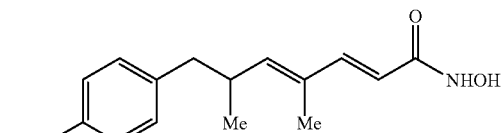

(4)

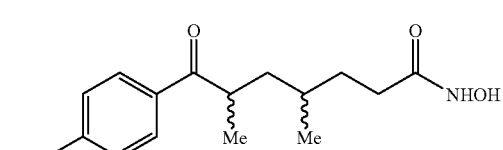

(5)

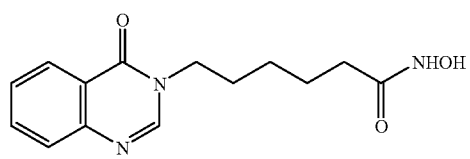

(6)

-continued (7)

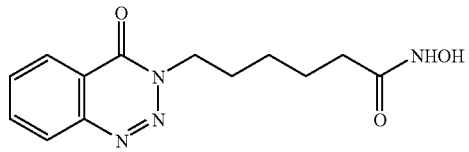

Synthesis

Compounds of formula (1), wherein $Y^1$ has the structure

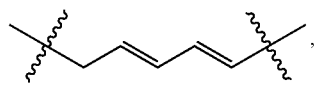

or formula (2), wherein $Y^2$ has the structure

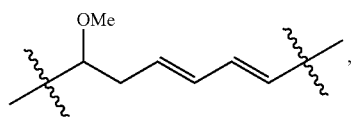

preferably may be prepared according to the synthetic route depicted in Scheme 1. Thus, a dialkyl acetal I is treated with 1-trimethylsilyloxy-1,3-butadiene in the presence of zinc bromide to afford the aldehyde II. Wittig reaction of II with a carboalkoxy phosphorous ylid such as ethyl (triphenylphosphoranylidene)acetate affords the diene ester III. Hydrolysis of the ester function in III can be effected by treatment with a hydroxide base, such as lithium hydroxide, to afford the corresponding acid IV.

The acid IV is converted to the corresponding acid chloride V according to standard methods, e.g., by treatment with sodium hydride and oxalyl chloride.

Treatment of V with 2-aminopyridine and a tertiary base such as N-methyl-morpholine, preferably in dichloromethane at reduced temperature, then affords the pyridyl amide VII. In a similar fashion, the acid chloride IV may be treated with 1,2-phenylenediamine to afford the anilinyl amide VIII. Alternatively, the acid chloride V may be treated with a mono-protected 1,2-phenylenediamine, such as 2-(t-BOC-amino)aniline, followed by deprotection, to afford VIII.

In another alternative procedure, the acid IV may be activated by treatment with carbonyldiimidazole (CDI), followed by treatment with 1,2-phenylenediamine and trifluoroacetic acid to afford the anilinyl amide VIII.

Similar procedures may be employed for the preparation of the hydroxamic El acid VI. Thus, in some embodiments, the acid IV is converted to the corresponding acid chloride V, followed by the addition of a protected hydroxylanine such as O-trimethylsilylhydroxylamine in a solvent such as methylene chloride to form an O-silyl hydroxamate, which then provides the hydroxamic acid VI upon workup.

Scheme 1

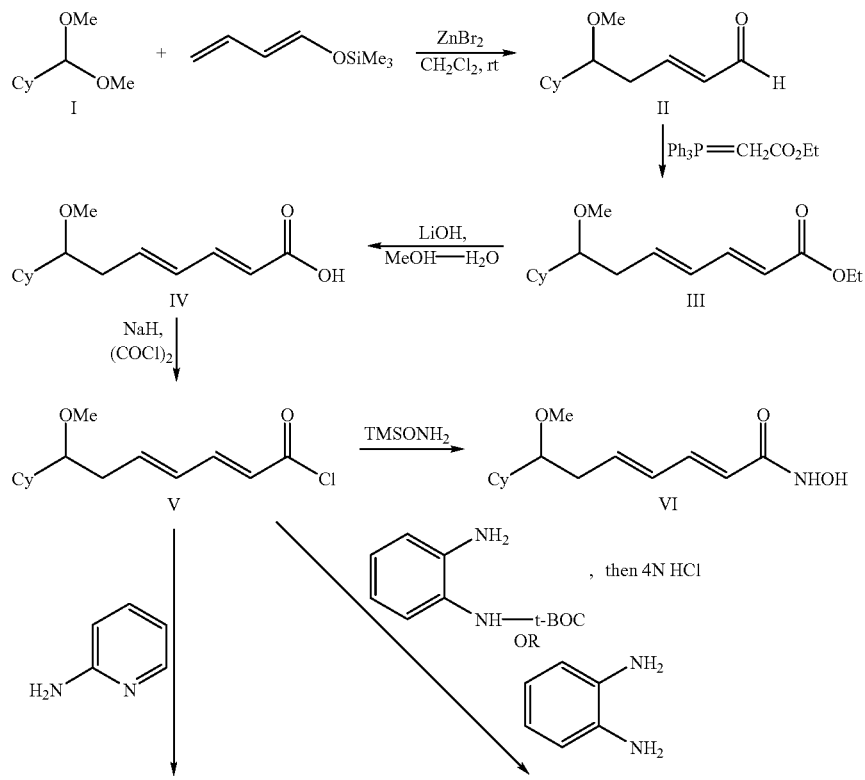

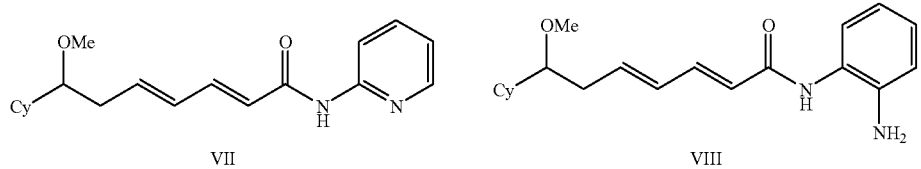

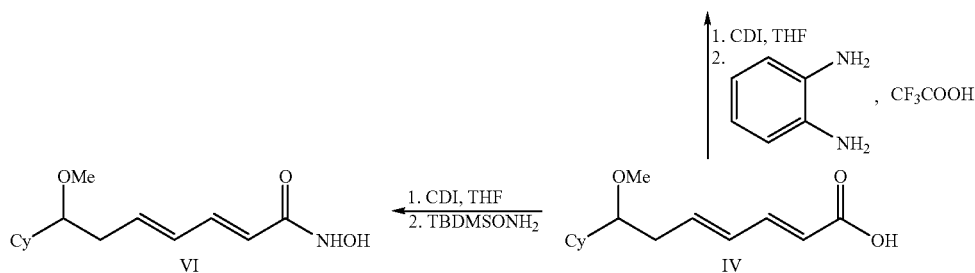

Alternatively, in some other embodiments, the acid IV is directly coupled with a protected hydroxylamine, such as tert-butyldimethylsilylhydroxylamine (TBDMSONH$_2$). The coupling reaction is preferably accomplished with a coupling reagent such as carbonyldiimidazole (CDI) in a solvent such as tetrahydrofuran (THF). Other coupling reagents are known in the art and may also be used for this reaction. When the protected hydroxylamine is a silylhydroxylamine, hydrolysis of the silyl ester occurs upon workup to afford the hydroxamic acid VI. When other protected hydroxylamines are employed, a separate deprotection step may be required.

Compounds of formula (1), wherein $Y^1$ has the structure

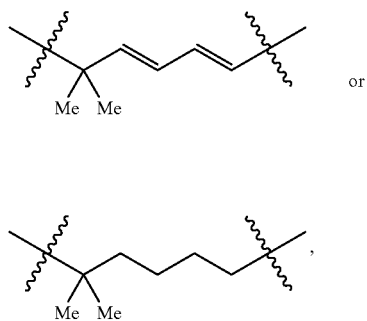

and compounds of formula (2), wherein $Y^2$ has the structure

preferably may be prepared according to the synthetic route depicted in Scheme 2. Thus, a dialkyl acetal I is treated with 2-methyl-1-(trimethylsilyloxy)-1-propene in the presence of zinc bromide to afford the aldehyde IX. Wittig reaction of IX with a carboalkoxy phosphorous ylid such as ethyl (triphenylphosphoranylidene)acetate affords the α,β-unsaturated ester X. The ester function in X is reduced to the alcohol with a reducing agent such as DIBAL-H, and then reoxidized to the corresponding aldehyde with an oxidizing agent such as pyridinium sulfur trioxide complex. Other reducing and oxidizing agents are well known in the art, and may also be used in these reactions.

Homologation of the resultant aldehyde is accomplished by treatment with a carboalkoxy phosphorous ylid such as ethyl (triphenylphosphoranylidene)acetate to afford the diene ester XI, which is hydrolyzed by treatment with a hydroxide base, such as lithium hydroxide to provide the corresponding acid XII. The remaining synthetic steps proceed as described above for Scheme 1.

Scheme 2

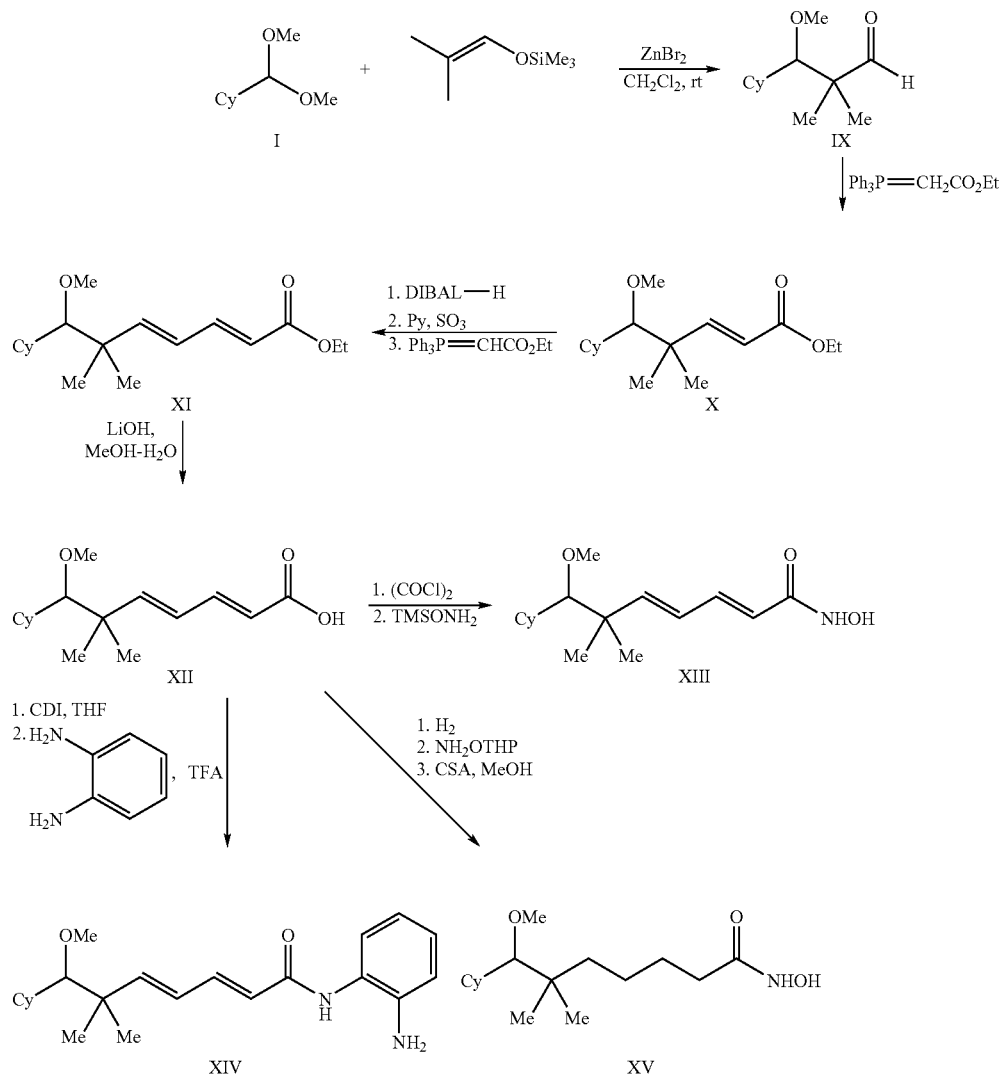

Compounds of formula (1), wherein $Y^1$ has the structure

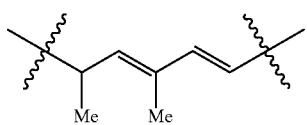

and compounds of formula (2), wherein $Y^2$ has the structure

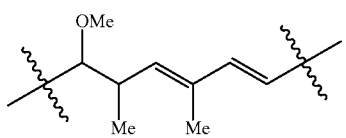

preferably may be prepared by procedures analogous to those already described, as illustrated in Scheme 3. Compounds XXII, wherein $Y^2$ has the structure

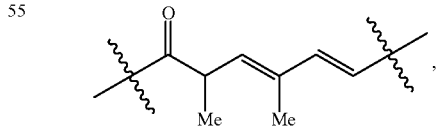

may be prepared from the corresponding methoxy substituted compounds XXI by oxidation with 2,3dichloro-5,6dicyano-1,4-benzoquinone (DDQ).

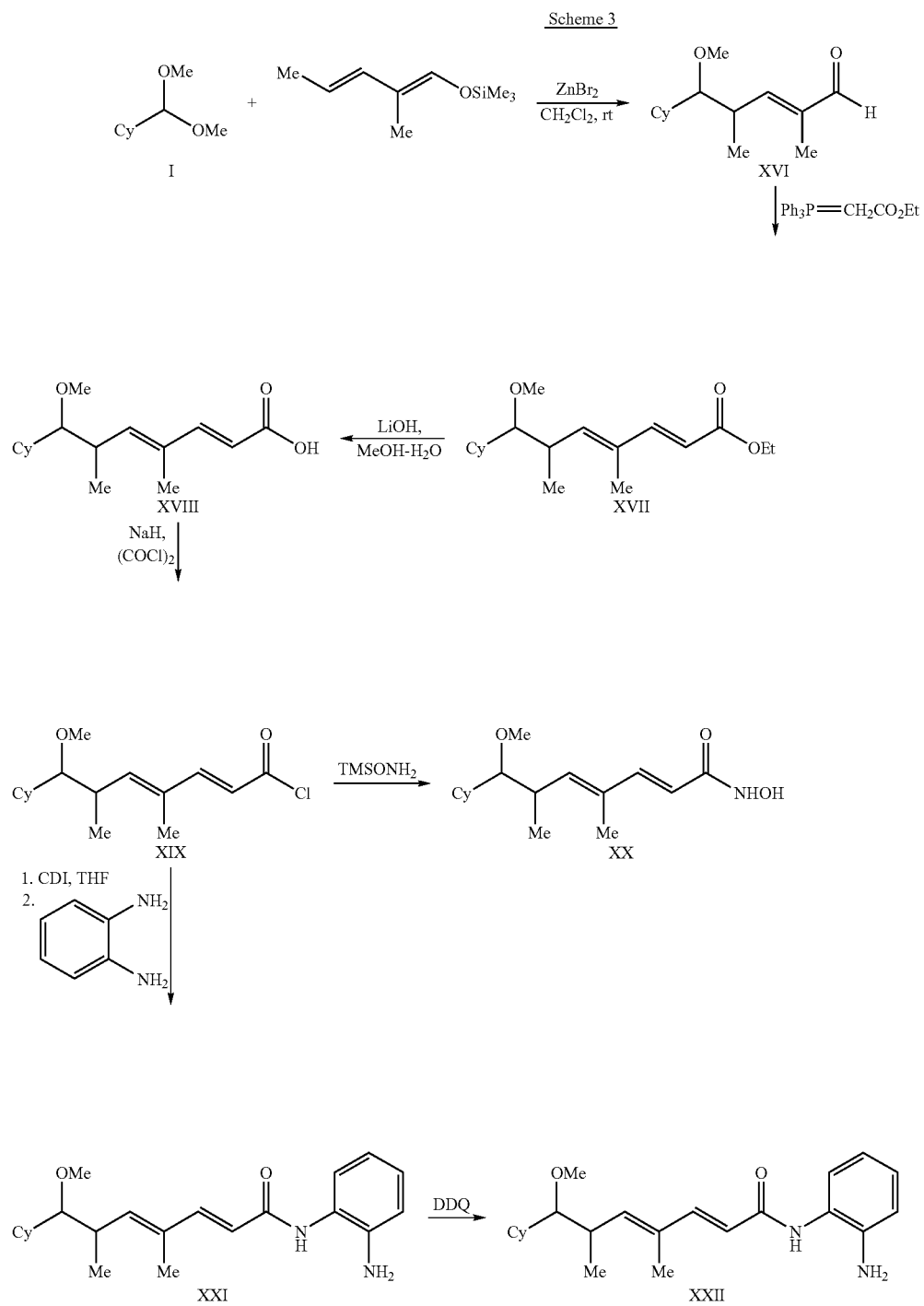

Compounds of formula (2), wherein $Y^2$ has the structure

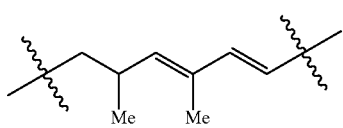

preferably may be prepared as outlined in Scheme 4. Thus, the methoxy substituted diene ester XVII, prepared as described in Scheme 3, is treated with triethylsilane and boron trifluoride etherate to afford the deoxygenated compound XXIII. Conversion of XXIII to the hydroxamic acid XXV and the anilinylamide XXVI is accomplished by procedures analogous to those described above for Schemes 1-3.

Scheme 4

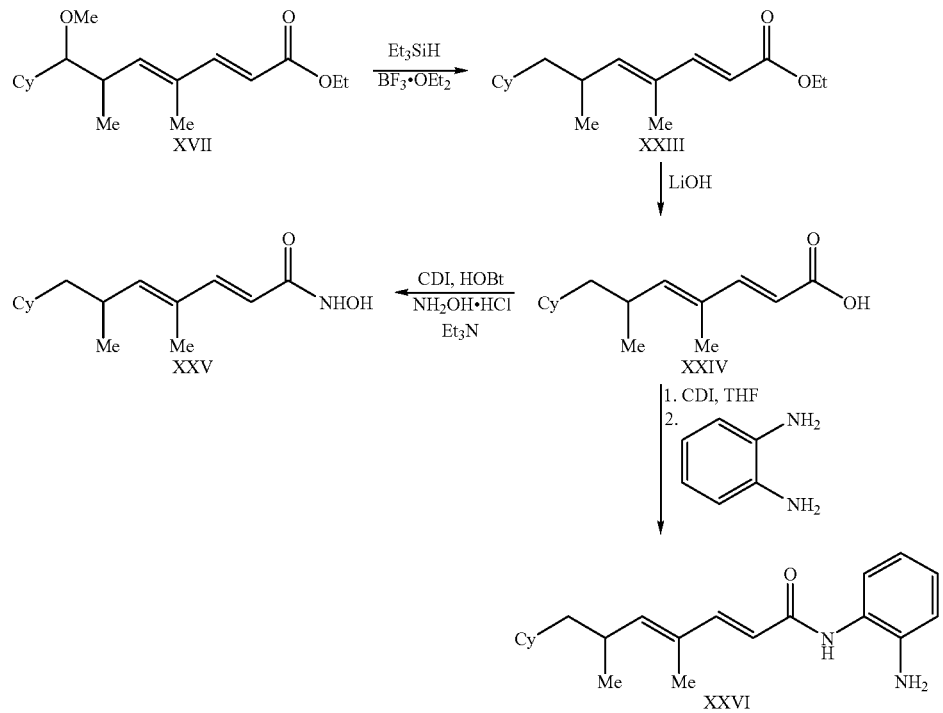

The compounds of formula (3) are preferably prepared as outlined in Scheme 5. Thus, an acid of formula XXIX is esterified and then treated with a sulfonyl chloride, preferably in the presence of a tertiary amine such as triethylamine. Saponification with a base such as LiOH then affords the acid XXXI. Conversion of XXXI to the hydroxamic acid XXXII and the anilinylamide XXXIII is accomplished by procedures analogous to those described above for Schemes 1-3.

Scheme 5

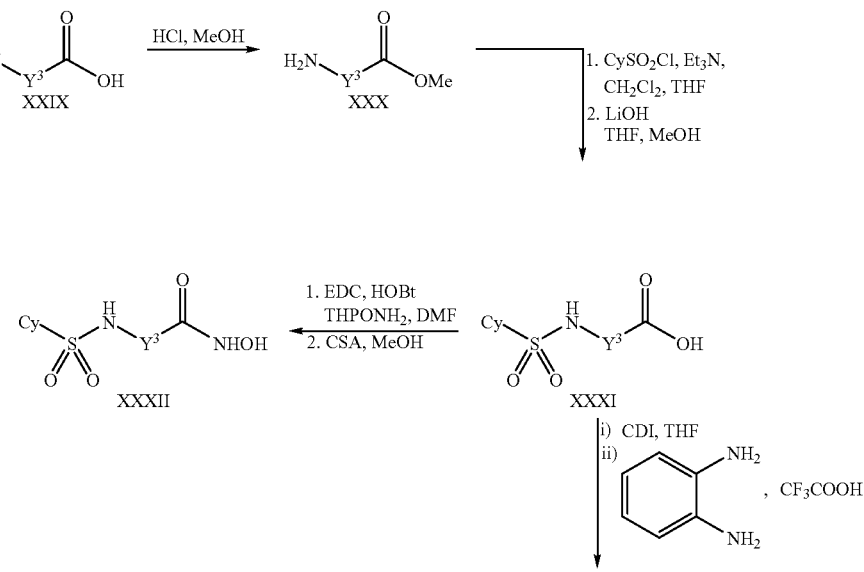

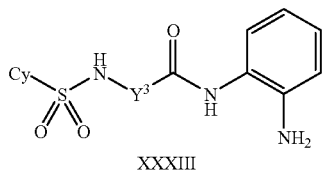

Compounds of formula (1), wherein X is C=O or C=N(OH) are preferably prepared as outlined in Schemes 6 and 7. Thus, an acyl chloride is treated with the heterocuprate reagent XXXIV in a solvent such as THF to afford the ketone XXXV. Ester hydrolysis affords the acid XXXVI, which may be coupled with hydroxylamine or with 1,2-phenylenediamine to afford the hydroxamic acid XXXVIII or the anilinylamide XXXIX, respectively. Alternatively, coupling of the acid XXXVI with an excess of hydroxylamine affords the oximino hydroxamic acid XXXVII.

Hydrogenation of the dienyl ester XI affords the saturated derivative XL, which is deoxygenated by treatment with triethylsilane and borontrifluoride etherate. Benzylic oxidation is then accomplished by treatment with N-bromosuccinimide in carbon tetrachloride, followed by treatment with bis(tetrabutylammonium) dichromate to afford the ketone XLII. Ester hydrolysis and conversion to the hydroxamic acid are then accomplished by procedures analogous to those described above for Schemes 1-3.

Scheme 6

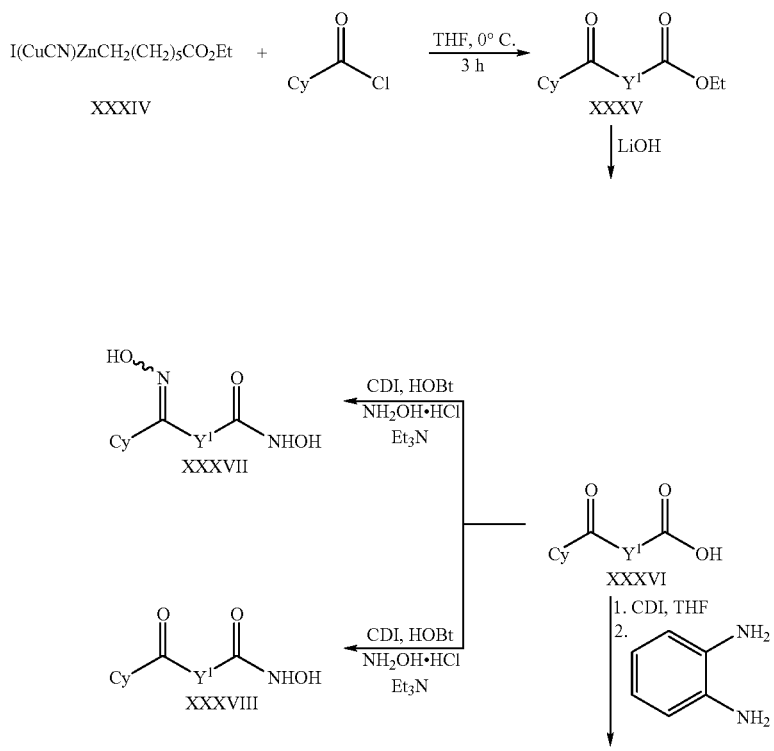

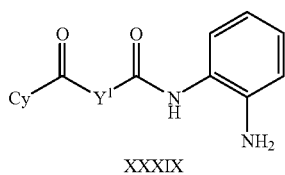

Scheme 7

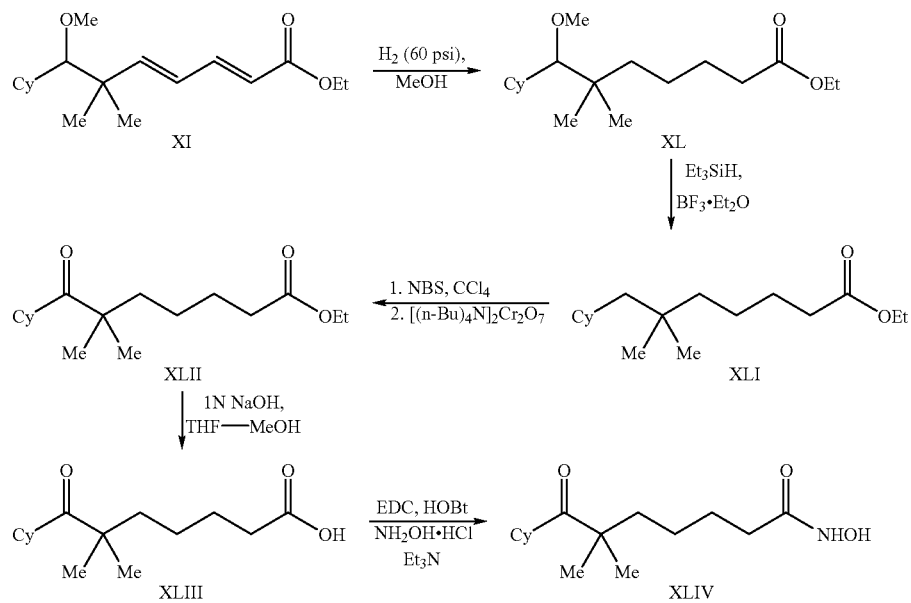

The compound of formula (4) is preferably prepared as described in the Examples.

Compounds of formula (1), wherein W is —NH-Z are preferably prepared as outlined in Scheme 8. Reduction of the ketoester XLV affords the diol XLVI, which is oxidized selectively at the benzylic position with manganese (IV) oxide to give the ketone XLVII. The primary alcohol is substituted for the bromide group to afford XLVIII which is then converted to the aniline XLIX.

Scheme 8

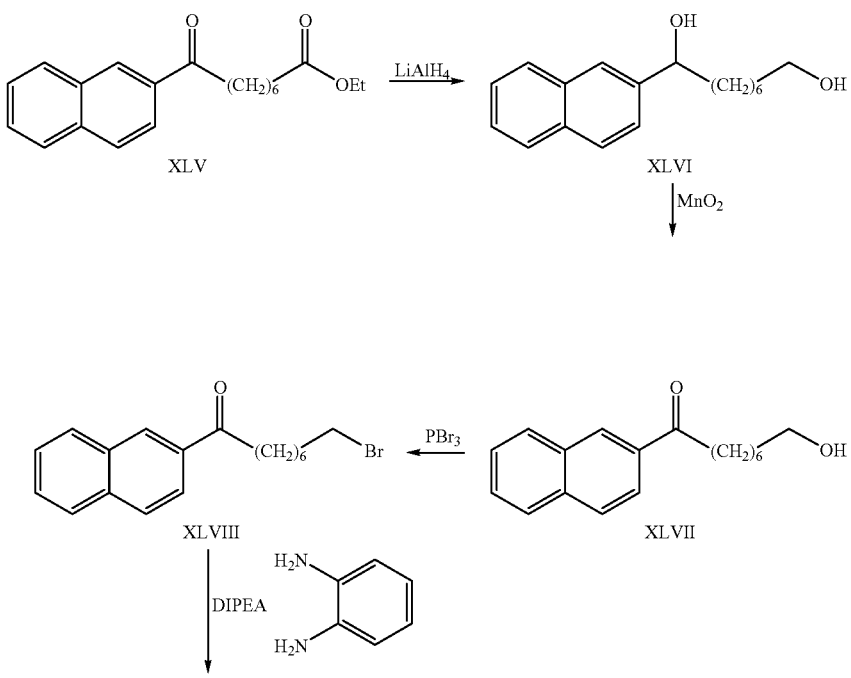

-continued

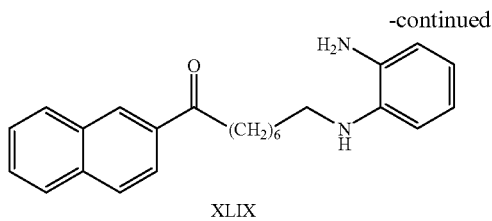

XLIX

Carbamates (LI, X=O) and ureas (LI, X=NH) are preferably synthesized according to the route outlined in Scheme 9. Treatment of the carboxylic acid L with diphenylphosphoryl azide in the presence of triethylamine followed by in situ trapping of the resulting isocyanate with 1,2-phenylenediamine or 2-aminophenol affords the ureas LI. A similar procedure may be employed for the preparation of carbamates, by treating the isocyanate with pyridylcarbinol.

-continued

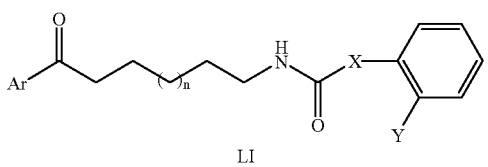

LI

Scheme 9

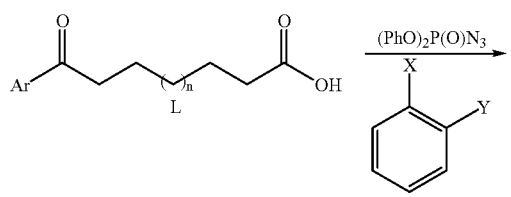

Compounds LV and LVI, wherein Cy is a biaryl moiety, may be prepared according to the synthetic route depicted in Scheme 10. The bromobenzoyl ester LII is treated with an heteroaryl- or arylboronic acids in presence of palladium(0) catalyst to afford esters LIII. Ester hydrolysis affords the acid LIV, which may be coupled with 1,2-phenylenediamine or with hydroxylamine to afford respectively the anilinyl amide LV or the hydroxamic acid LVI.

Scheme 10

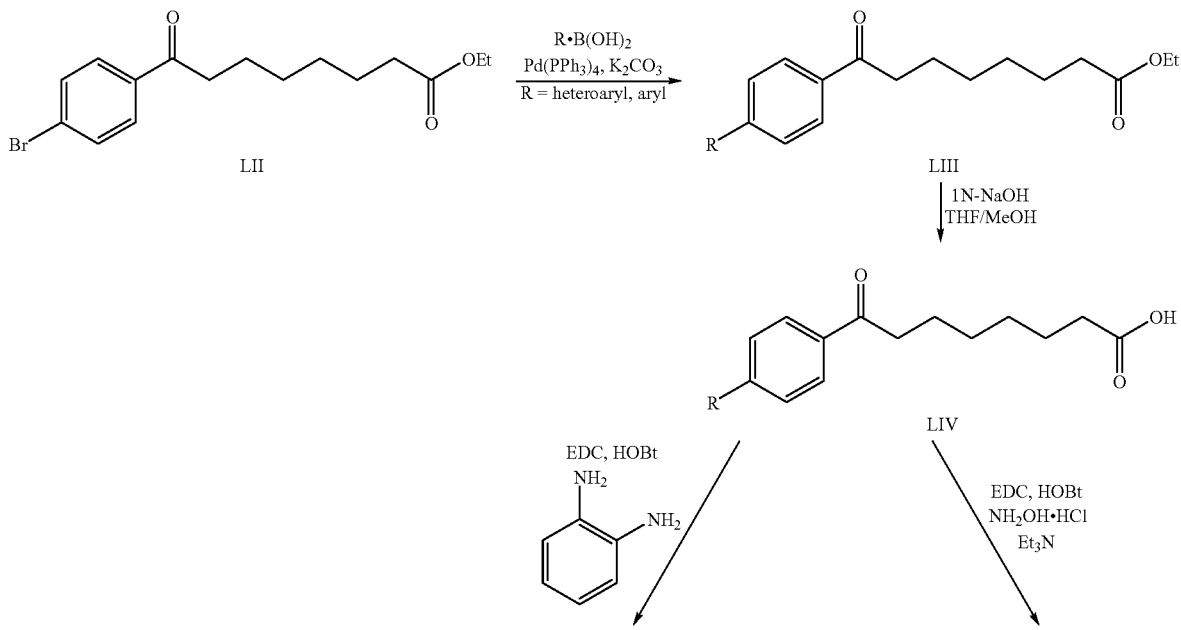

-continued

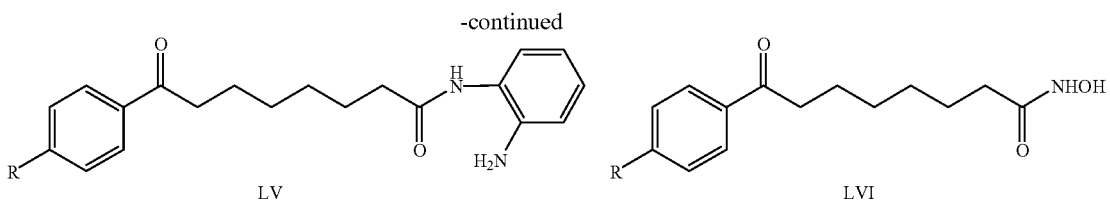

LV    LVI

Compounds LIX, wherein Cy is an aminophenyl moiety, preferably may be prepared according to the synthetic route depicted in Scheme 11. The bromobenzoyl ester LII is coupled with an amine in the presence of dibenzylacetone palladium and 2,2'-bis(diphenylphosphino)-1,1'-binaphtyl to afford esters LVII. Ester hydrolysis affords the acid LVIII, which may be coupled with hydroxylamine to afford the hydroxamic acid LIX.

is treated with n-butyllithium followed by trimethyltin chloride to give the aryltin compound, which may coupled with the acid chloride LX to afford the arylketoester LXI. Ester hydrolysis and the subsequent treatment of the acid LXII with hydroxylamine or 1,2-phenylenediamine affords respectively the hydroxamic acid LXIII or the anilinyl amide LXIV. The amides LXIV are easily converted to the oximes Scheme 11

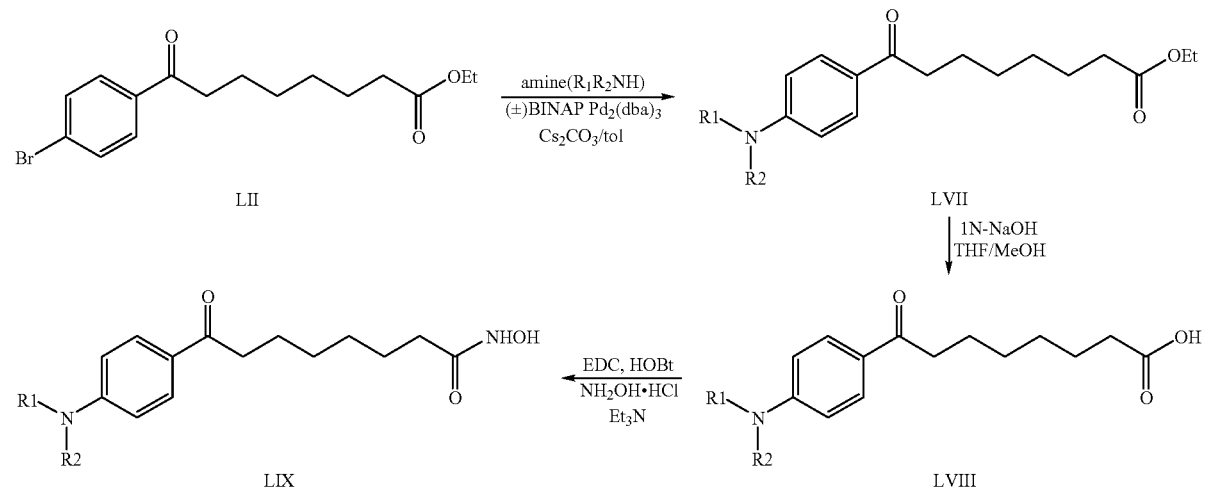

Compounds LXIII-LXVII may be prepared according to the synthetic route depicted in Scheme 12. The aryl bromide LXV and LXVI. Reduction of LXIV with sodium borohydride affords the alcohol LXVI.

Scheme 12

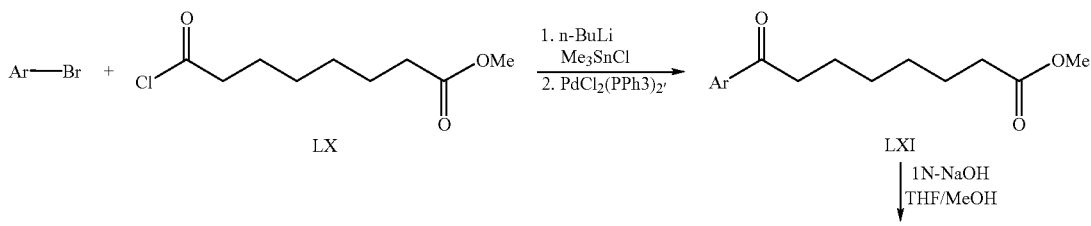

-continued

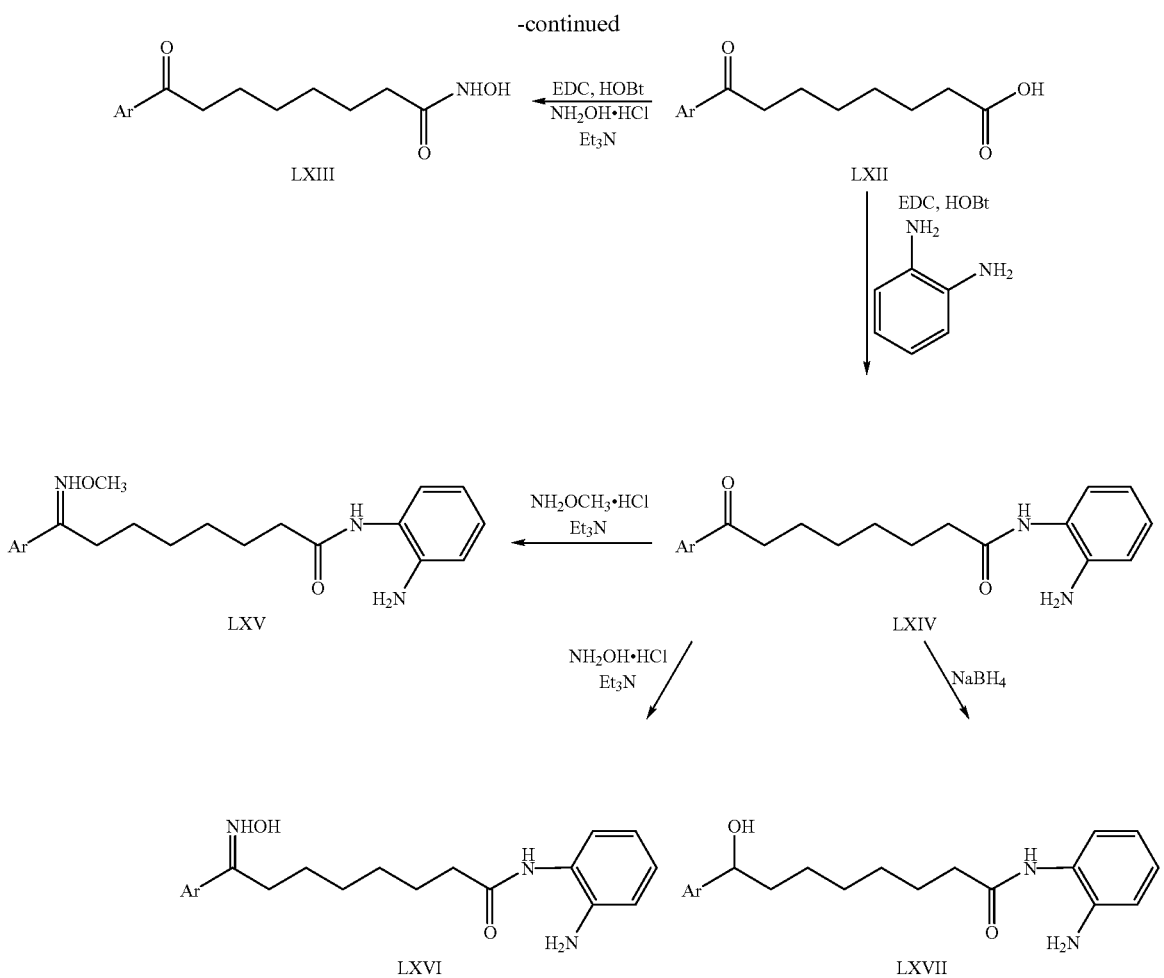

Compounds LXX, wherein W is —C(O)—CH$_2$SR$^2$, may be prepared according to the synthetic route depicted in Scheme 13. The carboxylic acid LXVIII is converted to α-chloromethylketone LXIX by the successive treatment of oxalyl chloride, diazomethane and hydrochloric acid. Replacement of chloride by a thiol in the presence of triethylamine affords the α-thiomethylketones LXX.

Scheme 13

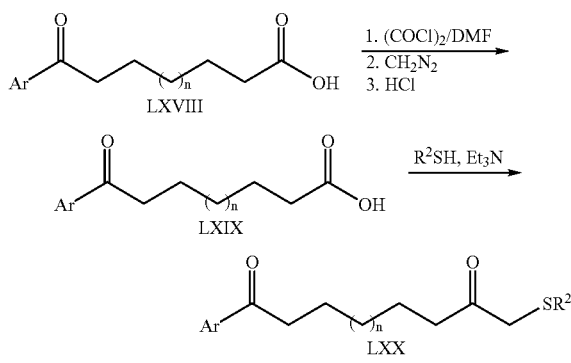

Compounds such as the compounds of formula LXXIV and LXXIX preferably may be prepared according to the route depicted in Scheme 14. Thus, the ketone LXXI is subjected to a Wittig reaction in the presence of methyl phosphonium bromide to afford the ester LXXII. Ester hydrolysis affords the acid LXXIII, which may be coupled with hydroxylamine to afford the hydroxamic acid LXXIV.

Protection of the ketone LXXI by treatment with ethylene glycol in presence of borontrifluoride etherate and trimethyl orthoformate afford the acetal LXXV. α-Methylation to LXXVI is then accomplished by treatment of LXXV with methyl iodide in the presence of lithium diisopropylethylamine. Deprotection of the acetal in acidic media, followed by the saponification of ester LXXVII and the subsequent conversion of the carboxylic acid LXXVIII to the hydroxamic acid afford LXXIX.

Scheme 14

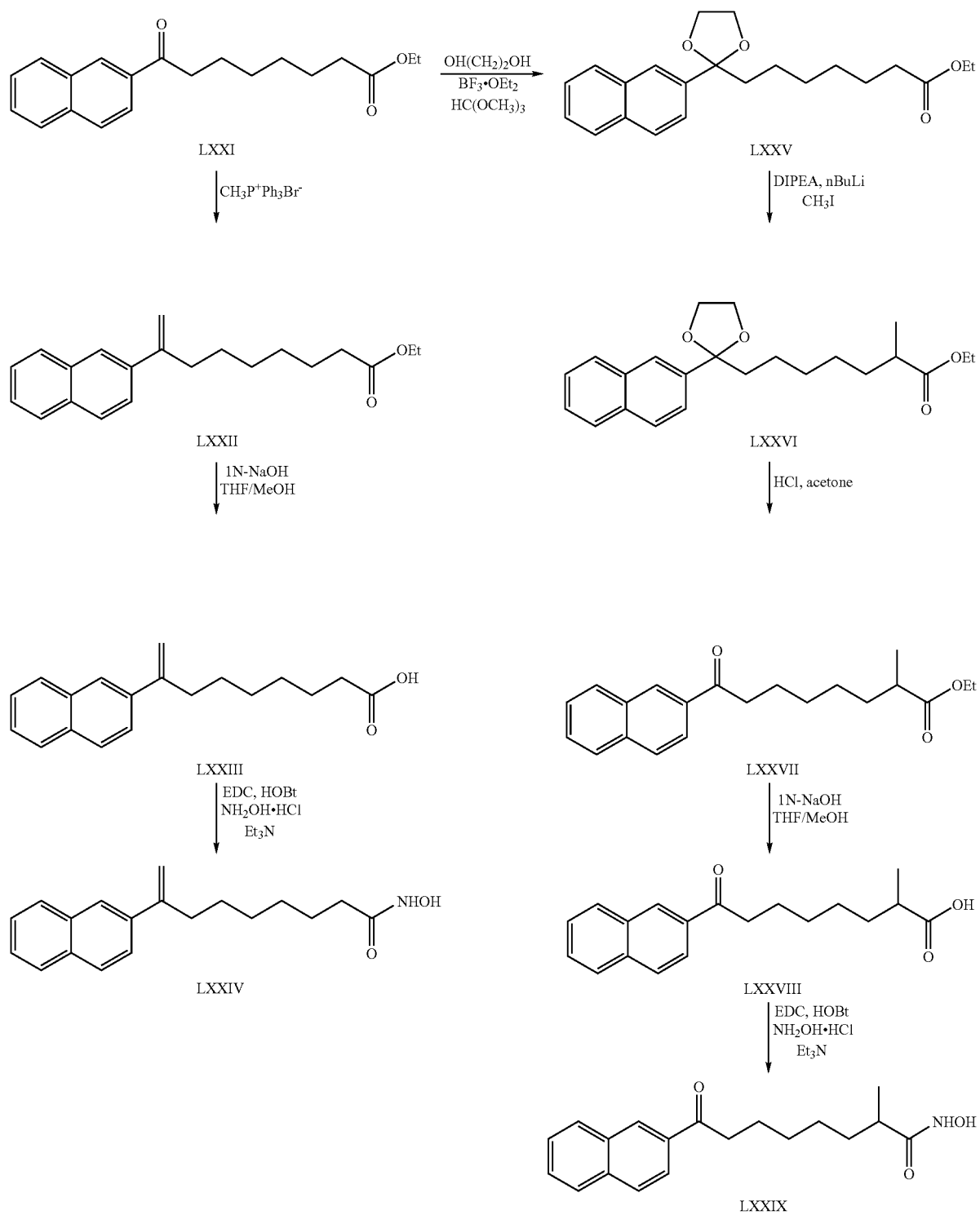

Compounds LXXXIV and LXXXV may be prepared according to the synthetic route depicted in Scheme 15. The aldehyde LXXXI was subjected to a Wittig reaction in the presence of the phosphonium bromide LXXX to afford a (E/Z) mixture of alkene LXXXII. Conversion of LXXXII to the hydroxamic acid LXXXIV is accomplished by a two steps procedure involving hydrolysis and coupling reaction with hydroxylamine. Reduction of LXXXIV by hydrogenation affords LXXXV.

Scheme 15

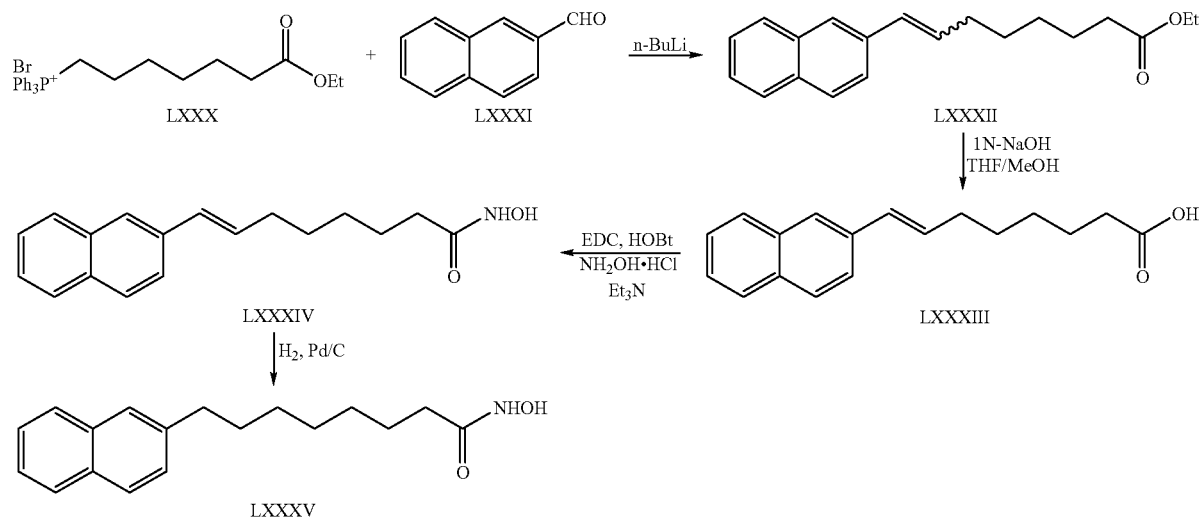

Compounds of formula (1) wherein X is CH(OH) may be prepared according to the synthetic route depicted for compounds XCII and XCIII in Scheme 16. The alcohol LXXXVI, prepared via a Grignard reaction of aldehyde LXXXI with 6-bromohexene, is protected by tert-butyldimethylsilyl group. Oxidative cleavage of olefin LXXXVII affords aldehyde LXXXVIII, which undergoes the Wittig reaction to give ester LXXXIX. Conversion of LXXXIX to the hydroxamic acid XCI is accomplished by procedure analogous to those described above for Scheme 1-3. Deprotection of silyl ether group of XCI affords XCII, which is reduced with sodium borohydride to give XCIII.

Scheme 16

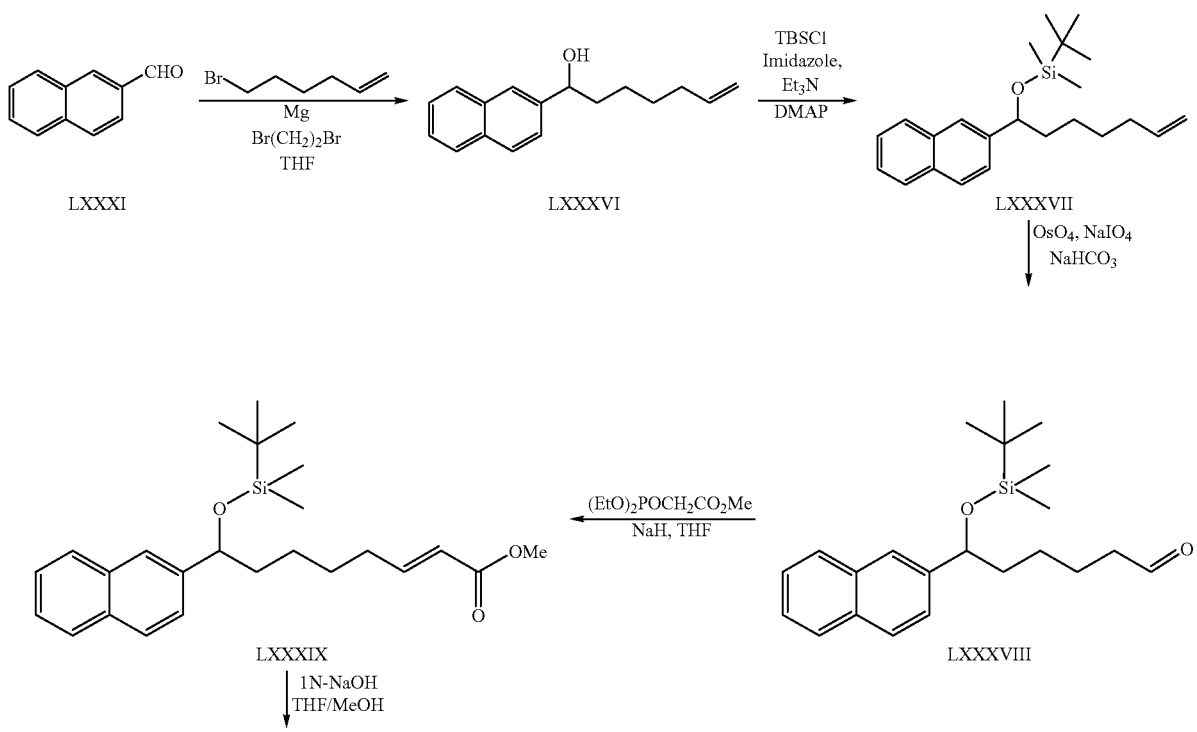

-continued

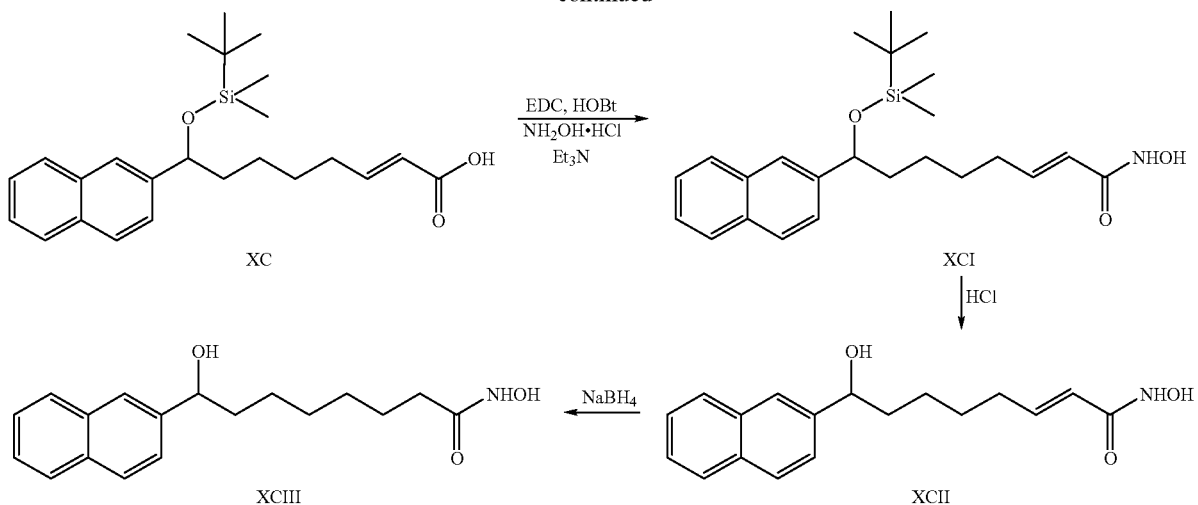

Compounds of formula (1), wherein $Y^1$ is a substituted alkylene, preferably may be prepared as outlined for compounds XCIX, CIII and CIV in Scheme 17. Hydroboration of the alkene XCIV with 9-BBN and the subsequent cross-coupling reaction with vinyl triflate XCV in the presence of palladium(0) catalyst affords the ester XCVI. Hydrolysis of ester XCVI followed by a Dess Martin oxidation gives the acid XCVIII, which is converted to the amide XCIX. Reduction of XCVI with sodium borohydride and nickel chloride affords the ester C. Conversion of CII to the anilinyl amide CIII and to the hydroxamic acid CIV is accomplished by procedure analogous to those described above for Scheme 1-3.

Scheme 17

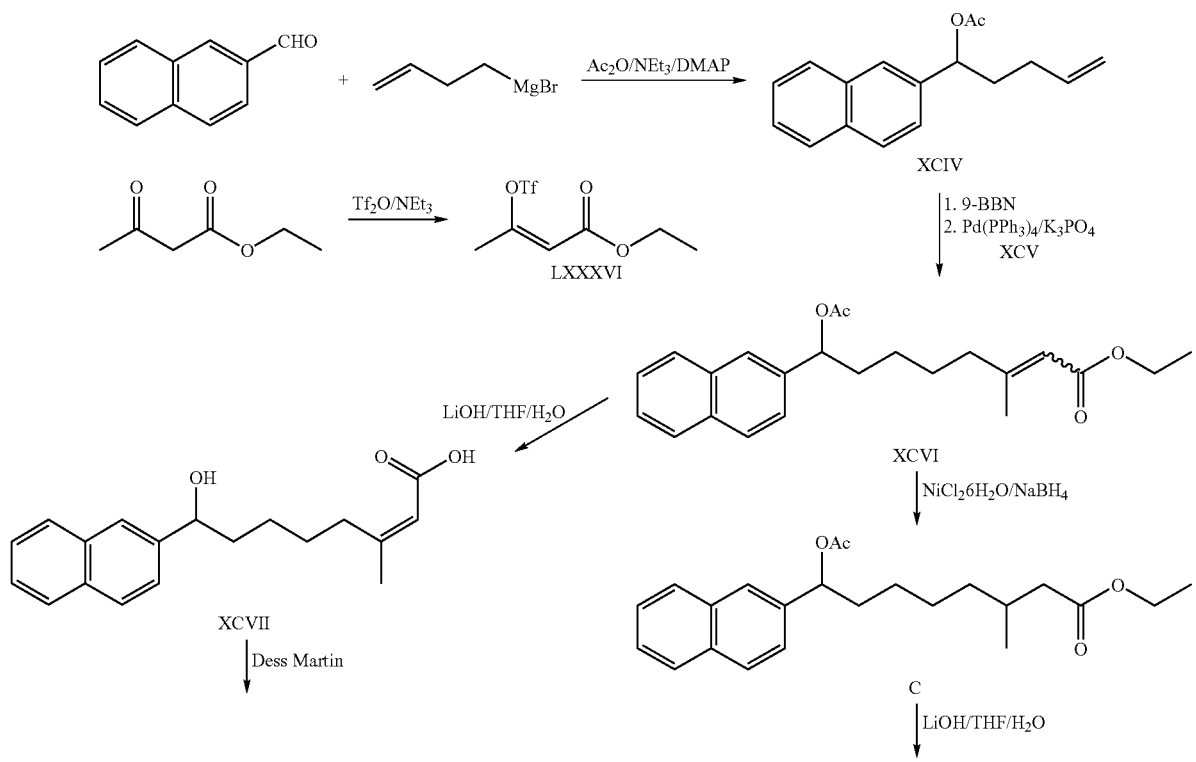

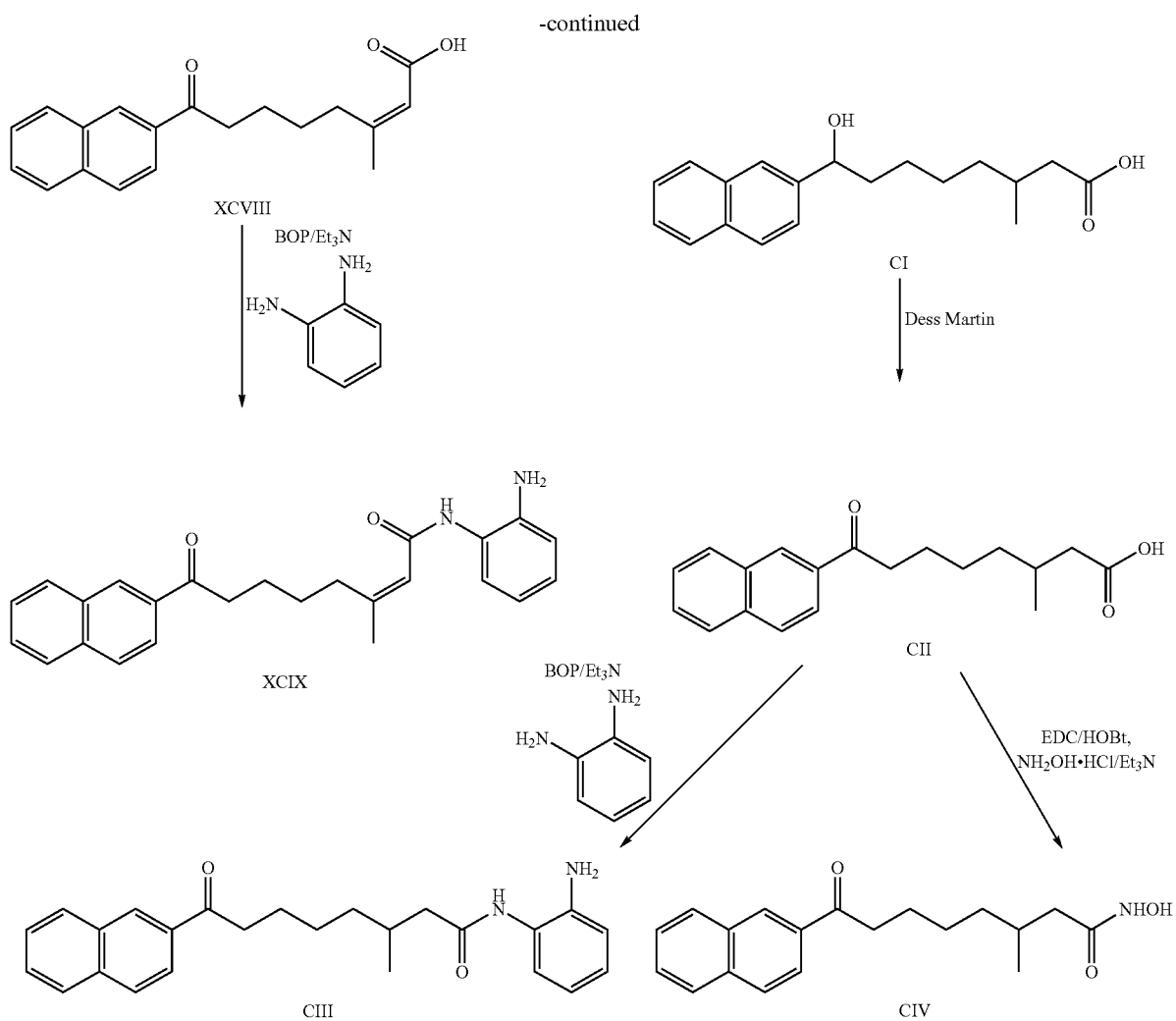

Compounds CIX and CX may be prepared according to the synthetic route depicted in Scheme 18. The alcohol CV is prepared by treatment of bromobiphenyl with γ-butyrolactone in the presence of n-butyllithium. Oxidation of CV with pyridinium dichromate in the presence of sodium acetate affords the aldehyde CVI, which undergoes the Wittig reaction to give the diene ester CVII. Conversion of CVII to the anilinyl amide CIX and to the hydroxamic acid CX is accomplished by procedure analogous to those described above for Scheme 1-3.

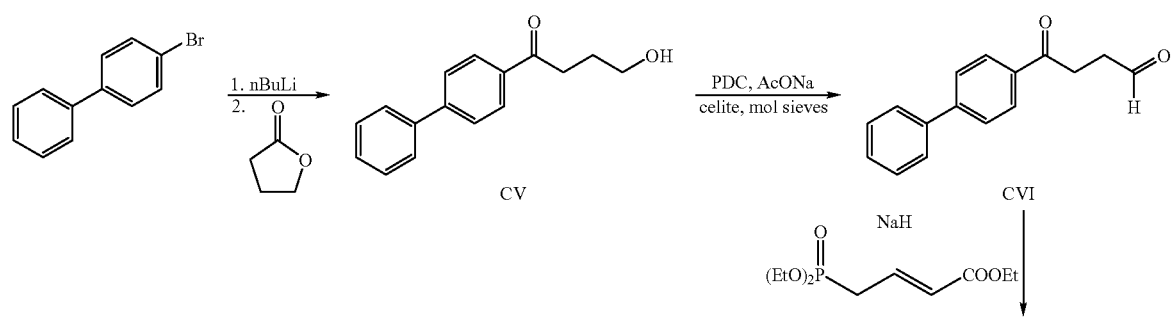

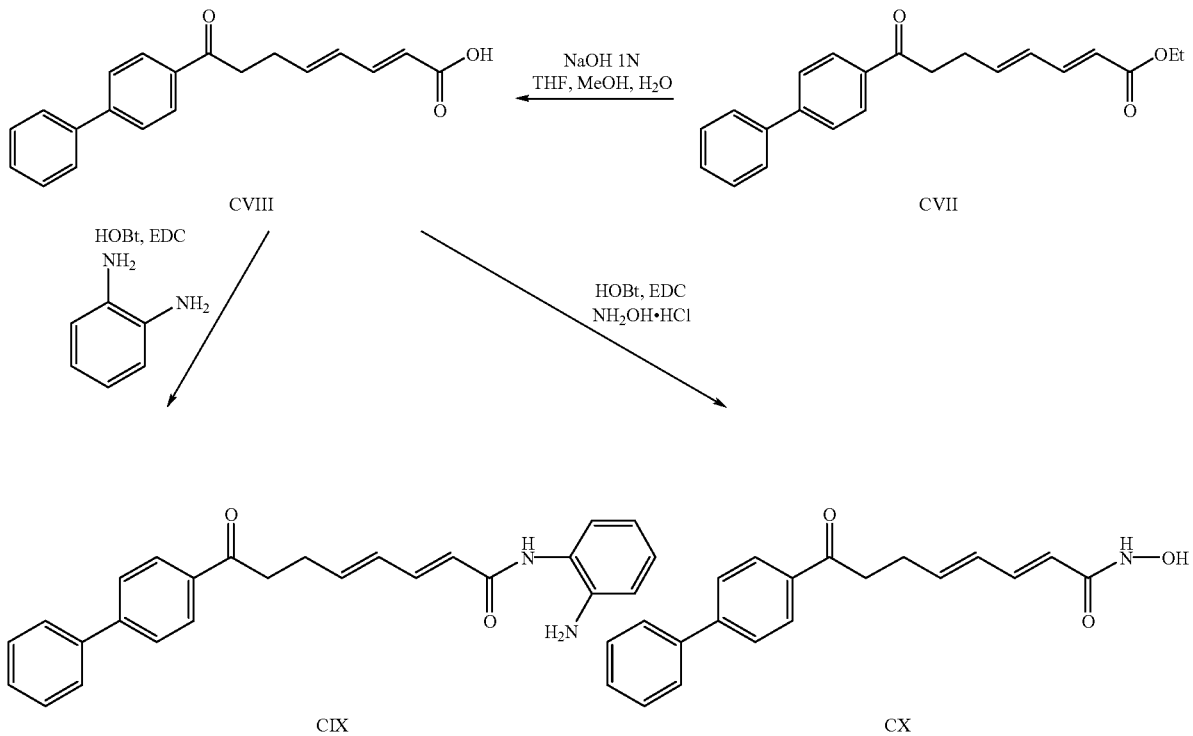

Compounds of formula (2), wherein one carbon atom in the linear chain connecting Cy and W is replaced by $NR^3$, preferably may be prepared as outlined for compounds CXVII-CXX in Scheme 19. The lactone CXI is N-alkylated with methyl iodide or 2-bromomethylnaphthalene in the presence of a base to afford CXII, which is hydrolyzed under acid condition to give the amino acid CXIII. A subsequent N-alkylation or N-acylation affords respectively the tertiary amine CXIV and CXV or the carbamate CXVI. Conversion of CXIV, CXV and CXVI to the anilinyl amide or hydroxamic acid, respectively, CXVII, CXVIII and CXIX is accomplished by procedure analogous to those described above for Scheme 1-3. Deprotection of CXIX using trifluoroacetic acid affords CXX.

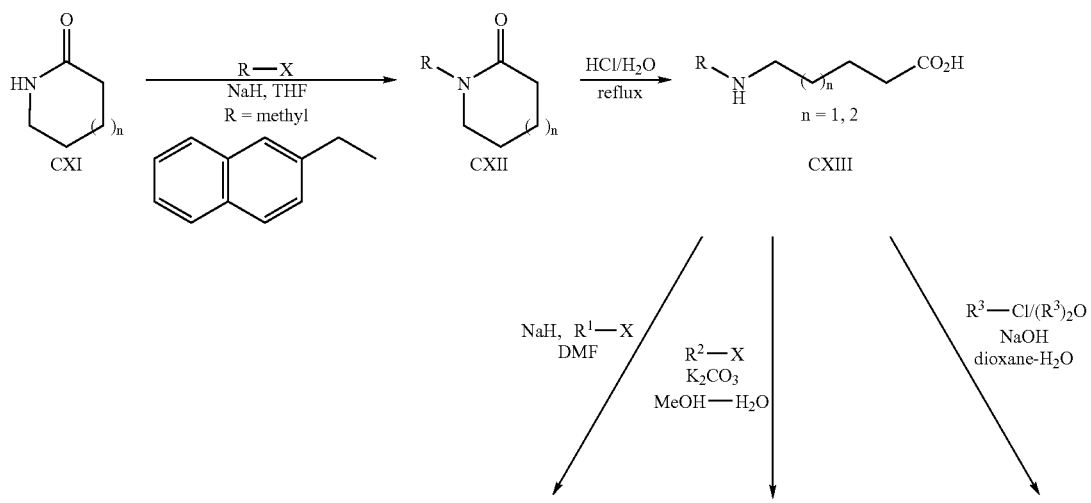

Scheme 19

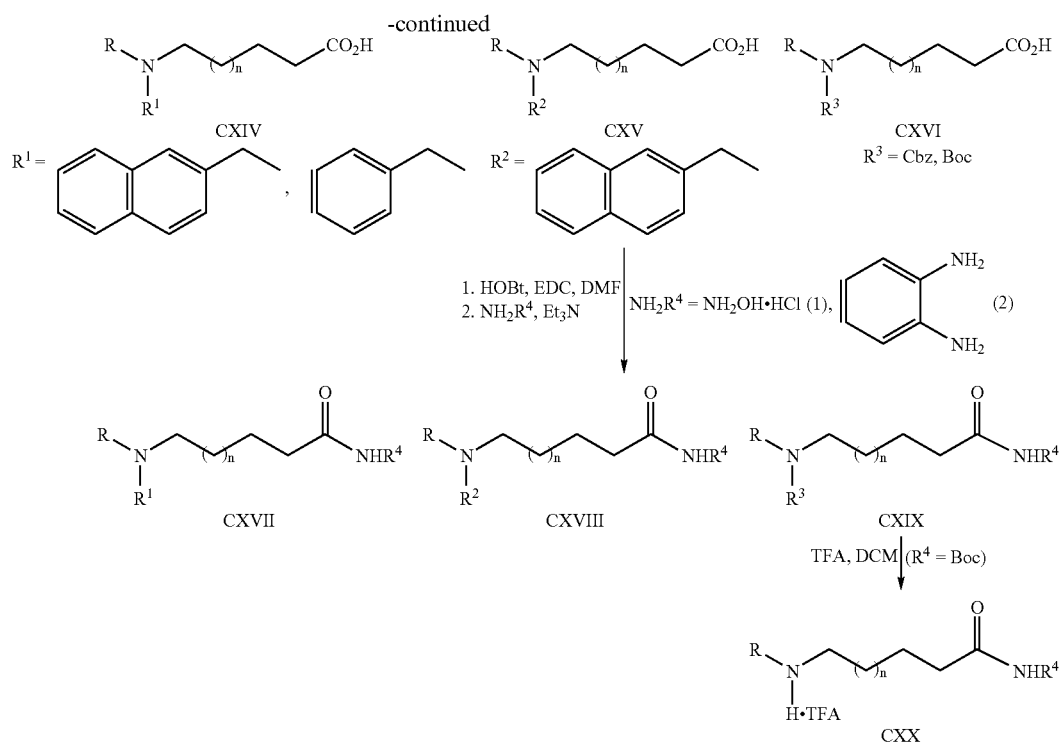

Compounds of formula (1), wherein one carbon atom in the linear chain connecting X and W is replaced by $S(O)_n$, preferably may be prepared as outlined in Scheme 20. The acid CXXI is prepared by treatment of 5-mercaptovaleric acid and the aryl ketone in the presence of a base. The oxidation of the sulfide of CXXI with oxone affords the acid CXXIV. Conversion of CXXI and CXXIV respectively to the anilinyl amide CXXIII and CXXVI and to the hydroxamic acid CXXII and CXXV is accomplished by the procedures analogous to those described above for Scheme 1-3.

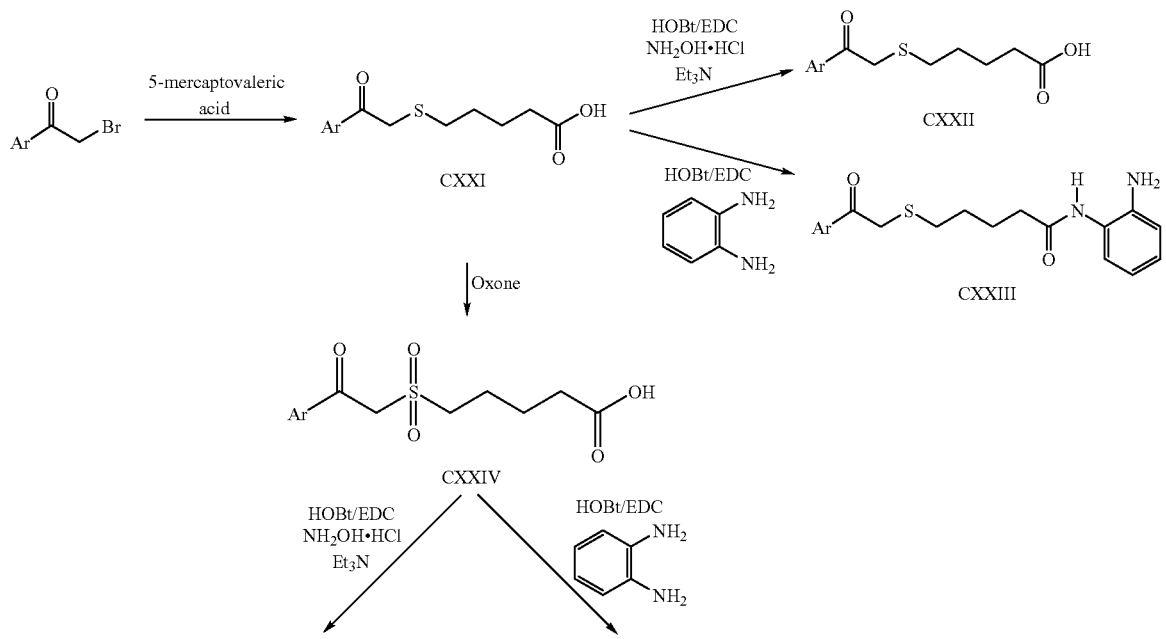

Scheme 20

-continued

CXXV

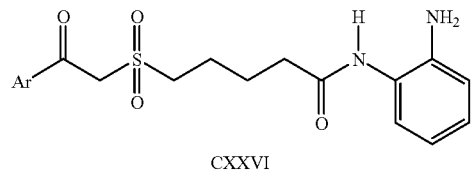
CXXVI

Compounds of formula (2), wherein one carbon atom in the linear chain connecting Cy and W is replaced by an oxygen atom, preferably may be prepared as outlined for compounds CXXIX and CXXX in Scheme 21. The ester CXXVII is prepared by treatment of ethyl-7-bromoheptanoate and the 4-phenylphenol in the presence of a base. Hydrolysis of ester and the subsequent conversion of the carboxylic acid CXXVIII to the anilinyl amide and hydroxamic acid affords respectively CXXIX and CXXX.

Compounds of formula (2), wherein Cy is an N-linked heterocycle, preferably may be prepared according to routes analogous to those depicted in Schemes 22-24. Treatment of 6-aminocaproic acid and the anhydride CXXXI in the presence of a base, followed by a reflux in formic acid or diazotization afford the acid CXXXII (wherein X=CH or X=N respectively). The conversion of the carboxylic acid CXXXII to the hydroxamic acid and anilinyl amide afford respectively CXXXIII and CXXXIV.

Scheme 21

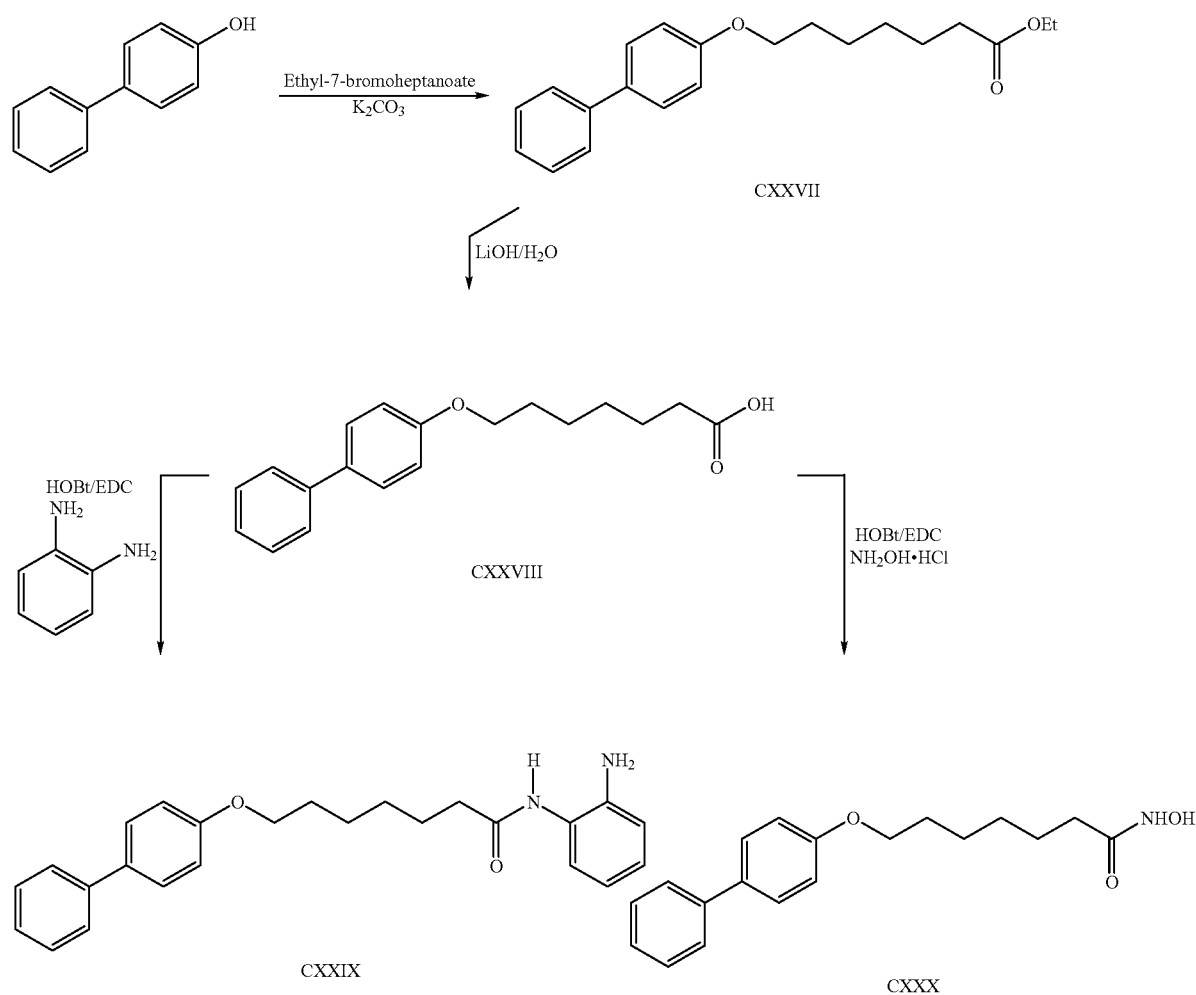

Scheme 22

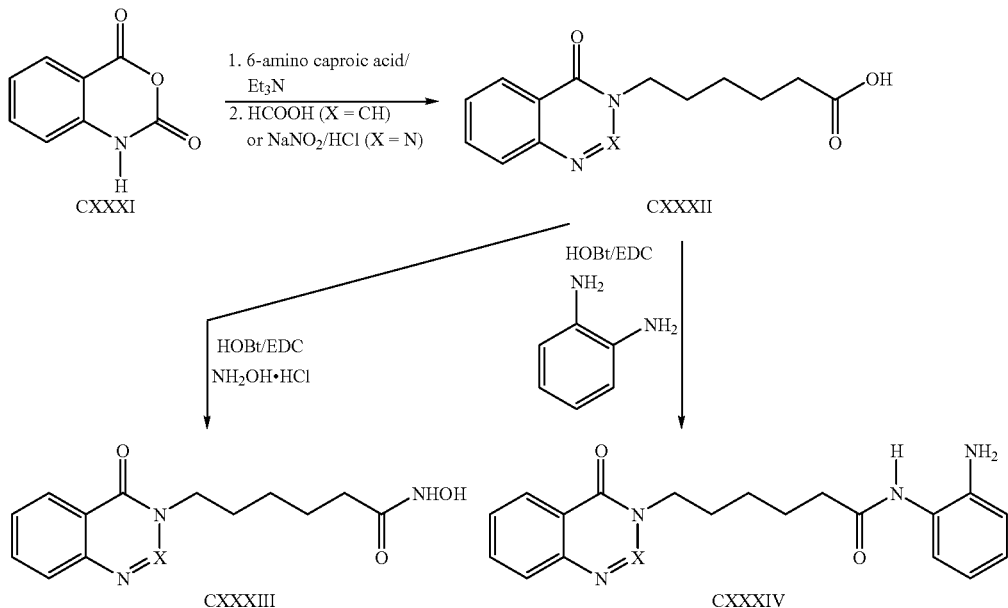

The anhydride CXXXVI is prepared by heating of the diacid CXXXV, as shown in Scheme 23. The treatment of the anhydride CXXXVI with an amino acid in the presence of a base affords the acid CXXXVII. A subsequent treatment of the acid CXXXVII with 1-methylpiperidine in the presence of paraformaldehyde affords the acid CXXXVIII. The conversion of the carboxylic acid CXXXVII or CXXXVIII to the hydroxamic acid and anilinyl amide afford respectively CXXXIX.

Scheme 23

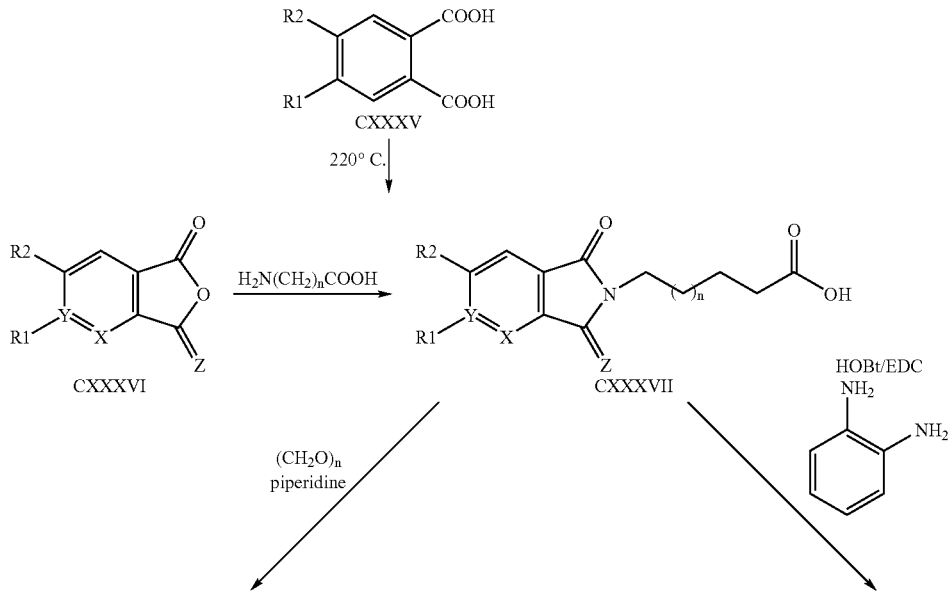

-continued

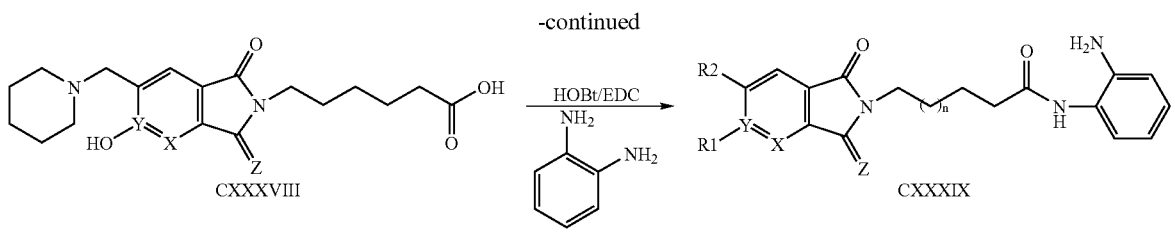

Treatment of the anhydride CXL with an amino acid in the presence of a base affords the acid CXLI, as shown in Scheme 24. The conversion of the carboxylic acid CXLI to the anilinyl amide then affords CXLII.

Scheme 24

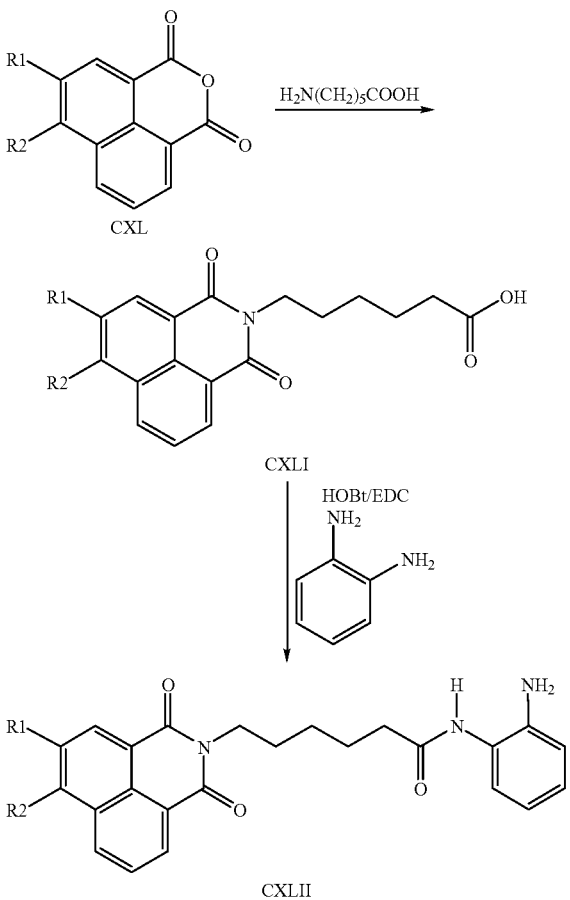

Pharmaceutical Compositions

In a second aspect, the invention provides a pharmaceutical composition comprising an inhibitor of histone deacetylase represented by any one of formulae (1)-(7) and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase represented by any one of formulae (1)-(7).

Measurement of the enzymatic activity of a histone deacetylase can be achieved using known methodologies. For example, Yoshida et al., *J. Biol. Chem.*, 265: 17174-17179 (1990), describes the assessment of histone deacetylase enzymatic activity by the detection of acetylated histones in trichostatin A treated cells. Taunton et al., *Science*, 272: 408-411 (1996), similarly describes methods to measure histone deacetylase enzymatic activity using endogenous and recombinant HDAC-1. Both of these references are hereby incorporated by reference in their entirety.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with and reduce the enzymatic activity of a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number or size). Most preferably, the phrase "inhibiting cell proliferation" includes a reduction in the number of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For example, the histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such a synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a daughter cell that is phylogenetically more advanced than the contacted cell.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (i.e., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense olignounleotides according to this aspect of the invention are complementary to regions of RNA or double-stranded DNA that encode HDAC-1, HDAC-2, HDAC-3, HDAC-4, HDAC-5, HDAC-6, HDAC-7, and/or HDAC-8 (see e.g., GenBank Accession Number U50079 for HDAC-1, Gen- Bank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1-6 saturated or unsaturated carbon atoms, or with an —O-aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active by quantitating the mRNA encoding a product of the gene, or in a Western blotting analysis assay for the product of the gene, or in an activity assay for an enzymatically active gene product, or in a soft agar growth assay, or in a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465-496).

Particularly preferred oligonucleotides have nucleotide sequences of from about 13 to about 35 nucleotides which include the nucleotide sequences shown in Table 1. Yet additional particularly preferred oligonucleotides have nucleotide sequences of from about 15 to about 26 nucleotides of the nucleotide sequences shown in Table 1.

TABLE 1

| Oligo | Target | Accession Number | Nucleotide Position | Sequence | position within Gene |
|---|---|---|---|---|---|
| HDAC1 AS1 | Human HDAC1 | U50079 | 1585-1604 | 5'-GAAACGTGAGGGACTCAGCA-3' | 3'-UTR |
| HDAC1 AS2 | Human HDAC1 | U50079 | 1565-1584 | 5'-GGAAGCCAGAGCTGGAGAGG-3' | 3'-UTR |
| HDAC1 MM | Human HDAC1 | U50079 | 1585-1604 | 5'-GTTAGGTGAGGCACTGAGGA-3' | 3'-UTR |
| HDAC2 AS | Human HDAC2 | U31814 | 1643-1622 | 5'-GCTGAGCTGTTCTGATTTGG-3' | 3'-UTR |
| HDAC2 MM | Human HDAC2 | U31814 | 1643-1622 | 5'-CGTGAGCACTTCTCATTTCC-3' | 3'-UTR |
| HDAC3 AS | Human HDAC3 | AF039703 | 1276-1295 | 5'-CGCTTTCCTTGTCATTGACA-3' | 3'-UTR |
| HDAC3 MM | Human HDAC3 | AF039703 | 1276-1295 | 5'-GCCTTTCCTACTCATTGTGT-3' | 3'-UTR |
| HDAC4 AS1 | Human HDAC4 | AB006626 | 514-33 | 5'-GCTGCCTGCCGTGCCCACCC-3' | 5'-UTR |
| HDAC4 MM1 | Human HDAC4 | AB006626 | 514-33 | 5'-CGTGCCTGCGCTGCCCACGG-3' | 5'-UTR |

TABLE 1-continued

| Oligo | Target | Accession Number | Nucleotide Position | Sequence | position within Gene |
|---|---|---|---|---|---|
| HDAC4 AS2 | Human HDAC4 | AB006626 | 7710-29 | 5'-TACAGTCCATGCAACCTCCA-3' | 3'-UTR |
| HDAC4 MM4 | Human HDAC4 | AB006626 | 7710-29 | 5'-ATCAGTCCAACCAACCTCGT-3' | 3'-UTR |
| HDAC5 AS | Human HDAC5 | AF039691 | 2663-2682 | 5'-CTTCGGTCTCACCTGCTTGG-3' | 3'-UTR |
| HDAC6 AS | Human HDAC6 | AJ011972 | 3791-3810 | 5'-CAGGCTGGAATGAGCTACAG-3' | 3'-UTR |
| HDAC6 MM | Human HDAC6 | AJ011972 | 3791-3810 | 5'-GACGCTGCAATCAGGTAGAC-3' | 3'-UTR |
| HDAC7 AS | Human HDAC7 | AF239243 | 2896-2915 | 5'-CTTCAGCCAGGATGCCCACA-3' | 3'-UTR |
| HDAC8 AS1 | Human HDAC8 | AF230097 | 51-70 | 5'-CTCCGGCTCCTCCATCTTCC-3' | 5'-UTR |
| HDAC8 A52 | Human HDAC8 | AF230097 | 1328-1347 | 5'-AGCCAGCTGCCACTTGATGC-3' | 3'-UTR |

The following examples are intended to further illustrate certain preferred embodiments of the invention, and are not intended to limit the scope of the invention.

EXAMPLES

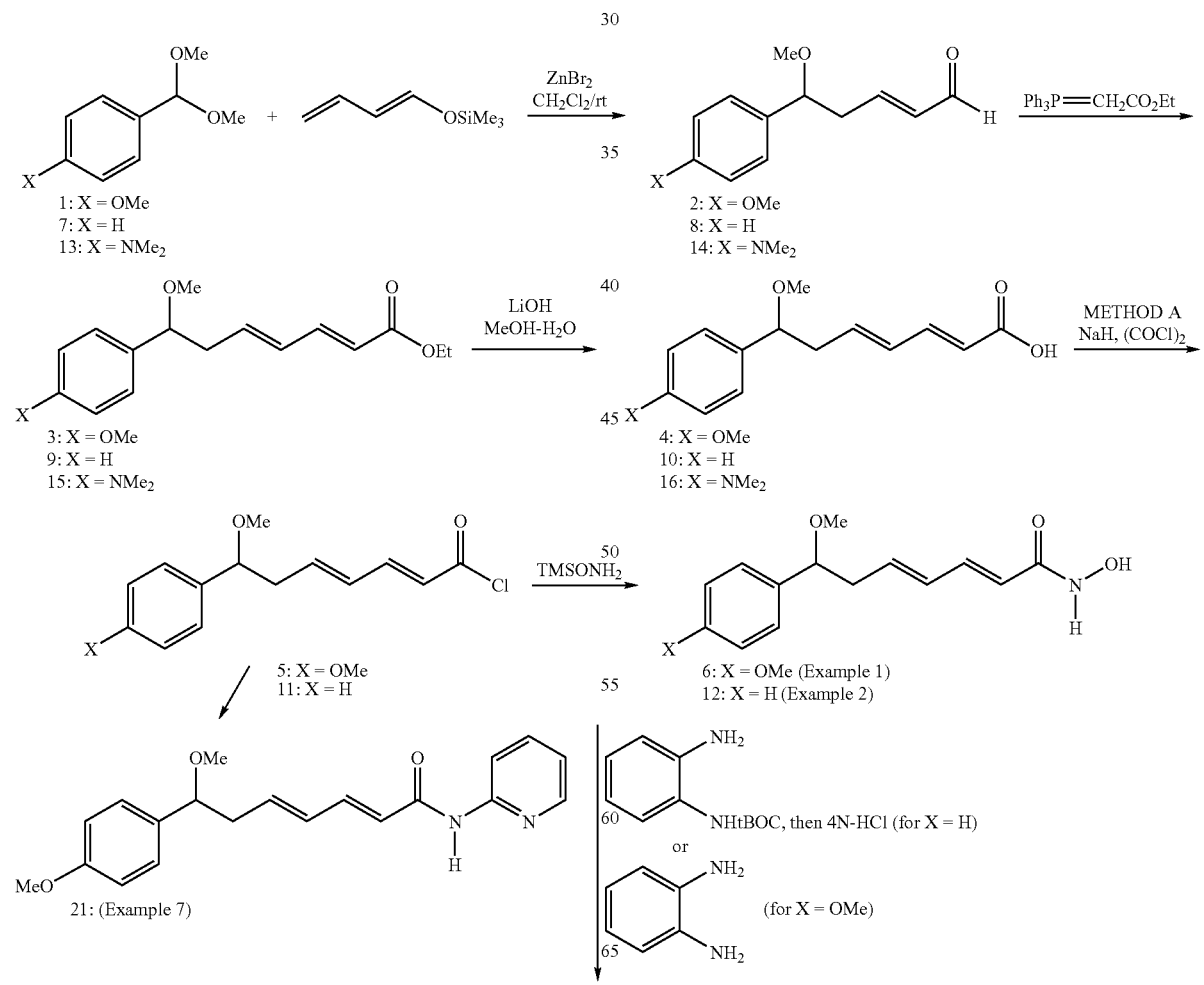

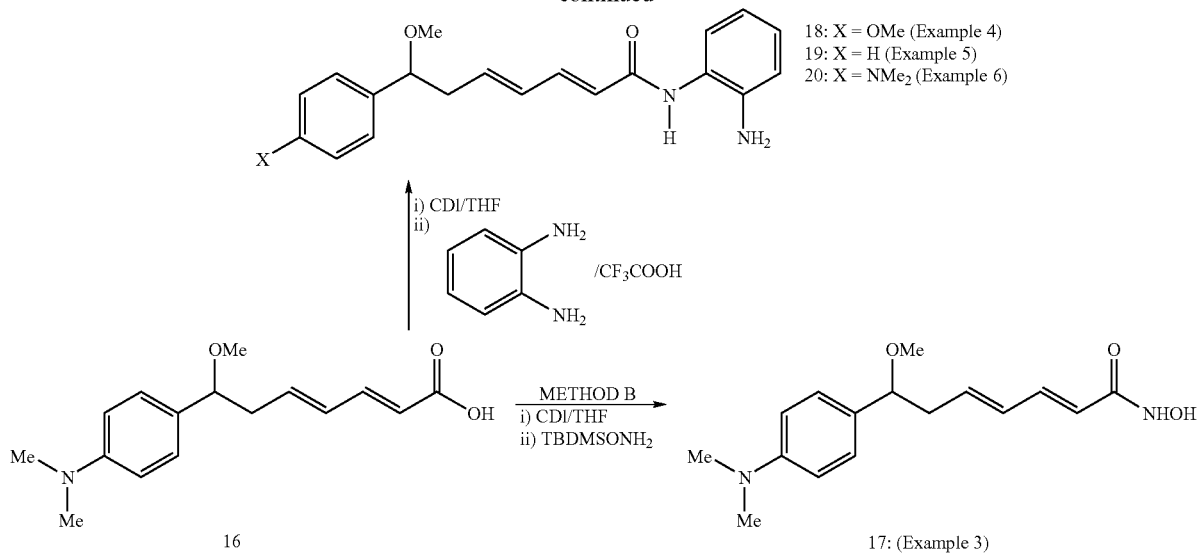

Example 1

N-Hydroxy-7-methoxy-7-(4-methoxyphenyl)-2,4-heptadienamide (6)

Step 1: 5-Methoxy-5-(4-methoxyphenyl)]-2-pentanal (2)

To a stirred solution of p-anisaldehyde dimethyl acetal (1) (1.82 g, 10 mmol) in dry $CH_2Cl_2$ (60 mL) at rt was added 1-trimethylsilyloxy-1,3-butadiene (1.42 g, 10 mmol) followed by catalytic amount of anhydrous $ZnBr_2$ (25 mg). After being stirred for 5 h at rt, the reaction was quenched with water (20 mL). The two phases were separated and the aqueous layer was extracted with $CH_2Cl_2$ (2×25 mL). The combined organic layers were washed with brine, dried over magnesium sulfate, filtered, and concentrated under reduced pressure. Purification of the crude product by flash silica gel chromatography (25% ethyl acetate in hexane) afforded the desired aldehyde 2 (1.15 g, 61% yield) as a colorless oil: $^1H$ NMR (300 MHz, $CDCl_3$) δ 9.48 (d, J=7.8 Hz, 1H), 7.21 (d, J=9.0 Hz, 2H), 6.90 (d, J=9.0 Hz, 2H), 6.81 (dt, J=15.6, 6.9 Hz, 1H), 6.12 (ddt, J=15.6, 7.8, 1.5 Hz, 1H), 4.23 (dd, J=8.1, 5.1 Hz, 1H), 3.81 (s, 3H), 3.20 (s, 3H), 2.78 (m, 1H), 2.65 (m, 1H).

Step 2: Ethyl-7-methoxy-7-(4-methoxyphenyl)-2,4-heptadienoate (3)

A mixture of aldehyde 2 (1.13 g, 5.14 mmol) and ethyl (triphenylphosphoranylidene)acetate (2.15 g, 6.16 mmol) in $CH_2Cl_2$ (25 mL) was heated at reflux for 5 h under $N_2$. After removal of the solvent under reduced pressure, the crude product obtained was purified by flash silica gel chromatography (10% ethyl acetate in hexane) to give the title compound 3 (1.10 g, 74% yield) as a colorless oil: $^1H$ NMR (300 MHz, $CDCl_3$) δ 7.20 (m, 3H), 6.88 (d, J=8.7 Hz, 2H), 5.99-6.21 (m, 2H), 5.76 (d, J=15.3 Hz, 1H), 4.18 (q, J=7.2 Hz, 2H), 4.13 (dd, J=8.4, 6.0 Hz, 1H) 3.81 (s, 3H), 3.18 (s, 3H), 2.64 (m, 1H), 2.48 (m, 1H), 1.28 (t, J=7.2 Hz, 3H).

Step 3: 7-Methoxy-7-(4-methoxyphenyl)-2,4-heptadienoic acid (4)

To a stirred solution of diene ester 3 (0.36 g, 1.24 mmol) in methanol (10 mL) at rt was added aqueous LiOH 0.5 N solution (3.4 mL, 1.7 mmol). After being stirred at 40° C. for 16 h, methanol was removed under reduced pressure and the resulting aqueous solution was acidified with 3N HCl (pH=ca. 4), extracted with ethyl acetate (25×3 mL), dried ($MgSO_4$), and concentrated under reduced pressure to give the desired carboxylic acid 4 (0.30 g, 92% yield). Without further purification, the crude product was used in the next step: $^1H$ NMR (300 MHz, $CD_3OD$): δ 7.23 (d, J=9.0 Hz, 2H), 7.00 (dd, J=15.3, 10.5 Hz, 1H), 6.93 (d, J=9.0 Hz, 2H), 6.17 (dd, J=15.3, 10.5 Hz, 1H), 5.93 (dd, J=15.3, 10.5 Hz, 1H), 5.85 (d, J=15.3 Hz, 1H), 4.20 (br t, J=6.6 Hz, 1H), 3.82 (s, 3 H), 3.20 (s, 3H), 2.61 (m, 1H), 2.48 (m, 1H).

Method A

Step 4: 7-Methoxy-7-(4-methoxyphenyl)-2,4-heptadienoic acid chloride (5)

To a suspension of 60% NaH (0.059 g, 1.47 mmol) washed previously with dry pentane (2×5 mL) in dry benzene (5 mL) at 5° C. was added dropwise a solution of carboxylic acid 4 (0.30 g, 1.14 mmol) in dry benzene (5 mL) via cannula. After 20 min, oxalyl chloride (117 μL, 1.34 mmol) was added via microsyringe, and then the reaction mixture was allowed to warm to rt over 30 min. After stirring for an additional 1.5 h at rt, the mixture was filtered and the filtrate was concentrated under reduced pressure to give the desired acid chloride 5 in 93% yield as a red-orange oil. Without further purification, this crude product was used in the next step: $^1H$ NMR (300 MHz, $CDCl_3$) δ 7.40 (dd, J=15.3, 10.5 Hz, 1H), 7.20 (d, J=8.4 Hz, 2H), 6.90 (d, J=8.4 Hz, 2H), 6.30 (m, 2H), 5.98 (d, J=15.3 Hz, 1H), 4.18 (dd, J=7.5, 4.8 Hz, 1H), 3.82 (s, 3 H), 3.20 (s, 3 H), 2.61 (m, 1H), 2.48 (m, 1H).

Step 5: N-Hydroxy-7-methoxy-7-(4-methoxyphenyl)-2,4-heptadienamide (6)

To a stirred solution of trimethylsilyloxy hydroxylamine (132 μL, 1.08 mmol) and N-methylmorpholine (44 μL, 0.40 mmol) in $CH_2Cl_2$ (5 mL) at 0° C. was added dropwise a solution of acid chloride 5 (101 mg, 0.36 mmol) via cannula. The reaction mixture was stirred for 1 h, and then was allowed to warm to rt over 1 h. After being stirred for an additional 1 h, the reaction mixture was diluted with $CHCl_3$: MeOH (20 mL: 1 mL), washed with saturated $NaHCO_3$ solution and then water, and the organic phase was dried ($MgSO_4$) and concentrated under reduced pressure. Purification by flash silica gel chromatography (5-10% MeOH in $CHCl_3$) gave the desired hydroxamic acid 6 (30 mg, 30%) as a colorless solid: $^1$H NMR (300 MHz, $CDCl_3$) δ 7.20 (m, 3H), 6.87 (d, J=7.5 Hz, 2H), 5.60-6.20 (m, 3H), 4.10 (m, 1H), 3.79 (s, 3H), 3.16 (s, 3H), 2.61 (m, 1H), 2.43 (m, 1H); $^{13}$C NMR (75.4 MHz, $CDCl_3$) δ 41.6, 55.2, 56.4, 82.7, 113.8, 117.9, 127.8, 130.4, 133.1, 139.3, 141.7, 159.2, 165.5.

Example 2

N-Hydroxy-7-methoxy-7-phenyl-2,4-heptadienamide (12)

Step 1: 5-Methoxy-5-phenyl-2-pentanal (8)

Following a procedure analogous to that described in Example 1, step1, but substituting benzaldehyde dimethyl acetal 7 for p-anisaldehyde dimethyl acetal 1, the title compound was obtained in 60% yield: $^1$H NMR (300 MHz, $CDCl_3$) δ 9.49 (d, J=8.1 Hz, 1H), 7.31 (m, 5H), 6.83 ( dt, J=15.6, 7.2 Hz, 1H), 6.12 (ddt, J=15.6, 8.1, 1.5 Hz, 1H), 4.30 (dd, J=8.1, 4.8 Hz, 1H), 3.24 (s, 3H), 2.79 (m, 1H), 2.67 (m, 1H).

Step 2: Ethyl-7-methoxy-7-phenyl-2,4-heptadienoate (9)

Following a procedure analogous to that described in Example 1, step 2, but substituting aldehyde 8 for aldehyde 2, the title compound was obtained in 63% yield: $^1$H NMR (300 MHz, $CDCl_3$) δ 7.30 (m, 6H), 6.11 (m, 2H), 5.76 (d, J=15.3 Hz, 1H), 4.18 (q, J=7.2 Hz, 2H), 4.16(dd, J=7.5, 5.4 Hz, 1H), 3.21(s, 3 H ), 2.64 (m, 1H), 2.50 (m, 1H), 1.28 (t, J=7.2 Hz, 3H).

Step 3: 7-Methoxy-7-phenyl-2,4-heptadienoic acid (10)

Following a procedure analogous to that described in Example 1, step 3, but substituting diene ester 9 for 3 the title compound was obtained in 79% yield: $^1$H NMR (300 MHz, $CD_3OD$) δ 7.29 (m, 5H), 7.18 (dd, J=15.3, 10.5 Hz, 1H), 6.16 (m, 2H), 5.75 (d, J=15.3 Hz, 1H), 4.22 (br t, J=6.6 Hz, 1H), 3.19 (s, 3H ), 2.61 (m, 1H), 2.48 (m, 1H).

Step 4: 7-Methoxy-7-phenyl-2,4-heptadienoic acid chloride (11)

Following a procedure analogous to that described in Example 1, step 4, but substituting carboxylic acid 10 for 4, the title compound was obtained in a quantitative yield: $^1$H NMR (300 MHz, $CDCl_3$) δ 7.25-7.45 (m, 6H), 6.30 (m, 2H), 6.10 (d, J=15.0 Hz, 1H), 4.23 (dd, J=7.5, 5.4 Hz, 1H), 3.22 (s, 3H), 2.63 (m, 1H), 2.49 (m, 1H).

Step 5: N-Hydroxy-7-methoxy-7-phenyl-2,4-heptadienamide (12)

Following a procedure analogous to that described in Example 1 step 5 but substituting acid chloride 11 for 5 the title compound was obtained in 45% yield: $^1$H NMR (300 MHz, $CDCl_3$) δ 7.28 (m, 5H), 7.15 ( dd, J=14.7, 10.5 Hz, 1H), 6.05 (m, 2H), 5.73 (d, J=14.7 Hz, 1H), 4.17 (dd, J=8.4, 4.8 Hz, 1H), 3.19 (s, 3H ), 2.61 (m, 1H), 2.43 (m, 1H); $^{13}$C NMR (75.4 MHz, $CDCl_3$) δ 41.6, 56.6, 83.1, 118.0, 126.5, 127.8, 128.4, 130.4, 139.0, 140.1, 141.6, 165.5.

Example 3

N-Hydroxy7-methoxy-7-[4-(N,N-dimethylamino)phenyl]-2,4-heptadienamide (17)

Step 1: 5-Methoxy-5-[4(N,N-dimethylamino)phenyl]-2-pentanal (14)

Following a procedure analogous to that described in Example 1, step 1, but substituting 4-dimethylaminobenzaldehyde dimethyl acetal (13) for p-anisaldehyde dimethyl acetal (1), the title compound 14 was obtained in 39% yield: $^1$H NMR (300 MHz, $CDCl_3$) δ 9.48 (d, J=8.1 Hz, 1H), 7.16 (d, J=8.7 Hz, 2H), 6.83 (dt, J=15.6, 6.9 Hz, 1H), 6.71 (d, J=8.7 Hz, 2H), 6.12 (ddt, J=15.6, 7.8, 1.5 Hz, 1H), 4.23 (dd, J=8.1, 5.1 Hz, 1H), 3.19 (s, 3H), 2.96 (s, 6H), 2.81 (m, 1H), 2.65 (m, 1H).

Step 2: Ethyl 7-methoxy-7-[4-(N,N-dimethylamino)phenyl]-2,4-heptadienoate (15)

Following a procedure analogous to that described in Example 1, step 2, but substituting aldehyde 14 for 2, the title compound 15 was obtained in 87% yield: $^1$H NMR (300 MHz, $CDCl_3$) δ 7.23 (dd, J=15.3, 10.2 Hz, 1H), 7.13 (d, J=9.0 Hz, 2H), 6.71 (d, J=9.0 Hz, 2H), 6.01-6.23 (m, 2H), 5.76 (d, J=15.3 Hz, 1H), 4.18 (q, J=7.2 Hz, 2H), 4.13 (dd, J=7.8, 6.0 Hz, 1H), 3.18 (s, 3H ), 2.96 (s, 3H), 2.66 (m, 1H), 2.50 (m, 1H), 1.28 (t, J=7.2 Hz, 3H).

Step 3: 7-Methoxy-7-[4-(N,N-dimethylamino)phenyl]-2,4-heptadienoic acid (16)

Following a procedure analogous to that described in Example 1, step 3, but substituting diene ester 15 for 3, the title compound 16 was obtained in 97% yield: $^1$H NMR (300 MHz, $CDCl_3$) δ 7.31 (dd, J=15.3, 10.2 Hz, 1H), 7.15 (d, J=9.0 Hz, 2H), 6.73 (d, J=9.0 Hz, 2H), 6.17 (m, 2H), 5.77 (d, J=15.3 Hz, 1H), 4.20 (m, 1H), 3.19 (s, 3H), 2.96 (s, 6H), 2.68 (m, 1H), 2.52 (m, 1H).

Method B

Step 4: N-Hydroxy-7-methoxy-[4-(N,N-dimethylamino)phenyl]-2,4-heptadienamide (17)

To a solution of carboxylic acid 16 (110 mg, 0.40 mmol) in anhydrous THF (5 mL) was added 1,1'-carbonyldiimidazole (77 mg, 0.439 mmol) at rt, and the mixture was stirred overnight. To this solution was added t-butyldimethylsilylhydroxylamine (200 mg, 1.36 mmol). The mixture was stirred at rt for 14 h and then at 45° C. for 3 h. The resulting yellow solution was diluted with water (5 mL), stirred for 20 minutes, and then extracted with ethyl acetate (3×15 mL), dried, and concentrated. Purification by flash silica gel chromatography (80% ethyl acetate in hexanes and then ethyl acetate only) afforded the title compound 17 (44 mg, 38% yield): $^1$H NMR (300 MHz, CDCl$_3$) δ 7.18 (dd, J=15.0, 10.2 Hz, 1H), 7.13 (d, J=8.7 Hz, 1H), 6.71 (d, J=8.7 Hz, 2H), 5.96-6.17 (m, 2H), 5.66 (br d, J=15.0 Hz, 1H), 4.09 (dd, J=7.5, 5.7 Hz, 1H), 3.17(s, 3H ), 2.94 (s, 6H), 2.61 (m, 1H),2.43 (m, 1H); $^{13}$C NMR (75.4 MHz, CDCl$_3$) δ 40.6, 41.5, 56.2, 82.9, 112.4, 117.4, 127.6, 128.7, 130.1, 139.9, 141.9, 150.3, 165.5.

Example 4

N-(2-Aminophenyl)-7-methoxy-7-(4-methoxyphenyl)-2,4-heptadienamide (18)

To a stirred solution of acid chloride 5 (115 mg,0.41 mmol) in CH$_2$Cl$_2$ (5 mL) at 0° C. was added 1,2-phenylenediamine (133 mg,1.23 mmol) followed by N-methylmorpholine (49 µL, 0.45 mmol). The mixture was stirred at 0° C. for 1 h, and then was allowed to warm to rt over 1 h. After being stirred for an additional 1 h at rt, the reaction mixture was partitioned between CHCl$_3$ (2×15 mL) and water (15 mL). The combined organic layers were dried (MgSO$_4$) and concentrated under reduced pressure to give the crude product. Purification by flash silica gel chromatography (50% ethyl acetate in hexane) afforded the desired benzamide 18 (21 mg, 15% yield): $^1$H NMR (300 MHz, CDCl$_3$) δ 6.65-7.40 (m, 9H), 5.96-6.20 (m, 2H), 5.92 (d, J=15.3 Hz, 1H), 4.18 (m, 1H), 3.82 (br s, 2H), 3.81 (s, 3H ), 3.19 (s, 3H), 2.61 (m, 1H), 2.43 (m, 1H); $^{13}$CNMR (75.4 MHz,CDCl$_3$) δ 41.7, 55.2, 56.4, 82.7, 113.8, 118.2, 119.5, 121.8, 124.4, 125.0, 127.0, 127.8, 130.1, 133.1, 139.5, 140.7, 142.4, 159.2, 164.6.

Example 5

N-(2-Aminophenyl)-7-methoxy-7-phenyl-2,4-heptadienamide (19)

Step 1: N-[2-(N-tert-Butoxycarbonyl)aminophenyl]-7-methoxy-7-phenyl-2,4-heptadienamide Following a procedure analogous to that described in Example 4, but substituting acid chloride 11 for 5 and t-Boc protected phenylenemonoamine for 1,2-phenylenediamine, the title compound was obtained as a light yellow solid in 84% yield: $^1$H NMR (300 MHz, CDCl$_3$) δ 8.23 (br s, 1H), 7.01-7.49 (m, 10H), 6.09 (m, 2H), 5.87 (d, J=15.3 Hz, 1H), 4.21 (dd, J'7.5, 5.7 Hz, 1H), 3.23 (s, 3H), 2.66 (m, 1H), 2.52 (m, 1H), 1.51 (s, 9H).

Step 2: N-(2-Aminophenyl)-7-methoxy-7-phenyl-2,4-heptadienamide (19)

The t-Boc protected aniline obtained in step 1 (200 mg, 0.473 mmol) was dissolved in a mixture of methanol (2 mL) and 4N HCl solution in 1,4-dioxane (3.55 mL, 14.2 mmol) and stirred at rt for 1 h. The reaction mixture was diluted with water (2 mL), neutralized with 1N NaOH (pH 7-8), and extracted with CHCl$_3$. The organic extract was dried (MgSO$_4$) and concentrated. Purification by flash silica gel chromatography (50% ethyl acetate in hexane) afforded the title compound 19 (128 mg, 84% yield): $^1$H NMR (300 MHz, CDCl$_3$) δ 7.48 (br s, 1H), 7.01-7.39 (m, 10H), 6.09 (m, 2H), 5.91 (d, J=14.7 Hz, 1H), 4.20 (br. t, J=6.3 Hz, 1H), 3.81 (br. s, 2H), 3.21 (s, 3H), 2.66 (m, 1H), 2.52 (m, 1H); $^{13}$C NMR (75.4 MHz, CDCl$_3$) δ 41.7, 56.7, 83.2, 118.1, 119.4, 121.9, 124.4, 125.1, 126.6, 127.1, 127.8, 128.5, 130.3, 139.2, 140.8, 141.2, 142.3, 164.6.

Example 6

N-(2-Aminophenyl)-7-methoxy-7-[4-(N,N-dimethylamino)phenyl]-2,4-heptadienamide (20)

To a solution of carboxylic acid 16 (207 mg, 0.753 mmol) in anhydrous THF (10 mL) was added 1,1'-carbonyldiimidazole (128 mg, 0.790 mmol) at rt, and the mixture was stirred overnight. To the resulting solution was added 1,2-phenylenediamine (570 mg, 5.27 mmol), followed by trifluoroacetic acid (52 µl ), and the reaction mixture was stirred for 16 h at rt. The reaction mixture was diluted with ethyl acetate (30 mL), washed with saturated NaHCO$_3$ solution (5 mL) and then water (10 mL), dried (MgSO$_4$), and concentrated. Purification by flash silica gel chromatography (50% ethyl acetate in toluene) afforded the title compound 20 (115 mg, 42% yield): $^1$H NMR (300 MHz, CDCl$_3$) δ 7.44 (br. s, 1H), 7.01-7.29 (m, 5H), 6.70-6.78 (m, 4H), 6.09 (m, 2H), 5.90 (d, J=15.0 Hz, 1H), 4.10 (br. t, J=6.6 Hz, 1H), 3.89 (br. s, 2H), 3.18 (s, 3H), 2.95 (s, 3H), 2.66 (m, 1H), 2.50 (m, 1H); $^{13}$C NMR (75.4 MHz, CDCl$_3$) δ 40.5, 41.6, 82.8, 112.3, 118.1, 119.4, 121.7, 124.4, 125.1, 127.0, 127.6, 128.6, 130.0, 140.0, 140.8, 142.5, 150.2, 164.7.

Example 7

N-(2-Aminopyridinyl)-7-methoxy-7-(4-methoxyphenyl)-2,4-heptadienamide (21)

Following a procedure analogous to that described in Example 1, step 5, but substituting 2-aminopyridine for trimethylsilyloxyhydroxylamine, the title compound was obtained in 5% yield: $^1$H NMR (300 MHz, CDCl$_3$) δ 8.31-8.23 (m, 3H), 7.70 (m, 1H), 7.31 (dd, J=15.0, 10.5 Hz, 1H), 7.19 (d, J=9.0 Hz, 2H), 7.02 (m, 1H), 6.89 (d, J=9.0 Hz, 2H), 6.13 (m, 2H), 5.90 (d, J=15.0 Hz, 1H), 4.16 (dd, J=7.2, 6.0 Hz, 1H), 3.82 (s, 3H), 3.20 (s, 3H), 2.62 (m, 1H), 2.47 (m, 1H).

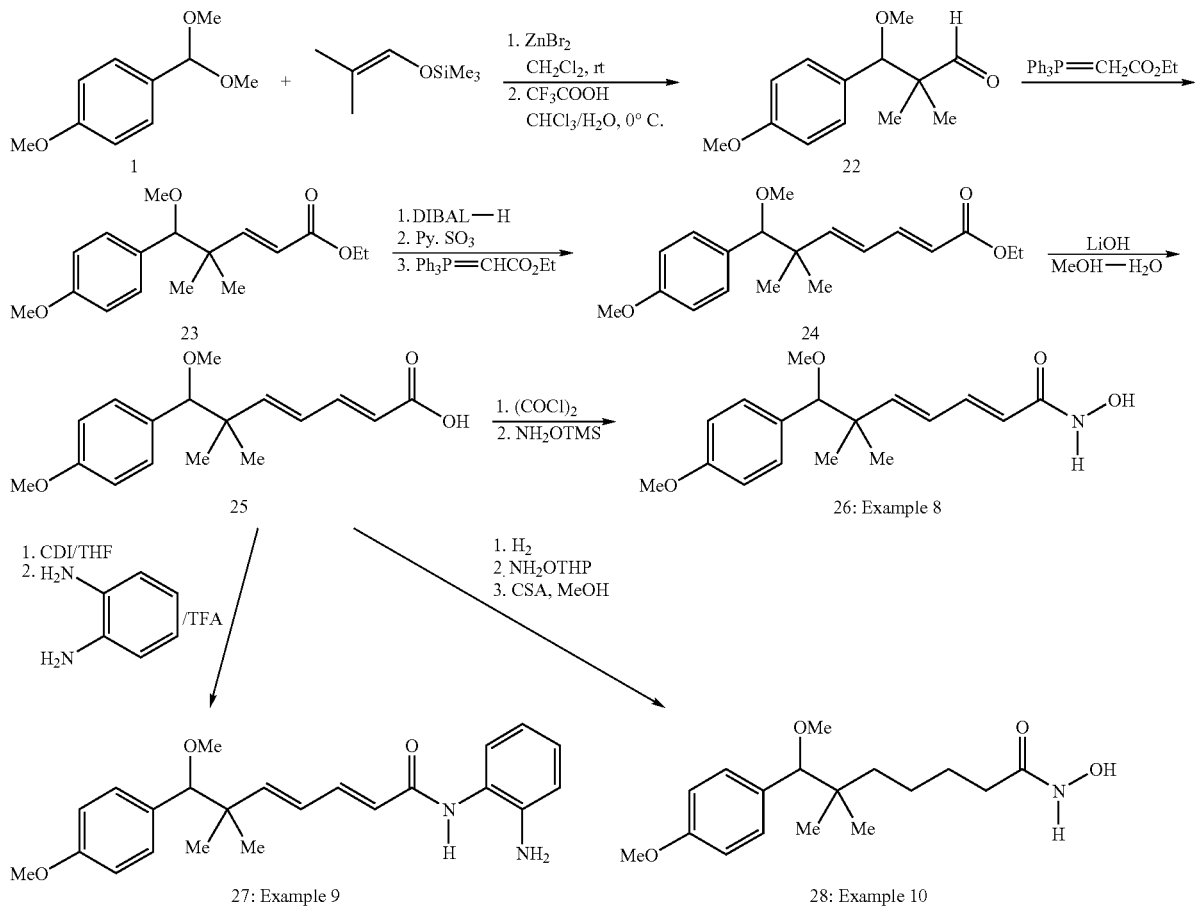

Example 8

N-Hydroxy-6,6-dimethyl-7-methoxy-7-(4-methoxyphenyl)-2,4-heptadienamide (26)

Step 1: 2,2-Dimethyl-3-methoxy-3-(4-methoxyphenyl)propanal (22)

Following a procedure analogous to that described in Example 1, step 1, but substituting 2-methyl-1-(trimethylsilyloxy)-1-propene for 1-trimethylsilyloxy-1,3-butadiene, the title compound 22 was obtained in 65% yield: $^1$H NMR (300 MHz, CDCl$_3$) δ 9.67 (s, 1H), 7.17 (d, J=8.4 Hz, 2H), 6.89 (d, J=8.4 Hz), 4.26 (s, 1H), 3.82(s, 3H), 3.17 (s, 3H), 1.00 (s, 3H), 0.89 (s, 3H).

Step 2: Ethyl 4,4-dimethyl-5-methoxy-5-(4-methoxyphenyl)-2-pentenoate (23)

Following a procedure analogous to that described in Example 1, step 2, but substituting aldehyde 22 for aldehyde 2 and conducting the reaction in refluxing toluene, the title compound 23 was obtained in 93% yield: $^1$H NMR (300 MHz, CDCl$_3$) δ 7.28 (d, J=15.9 Hz, 1H), 7.26 (d, J=8.7 Hz, 2H), 7.00 (d, J=8.7 Hz, 2H), 5.83 (d, J=15.9 Hz, 1H), 4.34 (q, J=7.2 Hz, 2H), 4.04 (s, 1H), 3.9 7 (s, 3H), 3.32 (s, 3H), 1.45 (t, J=7.2 Hz, 3H), 1.20 (s, 3H), 1.14 (s, 3H).

Step 3: Ethyl 6,6-dimethyl-7-methoxy-7-(4-methoxyphenyl)-2,4-heptadienoate (24)

i) DIBAL-H Reduction

To a stirred solution of ester 23 (2.14 g, 7.32 mmol) in anhydrous THF (40 mL) was added dropwise a solution of DIBAL-H (1.0 M solution in THF, 16 mL, 16 mmol) via syringe at −78° C., and the mixture was slowly warmed to rt over 3 h with stirring. The reaction was quenched carefully with water (20 mL), extracted with ethyl acetate (30×3 mL), dried (MgSO$_4$), and concentrated. Purification by flash silica gel chromatography (25% ethyl acetate in hexane) afforded the corresponding alcohol (1.46 g, 80% yield) as a colorless oil: $^1$H NMR (300 MHz, CDCl$_3$) δ 7.12 (d, J=8.7 Hz, 2H), 6.84 (d, J=8.7 Hz, 2H), 5.80 (dt, J=15.9, 1.4 Hz, 1H), 5.48 (dt, J=15.9, 6.0 Hz, 1H), 4.10 (d, J=6.0 Hz, 2H), 3.82 (s, 1H), 3.81 (s, 3H), 3.16 (s, 3H), 1.45 (t, J=7.2 Hz, 3H), 1.00 (s, 3H), 0.95 (s, 3H).

ii) Oxidation

To a stirred solution of the alcohol (1.21 g, 4.84 mmol) in anhydrous DMSO (25 mL) containing triethylamine (4.3 mL) was added pyridinium sulfur trioxide complex (2.31 g, 14.5 mmol) at rt, and the mixture was stirred for 10 min. at the same temperature. The reaction was quenched by adding cold water (15 mL). Extraction with ethyl ether (3×30 mL), followed by drying and concentration gave the corresponding aldehyde, which was used without further purification in the next step.(1.03 g, 86% yield).

iii: Wittig Reaction

The aldehyde was treated with ethyl (triphenylphosphoranylidene)acetate in toluene at 70° C. by a procedure analogous to that described in Example 1, step 2, to give the title compound 24 in 93% yield: $^1$H NMR (300 MHz, CDCl$_3$) δ 7.28 (dd, J=15.3, 10.5 Hz, 1H), 7.10 (d, J=8.7 Hz, 2H), 6.84 (d, J=8.7 Hz, 2H), 6.25 (d, J=15.6 Hz, 1H), 6.01 (dd, J=15.6, 10.5 Hz, 1H), 5.76 (d, J=15.3 Hz, 1H), 4.19 (q, J=7.2 Hz, 2H), 3.83 (s, 1H), 3.81 (s, 3H), 3.15 (s, 3H), 1.29 (t, J=7.2 Hz, 3H), 1.06 (s, 3H), 0.96 (s, 3H), Step 4: 6,6-Dimethyl-7-methoxy-7-(4-methoxyphenyl)-2,4-heptadienoic acid (25)

Following the procedure described in Example 1, step 3, but substituting compound 24 for diene ester 3, the title compound 25 was obtained in 95% yield: $^1$H NMR (300 MHz, CDCl$_3$) δ 7.38 (dd, J=15.0, 10.8 Hz, 1H), 7.10 (d, J=9.0 Hz, 2H), 6.84 (d, J=9.0 Hz, 2H), 6.32 (d, J=15.6 Hz, 1H), 6.06 (dd, J=15.6, 10.8 Hz, 1H), 5.78 (d, J=15.3 Hz, 1H), 3.85 (s, 1H), 3.81 (s, 3H), 3.16 (s, 3H), 1.08 (s, 3H), 0.98 (s, 3H); $^{13}$C NMR (75.4 MHz, CDCl$_3$) δ 22.9, 24.4, 42.2, 55.1, 57.2, 90.6, 113.9, 118.7, 125.7, 129.4, 130.3, 147.9, 152.4, 159.0, 172.8.

Step 5: N-Hydroxy-6,6-dimethyl-7-methoxy-7-(4-methoxyphenyl)-2,4-heptadienamide (26)

Following the procedure described in Example 1, step 4 (Method A), but substituting compound 25 for carboxylic acid 4, the title compound 26 was obtained as a colorless solid in 63% overall yield: $^1$H NMR (300 MHz, CD$_3$OD) δ 7.21 (dd, J=15.3, 10.8 Hz, 1H), 7.15 (d, J=8.7 Hz, 2H), 6.88 (d, J=8.7 Hz, 2H), 6.25 (d, J=15.6 Hz, 1H), 6.03 (dd, J=15.6, 10.8 Hz, 1H), 5.83 (d, J=15.3 Hz, 1H), 3.93 (s, 1H), 3.80 (s, 3H), 3.17 (s, 3H), 1.09 (s, 3H), 1.00 (s, 3H); $^{13}$C NMR (75.4 MHz, CD$_3$OD) δ 23.7, 24.9, 43.0, 55.6, 57.4, 91.9, 114.0, 119.7, 127.1, 130.6, 131.7, 142.6, 150.7, 160.6, 166.8.

Example 9

N-(2-Aminophenyl)-6,6-dimethyl-7-methoxy-7-(4-methoxyphenyl)-2,4-heptadienamide (27)

Following the procedure described in Example 6, but substituting carboxylic acid 25 for carboxylic acid 16, the title compound 27 was obtained as a light yellow solid in 67% yield: $^1$H NMR (300 MHz, CD$_3$OD) δ 7.56 (br. s, 1H), 7.29 (dd, J=15.0, 10.8 Hz, 1H), 6.72-7.20 ( m, 8H), 6.20 (d, J=15.0 Hz, 1H), 5.98 (dd, J=15.0, 10.8 Hz, 1H), 5.90 (d, J=15.0 Hz, 1H), 3.91 (br s, 2H), 3.83 (s, 1H), 3.80 (s, 3H), 3.16(s, 3H), 1.06 (s, 3H), 0.97 (s, 3H); $^{13}$C NMR (75.4 MHz, CDCl$_3$) δ 23.2, 24.3, 42.1, 55.1, 57.2, 90.6, 112.9, 118.0, 119.4, 121.6, 124.4, 125.2, 125.6, 127.0, 129.4, 130.5, 140.8, 143.1, 150.3, 158.9, 164.9.

Example 10

N-Hydroxy-6,6-dimethyl-7-methoxy-7-(4-methoxyphenyl)heptanamide (28)

Step 1: 6,6-Dimethyl-7-methoxy-7-(4-methoxyphenyl)heptanoic acid

To a solution of carboxylic acid 25 (100 mg, 0.345 mmol) in MeOH (6 mL), at room temperature was added a solution of Pd/C 10% (50 mg, 1 mL in MeOH). The system was then purged with H$_2$ several times to a final pressure of 50 psi. The reaction mixture was stirred for 3 h at room temperature, and then the solid was filtered through a Celite pad in a fritted glass funnel. The solvents were evaporated, and the crude material (100 mg, 99%) was pure enough for use in the next step: $^1$H NMR (300 MHz d$_6$-acetone) δ 7.18 (d, J=8 Hz, 2H), 6.89 (d, J=8 Hz, 2H), 3.85 (s, 1H), 3.78 (s, 3H), 3.11 (s, 3H), 2.30 (br. t, J=7.5 Hz, 2H), 1.58-1.53 (m, 2H), 1.37-1.25 (m, 4H), 0.84 (s, 3H), 0.77 (s, 3H).

Step 2: N-Hydroxy-6,6-dimethyl-7-methoxy-7-(4-methoxyphenyl)heptanamide (28)

To a solution of the carboxylic acid from step 1 (100 mg, 0.344 mmol), in DMF (10 mL) at room temperature were added 1-(3-dimethylaminopropyl)-3-ethylcarbodiimide hydrochloride (EDC, 79 mg, 0.414 mmol) and 1-hydroxybenzotriazole hydrate (HOBt, 70 mg, 0.516 mmol). The mixture was stirred for 20 min. at room temperature, and then NH$_2$OTHP (60 mg, 0.516 mmol) was added. The resulting mixture was heated overnight at 50° C., and then concentrated. The crude material was dissolved in CH$_2$Cl$_2$ and washed with a saturated aqueous solution of NaHCO$_3$. The aqueous layer was extracted several times with CH$_2$Cl$_2$ and the combined organic extracts were dried over anhydrous MgSO$_4$ and concentrated. The crude material was purified by flash chromatography using hexane/acetone (7:3) as the solvent mixture. The pure protected hydroxamate was then dissolved in MeOH (10 mL), and 10-camphorsulfonic acid (CSA, 40 mg, 0.172 mmol) was added. The mixture was stirred for 2 h at room temperature, and then the solvents were evaporated under reduced pressure at room temperature to avoid thermal decomposition. The crude mixture was purified by flash chromatography using CH$_2$Cl$_2$/MeOH (9:1) as the solvent mixture, giving compound 28 as colorless oil (212 mg, 68%): $^1$H NMR: (300 MHz, d$_6$-acetone) δ 7.18 (d, J=8 Hz, 2H), 6.89 (d, J=8 Hz, 2H), 3.85 (s, 1H), 3.79 (s, 3H), 3.11 (s, 3H), 2.11-2.05 (m, 2H), 1.45 (br. s, 2H), 1.34 (br. s, 4H), 0.83 (s, 3H), 0.76 (s, 3H).

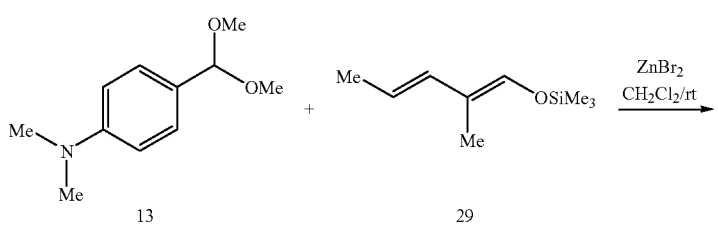

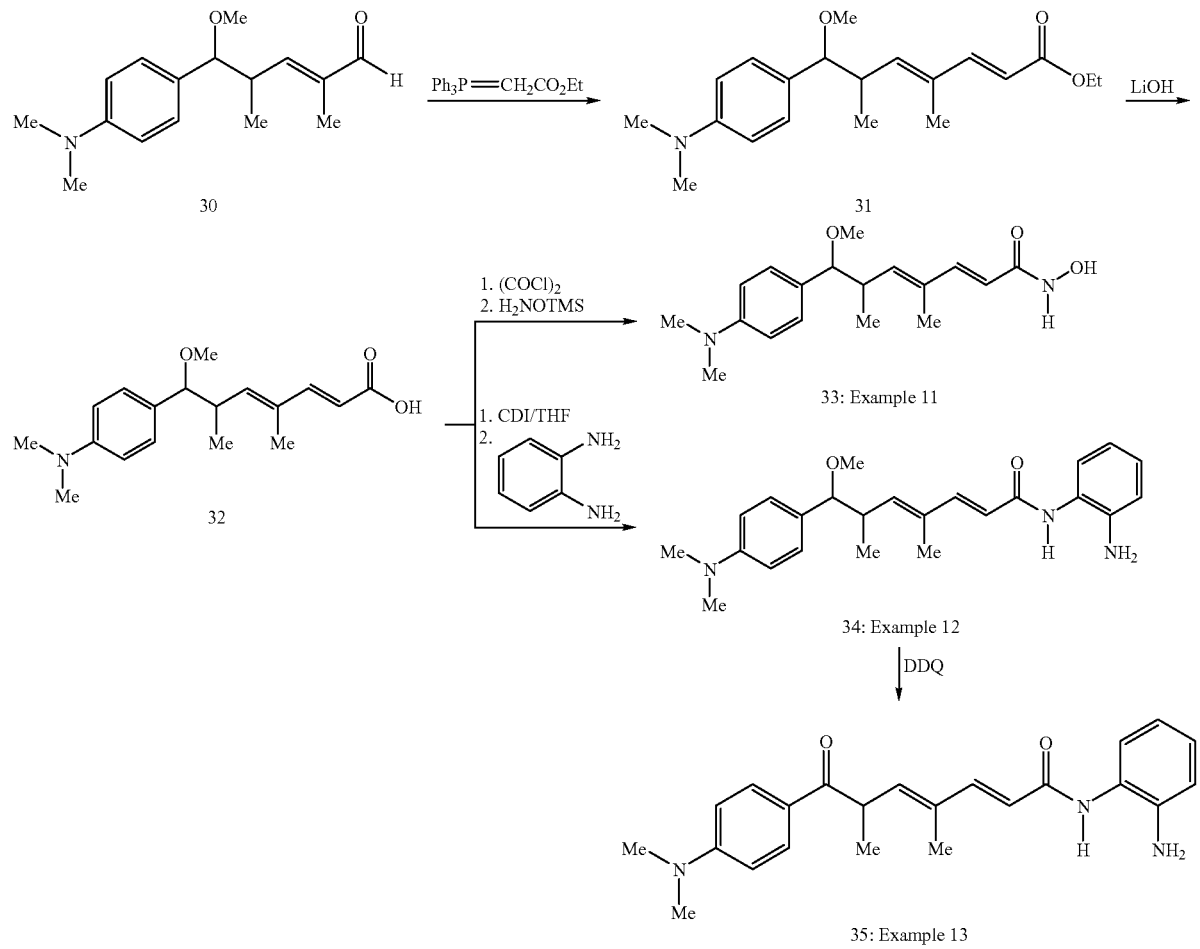

Example 11

N-Hydroxy-4,6-dimethyl-7-methoxy-7-[4-(N,N-dimethylamino)phenyl]-2,4-heptadienamide (33)

Step 1: 2,4-Dimethyl-5-methoxy-5-[4-(N,N-dimethylamino)phenyl]-2-pentenal (30)

Following the procedure described in Example 1, step 1, but substituting 2-methyl-1-trimethylsilyloxypenta-1,3-diene (29) (*Tetrahedron*, 39: 881 (1983)) for 1-trimethylsilyloxy-1,3-butadiene, the title compound 30 was obtained in 68% yield as a mixture of two isomers in a ca. 2.5:1 ratio: major isomer: $^1$H NMR (300 MHz, CDCl$_3$) δ 9.29 (s, 1H), 7.08 (d, J=8.4 Hz, 2H), 6.67 (d, J=8.4 Hz, 2H), 6.29 (dq, J=9.9, 1.2 Hz, 1H), 3.96 (d, J=6.6 Hz, 1H), 3.20 (s, 3H), 3.05 (m, 1H), 2.94 (s, 6H), 1.60 (d, J=0.9 Hz, 3H), 1.12 (d, J=6.9 Hz, 3H).

Step 2: Ethyl 4,6-dimethyl-7-methoxy-7-[4-(N,N-dimethylamino)phenyl]-2,4-heptadienoate (31)

Following the procedure described in Example 1, step 2, but substituting aldehyde 30 for aldehyde 2 and heating the reaction mixture at reflux in toluene overnight under N$_2$, the title compound 31 was obtained in 96% yield as a mixture of two isomers in a ca. 2.5:1 ratio: major isomer: $^1$H NMR (300 MHz, CDCl$_3$) δ 7.21 (dd, J=15.6, 0.9 Hz, 1H), 7.06 (d, J=8.7 Hz, 2H), 6.66 (d, J=8.7 Hz, 2H), 5.69 (d, J=15.6 Hz, 1H), 5.67 (br. d, J=9.0 Hz, 1H), 4.17 (q, J=7.2 Hz, 2H), 3.87 (d, J=6.9 Hz, 1H), 3.18 (s, 3H), 2.93 (s, 6H), 2.81 (m, 1H), 1.59 (d, J=1.2 Hz, 3H), 1.27 (t, J=7.2 Hz, 3H), 1.05 (d, 6.6 Hz, 3H).

Step 3: 4,6-Dimethyl-7-methoxy-7-(4N,N-imethylaminophenyl)-2,4-heptadienoic acid (32)

Following the procedure described in Example 1, step 3, but substituting ester 31 for ester 3, the title compound 32 was obtained in 98% yield: major isomer: $^1$H NMR (300 MHz, CD$_3$OD) δ 7.21 (d, J=15.6, 0.6 Hz, 1H), 7.04 (d, J=8.7 Hz, 2H), 6.70 (d, J=8.7 Hz, 2H), 5.61 (d, J=15.6 Hz, 1H), 5.60 (br. d, J=10.0 Hz, 1H), 3.85 (d, J=7.5 Hz, 1H), 3.13 (s, 3H), 2.87 (s, 6H), 2.81 (m, 1H), 1.52 (d, J=1.5 Hz, 3H), 1.06 (d, J=6.6 Hz, 3H).

Step 4: N-Hydroxy-4,6-dimethyl-7-methoxy-7-[4-(N,N-dimethylamino)phenyl]-2,4-heptadienamide (33)

Following the procedure described in Example 1, step 4 (Method A), but substituting compound 32 for carboxylic acid 4, the title compound 33 was obtained in 5% yield, as a mixture of two isomers in a ca. 3:1 ratio: major isomer: $^1$H NMR (300 MHz, CD$_3$OD) δ 7.23-7.21 (m, 3H), 6.67 (d, J=8.7 Hz, 2H), 5.70 (d, J=15.6 Hz, 1H), 5.62 (d, J=10.2 Hz, 1H), 3.90 (d, J=7.8 Hz, 1H), 3.20 (s, 3H), 2.93 (s, 6H), 2.81 (m, 1H), 1.58 (br. s, 3H), 1.13 (d, J=6.6 Hz, 3H).

Example 12

N-(2-Aminophenyl)-4,6-dimethyl-7-methoxy-7-[4-(N,N-dimethylamino)phenyl]-2,4-heptadienamide (34)

Following the procedure described in Example 6, but substituting carboxylic acid 32 for carboxylic acid 16, the title compound 34 was obtained in 61% yield, as a mixture of two isomers in a ca.3:1 ratio: major isomer: $^1$H NMR (300 MHz, CD$_3$OD) δ 7.28-7.02 (m, 5H), 6.79 (m, 2H), 6.68 (d, J=8.7 Hz, 2H), 5.83 (d, J=15.0 Hz, 1H), 5.69 (d, J=9.6 Hz, 1H), 3.87 (d, J=6.9 Hz, 1H), 3.19 (s, 3H), 2.94 (s, 6H), 2.80 (m, 1H), 1.61 (br. s, 3H), 1.07 (d, J=6.6 Hz, 3H).

Example 13

N-(2-Aminophenyl)-4-methyl-6-[4-(N,N-dimethylamino)benzoyl]-2,4-heptadienamide (35)

To a stirred solution of compound 34 (85 mg, 0.216 mmol) in wet benzene (2 mL, benzene: H$_2$O=9:1) at room temperature was added 2,3-dichloro-5,6-dicyano-1,4-benzoquinone (DDQ, 98 mg, 0.432 mmol). After being stirred vigorously for 15 min., the mixture was diluted with ethyl acetate (30 mL), washed with water (2×5 mL), dried (anhydr.MgSO$_4$), and concentrated. Purification by flash silica gel chromatography (50% ethyl acetate in hexanes, and then ethyl acetate only) afforded the title compound 35 (6 mg, 7% yield): $^1$H NMR (300 MHz, CDCl$_3$) δ 7.83 (d, J=9.0, 2H), 7.87 (br. s, 1H), 7.29 (d, J=15.6 Hz, 1H), 7.27 (d, 7.8 Hz, 1H), 7.00 (m, 1H), 6.72 (m, 2H), 6.62 (d, J=9.0 Hz, 2H), 5.97 (d, J=15.6 Hz, 1H), 5.97 (d, J=9.3 Hz, 1H), 4.34 (dq, J=9.3, 6.9 Hz, 1H), 3.03 (s, 3H), 1.87 (br. s, 3H), 1.29 (d, J=6.9 Hz, 3H); $^{13}$C NMR (75 MHz, CDCl$_3$) δ 12.6, 17.6, 39.9, 40.8, 110.7, 118.0, 119.0, 119.3, 123.8, 124.4, 125.1, 126.9, 130.6, 132.5, 140.8, 146.2, 153.4, 164.8, 198.6.

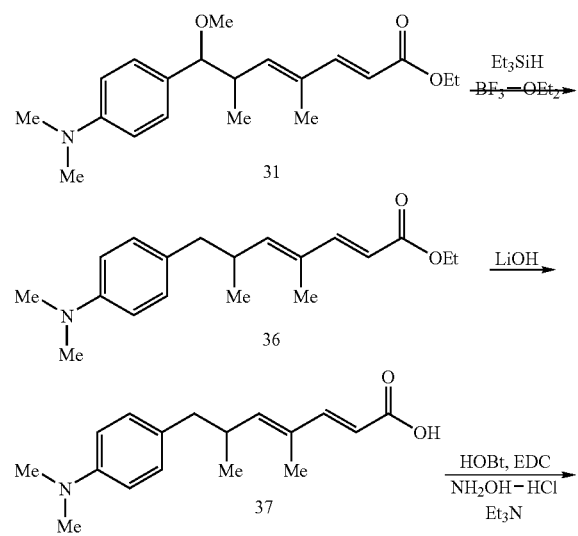

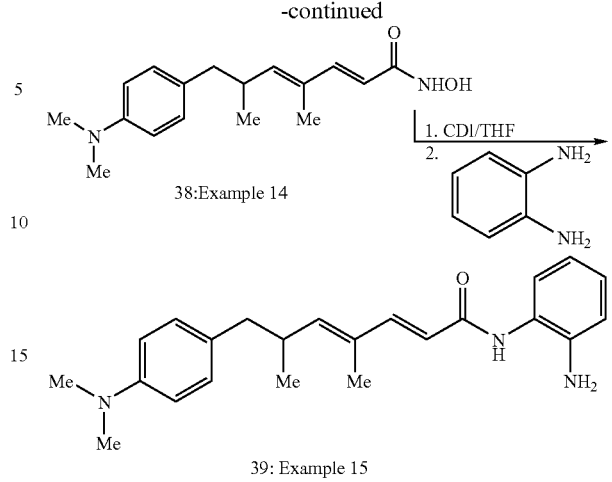

38:Example 14

39: Example 15

Example 14

N-Hydroxy-4,6-dimethyl-7-[4-(N,N-dimethylamino)phenyl]-2,4-heptadienamide (38)

Step 1: Ethyl 4,6dimethyl-7-[4-(N,N-dimethylamino)phenyl]-2,4-heptadienoate (36)

To a stirred solution of ester compound 31 (99 mg, 0.299 mmol) in CH$_2$Cl$_2$ (3 mL) at 0° C. was added triethylsilane (41.9 mg, 0.36 mmol) followed by BF$_3$.Et$_2$O (51 mg, 0.36 mmol) dropwise via microsyringe, and the mixture was stirred at 0° C. for 30 min. The reaction was quenched with saturated NaHCO$_3$ solution (3 mL), diluted with CH$_2$Cl$_2$ (20 mL), and washed with water, and the organic phase was dried and concentrated. Purification by flash silica gel chromatography (10% ethyl acetate in hexane) afforded the title compound 36 (87 mg, 97% yield) as a yellow oil: $^1$H NMR (300 MHz, CDCl$_3$) δ 7.29 (dd, J=15.6, 0.6 Hz, 1H), 6.98 (d, J=8.7 Hz, 2H), 6.64 (d, J=8.7 Hz, 2H), 5.74 (d, J=15.6 Hz, 1H), 5.73 (br d, J=10.2 Hz, 1H), 4.20 (q, J=6.9 Hz, 2H), 2.90 (s, 6H), 2.73 (m, 1H), 2.53 (d, J=7.2 Hz, 2H), 1.61 (d, J=0.6 Hz, 3H), 1.29 (t, J=6.9 Hz, 3H), 1.00 (d, J=6.6 Hz, 3H); $^{13}$C NMR (75 MHz, CDCl$_3$) δ 12.1, 14.3, 20.0, 35.5, 40.8, 42.2, 60.1, 112.7, 115.5, 128.1, 129.7, 131.6, 147.5, 149.0, 149.8, 167.5.

Step 2: 4,6-Dimethyl-7-[4-(N,N-dimethylamino)phenyl]-2,4-heptadienoic acid (37)

Following the procedure described in Example 1, step 3, but substituting compound 36 for ester 3, the title compound 37 was obtained in 98% yield as a yellow oil: $^1$H NMR (300 MHz, CDCl$_3$) δ 7.38 (dd, J=15.6, 0.6 Hz, 1H), 6.98 (d, J=9.0 Hz, 2H), 6.67 (d, J=9.0 Hz, 2H), 5.79 (br. d, J=9.6 Hz, 1H), 5.73 (d, J=15.6 Hz, 1H), 2.91 (s, 6H), 2.76 (m, 1H), 2.57 (d, J=7.2 Hz, 2H), 1.62 (d, J=0.6 Hz, 3H), 1.01 (d, J=6.6 Hz, 3H); $^{13}$C NMR (75 MHz, CDCl$_3$) δ 12.2, 20.0, 35.7, 40.9, 42.17, 112.9, 114.7, 128.2, 129.7, 131.7, 148.9, 149.1, 152.1, 172.7.

Step 3: N-Hydroxy-4,6-dimethyl-7-[4-(N,N-dimethylamino)phenyl]-2,4-heptadienamide (38)

To a stirred solution of carboxylic acid 37 (70 mg, 0.256 mmol) at rt in anhydrous DMF (2 mL) was added 1-hydroxybenzotriazole hydrate (41.5 mg, 0.307 mmol) followed by 1-(3-dimethylaminopropyl)-3-ethyl-carbodiimide hydrochloride(65 mg, 0.340 mmol). After 1 h, hydroxylamine hydrochloride (89 mg, 1.28 mmol) and Et$_3$N (0.27 mL, 1.92 mmol) was added, and stirring was continued at rt overnight. The solvent was removed in vacuo, and the residue was diluted with ethyl acetate (30 mL), and washed with water and saturated NaHCO$_3$ solution (5 mL). After drying and concentration, the crude product was purified by flash silica gel chromatography (2-10% methanol in chloroform) to give the title compound 38 (30 mg, 41% yield) as a yellow oil: $^1$H NMR (300 MHz, CDCl$_3$:CD$_3$OD=5:1) δ 7.10 (d, J=14.4 Hz, 1H), 6.88 (d, J=8.7 Hz, 2H), 6.58 (d, J=8.7 Hz, 2H), 5.59 (d, J=9.3 Hz, 1H), 5.55 (br. d, J=14.4 Hz, 1H), 2.78 (s, 6H), 2.63 (m, 1H), 2.40 (d, J=6.9 Hz, 2H), 1.48 (s, 3H), 0.89 (d, J=6.6 Hz, 3H); $^{13}$C NMR (75 MHz, CDCl$_3$: CD$_3$OD=5:1) δ 11.8, 19.7, 35.3, 40.8, 42.0, 14.3, 20.0, 35.5, 40.8, 42.2, 113.1, 113.7, 128.7, 129.5, 131.1, 145.9, 146.3, 148.9, 165.5.

Example 15

N-(2-Aminophenyl)-7-[4-(N,N-dimethylamino)phenyl)]-4,6-methyl-2,4-heptadienamide (39)

Following the procedure described in Example 6, but substituting carboxylic acid 37 for carboxylic acid 16, the title compound 39 was obtained in 75% yield: $^1$H NMR (300 MHz, CDCl$_3$) δ 7.42 (br. s, 1H), 7.32 (d, J=15.0 Hz, 1H), 7.20 (d, J=7.2 Hz, 1H), 7.04 (t, J=7.2 Hz, 1H), 6.98 (d, J=9.0 Hz, 2H), 6.76 (m, 2H), 6.66 (d, J=9.0 Hz, 2H), 5.85 (d, J=15.0 Hz, 1H), 5.72 (d, J=9.6 Hz, 1H), 3.90 (br. s, 2H), 2.90 (s, 6H), 2.75 (m, 1H), 2.52 (d, J=7.2 Hz, 2H), 1.61 (d, J=0.6 Hz, 3H), 1.00 (d, J=6.6 Hz, 3H); $^{13}$C NMR (75 MHz, CDCl$_3$) δ 12.3, 20.1, 35.6, 40.9, 42.2, 112.7, 117.5, 118.1, 119.4, 124.6, 125.1, 126.9, 128.2, 129.7, 131.3, 140.8, 147.1, 147.4, 149.0, 165.0.

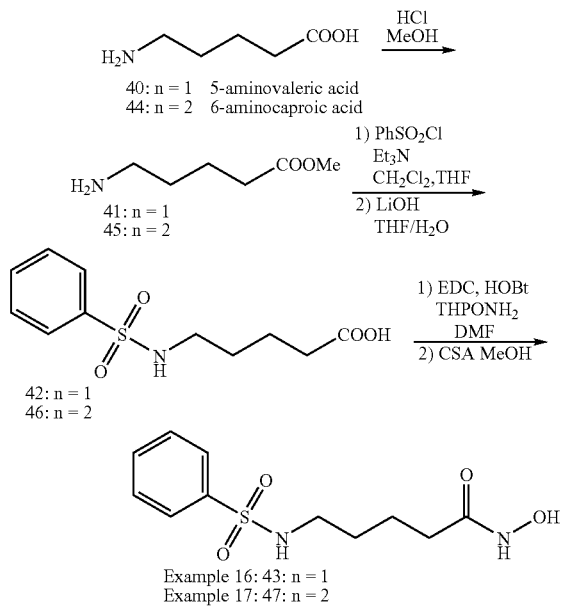

Example 16

N-Hydroxy-5-(benzenesulfonylamino)pentanamide (43)

Step 1: Methyl 5-aminovalerate (41)

To a solution of 5-aminovaleric acid (5 g, 42.68 mmol) in MeOH (100 mL) at room temperature was added HCl conc. (37%, 16 mL). The solution was stirred for 48 h at room temperature and monitored by HPLC-MS. The resulting solution was treated with a saturated aqueous solution of NaHCO$_3$ then the solvents were evaporated under reduced pressure. The aqueous layer was washed several times with CH$_2$Cl$_2$ and AcOEt. The aqueous phase was concentrated to produce a solid containing the desired product, NaCl, and NaHCO$_3$. The solid was washed with MeOH, and the organic filtrate was concentrated to afford the title compound (36) as a white solid (7.88 g, 100%): $^1$H NMR: (300 MHz, CD$_3$OD) δ 3.34 (s, 3H), 2.61 (br. s, 2H), 2.10-2.06 (m, 2H), 1.39-1.34 (m, 4H); MS (ES) m/z 132.2 (M$^+$).

Step 2: 5-(Benzenesulfonylamino)pentanoic acid (42)

To a solution of 41 (3 g, 22.90 mmol), in a solvent mixture of CH$_2$Cl$_2$ (100 mL) and THF (50 mL) at room temperature were added Et$_3$N (7.96 mL, 57.25 mmol), followed by benzenesulfonyl chloride (6.13 mL, 48.09 mmol). The mixture was stirred overnight at room temperature and then treated with a saturated aqueous solution of NH$_4$Cl. The phases were separated and the aqueous layer was extracted several times with CH$_2$Cl$_2$. The combined organic extracts were dried over (MgSO$_4$) and evaporated under reduced pressure giving a mixture of mono- and bis-alkylated products. The residue was dissolved in THF (50 mL) and water (50 mL), and LiOH was added. The resulting mixture was stirred for 4 h at room temperature, and then was treated with 1N HCl until pH 1. The phases were separated and the aqueous layer was extracted several times with AcOEt. The combined organic extracts were dried over (MgSO$_4$) and then evaporated under reduced pressure, yielding compound 42 (2.95 g, 48%) as a white powder: $^1$H NMR (300 MHz, acetone-d$_6$) δ 7.86 (d, J=7 Hz, 2H), 7.64-7.57 (m, 3H), 6.47 (br. s, 1H), 2.96-2.89 (m, 2H), 2.27-2.23 (m, 2H), 1.60-1.50 (m, 4H).

Step 3: N-Hydroxy-5-(benzenesulfonylamino)pentanamide (43)

To a solution of 42 (500 mg, 1.95 mmol) in DMF (20 mL) at room temperature were added 1-(3-dimethylaminopropyl)-3-ethylcarbodiimide hydrochloride (EDC, 448 mg, 2.33 mmol), and 1-hydroxybenzotriazole hydrate (HOBT, 395 mg, 2.93 mmol). The mixture was stirred 20 min. at room temperature, and then THPONH$_2$ (342 mg, 2.93 mmol) was added. The resulting mixture was heated at 50° C. for 24 h, and then the DMF solvent was evaporated under reduced pressure and the residue was dissolved in CH$_2$Cl$_2$ and washed with brine and a saturated aqueous solution of NaHCO$_3$. The combined organic extracts were dried over (MgSO$_4$) and then evaporated. The crude compound was purified by flash chromatography using hexane-acetone (1:1) as the solvent mixture. The residue was then dissolved in MeOH (10 mL), and 10-camphorsulfonic acid (CSA, 226 mg, 975 mmol) was added. The mixture was stirred for 2 h at room temperature, and then the solvents were evaporated under reduced pressure at room temperature to avoid thermal decomposition. The crude product was purified by flash chromatography using $CH_2Cl_2$/MeOH (9:1) as solvent mixture giving compound 43 as a yellowish oil (259 mg, 48% isolated): $^1$H NMR: (300 MHz, acetone-$d_6$) δ 9.99 (br. s, 1H), 7.87 (br. s, 2H), 7.62 (br. s), 2.90 (br. s, 2H), 2.05 (br. s, 2H), 1.59-1.49 (m, 4H).

Example 17

N-Hydroxy-6-(benzenesulfonylamino)hexanamide (47)

Step 1: Methyl 6-aminocaproate (45)

Compound 45 was prepared in 100% yield, using the procedure described in Example 16, step 1, but substituting 6-aminocaproic acid for 5-aminovaleric acid. $^1$H NMR (300 MHz, $CD_3OD$) δ 3.33 (s, 3H), 2.56-2.51 (m, 2H), 2.06-2.01 (m, 2H, 1.35-1.28 (m, 4H), 1.10-1.00 (m, 2H); MS (ES) m/z 146.2 ($M^+$).

Step 2: 6-(benzenesulfonylamino)hexanoic acid (46)

Compound 46 was prepared in 69% yield, using the procedure described in Example 16, step 2, but substituting compound 45 for compound 40. $^1$H NMR: (300 MHz, acetone-$d_6$) δ 7.92-7.85 (m, 2H), 7.61-7.56 (m, 3H), 6.57 (br. s, 1H), 6.44 (br. s, 1H), 2.94-2.88 (m, 2H), 2.26-2.21 (m, 2H), 1.55-1.46 (m, 4H), 1.38-1.33 (m, 2H).

Example 18

N-Hydroxy-8-oximino-8-aryloctanamides (51) and N-Hydroxy-7-aroylheptanamides (52)

Step 1: Preparation of Organocopper Reagent 48

To a suspension of zinc foil (3.40 g, 52 mmol) in THF (4 mL) was added 1,2-dibromoethane (0.38 g, 2.0 mmol), and the mixture was heated at 65° C. for one minute. After cooling to ambient temperature, chlorotrimethylsilane (0.2 mL, 1.6 mmol) was added and the mixture was stirred for 15 min. To this, a solution of ethyl 7-iodoheptanoate (14.21 g, 50 mmol) in THF (20 mL) was added slowly at ambient temperature, and the mixture was heated at 65° C. for 16 h and then cooled to −10° C. A solution of CuCN (3.96 g, 44 mmol) and anhydrous LiCl (3.80 g, 88 mmol) in THF (44 mL) was added. The resulting solution was stirred at 0° C. for 10 min and used for the coupling reactions with acid chlorides.

Step 2: Ethyl 7-aroylheptanoates (49)

Ethyl 7-benzoylheptanoate (49a)

To a stirred solution of the organocopper reagent 48 (2.0 mmol) in THF (4 mL) at −25° C. was added benzoyl chloride (253 mg, 0.21 mmol) and the reaction mixture was warmed to 0° C. over 30 min. After being stirred for additional 3 h at 0° C., the reaction mixture was quenched with saturated $NH_4Cl$ solution and extracted with ethyl acetate. The combined organic extracts were washed with brine, dried and concentrated under reduced pressure. The crude product was purified by flash silica gel chromatography (10% ethyl acetate in hexanes) to afford the title compound (376 mg, 80% yield): $^1$H NMR (300 MHz, $CDCl_3$) δ 7.42-7.97 (m, 5H), 4.12(q, J=6.9 Hz, 2H), 2.97 (t, J=7.2 Hz, 2H), 2.30(t, J=7.5 Hz, 2H), 1.74 (m, 2H), 1.65 (m, 2H), 1.39 (m, 4H), 1.25(t, J=6.9 Hz, 3H); $^{13}$C NMR (75.4 MHz, $CDCl_3$) δ 14.19, 24.04, 24.75, 28.90(2), 34.12, 38.39, 60.11, 127.96, 128.49, 132.84, 136.95, 173.70, 200.29.

Ethyl 7-(p-anisoyl)heptanoate (49b)

Following a procedure analogous to that described above for 49a, but substituting p-anisoyl chloride for benzoyl

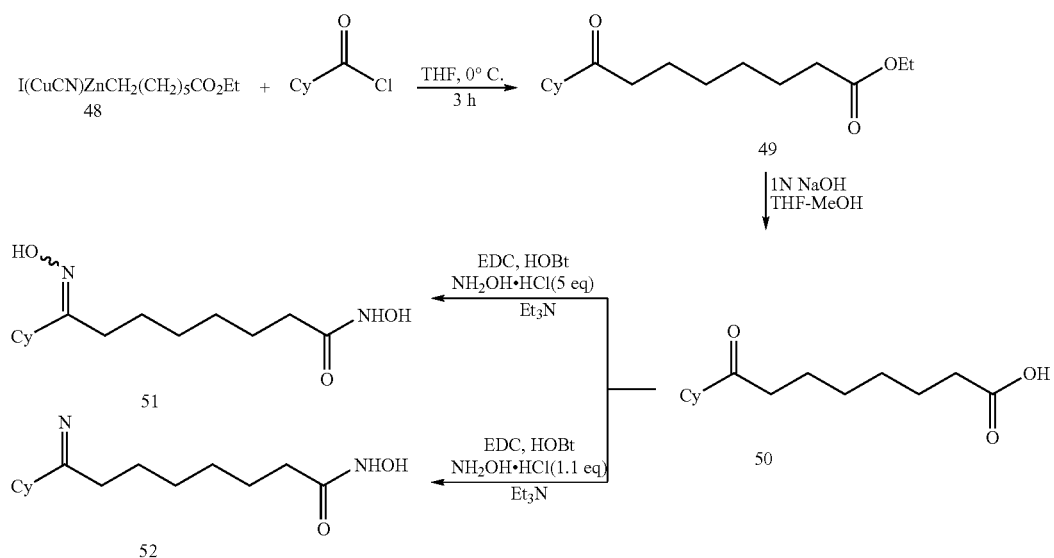

chloride, the title compound was obtained as a light yellow solid in 59% yield: $^1$H NMR (300 MHz, CDCl$_3$) δ 7.94 (d, J=9.0 Hz, 2H), 6.93 (d, J=9.0 Hz, 2H), 4.12 (q, J=6.9 Hz, 2H), 3.87 (s, 3H), 2.91 (t, J=7.2 Hz, 2H), 2.30(t, J=7.5 Hz, 2H), 1.74 (m, 2H), 1.65 (m, 2H), 1.39 (m, 4H), 1.25 (t, J=6.9 Hz, 3H); $^{13}$C NMR (75.4 MHz, CDCl$_3$) δ 14.19, 24.29, 24.75, 28.91, 28.96, 34.21, 38.06, 55.37, 60.10, 113.58, 130.02, 130.21, 163.23, 173.71, 198.93.

Ethyl 7-(4-(trifluoromethyl)benzoyl)heptanoate (49c)

Following a procedure analogous to that described above for 49a, but substituting p-(trifluoromethyl)benzoyl chloride for benzoyl chloride, the title compound was obtained as a white solid in 67% yield: $^1$H NMR (300 MHz, CDCl$_3$) δ 8.06 (d, J=8.1 Hz, 2H), 7.72 (d, J=8.1 Hz, 2H), 4.13 (q, J=6.9 Hz, 2H), 3.01 (t, J=7.2 Hz, 2H), 2.31 (t, J=7.2 Hz, 2H), 1.76 (m, 2H), 1.66 (m, 2H), 1.41 (m, 4H), 1.25(t, J=6.9 Hz, 3H); $^{13}$C NMR (75.4 MHz, CDCl$_3$) δ 14.00, 23.63, 24.56, 28.66, 28.71, 33.98, 38.48, 59.93, 123.46 (q, $J_{CF}$=272 Hz), 125.42 (q, $J_{CF}$=3.7 Hz), 128.15, 133.93 (q, $J_{CF}$=33.5 Hz), 139.52, 173.42, 198.91.

Ethyl 7-(4-bromobenzoyl)heptanoate (49d)

Following a procedure analogous to that described above for 49a, but substituting p-bromobenzoyl chloride for benzoyl chloride, the title compound was obtained as a white solid in 70% yield: $^1$H NMR (300 MHz, CDCl$_3$): δ 7.80 (d, J=8.7 Hz, 2H), 7.59 (d, J=8.7 Hz, 2H), 4.12 (q, J=6.9 Hz, 2H), 2.92 (t, J=7.2 Hz, 2H), 2.30 (t, J=7.5 Hz, 2H), 1.73 (m, 2H), 1.64 (m, 2H), 1.38 (m, 4H), 1.25 (t, J=6.9 Hz, 3H); $^{13}$C NMR (75.4 MHz, CDCl$_3$) δ 14.21, 23.95, 24.73, 28.87(2), 34.21, 38.37, 60.14, 127.98, 129.53, 131.82, 135.69, 173.66, 199.18.

Ethyl 7-(2-acetoxybenzoyl)heptanoate (49e)

Following a procedure analogous to that described above for 49a, but substituting o-acetoxybenzoyl chloride for benzoyl chloride, the title compound was obtained as a colorless oil in 58% yield: $^1$H NMR (300 MHz, CDCl$_3$) δ 7.76 (dd, J=8.4, 1.5 Hz, 1H), 7.51 (m, 1H), 7.31 (m, 1H), 7.10 (dd, J=7.8, 1.2 Hz, 1H), 4.12(q, J=6.9 Hz, 2H), 2.87 (t, J=7.2 Hz, 2H), 2.33 (s, 3H), 2.29 (t, J=7.5 Hz, 2H), 1.65 (m, 4H), 1.36 (m, 4H), 1.25(t, J=6.9 Hz, 3H); $^{13}$C NMR (75.4 MHz, CDCl$_3$) δ 14.20, 21.07, 23.79, 24.73, 28.79, 28.87, 34.20, 40.18, 60.12, 123.77, 125.95, 129.60, 130.98, 132.95, 148.74, 169.44, 173.66, 200.21.

Ethyl 7-(1-naphthoyl)heptanoate (49f)

Following a procedure analogous to that described above for 49a, but substituting 1-naphthoyl chloride for benzoyl chloride, the title compound was obtained as a white solid in 58% yield: $^1$H NMR (300 MHz, CDCl$_3$) δ 8.56 (d, J=8.7 Hz, 1H), 7.42-7.92 (m, 6H), 4.10 (q, J=6.9 Hz, 2H), 2.98 (m, 2H), 2.26(t, J=7.5 Hz, 2H), 1.75 (m, 2H), 1.62 (m, 2H), 1.36 (m, 4H), 1.22 (t, J=6.9 Hz, 3H); $^{13}$C NMR (75.4 MHz, CDCl$_3$) δ 14.02, 24.23, 24.55, 28.70(2), 33.98, 41.79, 59.89, 124.12, 125.51, 126.12, 126.99, 127.51, 128.14, 129.87, 132.06, 133.69, 136.00, 173.39, 204.44.

Ethyl 7-(2-naphthoyl)heptanoate (49g)

Following a procedure analogous to that described above for 49a, but substituting 2-naphthoyl chloride for benzoyl chloride, the title compound was obtained as a white solid in 54% yield: 1H NMR (300 MHz, CDCl$_3$): δ 8.47 (s, 1H), 7.86-8.05 (m, 4H), 7.51-7.62 (m, 2H), 4.12 (q, J=6.9 Hz, 2H), 3.10 (t, J=7.5 Hz, 2H), 2.31 (t, J=7.5 Hz, 2H), 1.80 (m, 2H), 1.62 (m, 2H), 1.41 (m, 4H), 1.25 (t, J=6.9 Hz, 3H).

Ethyl 7-(4-biphenyl)carbonylheptanoate (49h)

Following a procedure analogous to that described above for 49a, but substituting 4-biphenylcarbonyl chloride for benzoyl chloride, the title compound was obtained as a white solid in 41% yield: $^1$H NMR (300 MHz, CDCl$_3$) δ 8.01 (d, J=7.2 Hz, 2H), 7.39-7.69 (m, 7H), 4.12 (q, J=6.9 Hz, 2H), 2.99 (t, J=7.2 Hz, 2H), 2.30(t, J=7.5 Hz, 2H), 1.76 (m, 2H), 1.65 (m, 2H), 1.40 (m, 4H), 1.25 (t, J=7.2 Hz, 3H).

Ethyl 7-(2-furanoyl)heptanoate (49i)

Following a procedure analogous to that described above for 49a, but substituting 2-furanoyl chloride, the title compound was obtained in 71% yield: $^1$H NMR (300 MHz, CDCl$_3$) δ 7.59 (d, J=1.8 Hz, 1H), 7.19 (d, J=3.3 Hz, 1H), 6.54 (dd, J=3.3, 1.8 Hz), 4.12 (q, J=6.9 Hz, 2H), 2.82 (t, J=7.5 Hz, 2H), 2.30 (t, J=7.5 Hz, 2H), 1.72 (m, 2H), 1.64 (m, 2H), 1.38 (m, 4H), 1.25 (t, J=6.9 Hz, 3H); $^{13}$C NMR (75.4 MHz, CDCl$_3$) δ 14.07, 23.87, 24.58, 28.68, 28.72, 34.05, 38.14, 59.98, 111.97, 116.68, 146.05, 152.60, 173.52, 189.39.

Ethyl 7-(3-furanoyl)heptanoate (49j)

Following a procedure analogous to that described above for 49a, but substituting 3-furanoyl chloride for benzoyl chloride, the title compound was obtained as a yellow oil in 24% yield: $^1$H NMR (300 MHz, CDCl$_3$) δ 8.03 (m, 1H), 7.44 (m, 1H), 6.76 (m, 1H), 4.12 (q, J=6.9 Hz, 2H), 2.74 (t, J=7.5 Hz, 2H), 2.29 (t, J=7.5 Hz, 2H), 1.71 (m, 2H), 1.63 (m, 2H), 1.37 (m, 4H), 1.25 (t, J=6.9 Hz, 3H); $^{13}$C NMR (75.4 MHz, CDCl$_3$) δ 14.18, 24.04, 24.69, 28.82(2), 34.18, 40.23, 60.13, 108.56, 127.69, 144.09, 146.98, 173.68, 195.10.

Ethyl 7-(2-thiophene)carbonylheptanoate (49k)

Following a procedure analogous to that described above for 49a, but substituting 2-thiophenecarbonyl chloride for benzoyl chloride, the title compound was obtained as a colorless oil in 66% yield: $^1$H NMR (300 MHz, CDCl$_3$) δ 7.70 (dd, J=3.9, 1.2 Hz, 1H), 7.62 (dd, J=4.8, 1.2 Hz, 1H), 7.13 (dd, J=4.8, 3.9 Hz), 4.12(q, J=7.2 Hz, 2H), 2.90 (t, J=7.2 Hz, 2H), 2.30 (t, J=7.5 Hz, 2H), 1.75 (m, 2H), 1.64 (m, 2H), 1.39 (m, 4H), 1.25 (t, J=7.2 Hz, 3H); $^{13}$C NMR (75.4 MHz, CDCl$_3$) δ 14.23, 24.48, 24.75, 28.87, 28.90, 34.24, 39.23, 60.17, 128.01, 131.65, 133.34, 144.42, 173.73, 193.31.

Ethyl 7-(2-benzofuran)carbonylheptanoate (49l)

Following a procedure analogous to that described above for 49a, but substituting 2-benzofurancarbonyl chloride for benzoyl chloride, the title compound was obtained in 45% yield: $^1$H NMR (300 MHz, CDCl$_3$) δ 7.15-7.65 (m, 5H), 4.02 (q, J=7.2 Hz, 2H), 2.83 (t, J=7.2 Hz, 2H), 2.20(t, J=7.5 Hz, 2H), 1.70 (m, 2H), 1.54 (m, 2H), 1.30 (m, 4H), 1.15 (t, J=7.2 Hz, 3H).

Ethyl 7-(2-benzothiophene)carbonylheptanoate (49m)

Following a procedure analogous to that described above for 49a, but substituting 2-benzothiophenecarbonyl chloride for benzoyl chloride, the title compound was obtained in 44% yield: $^1$H NMR (300 MHz, CDCl$_3$) δ 7.87 (s, 1H), 7.79 (m, 2H), 7.35 (m, 2H), 4.05 (q, J=7.2 Hz, 2H), 2.90 (t, J=7.2 Hz, 2H), 2.23 (t, J=7.5 Hz, 2H), 1.70 (m, 2H), 1.57 (m, 2H), 1.30 (m, 4H), 1.19 (t, J=7.2 Hz, 3H).

Step 3: 7-Aroylheptanoic acids (50a-m)

7-(2-Benzoyl)heptanoic acid (50a)

To a stirred solution of 49a (610 mg, 2.3 mmol) in THF (3.5 mL) and MeOH (3.5 mL) at ambient temperature was added 1N NaOH (3.5 mL, 3.5 mmol), and the mixture was stirred for 2 h. After removal of organic solvents, the resulting aqueous solution was acidified with 1N HCl and then extracted with ethyl acetate. The combined organic layers were dried, concentrated under reduced pressure to give the crude product. Purification by flash silica gel chromatography (7% MeOH in chloroform) afforded the title compound (511 mg, 94% yield) as a white solid: $^1$H NMR (300 MHz, CDCl$_3$) δ 7.96 (d, J=6.9 Hz, 2H), 7.41-7.61 (m, 3H), 2.97 (t, J=7.5 Hz, 2H), 2.36 (t, J=7.5 Hz, 2H), 1.75 (m, 2H), 1.66 (m, 2H), 1.40 (m, 4H); $^{13}$C NMR (75.4 MHz, CDCl$_3$) δ 24.01, 24.43, 28.80, 28.86, 33.92, 38.37, 127.98, 128.50, 132.88, 136.91, 179.95, 200.44.

7-(p-Anisoyl)heptanoic acid (50b)

Following a procedure described above in 50a, but substituting ester 49b for ester 49a, the title compound was obtained as a white solid in 51% yield: $^1$H NMR (300 MHz, CDCl$_3$) δ 7.94 (d, J=9.0 Hz, 2H), 6.93 (d, J=9.0 Hz, 2H), 3.86 (s, 3H), 2.91(t, J=7.5 Hz, 2H), 2.36(t, J=7.5 Hz, 2H), 1.73 (m, 2H), 1.65 (m, 2H), 1.40 (m, 4H); $^{13}$C NMR (75.4 MHz, CDCl$_3$) δ 24.25, 24.40, 28.76, 28.86, 33.83, 37.99, 55.33, 113.58, 129.93, 130.24, 163.26, 179.40, 199.22.

7-(4-Trifluoromethylbenzoyl)heptanoic acid (50c)

Following a procedure described above in 50a, but substituting ester 49c for ester 49a, the title compound was obtained as a white solid in 68% yield: $^1$H NMR (300 MHz, CDCl$_3$) δ 8.06(d, J=8.1 Hz, 2H), 7.73 (d, J=8.1 Hz, 2H), 3.00(t, J=7.5 Hz, 2H), 2.37 (t, J=7.5 Hz, 2H), 1.76(m, 2H), 1.67 (m, 2H), 1.42 (m, 4H); $^{13}$C NMR (75.4 MHz, CDCl$_3$) δ 23.75, 24.39, 28.78(2), 33.90, 38.67, 123.69(q, $J_{CF}$=272 Hz), 125.62(q, $J_{CF}$=3.7 Hz), 128.33, 134.21(q, $J_{CF}$=32.6 Hz), 139.59, 180.07, 199.28.

7-(4-Bromobenzoyl)heptanoic acid (50d)

Following a procedure described above in 50a, but substituting ester 49d for ester 49a, the title compound was obtained as a white solid in 91% yield: $^1$H NMR (300 MHz, CDCl$_3$) δ 7.81 (d, J=9.0 Hz, 2H), 7.60 (d, J=9.0 Hz, 2H), 2.93 (t, J=7.5 Hz, 2H), 2.37 (t, J=7.5 Hz, 2H), 1.74(m, 2H), 1.66(m, 2H), 1.40(m, 4H); $^{13}$C NMR (75.4 MHz, CDCl$_3$) δ 23.92, 24.43, 28.80, 28.84, 33.87, 38.35, 128.04, 129.56, 131.85, 135.69, 179.74, 199.26.

7-(2-Acetoxybenzoyl)heptanoic acid (50e)

Following a procedure described above in 50a, but substituting ester 49e for ester 49a and using 2.5 equivalent of 1N NaOH, the title compound was obtained as a white solid in 94% yield: $^1$H NMR (300 MHz, CDCl$_3$): δ 12.39 (s, 1H), 10.65 (br s, 1H), 7.75 (dd, J=8.1, 1.5 Hz, 1H), 7.45 (m, 1H), 6.98 (dd, J=8.4, 0.9 Hz, 1H), 6.89 (m, 1H), 2.98 (t, J=7.5 Hz, 2H), 2.37 (t, J=7.5 Hz, 2H), 1.76 (m, 2H), 1.66 (m, 2H), 1.41 (m, 4H); $^{13}$C NMR (75.4 MHz, CDCl$_3$) δ 24.13, 24.39, 28.75, 28.18, 33.90, 38.08, 118.47, 118.81, 119.25, 129.90, 136.18, 162.42, 180.04, 206.67.

7-(1-Naphthoyl)heptanoic acid (50f)

Following a procedure described above in 50a, but substituting ester 49f for ester 49a, the title compound was obtained as a white solid in 97% yield: $^1$H NMR (300 MHz, CDCl$_3$): δ 8.53 (d, J=8.7 Hz, 1H), 7.95(d, J=8.1 Hz, 1H), 7.80-7.87 (m, 2H), 7.44-7.60 (m, 3H), 3.03 (t, J=7.5 Hz, 2H), 2.34(t, J=7.5 Hz, 2H), 1.79(m, 2H), 1.64(m, 2H), 1.41(m, 4H). $^{13}$C NMR (75.4 MHz, CDCl$_3$): δ 24.42(2), 28.80, 28.87, 33.92, 42.05, 124.31, 125.68, 126.35, 127.13, 127.75, 128.34, 130.05, 132.29, 133.90, 136.27, 180.05, 204.87.

7-(2-Naphthoyl)heptanoic acid (50g)

Following a procedure described above in 50a, but substituting ester 49g for ester 49a, the title compound was obtained as a white solid in 78% yield: $^1$H NMR (300 MHz, CDCl$_3$) δ 8.47 (s, 1H), 7.85-8.05 (m, 4H), 7.57 (m, 2H), 3.10 (t, J=7.5 Hz, 2H), 2.37 (t, J=7.5 Hz, 2H), 1.80 (m, 2H), 1.67 (m, 2H), 1.43 (m, 4H); $^{13}$C NMR (7.54 MHz, CDCl$_3$) δ 24.20, 24.48, 28.27, 28.95, 33.92, 38.48, 123.89, 126.69, 127.73, 128.33, 128.39, 129.52, 129.60, 132.51, 134.30, 135.50, 179.85, 200.36.

7-(4-Biphenyl)carbonylheptanoic acid (50h)

Following a procedure described above in 50a, but substituting ester 49h for ester 49a, the title compound was obtained as a white solid in 93% yield: $^1$H NMR (300 MHz, CDCl$_3$): δ 8.02 (d, J=9.0 Hz, 2H), 7.26-7.61 (m, 7H), 3.00 (t, J=7.5 Hz, 2H), 2.36 (t, J=7.5 Hz, 2H), 1.75 (m, 2H), 1.66 (m, 2H), 1.42 (m, 4H).

7-(2-Furanoyl)heptanoic acid (50i)

Following a procedure described above in 50a, but substituting ester 49i for ester 49a, the title compound was obtained as a white solid in 88% yield: $^1$H NMR (300 MHz, CDCl$_3$) δ 11.4 (br s, 1H), 7.54 (d, J=0.9 Hz, 1H), 7.15 (dd, J=3.6, 0.9 Hz, 1H), 6.49 (d, J=3.6 Hz, 1H), 2.78 (t, J=7.5 Hz, 2H), 2.31 (t, J=7.5 Hz, 1.65 (m, 2H), 1.59 (m, 2H), 1.35 (m, 4H); $^{13}$C NMR (75.4 MHz, CDCl$_3$) δ 23.91, 24.32, 28.64, 28.73, 33.84, 38.16, 112.05, 116.89, 146.18, 152.61, 179.81, 189.64.

7-(3-Furanoyl)heptanoic acid (50j)

Following a procedure described above in 50a, but substituting ester 49j for ester 49a, the title compound was obtained as a white solid in 63% yield: $^1$H NMR (300 MHz, CDCl$_3$) δ 8.03 (br s, 1H), 7.43 (m, 1H), 6.77 (d, J=1.8 Hz, 1H), 2.74 (t, J=7.5 Hz, 2H), 2.36 (t, J=7.5 Hz, 2H), 1.72 (m, 2H), 1.65 (m, 2H), 1.38 (m, 4H); $^{13}$C NMR (75.4 MHz, CDCl$_3$) δ 24.02, 24.39, 28.74, 28.80, 33.88, 40.21, 108.58, 127.68, 144.12, 147.06, 179.84, 195.26.

7-(2-Thiophene)carbonylheptanoic acid (50k)

Following a procedure described above in 50a, but substituting ester 49k for ester 49a, the title compound was obtained as a white solid in 77% yield: $^1$H NMR (300 MHz, CDCl$_3$) δ 7.71 (dd, J=3.6, 0.9 Hz, 1H), 7.62 (m, 1H), 7.12 (m, 1H), 2.90 (t, J=7.5 Hz, 2H), 2.36 (t, J=7.5 Hz, 2H), 1.75 (m, 2H), 1.65 (m, 2H), 1.40 (m, 4H); $^{13}$C NMR (75.4 MHz, CDCl$_3$): δ 24.31, 24.34, 28.64, 28.72, 33.83, 39.05, 127.96, 131.72, 133.37, 144.20, 179.92, 193.35.

7-(2-Benzofuran)carbonylheptanoic acid (50l)

Following a procedure described above in 50a, but substituting ester 49l for ester 49a, the title compound was obtained as a white solid in 84% yield: $^1$H NMR (300 MHz, acetone-d$_6$) δ 10.6 (br s, 1H), 7.25-7.80 (m, 5H), 3.00 (t, J=7.5 Hz, 2H), 2.24 (t, J=7.5 Hz, 2H), 1.60-1.80 (m, 4H), 1.40 (m, 4H).

7-(2-Benzothiophene)carbonylheptanoic acid (50m)

Following a procedure described above in 50a, but substituting ester 49m for ester 49a, the title compound was obtained as a white solid in 90% yield: $^1$H NMR (300 MHz, acetone-d$_6$) δ 10.5(br s, 1H), 7.40-8.25 (m, 5H), 3.10 (t, J=7.5 Hz, 2H), 2.14 (t, J=7.5 Hz, 2H), 1.50-1.80 (m, 4H), 1.40 (m, 4H).

Step 4: N-Hydroxy-8-oximino-8-aryloctanamides (51) and N-Hydroxy-7-aroylheptanamides (52a-m)

N-Hydroxy-8-oximino-8-phenyloctanamide (51a)

Following the procedure described in Example 14, step 3, but substituting carboxylic acid 50a for 37, the title compound was obtained as light yellow oil in 54% yield: $^1$H NMR (300 MHz, CD$_3$OD/CDCl$_3$=5/1) δ 7.55 (m, 2H), 7.36 (m, 3H), 2.79 (t, J=7.5 Hz, 2H), 2.07 (t, J=7.5 Hz, 2H), 1.56 (m, 4H), 1.35 (m, 4H); $^{13}$C NMR (75.4 MHz, CD$_3$OD/CDCl$_3$=5/1) δ 25.09, 25.78, 25.92, 28.43, 28.95, 32.55, 126.12, 128.21, 128.75, 135.85, 159.52, 171.25.

N-Hydroxy-8-(E)-oximino-8-(4-biphenyl)octanamide (E-51h) and N-Hydroxy-8-(Z)-oximino-8-(4-biphenyl)octanamide (Z-51h)

Following the procedure described in Example 14, step 3, but substituting carboxylic acid 50h for 37 the title compound 51h was obtained as a white solid in 45% yield, along with 52h (19%). Data for 51h: $^1$H NMR (300 MHz, CD$_3$OD/CDCl$_3$=5/1) δ 7.25-7.67(m, 9H), 7.36 (m, 3H), 2.82 (t, J=7.5 Hz, 2H), 2.06 (br t, J=6.9 Hz, 2H), 1.59 (m, 4H), 1.37 (m, 4H); $^{13}$C NMR (75.4 MHz, CDCl$_3$/CDCl$_3$=5/1) δ 25.13, 25.78, 25.88, 28.47, 29.00, 32.58, 126.51, 126.72, 126.85, 127.33, 128.59, 134.72, 140.14, 141.47, 159.17, 171.24. Data for 52h: $^1$H NMR (300 MHz, CD$_3$OD/CDCl$_3$=5/1) δ 7.35-7.68 (m, 9H), 2.83 (t, J=7.8 Hz, 2H), 2.29(t, J=7.5 Hz, 2H), 1.62 (m, 2H), 1.60 (m, 2H), 1.40 (m, 4H); $^{13}$C NMR (75.4 MHz, CDCl$_3$/CDCl$_3$=5/1) δ 24.55, 25.92, 28.58(2), 29.29, 33.79, 126.52, 126.75, 126.86, 127.31, 128.58, 134.76, 140.17, 141.46, 159.20, 176.54.

N-Hydroxy-8-oximino-8-(2-furanyl)octanamide (51i) and N-hydroxy-7-(2-furanoyl)-heptanamide (52i)

Following the procedure described in Example 14, step 3, but substituting carboxylic acid 50i for 37, the title compound 51i was obtained as a 6:4 mixture of E- and Z-isomers in 26% yield, along with 52i (11%). Data for 51i: $^1$H NMR (300 MHz, CD$_3$OD/CDCl$_3$=5/1) δ 6.31-7.35 (m, 3H), 2.50 (m, 2H), 1.98 (m, 2H), 1.47 (m, 4H), 1.24 (m, 4H). Data for 52i: $^1$H NMR (300 MHz, CD$_3$OD/CDCl$_3$=5/1) δ 7.61 (d, J=1.2 Hz, 1H), 7.21 (d, J=3.3 Hz, 1H), 6.55 (dd, J=3.3, 1.2 Hz, 1H), 2.82 (t, J=7.5 Hz, 2H), 2.10 (t, J=7.5 Hz, 2H), 1.60-1.72 (m, 4H), 1.36 (m, 4H); $^{13}$C NMR (75.4 MHz, CD$_3$OD/CDCl$_3$=5/1) δ 23.84, 25.00, 28.49(2), 32.47, 37.98, 112.08, 117.45, 146.53, 152.27, 171.09, 190.25.

N-hydroxy-7-benzoylheptanamide (52a)

Following the procedure described in Example 14, step 3, but substituting carboxylic acid 50a for 37 and using 1.1 equivalent of NH$_2$OH.HCl and triethylamine each, the title compound was obtained as light yellow solid in 46% yield: $^1$H NMR (300 MHz, CD$_3$OD/CDCl$_3$=5/1): δ 7.95 (d, J=7.2 Hz, 2H), 7.57 (m, 1H), 7.47 (m, 2H), 2.98 (t, J=7.5 Hz, 2H), 2.13 (m, 2H), 1.72 (m, 2H), 1.64 (m, 2H), 1.38 (m, 4H); $^{13}$C NMR (75.4 MHz, CD$_3$OD/CDCl$_3$=5/1) δ 23.77, 24.98, 28.49(2), 32.49, 38.13, 127.73, 128.29, 132.86, 136.46, 171.23, 201.16.

N-hydroxy-7-(p-anisoyl)heptanamide (52b)

Following the procedure described in Example 14, step 3, but substituting carboxylic acid 50b for 37 and using 1.1 equivalent of NH$_2$OH.HCl and triethylamine each, the title compound was obtained as light yellow solid in 48% yield: $^1$H NMR (300 MHz, CD$_3$OD/CDCl$_3$=5/1) δ 7.94 (d, J=9.0 Hz, 2H), 6.95 (d, J=9.0 Hz, 2H), 3.88 (s, 3H), 2.93 (t, J=7.2 Hz, 2H), 2.11 (t, J=7.5 Hz, 2H), 1.59-1.79(m, 4H), 1.37 (m, 4H); $^{13}$C NMR (75.4 MHz, CD$_3$OD/CDCl$_3$=5/1) δ 24.15, 25.04, 28.59(2), 32.51, 37.88, 55.21, 113.54, 129.58, 130.20, 163.39, 171.10, 200.06.

N-hydroxy-7-(4-trifluoromethylbenzoyl)heptanamide (52c)

Following the procedure described in Example 14, step 3, but substituting carboxylic acid 50c for 37 and using 1.1 equivalent of NH$_2$OH.HCl and triethylamine each, the title compound was obtained as light yellow solid in 35% yield: $^1$H NMR (300 MHz, CD$_3$OD/CDCl$_3$=5/1) δ 8.07 (d, J=8.4 Hz, 2H), 7.74 (d, J=8.4 Hz, 2H), 3.02 (t, J=7.5 Hz, 2H), 2.12 (t, J=7.5 Hz, 2H), 1.75 (m, 2H) 1.65 (m, 2H), 1.40 (m, 4H); $^{13}$C NMR (75.4 MHz, CD$_3$OD/CDCl$_3$=5/1) δ 23.57, 25.03, 28.51, 28.59, 32.50, 38.50, 123.37(q, J$_{CF}$=273 Hz),125.43 (q, J$_{CF}$=3.7 Hz), 128.18, 134.09 (q, J$_{CF}$=32.6 Hz), 139.32, 171.15, 199.93.

N-hydroxy-7-(4-bromobenzoyl)heptanamide (52d)

Following the procedure described in Example 14, step 3, but substituting carboxylic acid 50d for 37 and using 1.1 equivalent of NH$_2$OH.HCl and triethylamine each, the title compound was obtained as light yellow solid in 31% yield: $^1$H NMR (300 MHz, CD$_3$OD/CDCl$_3$=5/1) δ 7.82 (d, J=7.5 Hz, 2H), 7.62 (d, J=7.5 Hz, 2H), 2.95 (t, J=7.2 Hz, 2H), 2.11 (m, 2H), 1.55-1.79 (m, 4H), 1.38 (m, 4H).

N-hydroxy-7-(2-acetoxybenzoyl)heptanamide (52e)

Following the procedure described in Example 14, step 3, but substituting carboxylic acid 50e for 37 and using 1.1 equivalent of $NH_2OH \cdot HCl$ and triethylamine each, the title compound was obtained as light yellow solid in 43% yield: $^1$H NMR (300 MHz, $CD_3OD/CDCl_3$=5/1) δ 7.78 (dd, J=8.1, 1.2 Hz, 1H), 7.47 (m, 1H), 6.96 (dd, J=8.4, 1.2 Hz, 1H), 6.91 (m, 1H), 3.00 (t, J=7.2 Hz, 2H), 2.12 (t, J=7.5 Hz, 2H), 1.59-1.79 (m, 4H), 1.40 (m, 4H); $^{13}$C NMR (75.4 MHz, $CD_3OD/CDCl_3$=5/1) δ 23.97, 32.51, 37.94, 118.02, 118.84, 119.01, 129.86, 136.09, 161.76, 171.15, 206.79.

N-hydroxy-7-(1-naphthoyl)heptanamide (52f)

Following the procedure described in Example 14, step 3, but substituting carboxylic acid 50f for 37 and using 1.1 equivalent of $NH_2OH \cdot HCl$ and triethylamine each, the title compound was obtained as light yellow solid in 58% yield: $^1$H NMR (300 MHz, $CD_3OD/CDCl_3$=5/1) δ 8.50 (d, J=8.1 Hz, 1H), 7.40-7.90 (m, 6H), 2.93(t, J=7.5 Hz, 2H), 2.12 (m, 2H), 1.69 (m, 2H), 1.59 (m, 2H), 1.30 (m, 4H); $^{13}$C NMR (75.4 MHz, $CD_3OD/CDCl_3$=5/1) δ 24.27, 25.08, 28.63(2), 32.65, 41.88, 124.29, 125.53, 126.27, 127.33, 127.70, 128.30, 129.91, 132.32, 133.77, 135.91, 171.87, 205.28.

N-hydroxy-7-(2-naphthoyl)heptanamide (52g)

Following the procedure described in Example 14, step 3, but substituting carboxylic acid 50 g for 37 and using 1.1 equivalent of $NH_2OH \cdot HCl$ and triethylamine each, the title compound was obtained as light yellow solid in 31% yield: $^1$H NMR (300 MHz, $CD_3OD/CDCl_3$=5/1) δ 8.47 (s, 1H), 7.53-8.01 (m, 6H), 3.10 (t, J=7.5 Hz, 2H), 2.12 (m, 2H), 1.78 (m, 2H), 1.66 (m, 2H), 1.42 (m, 4H); $^{13}$C NMR (75.4 MHz, $CD_3OD/CDCl_3$=5/1) δ 24.01, 25.07, 28.62(2), 32.54, 38.27, 123.47, 126.56, 127.48, 128.22, 128.28, 129.03, 129.60, 132.27, 133.86, 135.37, 171.19, 201.18.

N-hydroxy-7-(3-furanoyl)heptanamide (52j)

Following the procedure described in Example 14, step 3, but substituting carboxylic acid 50j for 37 and using 1.1 equivalent of $NH_2OH \cdot HCl$ and triethylamine each, the title compound was obtained as light yellow solid in 33% yield: $^1$H NMR (300 MHz, $CD_3OD/CDCl_3$=5/1) δ 8.09 (br s, 1H), 7.46 (m, 1H), 6.75 (m, 1H), 2.76 (t, J=7.5 Hz, 2H), 2.10 (t, J=7.5 Hz, 2H), 1.60-1.72 (m, 4H), 1.36 (m, 4H); $^{13}$C NMR (75.4 MHz, $CD_3OD/CDCl_3$=5/1) δ 23.90, 24.99, 28.45(2), 32.48, 39.98, 108.19, 127.37, 144.15, 147.43, 171.08, 196.21.

N-hydroxy-7-(2-thiophene)carbonylheptanamide (52k)

Following the procedure described in Example 14, step 3, but substituting carboxylic acid 50k for 37 and using 1.1 equivalent of $NH_2OH \cdot HCl$ and triethylamine each, the title compound was obtained as light yellow solid in 56% yield: $^1$H NMR (300 MHz, $CD_3OD/CDCl_3$=5/1) δ 7.76 (d, J=2.7 Hz, 1H), 7.68 (d J=4.5 Hz, 1H), 7.16 (m, 1H), 2.92(t, J=7.5 Hz, 2H), 2.10 (t, J=7.5 Hz, 2H), 1.74 (m, 2H), 1.64 (m, 2H), 1.36 (m, 4H).

N-hydroxy-7-(2-benzofuran)carbonylheptanamide (52l)

Following the procedure described in Example 14, step 3, but substituting carboxylic acid 50 l for 37 and using 1.1 equivalent of $NH_2OH \cdot HCl$ and triethylamine each, the title compound was obtained as light yellow solid in 20% yield: $^1$H NMR (300 MHz, acetone-$d_6$) δ 7.35-7.85 (m, 5H), 2.99 (t, J=7.5 Hz, 2H), 2.10(t, J=7.5 Hz, 2H), 1.50-1.80 (m, 4H), 1.36 (m, 4H).

N-hydroxy-7-(2-benzothiophene)carbonylheptanamide (52m)

Following the procedure described in Example 14, step 3, but substituting carboxylic acid 50m for 37 and using 1.1 equivalent of $NH_2OH \cdot HCl$ and triethylamine each, the title compound was obtained as light yellow solid in 31% yield: $^1$H NMR (300 MHz, $CD_3OD/CDCl_3$=5/1) δ 8.23 (s, 1H), 8.00 (m, 2H), 7.49 (m, 2H), 3.05 (t, J=7.5 Hz, 2H), 2.10 (t, J=7.5 Hz, 2H), 1.50-1.80 (m, 4H), 1.40 (m, 4H).

Example 19

N-(2-Aminophenyl)-7-aroylheptanamides (53)

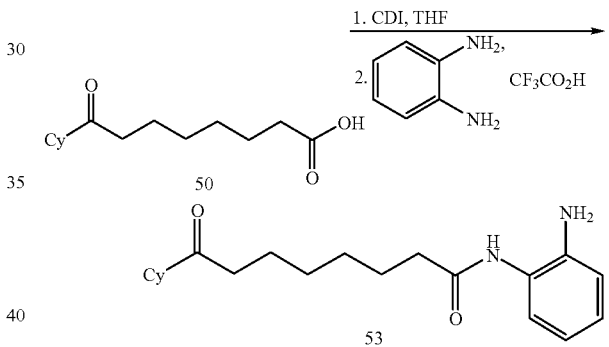

N-(2-Aminophenyl)-7-benzoylheptanamide (53a)

Following the procedure described in Example 6, but substituting carboxylic acid 50a for 16, the title compound was obtained in 23% yield: $^1$H NMR (300 MHz, $CDCl_3$) δ 7.93 (d, J=8.4 Hz, 2H), 7.82 (br s, 1H), 6.70-7.55 (m, 7H), 3.90 (br s, 2H), 2.94 (t, J=7.5 Hz, 2H), 2.29 (t, J=7.5 Hz, 2H), 1.60-1.80 (m, 4H), 1.43 (m, 4H); $^{13}$C NMR (75.4 MHz, $CDCl_3$) δ 23.94, 25.47, 28.79, 28.87, 36.49, 38.29, 117.78, 119.01, 124.16, 125.36, 126.89, 127.90, 128.45, 132.87, 136.80, 140.88, 172.07, 200.52.

N-(2-Aminophenyl)-7-(p-anisoyl)heptanamide (53b)

Following the procedure described in Example 6, but substituting carboxylic acid 50b for 16, the title compound was obtained in 40% yield: $^1$H NMR (300 MHz, $CDCl_3$) δ 7.94 (d, J=8.7 Hz, 2H), 7.35 (br s, 1H), 7.19 (m, 1H), 7.05 (m, 1H), 6.92 (d, J=8.7 Hz, 2H), 6.70-6.80 (m, 2H), 3.86 (s, 3H), 3.85 (br s, 2H), 2.92 (t, J=7.5 Hz, 2H), 2.40 (t, J=7.5 Hz, 2H), 1.65-1.80 (m, 4H), 1.43 (m, 4H); $^{13}$C NMR (75.4 MHz, $CDCl_3$) δ 24.23, 25.56, 28.88, 28.92, 37.00, 38.03, 55.43, 113.67, 118.13, 119.43, 124.37, 125.18, 127.05, 130.06, 130.29, 140.78, 163.34, 171.82, 199.13.

N-(2-Aminophenyl)-7-(1-naphthoyl)heptanamide (53f)

Following the procedure described in Example 6, but substituting carboxylic acid 50f for 16, the title compound was obtained in 60% yield: $^1$H NMR (300 MHz, CDCl$_3$) δ 8.53 (d, J=7.8 Hz, 1H), 8.05 (br s, 1H), 7.89 (d, J=8.4 Hz, 1H), 6.60-7.82 (m, 9H), 3.69 (br s, 2H), 2.94 (t, J=7.5 Hz, 2H), 2.18 (t, J=7.5 Hz, 2H), 1.55-1.80 (m, 4H), 1.28 (m, 4H); $^{13}$C NMR (75.4 MHz, CDCl$_3$) δ 24.20, 25.30, 28.64, 28.69, 36.16, 41.78, 117.37, 118.62, 123.87, 124.14, 125.35, 125.42, 126.13, 126.70, 127.06, 127.52, 128.18, 129.74, 132.13, 133.61, 135.85, 140.89, 172.15, 204.96.

(m, 2H), 1.26 (t, J=7.2 Hz, 3H), 1.15-1.40 (m, 4H), 0.82 (s, 6H); $^{13}$C NMR (75.4 MHz, CDCl$_3$) δ 14.26, 23.76, 25.81, 26.69, 34.07, 34.41, 41.50, 47.40, 55.16, 60.16, 113.01, 131.37, 131.40, 157.73, 173.83.

Step 3: Ethyl 6-Methyl-6-(4-methoxybenzoyl)heptanoate (56)

A mixture of ester 55 (190 mg, 0.65 mmol) and N-bromosuccinimide (150 mg, 0.85 mmol) in CCl$_4$ was heated at reflux overnight in the presence of a catalytic amount of AIBN (7 mg). The reaction mixture was cooled to ambient temperature, and the floating solid was filtered off. The

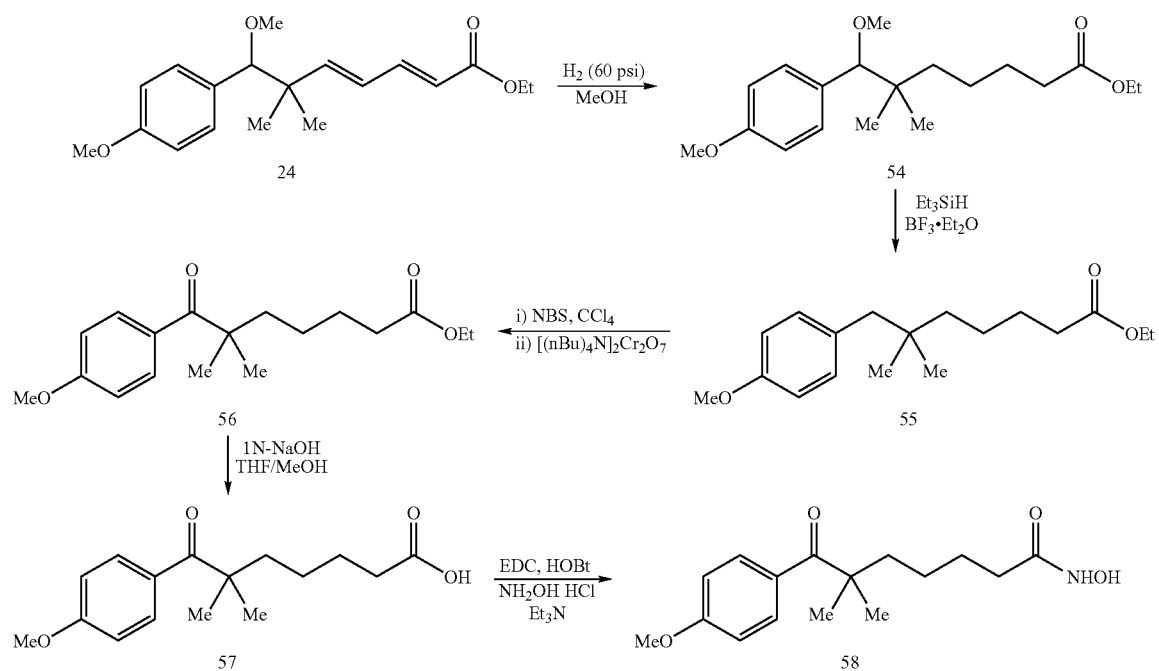

filtrate was then concentrated to give the crude benzylic bromide: $^1$H NMR (300 MHz, CDCl$_3$) δ 7.28 (d, J=8.7 Hz, 2H), 6.81 (d, J=8.7 Hz, 2H), 4.89 (s, 1H), 4.13 (q, J=7.2 Hz, 2H), 3.80 (s, 3H), 2.31 (t, J=7.5 Hz, 2H), 1.60 (m, 2H), 1.26 (t, J=7.2 Hz, 3H), 1.10-1.40 (m, 4H), 1.05 (s, 3H), 0.93 (s, 3H).

A mixture of crude bromide obtained above and bis(tetrabutylammonium)-dichromate (1.68 g, 2.4 mmol) was heated at reflux in CHCl$_3$ (10 mL) for 4 h. After removal of the solvent, the residue was dissolved in ethyl ether (50 mL), washed with water, dried and concentrated. Purification by flash silica gel chromatography (15% ethyl acetate in hexanes) gave the title compound (230 mg, 63% yield) as light yellow oil: $^1$H NMR (300 MHz, CDCl$_3$) δ 7.81 (d, J=9.0 Hz, 2H), 6.89 (d, J=9.0 Hz, 2H), 4.08 (q, J=7.2 Hz, 2H), 3.86 (s, 3H), 2.23 (t, J=7.5 Hz, 2H), 1.79 (m, 2H), 1.55 (m, 2H), 1.32 (s, 6H), 1.23 (t, J=7.2 Hz, 3H), 1.21 (m, 2H).

Step 4: 6-Methyl-6-(4-methoxybenzoyl)heptanoic acid (57)

Following a procedure analogous to that described for 50a but substituting ester 56 for ester 49a, the title compound was obtained in 93% yield: $^1$H NMR (300 MHz, CDCl$_3$) δ

Example 20

N-Hydroxy-6,6-dimethyl-7-(4-methoxybenzoyl)heptanamide (58)

Step 1: Ethyl 6,6-dimethyl-7-methoxy-7-(4-methoxyphenyl)-heptanoate (54)

Following the procedure described in Example 10, step 1, but substituting ester 24 for carboxylic acid 16, the title compound was obtained in 94% yield: 1H NMR (300 MHz, CDCl$_3$) δ 7.24 (d, J=8.7 Hz, 2H), 6.86 (d, J=8.7 Hz, 2H), 4.12 (q, J=7.2 Hz, 2H), 3.82 (s, 3H), 3.78 (s, 1H), 3.15 (s, 3H), 2.30 (t, J=7.2 Hz, 2H), 1.59 (m, 2H), 1.26 (t, J=7.2 Hz, 3H), 1.25-1.40 (m, 4H), 0.83 (s, 3H), 0.76 (s, 3H).

Step 2: Ethyl 6,6-dimethyl-7-(4-methoxyphenyl)heptanoate (55)

Following the procedure described in Example 14, step 1, but substituting ester 54 for ester 31, the title compound was obtained in 64% yield. $^1$H NMR (300 MHz, CDCl$_3$) δ 7.01 (d, J=8.7 Hz, 2H), 6.81 (d, J=8.7 Hz, 2H), 4.13 (q, J=7.2 Hz, 2H), 3.79 (s, 3H), 2.43 (s, 2H), 2.31 (t, J=7.5 Hz, 2H), 1.60

7.67 (d, J=9.0 Hz, 2H), 6.78 (d, J=9.0 Hz, 2H), 3.73 (s, 3H), 2.10 (t, J=7.5 Hz, 2H), 1.67 (m, 2H), 1.42 (m, 2H), 1.19 (s, 6H), 1.13 (m, 2H); $^{13}$C NMR (75.4 MHz, CDCl$_3$) δ 24.15, 25.13, 26.16, 33.57, 40.81, 47.32, 55.08, 113.11, 130.27, 130.31, 161.90, 176.12, 207.01.

Step 5: N-Hydroxy-6-methyl-6-(4-methoxybenzoyl)-heptanamide (58)

Following the procedure described in Example 14, step 3, but substituting carboxylic acid 57 for 37, the title compound was obtained in 39% yield: $^1$H NMR (300 MHz, CD$_3$OD/CDCl$_3$=5/1): δ 7.80 (d, J=9.0 Hz, 2H), 6.91 (d, J=9.0 Hz, 2H), 3.86 (s, 3H), 2.05 (t, J=7.5 Hz, 2H), 1.77 (m, 2H), 1.47 (m, 2H), 1.32 (s, 6H), 1.23 (m, 2H); $^{13}$C NMR (75.4 MHz, CD$_3$OD/CDCl$_3$=5/1) δ 24.14, 25.71, 26.17, 29.40, 32.40, 40.75, 55.08, 113.12, 130.15, 130.32, 161.94, 170.94, 207.08.

CDCl$_3$) δ 7.09 (d, J=9.0 Hz, 2H), 6.70 (d, J=9.0 Hz, 2H), 4.10 (q, J=7.2 Hz, 2H), 3.74 (d, J=6.9 Hz, 1H), 3.16 (s, 3H), 2.95 (s, 6H), 2.21 (m, 2H), 1.23 (t, J=7.2 Hz, 3H), 1.00-1.83 (m, 6H), 0.90 (d, J=6.6 Hz, 3H), 0.76 (d, J=6.0 Hz, 3H).

Step 2: Ethyl 4-methyl-6-[4-(N,N-dimethylamino)benzoyl]heptanoate (60)

Following the procedure described in Example 13, but substituting ester 59 for compound 34, the title compound was obtained as a ca. 3:1 mixture of isomers in 42% yield: major isomer: $^1$H NMR (300 MHz, CDCl$_3$) δ 7.88 (d, J=9.0 Hz, 2H), 6.64 (d, J=9.0 Hz, 2H), 4.18 (q, J=7.2 Hz, 2H), 3.45 (m, 1H), 3.05 (s, 6H), 2.13 (m, 2H), 1.22 (t, J=7.2 Hz, 3H), 1.20-1.83 (m, 5H), 1.02 (d, J=6.6 Hz, 3H), 0.81 (d, J=6.3 Hz, 3H); $^{13}$C NMR (75.4 MHz, CDCl$_3$) δ 14.13, 17.53, 19.02, 30.33, 31.80, 32.16, 37.06, 39.91, 40.06, 60.08, 110.66, 124.15, 130.32, 153.19, 173.81, 202.28.

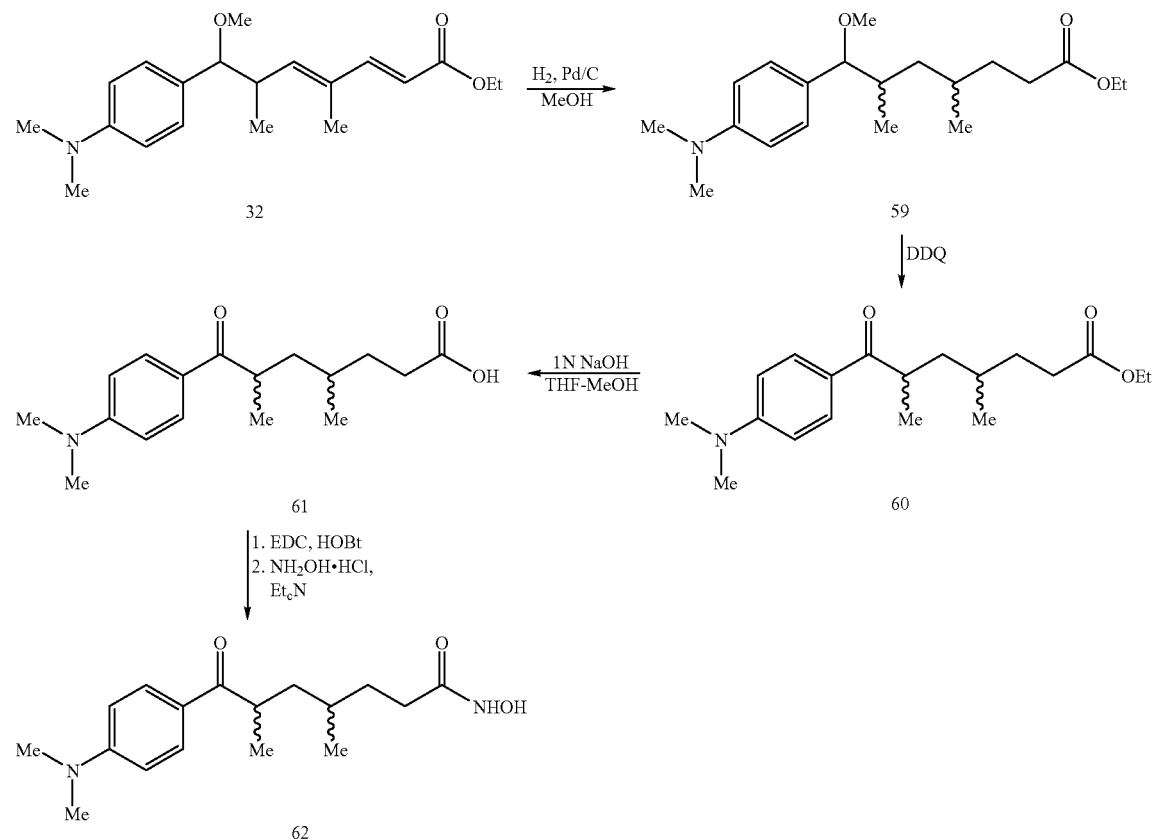

Example 21

N-Hydroxy-4,6-dimethyl-6-[4-(N,N-dimethyl)benzoyl]heptanamide (62)

Step 1: Ethyl 4,6-dimethyl-7-methoxy-7-[4-(N,N-dimethylamino)phenyl]heptanoic acid (59)

Following the procedure described in Example 10, step1, but substituting ester 32 for carboxylic acid 16, the title compound was obtained as an inseparable mixture of isomers in 99% yield: major isomer: $^1$H NMR (300 MHz, Step 3: 4-Methyl-6-[4-(N,N-dimethylamino)benzoyl]heptanoic acid (61)

Following the procedure described for 50, but substituting ester 60 for ester 49, the title compound was obtained in 94% yield: major isomer: $^1$H NMR (300 MHz, CDCl$_3$) δ 7.89 (d, J=9.0 Hz, 2H), 6.66 (d, J=9.0 Hz, 2H), 3.45 (m, 1H), 3.05 (s, 6H), 2.15 (m, 2H), 1.20-1.83 (m, 5H), 1.14 (d, J=6.6 Hz, 3H), 0.93 (d, J=6.3 Hz, 3H),-

Step 4: N-Hydroxy-4-Methyl-6-[4-(N,N-dimethylamino)benzoyl]heptanamide (62)

Following the procedure described in Example 14, step 3, but substituting carboxylic acid 61 for 37, the title compound was obtained in 44% yield: major isomer: $^1$H NMR (300 MHz, CD$_3$OD/CDCl$_3$=5/1) δ 7.82 (d, J=9.0 Hz, 2H), 6.62 (d, J=9.0 Hz, 2H), 3.40 (m, 1H), 3.01(s, 6H), 2.05 (m, 2H), 1.20-1.83 (m, 5H), 1.07 (d, J=6.6 Hz, 3H), 0.88 (d, J=6.3 Hz, 3H).

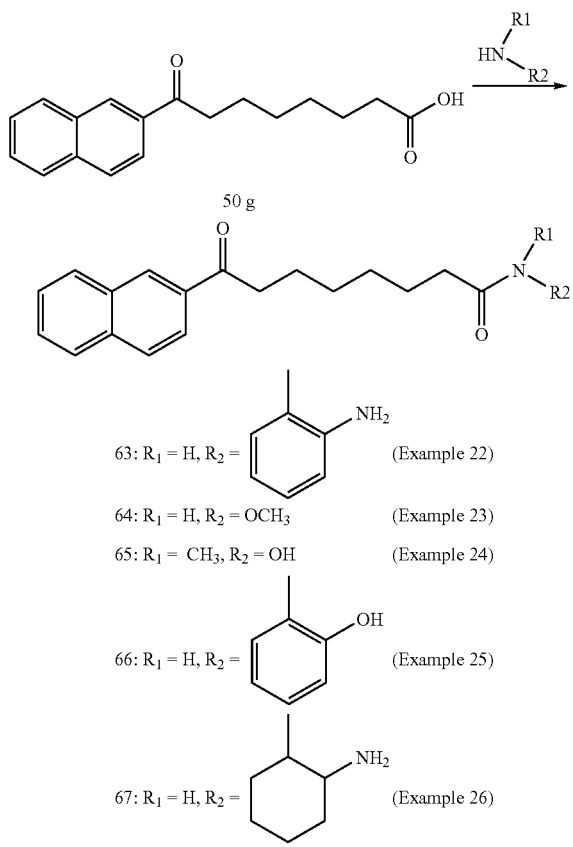

63: R$_1$ = H, R$_2$ = (2-methylphenyl-NH$_2$)  (Example 22)

64: R$_1$ = H, R$_2$ = OCH$_3$  (Example 23)

65: R$_1$ = CH$_3$, R$_2$ = OH  (Example 24)

66: R$_1$ = H, R$_2$ = (2-methylphenyl-OH)  (Example 25)

67: R$_1$ = H, R$_2$ = (2-aminocyclohexyl)  (Example 26)

Example 22

N-(2-Aminophenyl)-7-(2-naphthoyl)heptanamide (63)

To a solution of 7-(2-naphthoyl)heptanoic acid 50 g (1.00 g, 3.52 mmol) in DMF (15 mL) were added HOBT (950 mg, 7.04 mmol) and EDC (1.00 g, 5.28 mmol). The mixture was stirred at room temperature for 1 hour, after which 1,2-phenylenediamine (760 mg, 7.04 mmol) was added and the solution was stirred at room temperature for 16 hours. The DMF was evaporated under high vacuum, deionized water was added, and the mixture was extracted with ethyl acetate (2×30 mL). The combined organic layers were washed with saturated sodium bicarbonate (20 mL), washed with brine (20 mL), and dried (MgSO$_4$). The solvents were removed in vacuo and the title compound 63 (558 mg, 42%) was isolated by recrystallization from acetone and dichloromethane. $^1$H NMR (300 MHz, 20% CD$_3$OD in CDCl$_3$): δ 8.47 (s, 1H), 8.10-7.85 (m, 4H), 7.63-7.50 (m, 2H), 7.14-6.70 (m, 4H), 3.11 (t, J=7.2 Hz, 2H), 2.39 (t, J=7.5 Hz, 2H), 1.77 (m, 4H), 1.46 (m, 4H). $^{13}$C NMR (75 MHz, 20% CD$_3$OD in CDCl$_3$): δ 23.99, 25.40, 28.66, 28.74, 36.08, 38.23, 117.69, 119.09, 123.45, 124.01, 125.34, 126.53, 126.86, 127.45, 128.19, 128.23, 129.28, 129.56, 132.23, 133.85, 135.32, 140.58, 172.81, 201.11.

Example 23

N-Methoxy-7-(2-naphthoyl)heptanamide (64)

To a solution of 7-(2-naphthoyl)heptanoic acid 50 g (500 mg, 1.76 mmol) in DMF (10 mL) were added HOBT (309 mg, 2.29 mmol) and EDC (504 mg, 2.64 mmol). The mixture was stirred at room temperature for 1 hour, after which methoxylamine-HCl (176 mg, 2.11 mmol) and triethylamine (300 μL, 2.11 mmol) were added and the solution was stirred at room temperature for 16 hours, then at 45° C. for 2 hours. The DMF was evaporated under high vacuum, deionized water was added, and the mixture was extracted with ethyl acetate (2×30 mL). The combined organic layers were washed with saturated sodium bicarbonate (10 mL), washed with brine (10 mL), and dried (MgSO$_4$). The solvents were removed in vacuo and the title compound 64 (308 mg, 56%) was isolated by recrystallization from acetone. $^1$H NMR (400 MHz, 5:1 CDCl$_3$:CD$_3$OD): 8.37 (s, 1H), 7.89 (m, 2H), 7.78 (m, 2H), 7.48 (m, 2H), 3.59 (s, 3H), 3.01 (t, J=7.3 Hz, 2H), 1.96 (t, J=7.3 Hz, 2H), 1.67 (m, 2H), 1.54 (m, 2H), 1.31 (m, 4H).

Example 24

N-Hydroxy-N-methyl-7-(2-naphthoyl)heptanamide (65)

Following the procedure described in Example 23, but substituting N-methyl-hydroxylamine-HCl for methoxylamine-HCl, the title compound 65 was obtained in 34% yield. $^1$H NMR (400 MHz, 5:1 CDCl$_3$:CD$_3$OD): δ 8.37 (s, 1H), 7.88 (m, 2H), 7.78 (m, 2H), 7.47 (m, 2H), 3.10 (s, 3H), 3.01 (t, J=7.1 Hz, 2H), 2.36 (t, J=6.5 Hz, 2H), 1.67 (m, 2H), 1.52 (m, 2H), 1.32 (m, 4H).

Example 25

N-(2-Hydroxyphenyl)-7-(2-naphthoyl)heptanamide (66)

Following the procedure described in Example 22, but substituting 2-aminophenol for 1,2-phenylenediamine, the title compound 66 was obtained in 20% yield after purification by flash silica gel chromatography (3% methanol in dichloromethane) followed by crystallization in ethyl acetate. $^1$H NMR (CDCl$_3$): δ 8.38 (s, 1H), 7.89 (m, 2H), 7.81 (m, 2H), 7.48 (m, 3H), 6.81 (m, 3H), 3.03 (t, J=7.3 Hz, 2H), 2.34 (t, J=7.5 Hz, 2H), 1.68 (m, 4H), 1.37 (m, 4H).

Example 26

N-(2-Aminocyclohexyl)-7-(2-naphthoyl)heptanamide (67)

Following the procedure described in Example 6, but substituting the carboxylic acid 5g for the carboxylic acid 16 and 1,2-diaminocyclohexyl for 1,2-phenylenediamine, the title compound 67 was obtained in 16% yield. $^1$H NMR (300

MHz, CDCl$_3$): δ 8.44 (s, 1H), 8.0-7.82 (m, 4H), 7.65-7.48 (m, 3H), 3.80-3.70 (br s, 2H), 3.07 (t, J=6.9 Hz, 2H), 1.20-2.25 (m, 20H).

Example 27

N-(2-(N-Methyl-N-methyloxycarbonyl)aminophenyl)-7-(2-naphthoyl)heptanamide (69)

Step 1: 2-(N-Methyl-N-methyloxycarbonyl)aminoaniline (68)

i) Substitution Reaction

To a solution of N-methyl-2-nitroaniline (1.00 g, 6.58 mmol) in acetone (15 mL) was added methyl chloroformate (2.0 mL, 26 mmol) and potassium carbonate (5.45 g, 39.5 mmol). The reaction mixture was refluxed for 16 hours and then stirred at room temperature for 96 hours. The acetone was removed in vacuo, water was added, and the mixture was extracted with ethyl acetate (2×30 mL). The combined organic layers were washed with brine and dried (MgSO$_4$). The solvents were removed in vacuo and the compound (808 mg, 59%) was isolated by column chromatography (25% to 40% of ethyl acetate in hexane). $^1$H NMR: (400 MHz, DMSO-d$_6$): δ 8.02 (m, 1H), 7.78 (m, 1H), 7.63 (d, J=7.7 Hz, 1H), 7.55 (m, 1H), 3.66 and 3.45 (s, 3H), 3.29 and 3.23 (s, 3H).

ii) Hydrogenation

A solution of 2-(N-methyl-N-methyloxycarbonyl)nitroaniline (600 mg, 2.86 mmol) in methanol (6 mL) was hydrogenated over 10% Pd/C (51 mg, 0.048 mmol) for 2 hours. The reaction mixture was filtered through a short pad of Celite and the solvent was removed in vacuo to give the title compound 68 (489 mg, 95%). $^1$H NMR (400 MHz, DMSO-d$_6$): δ 6.94 (m, 2H), 6.70 (m, 1H), 6.50 (m, 1H), 5.01 (br s, 2H), 3.64 and 3.49 (s, 3H), 3.33 (s, 3H).

Step 2: N-(2-(N-Methyl-N-methyloxycarbonyl)aminophenyl)-7-(2-naphthoyl)-heptanamide (69)

Following the procedure described in Example 6, but substituting the carboxylic acid 50 g for the carboxylic acid 16 and the N-methyl, N-methyloxycarbonyl-1,2-phenylenediamine for 1,2-phenylenediamine, the title compound 69 was obtained in 32% yield. MS (ESI)=447.5 (MH$^+$)

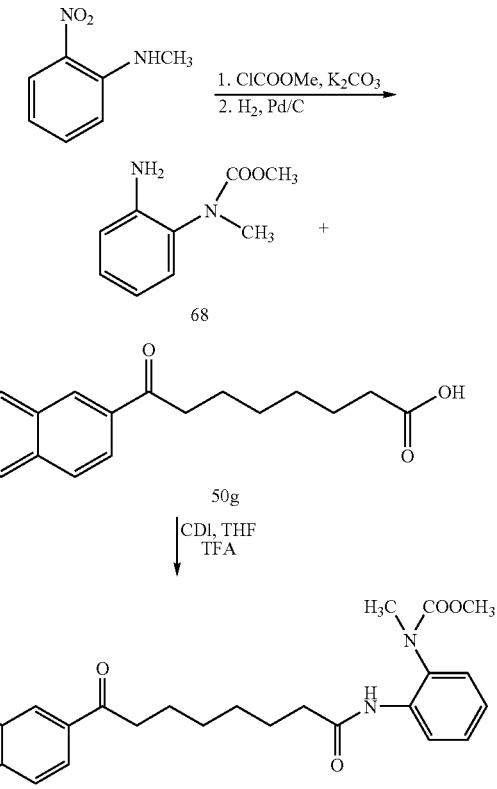

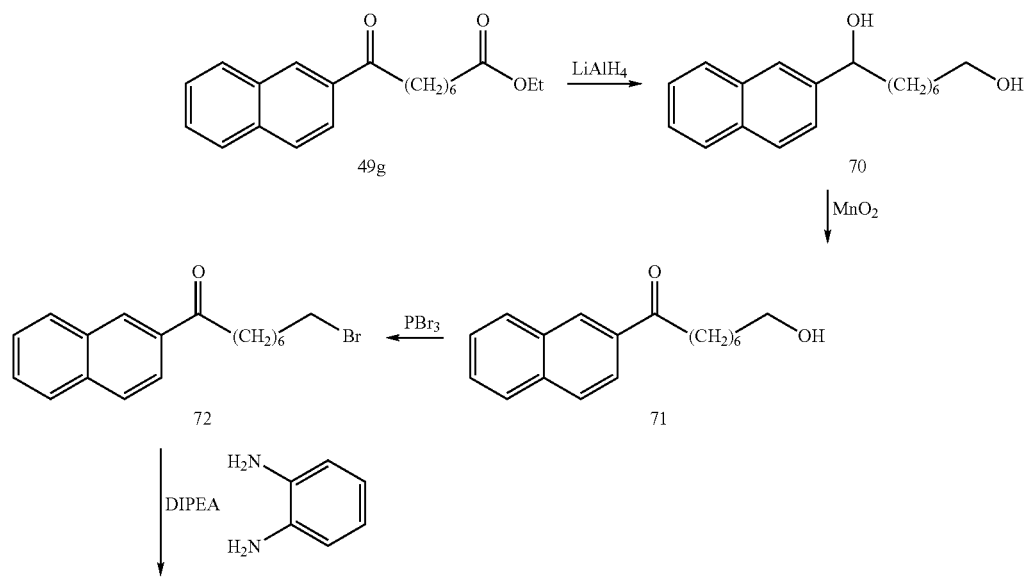

-continued

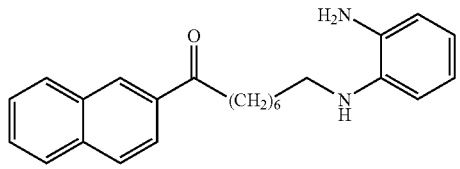

73: Example 28

Example 28

N-(2-Aminophenyl)-7-(2-naphthoyl)heptanamine (73)

Step 1: 1-Hydroxy-1-[(2-naphthyl)]-8-octanol (70)

Lithium aluminum hydride (114 mg, 3.00 mmol) was added to diethyl ether (3 mL) at 0° C. A solution of ethyl-7-(2-naphthoyl)-heptanoate 49 g (312 mg, 1.00 mmol) in ether (2 mL) was added dropwise at 0° C. and the reaction mixture was stirred at 0° C. for 1 hour, then at room temperature for 1 hour. Deionized water was added slowly dropwise (5 mL) followed by 2N NaOH (5 mL). The mixture was filtered through a short pad of Celite, washing with ether. The organic layer was separated and dried ($MgSO_4$). The solvents were removed in vacuo to give the title compound 70 (247 mg, 91%). $^1$H NMR (400 MHz, DMSO-$d_6$): δ 7.83 (m, 4H), 7.45 (m, 3H), 5.22 (m, 1H), 4.64 (m, 1H), 4.28 (m, 1H), 3.35 (m, 2H), 1.68 (m, 2H), 1.37 (m, 2H), 1.22 (m, 8H).

Step 2: 7-(2-Naphthoyl)-1-heptanol (71)

To a solution of 1-hydroxy-1-[(2-naphthyl)]-8-octanol 70 (715 mg, 2.63 mmol) in acetone (25 mL) was added manganese (IV) oxide (7.0 g, 81 mmol) and the reaction mixture was stirred at room temperature for 16 hours. The mixture was filtered through a short pad of Celite and the solvents were removed in vacuo. The title compound 71 (361 mg, 51%) was isolated by column chromatography (4:6 ethyl acetate:hexane). $^1$H NMR (400 MHz, DMSO-$d_6$): δ 8.68 (s, 1H), 8.11 (d, 1H), 8.00 (m, 3H), 7.64 (m, 2H), 4.32 (t, 1H), 3.15 (t, J=7.2 Hz, 2H), 1.67 (m, 2H), 1.40 (m, 2H), 1.32 (m, 8H).

Step 3: 1-Bromo-7-[(2-naphthoyl)]heptane (72)

To a solution of 7-(2-naphthoyl)-1-heptanol 71 (175 mg, 0.606 mmol) in ether (5 mL) at 0° C. was added a solution of phosphorous tribromide (86 μL, 0.908 mmol) in ether (1 mL) dropwise and the reaction mixture was stirred at room temperature for 6 hours. Saturated sodium bicarbonate solution was added slowly and the mixture was extracted with ether (2×20 mL). The combined organic layers were washed with brine and dried ($MgSO_4$). The solvents were removed in vacuo to give the title compound 72 (141 mg, 70%). $^1$H NMR (400 MHz, DMSO-$d_6$): δ 8.66 (s, 1H), 8.12 (m, 1H), 7.99 (m, 3H), 7.62 (m, 2H), 3.50 (t, 2H), 3.11 (t, 2H), 1.65 (m, 2H), 1.55 (m, 2H),1.31 (m, 6H).

Step 4: N-(2-Aminophenyl)-7-(2-naphthoyl)heptanamine (73)

To a solution of 1-bromo-7-[(2-naphthoyl)]heptane 72 (62 mg, 0.17 mmol) in toluene (2 mL) and DMF (1 mL) was added 1,2-phenylenediamine (60 mg, 0.56 mmol) and N,N-diisopropylethylamine (36 μL, 0.21 mmol) and the reaction mixture was stirred at room temperature for 2 hours then at 75° C. for two hours and finally refluxed for 5 hours. Saturated sodium bicarbonate solution (5 mL) was added and the mixture was extracted with dichloromethane (2×20 mL). The combined organic layers were washed with deionized water (20 mL), washed with brine (10 mL), and dried ($MgSO_4$). The solvents were removed in vacuo and the title compound 73 (2 mg, 3%) was isolated by column chromatography (3:7-4:6 ethyl acetate:hexane) followed by recrystallization from ether and hexane. $^1$H NMR (400 MHz, DMSO-$d_6$): δ 8.69 (s, 1H), 8.14 (d, J=8.0 Hz, 1H), 8.00 (m, 3H), 7.64 (m, 2H), 6.52 (m, 1H), 6.47 (m, 1H), 6.38 (m, 2H), 4.46 (s, 2H), 4.30 (m, 1H), 3.17 (t, J=7.4 Hz, 2H), 2.99 (m, 2H), 1.69 (m, 2H), 1.60 (m, 2H), 1.39 (m, 6H).

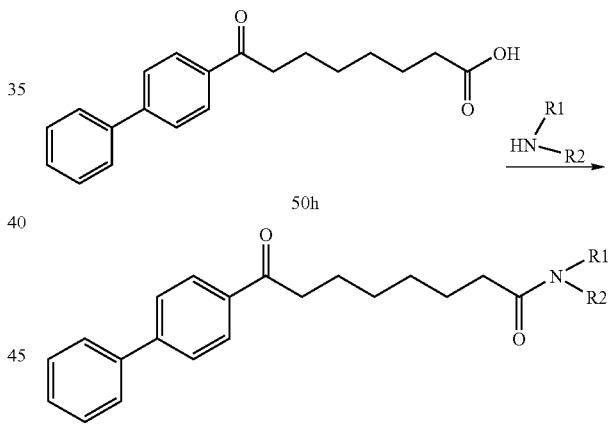

(Example 29)

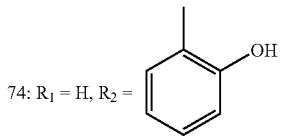

74: $R_1$ = H, $R_2$ =

(Example 30)

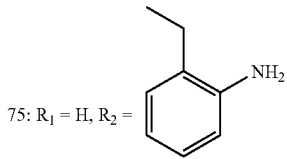

75: $R_1$ = H, $R_2$ =

(Example 31)

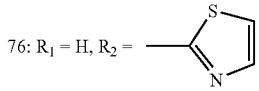

76: $R_1$ = H, $R_2$ =

-continued

77: R₁ = H, R₂ = 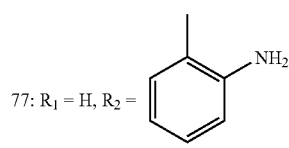 (Example 32)

78: R₁ = H, R₂ = NHOH (Example 33)

79: R₁ = H, R₂ = 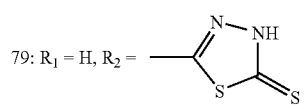 (Example 34)

80: R₁ = H, R₂ = 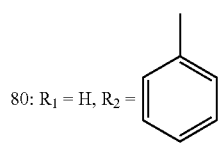 (Example 35)

81: R₁ = H, R₂ = 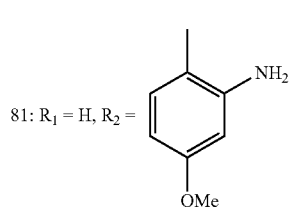 (Example 36)

82: R₁ = H, R₂ = 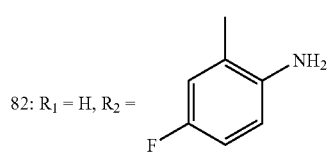 (Example 37)

83: R₁ = H, R₂ = 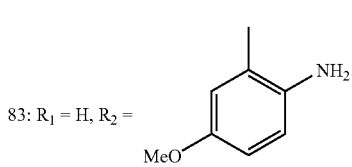 (Example 38)

Example 29

N-(2-Hydroxyphenyl)-7-[(4-biphenyl)carbonyl]heptanamide (74)

Following the procedure described in Example 22, but substituting carboxylic acid 50h for carboxylic acid 50g and 2-aminophenol for 1,2-phenylenediamine, the title compound 74 was obtained in 39% yield. $^1$H NMR (CDCl$_3$: CD$_3$OD 5:1): δ 7.99 (d, J=8.4 Hz, 2H), 7.60 (m, 4H), 7.41 (m, 4H), 7.02 (m, 1H), 6.91 (m, 1H), 6.81 (m, 1H), 2.98 (m, 2H), 2.41 (t, J=7.5 Hz, 2H), 1.74 (m, 4H), 1.42 (m, 4H).

Example 30

N-(2-Aminobenzyl)-7-[(4-biphenyl)carbonyl]heptanamide (75)

Following the procedure described in Example 22, but substituting carboxylic acid 50h for carboxylic acid 50g and 2-aminobenzylamine for 1,2-phenylenediamine respectively, the title compound 75 was obtained in 32% yield. $^1$H NMR (300 MHz, CDCl$_3$): δ 8.02 (d, J=8.4 Hz, 2H), 7.71-7.61 (m, 4H), 7.37-7.51 (m, 3H), 7.12-7.01 (m, 2H), 6.70-6.62 (m, 2H), 5.76 (br s, 1H), 4.38 (d, J=6.3 Hz, 2H), 2.97 (t, J=7.5 Hz, 2H), 2.19 (t, J=7.5 Hz, 2H), 1.80-1.58 (m, 4H), 1.45-1.32 (m, 4H).

Example 31

N-(2-Thiazolyl)-7-[(4-biphenyl)carbonyl]heptanamide (76)

Following the procedure described in Example 22, but substituting carboxylic acid 50h for carboxylic acid 50 g and 2-aminothiazole for 1,2-phenylenediamine respectively, the title compound 76 was obtained in 11% yield. $^1$H NMR (400 MHz, CDCl$_3$): δ 8.03 (d, J=8.4 Hz, 2H), 7.6-7.7 (m, 4H), 7.39-7.53 (m, 4H), 7.07 (d, J=4.2 Hz, 2H), 3.05 (t, J=7.5 Hz, 2 H), 2.67 (t, J=7.5 Hz, 2H), 1.72-1.82 (m, 4H), 1.42-1.50 (m, 4H).

Example 32

N-(2-Aminophenyl)-7-[(4-biphenyl)carbonyl]heptanamide (77)

Following the procedure described in Example 22, but substituting carboxylic acid 50h for carboxylic acid 50g, the title compound 77 was obtained in 31% yield. $^1$H NMR (300 MHz, CDCl$_3$): δ 8.02 (d, J=8.4 Hz, 2H), 7.68 (d, 8.4 Hz, 2H), 7.62 (m, 2H), 7.51-7.35 (m, 3H), 7.16 (m, 1H), 7.04 (m, 1H), 7.75-6.80 (m, 2H), 3.83 (br s, 2H), 3.00 (t, J=7.5 Hz, 2H), 2.39 (t, J=7.2 Hz, 2H), 1.78 (m, 4H), 1.45 (m, 4H). $^{13}$C NMR (75 MHz, CDCl$_3$) δ 24.08, 25.55, 28.87, 28.94, 36.79, 38.41, 118.13, 119.43, 124.38, 125.20, 127.05, 127.19, 127.21, 128.16, 128.62, 128.91, 135.61, 139.85, 140.78, 145.60, 171. 82, 200.09.

Example 33

N-Hydroxy-7-[(4-biphenyl)carbonyl]heptanamide (78)

Following the procedure described in Example 14, step 3, but substituting carboxylic acid 50h for carboxylic acid 37, and using 1.1 equivalent of NH$_2$OH.HCl and triethylamine each, the title compound 78 was obtained in 22% yield. $^1$H NMR (300 MHz, 20% CD$_3$OD in CDCl$_3$): δ 8.03 (d, J=7.8 Hz, 2H), 7.70 (d, J=7.8 Hz, 2H), 7.64 (d, J=7.2 Hz, 2H), 7.55-7.38 (m, 3H), 3.02 (t, J=6.9 Hz, 2H), 2.12 (t, J=7.2 Hz, 2H), 1.75 (m, 2H), 1.66 (m, 2H), 1.41 (m, 4H). $^{13}$C NMR (75 MHz, 20% CD$_3$OD in CDCl$_3$): δ 23.96, 25.06, 28.61(2), 32.54, 38.29, 126.98, 127.02, 128.02, 128.47, 128.71, 135.26, 139.55, 145.66, 171.09, 200.92.

Example 34

N-(4,5-Dihydro-5-thioxo-1,3,4-thiadiazol-2-yl)-7-[(4-biphenyl)carbonyl]-heptanamide (79)

Following the procedure described in Example 22, but substituting carboxylic acid 50h for carboxylic acid 50g and 5-amino-1,3,4thiadiazole-2-thiol for 1,2-phenylenediamine respectively, the title compound 79 was obtained in 34% yield. $^1$H NMR (300 MHz, 20% CD$_3$OD in CDCl$_3$): δ 7.91 (d, J=8.4 Hz, 2H), 7.58(d, J=8.4 Hz, 2H), 7.52 (m, 2H), 7.38-7.26 (m, 3H), 2.90 (t, J=7.2 Hz, 2H), 2.30 (t, J=7.2 Hz, 2H), 1.62 (m, 4H), 1.30 (m, 4H).

Example 35

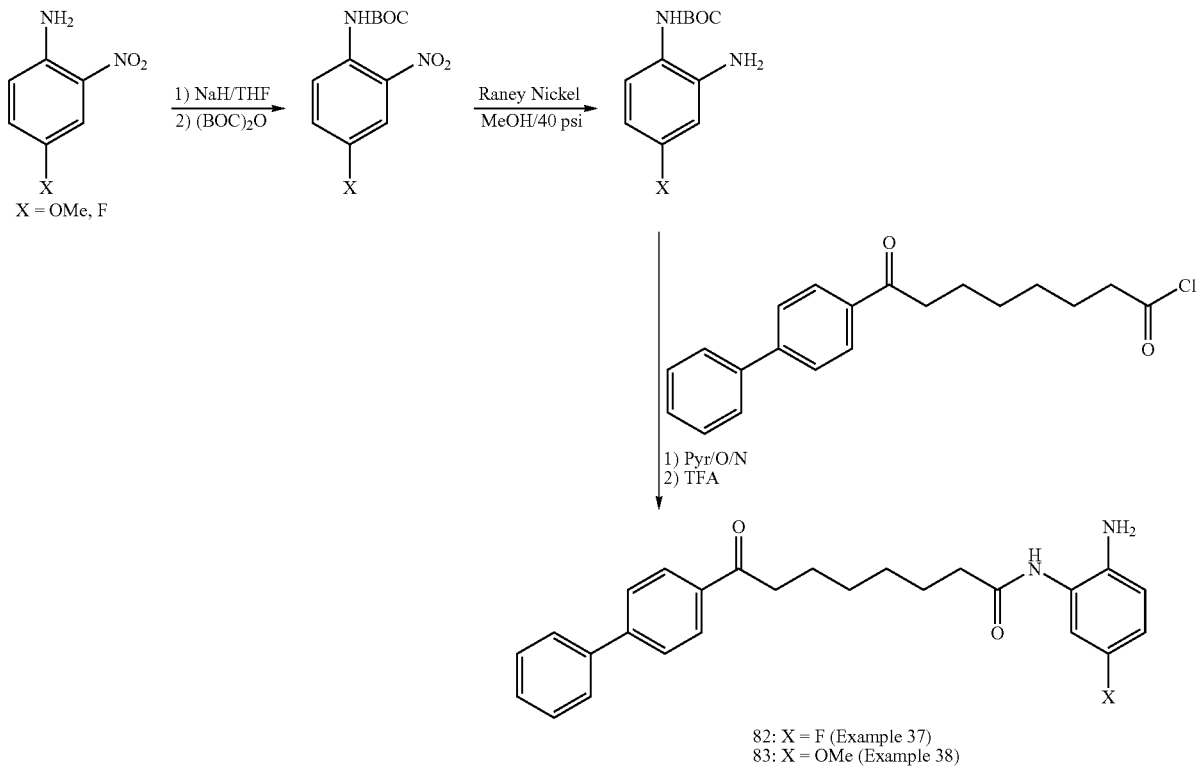

N-Phenyl-7-[(4-biphenyl)carbonyl]heptanamide (80)

To a solution of carboxylic acid 50h (310 mg, 1 mmol) in dichloromethane (5 mL) stirred at room temperature under nitrogen was added triethylamine (135 µL, 1 mmol), followed by BOP (442 mg, 1 mmol), aniline (108 µL, 1 mmol) and triethylamine (405 µL, 3 mmol). The resulting reaction mixture was stirred for 12 hours at room temperature. The solvent was removed and the mixture was quenched with water (5 mL), extracted with ethyl acetate (3×10 mL), dried (MgSO$_4$), concentrated. Purification by flash silica gel chromatography (5% methanol in dichloromethane) followed by crystallization from acetone afforded the corresponding amide 80 (20% yield). $^1$H NMR: (300 MHz, CDCl$_3$) δ 8.00 (m, 4H), 7.40-7.60 (m, 10H), 3.00 (m, 2H), 2.60 (m, 2H), 1.60 (m, 4H), 1.20 (m, 4H).

Example 36

N-(4-(3-Amino)anisole)-7-[(4-biphenyl)carbonyl]heptanamide (81)

Following the procedure described in Example 1, step 4, but substituting 4-biphenyl carboxylic acid for 5, the resulting carboxylic acid was substituted for 16 in Example 6. Then, to a solution of nitroamide (1 mmol) in THF/NH$_4$Cl was added iron (1 mmol) and the mixture was stirred at room temperature for 4 hours. After filtration over Celite, water was added and the mixture was extracted from ethyl acetate to give a residue which was flashed over silica gel to give the title compound 81 obtained in 30% yield. $^1$H NMR: (300 MHz, CDCl$_3$) δ 8.00 (m, 4H), 7.60-7.40 (m, 8H), 4.00 (s, 3H), 3.00 (m, 2H), 2.60 (m, 2H), 1.60 (m, 4H), 1.20 (m, 4H).

Example 37

N-[(2-Amino-5-fluoro-phenyl]-7-[(4biphenyl)carbonyl]heptanamide (82)

Step 1: N-tert-Butyloxycarbonyl-3-fluoro-2-nitro aniline

To a solution of 3-fluoro-2-nitro aniline (1 g, 6.4 mmol) in anhydrous THF (20 mL) was added dropwise at 0° C. a solution of sodium hydride (510 mg, 12.8 mmol) in THF (10 mL). After 15 minutes, di-tert-butyl dicarbonate (2.8 g, 13 mmol) was added dropwise and the mixture was refluxed overnight. Water was added and the mixture was extracted with ethyl acetate. The residue was flashed on silica gel to give the desired product in 93% yield. MS (ESI)=257 (MH$^+$)

Step 2: N-tert-Butyloxycarbonyl-3-fluoro-2-amino aniline

To a solution of the N-tert-Butyloxycarbonyl-3-fluoro-2-nitro aniline (950 mg, 2.5 mmol) in MeOH was added catalytic amount of Raney Nickel in water, hydrogen was applied at 40 psi and the mixture was stirred overnight. The mixture was filtered over Celite and the solvent was evaporated to give the desired product in 66% yield (550 mg). MS (ESI)=226 (MH$^+$)-

Step 3: N-[(2-Amino-5-fluoro-phenyl]-7-[(4-biphenyl)carbonyl]heptanamide (82)

Following the procedure described in Example 1, step 4, but substituting 50h for 5, followed by Example 4, but substituting N-tert-butyloxycarbonyl-3-fluoro-2-amino aniline for 1,2-phenylenediamine, the title compound 82 was obtained in 27% yield. $^1$H NMR: (300 MHz, CDCl$_3$) δ 8.00 (m, 4H), 7.60-7.40 (m, 8H), 3.00 (m, 2H), 2.60 (m, 2H), 1.60 (m, 4H), 1.20 (m, 4H).

Example 38

N-(3-(4-Amino)anisole)-7-[(4-biphenyl)carbonyl]heptanamide (83)

Step 1: N-tert-Butyloxycarbonyl-3-methoxy-2-nitro aniline

To a solution of 3-methoxy-2-nitro aniline (6.5 mmol) in anhydrous THF (20 mL) was added dropwise at 0° C. a solution of sodium hydride (13 mmol) in THF (10 mL). After 15 minutes, di-tert-butyl dicarbonate (13 mmol) was added dropwise and the mixture was refluxed overnight. Water was added and the mixture was extracted with ethyl acetate. The residue was flashed on silica gel to give the desired product in 95% yield. MS (ESI)=269 (MH$^+$).

Step 2: N-tert-Butyloxycarbonyl-3-methoxy-2-amino aniline

To a solution of the N-tert-Butyloxycarbonyl-3-methoxy-2-nitro aniline (4 mmol) in MeOH was added catalytic amount of Raney Nickel in water, hydrogen was applied at 40 psi and the mixture was stirred overnight. The mixture was filtered over Celite and the solvent was evaporated to give the desired product in 55% yield. MS (ESI)=239 (MH$^+$).

Step 3: N-(3-(4-Amino)anisole)-7-[(4-biphenyl)carbonyl]heptanamide (83)

Following the procedure described in Example 1, step 4, but substituting 50h for 5, followed by Example 4, step 1, 2, but substituting N-tert-butyloxycarbonyl-3-methoxy-2-amino aniline for 1,2-phenylenediamine, the title compound 83 was obtained in 32% yield. $^1$H NMR: (300 MHz, CDCl$_3$) δ 8.00 (m, 4H), 7.60-7.40 (m, 8H), 4.00 (s, 3H), 3.00 (m, 2H), 2.60 (m, 2H), 1.60 (m, 4H), 1.20 (m, 4H).

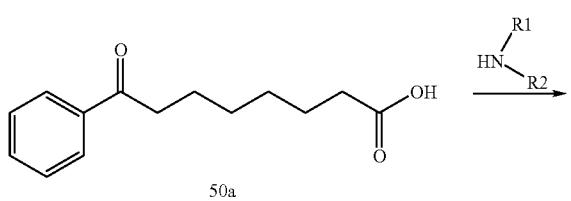

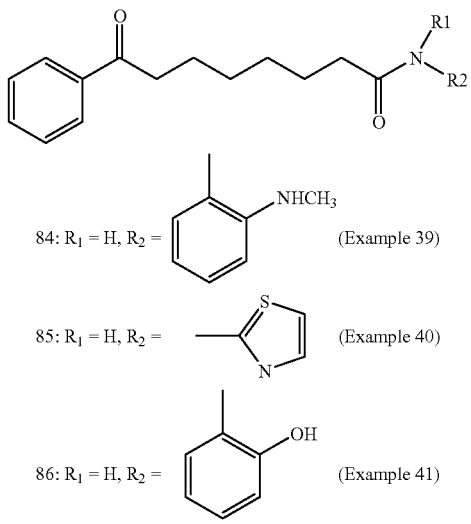

Example 39

N-(2-N-Methylaminophenyl)-7-(benzoyl)heptanamide (84)

Following the procedure described in Example 35, but substituting 50h for 80, and N-methyl-1,2-phenylenediamine for aniline respectively, the title compound 84 was obtained in 27% yield. $^1$H NMR (300 MHz, CDCl$_3$): δ7.98-7.92 (m, 2H), 7.59-7.52 (m, 1H), 7.41-7.50 (m, 2H), 7.24-7.13 (m, 2H), 7.05-6.98 (br s, 1H), 6.77 (d, J=7.8 Hz, 1H), 4.0 (br s, 1H), 2.99 (t, J=7.4 Hz, 2H), 2.84 (s, 3H), 2.41 (t, J=7.4 Hz, 2H), 1.85-1.70 (m, 4H), 1.48-1.35 (m, 4H).

Example 40

N-(2-Thiazolyl)-7-(benzoyl)heptanamide (85)

Following the procedure described in Example 35, but substituting respectively benzotriazol-1-yloxytripyrrolidinophosphonium hexafluorophosphate for the BOP reagent and 2-aminothiazole for aniline, the title compound 85 was obtained in 54% yield. $^1$H NMR (400 MHz, CDCl$_3$): δ 7.96 (d, J=7.9 Hz, 2H), 7.60-7.54 (m, 1H), 7.42-7.50 (m, 3H), 7.0 (d, J=3.7 Hz, 1H), 2.97 (t, J=7.3 Hz, 2H), 2.57 (t, J=7.4 Hz, 2H), 1.87-1.72 (m, 4H), 1.50-1.38 (m, 4H).

Example 41

N-(2-Hydroxyphenyl)-7-(benzoyl)heptanamide (86)

Following the procedure described in Example 40, but substituting the 1,2-aminophenol for the 2-aminothiazole, the title compound 86 was obtained in 36% yield.

$^1$H NMR (400 MHz, CDCl$_3$): δ 8.01 (br s, 1H), 7.97-7.93 (m, 2H), 7.59-7.42 (2 m, 3H), 7.13-7.07 (m, 2H), 7.02-6.98 (m, 1H), 6.87-6.81 (m, 1H), 2.98 (t, J=7.2 Hz, 2H), 2.45 (t, J=7.2 Hz, 2H), 1.81-1.68 (m, 4H), 1.45-1.38 (m, 4H).

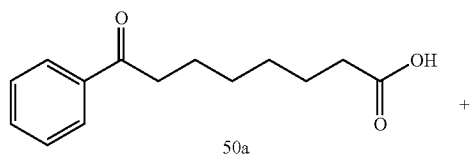

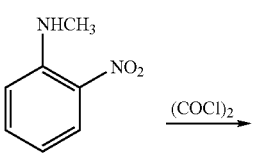

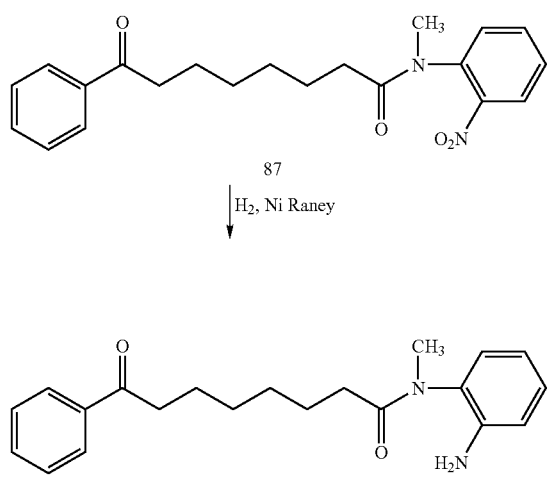

Example 42

N-Methyl-N-(2-aminophenyl)-7-(benzoyl)heptanamide (88)

Step 1: N-Methyl-N-(2-nitrophenyl)-7-(benzoyl)heptanamide (87)

To a solution of carboxylic acid 50a (1 g, 4.27 mmol) in dichloromethane (5 mL) was added DMF (100 μL) and oxalyl chloride (447 μL, 4.7 mmol). The mixture was stirred at room temperature for 12 hours and then cooled at 0° C. The N-methyl-2-nitroaniline (714 mg, 4.7 mmol) dissolved in pyridine (2 mL) was transferred over the mixture, and the mixture was stirred at 50° C. for 12 hours. The reaction was quenched by addition of 1N HCl and extracted with dichloromethane. The organic layer was washed with a saturated solution of sodium bicarbonate, dried (MgSO$_4$), and concentrated. Purification by flash silica gel chromatography (2% methanol in dichloromethane) afforded the corresponding amide 87 (963 mg, 62% yield). MS (ESI)=369 (MH$^+$).

Step 2: N-Methyl-N-(2-aminophenyl)-7-(benzoyl)heptanamide (88)

To a solution of amide 87 (420 mg, 1.14 mmol) in a mixture of ethyl acetate and methanol (5 mL, 9:1) was added catalytic amount of a suspension of Raney Nickel. The mixture was stirred at room temperature under hydrogen pressure for 2 hours and then without pressure for 10 hours. The reaction mixture was filtered through a short pad of Celite and the solvents were removed in vacuo. Purification by flash silica gel chromatography (2% methanol in dichloromethane) afforded the corresponding amide 88 (180 mg, 47% yield). $^1$H NMR (300 MHz, CDCl$_3$): δ 7.96-7.90 (m, 2H), 7.58-7.41 (2 m, 4H), 7.17-7.10 (m, 1H), 6.98 (dd, J=1.5, 7.5 Hz, 1H), 6.80-672 (m, 2H), 3.18 (s, 3H), 2.91 (t, J=7.2 Hz, 2H), 2.15-1.95 (m, 2H), 1.73-1.51 (m, 4H), 1.35-1.20 (m, 4H).

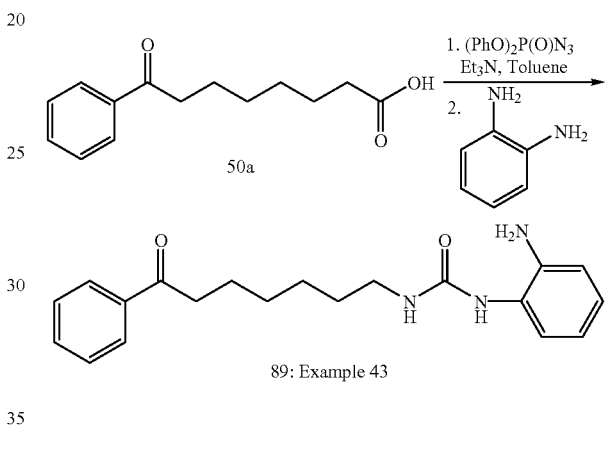

Example 43

N-(2-Aminophenyl)-N'-[6-(benzoyl)hexyl]urea (89)

To a stirred solution of carboxylic acid 50a (500 mg, 2.13 mmol) in toluene (1.5 mL) at room temperature under nitrogen was added triethylamine (295 μL, 2.13 mmol), followed by diphenylphosphoryl azide (461 μL, 2.13 mmol). The reaction mixture was heated at 80° C. for 5 hours and 1,2-phenylenediamine (253 mg, 2.34 mmol) dissolved in 1 mL of toluene was added. The reaction was stirred at 80° C. for 12 hours. The mixture was quenched with water (5 mL), extracted with ethyl acetate (3×10 mL), dried (MgSO$_4$), and concentrated. Purification by flash silica gel chromatography (5% methanol in dichloromethane) followed by recrystallization from ethyl acetate and hexane afforded the corresponding urea 89 (340 mg, 47% yield) as a brown powder. $^1$H NMR: (400 MHz, CDCl$_3$) δ 7.95 (d, 2H, J=7.2 Hz), 7.60-7.53 (m, 1H), 7.5-7.4 (m, 2H), 7.12-7.03 (m, 2H), 6.82-6.73 (m, 2H), 6.38 (br s, 1H), 4.92 (br s, 1H), 3.9 (br s, 2H), 3.23-3.12 (m, 2H), 2.95 (t, 2H, J=7.3 Hz), 1.80-1.60 (m, 2H), 1.55-1.25 (2m, 6H).

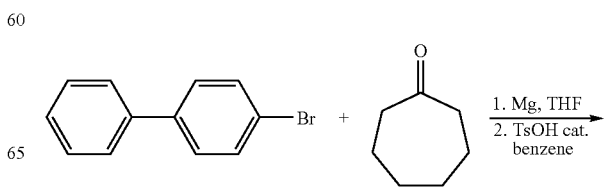

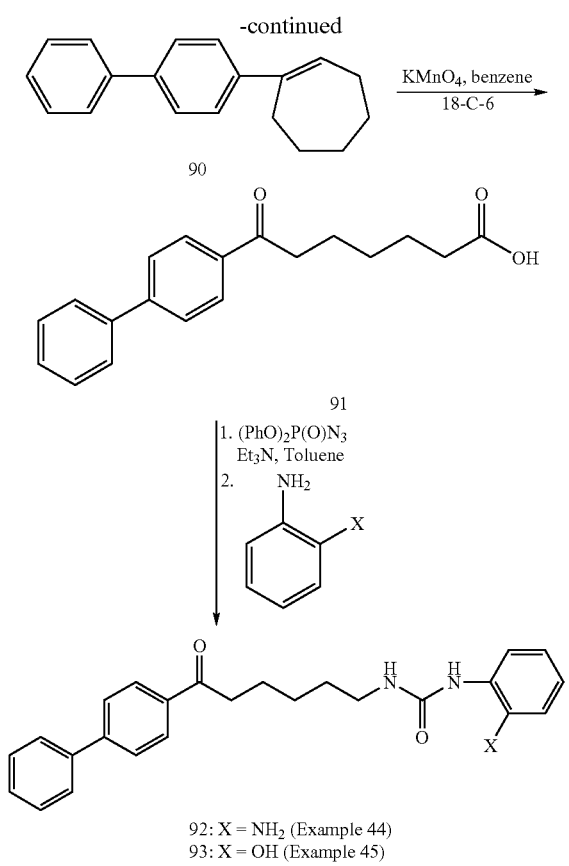

g, 84% yield). $^1$H NMR (400 MHz, CDCl$_3$: δ 7.70-7.35 (m, 9H), 6.15 (t, J=8.0 Hz, 1H), 2.75-2.68 (m, 2H), 2.43-2.35 (m, 2H), 1.80-1.60 (m, 6H).

Step 2: 6-[(4-Biphenyl)carbonyl]hexanoic acid (91)

To a solution of cyclic alkene 90 (1.5 g, 6 mmol) dissolved in benzene (200 mL) was added 18-crown-6 (111 mg, 0.42 mmol) and KMnO$_4$ (2.37 g, 15 mmol). The reaction mixture was stirred at room temperature for 10 hours, and then quenched by addition of an aqueous solution of NaHSO$_3$ (100 mL) followed by 6N HCl until decoloration. The organic layer was extracted and washed with 0.5 N NaOH until a white precipitate was formed. The extracted aqueous layer was acidified with 6N HCl and then extracted with dichloromethane (5×200 mL). The combined organic layers were dried (MgSO$_4$) and concentrated affording the corresponding acid 91 (480 mg, 27% yield) as a white solid. MS (ESI)=311 (MH$^+$).

Step 3: N-(2-Aminophenyl)-N'-[5-((4-biphenyl)carbonyl)pentyl]urea (92)

Following the procedure described in Example 43, but substituting carboxylic acid 91 for carboxylic acid 50a, and substituting 1,2-phenylenediamine for 2-aminophenol the title compound 92 was obtained in 28% yield. $^1$H NMR (400 MHz, CDCl$_3$): δ 8.0 (d, J=8.2 Hz, 2H), 7.70-7.60 (m, 5H), 7.52-7.38 (m, 4H), 7.2-7.00 (m, 3H), 6.93 (t, 1H), 5.73 (br s, 1H), 3.25-3.13 (m, 2H), 3.0 (t, 2H), 1.80-1.70 (m, 2H), 1.60-1.35 (m, 4H).

Example 45

N-(2-Hydroxyphenyl)-N'-[5-((4-biphenyl)carbonyl)pentyl]urea (93)

Following the procedure described in Example 43, but substituting carboxylic acid 91 for carboxylic acid 50a, the title compound 93 was obtained in 22% yield. $^1$H NMR (400 MHz, CDCl$_3$): δ 8.03 (d, J=8.2 Hz, 2H), 7.69 (d, J=8.2 Hz, 2H), 7.63 (d, J=7.1 Hz, 2H), 7.60-7.40 (m, 4H), 7.10-6.75 (3 m, 3H), 3.31 (t, J=6.7 Hz, 2H), 3.04 (t, J=6.9 Hz, 2H), 1.85-1.75 (m, 2H), 1.65-1.58 (m, 2H), 1.50-1.40 (m, 2H).

Example 44

N-(2-Aminophenyl)-N'-[5-((4biphenyl)carbonyl)pentyl]urea (92)

Step 1: 1-Phenylcycloheptene (90)

i) Grignard Reaction

A dry two neck round bottom flask fitted with a condenser, a drying tube and an addition funnel was charged with magnesium turnings (517 mg, 21.5 mmol). Around 10% of the 4-bromobiphenyl (5 g, 21.5 mmol) dissolved in anhydrous THF (15 mL) was added via the addition funnel. When the reflux was maintained, the balance of halide was dropwise added and the mixture was refluxed for 2 hours. After being cooled to room temperature, the heptanone (2.5 mL, 21.2 mmol) dissolved in dry THF (10 mL) was dropwise added, and the mixture was stirred for 10 hours at room temperature. The reaction was quenched with 2N HCl (5 mL), extracted with diethyl ether (3×30 mL), dried (MgSO$_4$), and concentrated. Purification by flash silica gel chromatography (10% ethyl acetate in hexane) afforded the corresponding alcohol (4 g, 70% yield).

ii) Dehydration

In a round bottom flask fitted with a Dean Stark and a condenser was added a solution of alcohol (obtained above) in benzene (90 mL) and a catalytic amount of p-toluenesulfonic acid. The reaction mixture was refluxed for 3 hours and then cooled to room temperature. The mixture was washed with water (30 mL), brine (30 mL), dried (MgSO$_4$), and concentrated to afford the corresponding alkene 90 (3.1

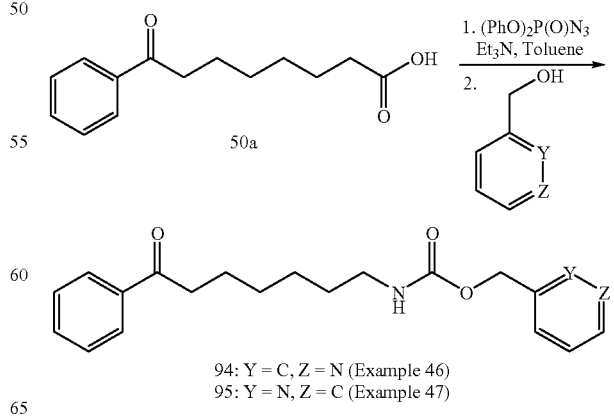

Example 46

3-Pyridylmethyl-N-[6-(benzoyl)hexyl]carbamate (94)

Following the procedure described in Example 43, but substituting 3-pyridylcarbinol for 2-aminophenol, the title compound 94 was obtained in 46% yield. $^1$H NMR (400 MHz, CDCl$_3$): δ 9.0 (s, 1H), 8.81 (d, J=5.4 Hz, 1H), 8.35 (d, J=8.4 Hz, 1H), 7.58-7.43 (m, 3H), 5.29 (s, 2H), 5.18 (br s, 1H), 3.23-3.16 (m, 2H), 2.97 (t, J=7.2 Hz, 2H), 1.80-1.68 (m, 2H), 1.60-1.47 (m, 2H), 1.47-1.3 (m, 4H).

Example 47

2-Pyridylmethyl-N-[6-(benzoyl)hexyl]carbamate (95)

Following the procedure described in Example 43, but substituting the 2-pyridylcarbinol for 2-aminophenol, the title compound 95 was obtained in 35% yield. $^1$H NMR (400 MHz, CDCl$_3$): δ 9.0 (dd, J=7.2 Hz; 1.2 Hz, 1H), 8.3 (dt, J=7.2 Hz; 1.2 Hz, 1H), 7.97-7.92 (m, 2H), 7.81-7.75 (m, 2H), 7.58-7.42 (m, 3H), 5.75 (br s, 1H), 5.45 (s, 2H), 3.23-3.14 (m, 2H), 2.96 (t, J=7.2 Hz, 2H), 1.78-1.68 (m, 2H), 1.58-1.48 (m, 2H), 1.42-1.34 (m, 4H).

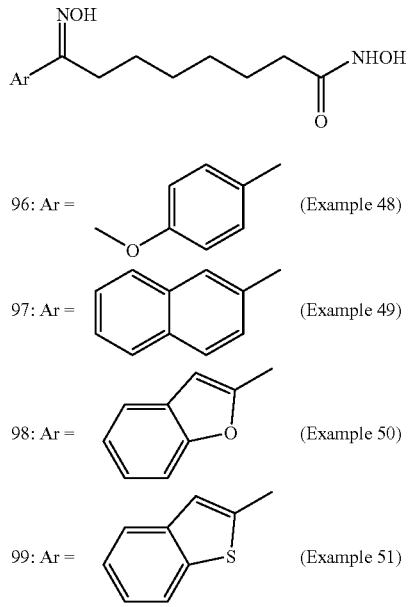

Example 48

N-Hydroxy-8-(E)-oximino-8-(4-methoxyphenyl)octanamide (E-96)

Following the procedure described in Example 18, step 2, 3, but substituting 4-methoxybenzoyl chloride for benzoyl chloride, and then the resulting carboxylic acid was substituted for 37 in Example 14, step 3, to afford the title compound 96 in 55% yield. $^1$H NMR (300 MHz, 20% CD$_3$OD in CDCl$_3$): δ 7.50 (d, J=8.1 Hz, 2H), 6.89 (d, J=8.1 Hz, 2H), 3.81 (s, 3H), 2.75 (t, J=7.2 Hz, 2H), 2.06 (m, 2H), 1.63-1.45 (m, 4H), 1.32 (m, 4H).

Example 49

N-Hydroxy-8-(E)-oximino-8-(2-naphthyl)octanamide (97)

Following the procedure described in Example 18, step 2, 3, but substituting 2-naphthoyl chloride for benzoyl chloride, and then the resulting carboxylic acid was substituted for 37 in Example 14, step 3, to afford the title compound 97 in 40% yield. $^1$H NMR (300 MHz, 20% CD$_3$OD in CDCl$_3$): δ 8.00 (s, 1H), 7.90-7.40 (m, 6H), 2.91 (t, J=7.2 Hz, 2H), 2.07 (t, J=6.9 Hz, 2H), 1.61 (m, 4H), 1.38 (m, 4H). $^{13}$C NMR (75 MHz, 20% CD$_3$OD in CDCl$_3$): δ 25.03, 25.46, 25.86, 28.37, 28.92, 32.39, 123.43, 125.38, 125.90, 126.08, 127.15, 127.62, 127.94, 132.79, 133.14, 133.17, 159.01, 171.17.

Example 50

N-Hydroxy-8-(E)-oximino-8-(2-benzofuryl)octanamide (E-98) and N-Hydroxy-8-(Z)-oximino-8-(2-benzofuryl)octanamide (Z-98)

Following the procedure described in Example 1, step 4, but substituting 2-benzofurancarboxylic acid for 5, followed by Example 18, step 2, 3, but substituting 2-benzofurancarbonyl chloride for benzoyl chloride, and then the resulting carboxylic acid was substituted for 37 in Example 14, step 3, to afford the title compound 98 in 20% yield as a mixture of E and Z isomer in a ca 9:1 ratio. $^1$H NMR (300 MHz, CDCl$_3$): δ 7.62 (m, 2H), 7.22-7.00 (m, 3H), 2.82 (m, 2H), 2.00 (m, 2H), 1.62 (m, 4H), 1.22 (m, 4H).

Example 51

N-Hydroxy-8-(Z)-oximino-8-(2-benzo[b]thiophene)octanamide (99)

Following the procedure described in Example 14, step 3, but substituting carboxylic acid 50m for 37, the title compound 99 was obtained in 30% yield. $^1$H NMR (300 MHz, CDCl$_3$): δ 7.62 (m, 2H), 7.22-7.00 (m, 3H), 2.82 (m, 2H), 2.00 (m, 2H), 1.62 (m, 4H), 1.22 (m, 4H).

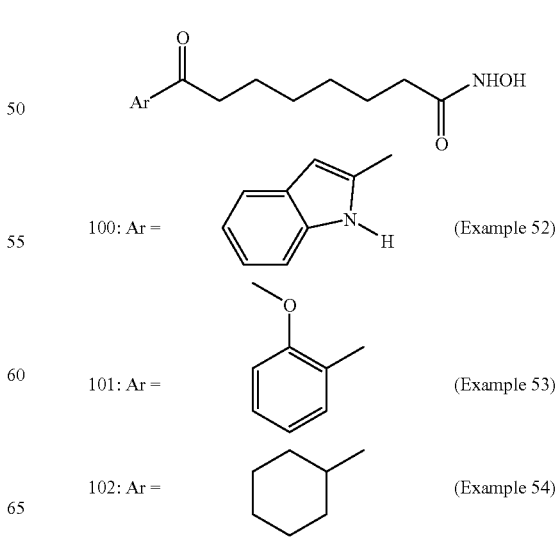

103: Ar = 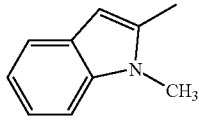 (Example 55)

104: Ar =  (Example 56)

105a: Ar = 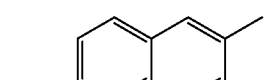 (Example 57a)

105b: Ar = 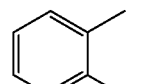 (Example 57b)

Example 52

N-Hydroxy-7-[2-(indolyl)carbonyl]heptanamide (100)

Following the procedure described in Example 18, steps 2, 3, but substituting indole-2-carbonyl chloride for benzoyl chloride, and then substituting the resulting carboxylic acid for 37 in Example 14, step 3, and using 1.1 equivalent each of NH$_2$OH.HCl and triethylamine, the title compound 100 was obtained in 15% yield. $^1$H NMR: (300 MHz, CDCl$_3$) δ 7.60 (m, 2H), 7.00-7.40 (m, 3H), 2.80 (m, 2H), 2.00-2.30 (m, 2H), 1.60 (m, 4H), 1.20 (m, 4H).

Example 53

N-Hydroxy-7-(2-methoxybenzoyl)heptanamide (101)

Following the procedure described in Example 18, step 2, 3, but substituting 2-methoxybenzoyl chloride for benzoyl chloride, and then the resulting carboxylic acid was substituted for 37 in Example 14, step 3, using 1.1 equivalent of NH$_2$OH.HCl and triethylamine each, to afford the title compound 101 obtained in 33% yield. $^1$H NMR (300 MHz, 20% CD$_3$OD in CDCl$_3$): δ 7.81 (dd, J=8.1, 1.8 Hz, 1H), 7.47 (m, 1H), 7.02-6.97 (m, 2H), 3.90 (s, 3H), 2.97 (t, J=7.2 Hz, 2H), 2.10 (t, J=7.2 Hz, 2H), 1.74-1.56 (m, 4H), 1.36 (m, 4H). $^{13}$C NMR (75 MHz, 20% CD$_3$OD in CDCl$_3$): δ 23.89, 25.05, 28.68, 28.60, 32.50, 43.28, 55.17, 111.35, 120.33, 128.03, 129.69, 133.26, 158.18, 171.18, 204.09.

Example 54

N-Hydroxy-7-[(cyclohexyl)carbonyl]heptanamide (102)

Following the procedure described in Example 18, step 2, 3, but substituting 2-cyclohexylcarbonyl chloride for benzoyl chloride, and then the resulting carboxylic acid was substituted for 37 in Example 14, step 3, using 1.1 equivalent of NH$_2$OH.HCl and triethylamine each, to afford the title compound 102 obtained in 38% yield. $^1$H NMR (300 MHz, CDCl$_3$): δ 2.45 (t, J=6.9 Hz, 2H), 2.36 (m, 2H), 2.10 (m, 2H), 1.80-1.25 (m, 17H). $^{13}$C NMR (75 MHz, 20% CD$_3$OD in CDCl$_3$): δ 23.13, 25.00, 25.35, 25.53, 28.22, 28.50, 28.51, 32.47, 40.27, 50.61, 177.11, 215.62.

Example 55

N-Hydroxy-7-[2-((N-methyl)indolyl)carbonyl]heptanamide (103)

Following the procedure described in Example 1, step 4, but substituting 1-methyl indole-2-carboxylic acid for 5, followed by Example 18, step 2, 3, but substituting N-methyl indole-2-carbonyl chloride for benzoyl chloride, and then the resulting carboxylic acid was substituted for 37 in Example 14, step 3, using 1.1 equivalent of NH$_2$OH.HCl and triethylamine each, to afford the title compound 103 obtained in 30% yield. $^1$H NMR: (300 MHz, CDCl$_3$) δ 7.60 (m, 2H), 7.00-7.20 (m, 3H), 2.90 (s, 3H), 2.80 (m, 2H), 2.00 (m, 2H), 1.60 (m, 4H), 1.20 (m, 4H).

Example 56

N-Hydroxy-7-(4-phenoxybenzoyl)heptanamide (104)

Following the procedure described in Example 1, step 4, but substituting 4-phenoxybenzoic acid for 5, followed by Example 18, step 2, 3, but substituting 4-phenoxybenzoyl chloride for benzoyl chloride, and then the resulting carboxylic acid was substituted for 37 in Example 14, step 3, using 1.1 equivalent of NH$_2$OH.HCl and triethylamine each, to afford the title compound 104 obtained in 44% yield. $^1$H NMR (300 MHz, 20% CD$_3$OD in CDCl$_3$): δ 7.81 (d, J=8.7 Hz, 2H), 7.23 (m, 2H), 7.08 (m, 1H), 6.94 (d, J=8.1 Hz, 2H), 6.87 (d, J=8.1 Hz, 2H), 2.81 (t, J=7.2 Hz, 2H), 1.99 (m, 2H), 1.59 (m, 2H), 1.52 (m, 2H), 1.25 (m, 4H). $^{13}$C NMR (75 MHz, 20% CD$_3$OD in CDCl$_3$): δ 24.00, 25.02, 28.56(2), 32.48, 37.96, 116.99, 119.89, 124.41, 129.79, 130.15, 131.15, 155.11, 161.83, 171.14, 199.86.

Example 57a

N-Hydroxy-7-[2-(6-methoxy)naphthoyl]heptanamide (105)

Following the procedure described in Example 1, step 4, but substituting 2-(6-methoxy)naphthoic acid for 5, followed by Example 18, step 2, 3, but substituting 2-(6-methoxy)naphthoyl chloride for benzoyl chloride, and then the resulting carboxylic acid was substituted for 37 in Example 14, step 3, using 1.1 equivalent of NH$_2$OH.HCl and triethylamine each, to afford the title compound 105 obtained in 43% yield. $^1$H NMR (300 MHz, 20% CD$_3$OD in CDCl$_3$): δ 8.39 (s, 1H), 7.98-7.16 (m, 5H), 7.56 (m, 1H), 3.95 (s, 3H), 3.06 (br t, J=7.5 Hz, 2H), 2.10 (m, 2H), 1.75 (mm, 2H), 1.65 (m, 2H), 1.40 (m, 4H). $^{13}$C NMR (75 MHz, 20% CD$_3$OD in CDCl$_3$) δ 24.09, 25.05, 28.59(2), 32.51, 38.07, 55.11, 105.49, 119.43, 124.19, 126.90, 127.57, 129.48, 130.87, 131.88, 137.09, 159.53, 171.20, 201.00.

Example 57b

N-Hydroxy-7-[3-(2-thiomethyl)pyridyl)carbonyl]heptanamide (105b)

Following the procedure described in Example 1, step 4, but substituting 3-(2-thiomethyl)pyridyl carboxylic acid for 5, followed by Example 18, step 2, 3, but substituting 3-(2-thiomethyl)pyridyl carbonyl chloride for benzoyl chloride, and then the resulting carboxylic acid was substituted for 37 in Example 14, step 3, using 1.1 equivalent of NH₂OH.HCl and triethylamine each, to afford the title compound 105 obtained in 39% yield. ¹H NMR (300 MHz, 20% CD₃OD in CDCl₃): δ 8.58 (br d, J=3.9 Hz, 1H), 8.74 (br d, J=7.5 Hz, 1H), 7.50 (dd, J=7.5, 4.8 Hz, 1H), 2.95 (t, J=7.5 Hz, 2H), 2.51 (s, 3H), 2.12 (br t, 2H), 1.72 (m, 2H), 1.64 (m, 2H), 1.38 (m, 4H). ¹³CNMR (75 MHz, 20% CD₃OD in CDCl₃) δ 13.61, 23.64, 24.97, 28.42, 28.51, 32.44, 39.12, 117.71, 129.12, 137.29, 151.35, 161.62, 171.13, 200.67.

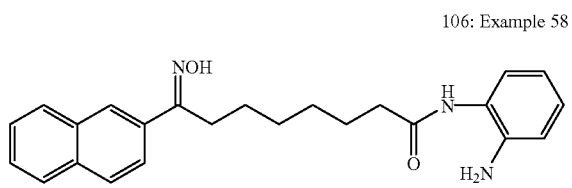

106: Example 58

Example 58

N-(2-Aminophenyl)-8-(E)-oximino-8-(2-naphthyl)octanamide (E-106) and N-(2-Aminophenyl)-8-(Z)-oximino-8-(2-naphthyl)octanamide (Z-106)

Following the procedure described in Example 14, step 3, but substituting amide 63 for 37, the title compound 106 was obtained in 30% yield (E/Z isomeric mixture, ca 5:1). ¹H NMR (300 MHz, 20% CD₃OD in CDCl₃): δ 7.99 (s, 1H), 7.90-6.70 (m, 10H), 2.93 (t, J=7.5 Hz, 2H), 2.37 (t, J=7.5 Hz, 2H), 1.71 (m, 2H), 1.64 (m, 2H), 1.44 (m, 4H).

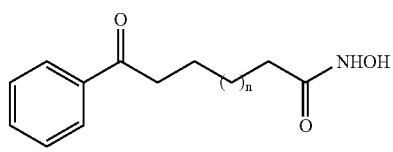

107: n = 1 (Example 59)
108: n = 2 (Example 60)
109: n = 4 (Example 61)

Example 59

N-Hydroxy-5-(benzoyl)pentanamide (107)

Following the procedure described in Example 14, step 3, but substituting 5-benzoylpentanoic acid for 37 and using 1.1 equivalent of NH₂OH.HCl and triethylamine each, the title compound 107 was obtained in 52% yield. ¹H NMR (300 MHz, 20% CD₃OD in CDCl₃): δ 7.86 (d, J=6.9 Hz, 2H), 7.59-7.43 (m, 3H), 3.01 (br t, 2H), 2.18 (br t, 2H), 1.72 (m, 4H). ¹³C NMR (75 MHz, 20% CD₃OD in CDCl₃): δ 23.24, 24.78, 32.39, 37.79, 127.76, 128.36, 133.00, 136.38, 170.85, 200.82.

Example 60

N-Hydroxy-6-(benzoyl)hexanamide (108)

Following the procedure described in Example 14, step 3, but substituting 6-benzoylhexanoic acid for 37 and using 1.1 equivalent of NH₂OH.HCl and triethylamine each, the title compound 108 was obtained in 40% yield. ¹H NMR (300 MHz, 20% CD₃OD in CDCl₃): δ 7.94 (d, J=7.5 Hz, 2H), 7.61-7.40 (m, 3H), 2.98 (t, J=6.9 Hz, 2H), 2.15 (t, J=6.6 Hz, 2H), 1.80-1.60 (m, 4H), 1.41 (m, 2H). ¹³C NMR (75 MHz, 20% CD₃OD in CDCl₃): 23.48, 25.04, 28.37, 32.39, 38.08, 127.87, 128.45, 133.03, 136.57, 171.16, 201.05.

Example 61

N-Hydroxy-8-(benzoyl)octanamide (109)

Following the procedure described in Example 14, step 3, but substituting 8-benzoyloctanoic acid for 37 and using 1.1 equivalent of NH₂OH.HCl and triethylamine each, the title compound 109 was obtained in 46% yield. ¹H NMR (300 MHz, 20% CD₃OD in CDCl₃): δ 7.86 (d, J=7.5 Hz, 2H), 7.51-7.35 (m, 3H), 2.89 (t, J=6.9 Hz, 2H), 2.02 (t, J=6.6 Hz, 2H), 1.70-1.45 (m, 4H), 1.26 (m, 6H). ¹³C NMR (75 MHz, 20% CD₃OD in CDCl₃): δ 23.95, 25.15, 28.59, 28.74, 28.78, 32.55, 38.27, 127.79, 128.36, 132.91, 136.55, 171.27, 201.32.

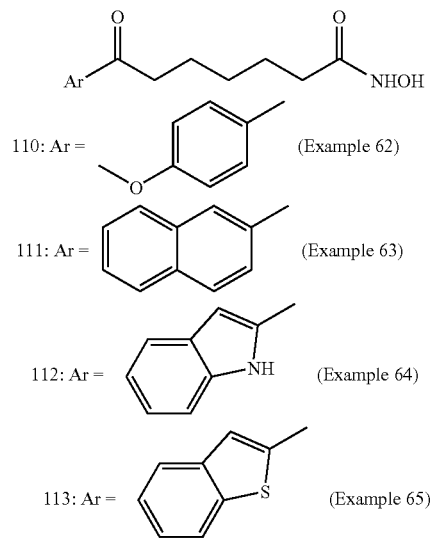

110: Ar = (Example 62)

111: Ar = (Example 63)

112: Ar = (Example 64)

113: Ar = (Example 65)

Example 62

N-Hydroxy-6-(4-methoxybenzoyl)hexanamide (110)

Following the procedure described in Example 18, step 1, 2, 3, but substituting respectively ethyl-6-iodohexanoate for ethyl-7-iodoheptanoate and 4-methoxybenzoyl chloride for benzoyl chloride, and then the resulting carboxylic acid was substituted for 37 in Example 14, step 3, using 1.1 equivalent of NH₂OH.HCl and triethylamine each, to afford the title compound 110 in 54% yield. ¹H NMR (300 MHz, 20% CD₃OD in CDCl₃): δ 7.86 (d, J=8.7 Hz, 2H), 6.88 (d, J=8.7 Hz, 2H), 3.81 (s, 3H), 2.87 (t, J=6.6 Hz, 2H), 2.07 (br t, 2H), 1.62 (m, 4H), 1.34 (m, 2H). ¹³C NMR (75 MHz, 20% CD₃OD in CDCl₃): δ 23.68, 24.96, 28.32, 32.28, 37.63, 55.14, 113.49, 129.48, 130.13, 163.35, 171.06, 199.81.

Example 63

N-Hydroxy-6-(2-naphthoyl)hexanamide (111)

Following the procedure described in Example 18, step 1, 2, 3, but substituting respectively ethyl-6-iodohexanoate for ethyl-7-iodoheptanoate and 2-naphthoyl chloride for benzoyl chloride, and then the resulting carboxylic acid was substituted for 37 in Example 14, step 3, using 1.1 equivalent of NH$_2$OH.HCl and triethylamine each, to afford the title compound 111 in 55% yield. $^1$H NMR (300 MHz, 20% CD$_3$OD in CDCl$_3$): δ 8.47 (s, 1H), 8.05-7.50 (m, 6H), 3.12 (br t, 2H), 2.15 (br t, 2H), 1.82-1.60 (m, 4H), 1.46 (m, 2H). $^{13}$C NMR (75 MHz, 20% CD30D in CDCl$_3$): δ 23.59, 25.02, 28.36, 32.33, 38.06, 123.40, 126.56, 127.46, 128.21, 128.29, 129.29, 129.60, 132.25, 133.78, 135.37, 171.04, 201.04.

Example 64

N-Hydroxy-6-[(2-indolyl)carbonyl]hexanamide (112)

Following the procedure described in Example 1, step 4, but substituting indole-2-carboxylic acid for 5, followed by Example 18, step 1, 2, 3, but substituting respectively ethyl-6-iodohexanoate for ethyl-7-iodoheptanoate and indole-2-carbonyl chloride for benzoyl chloride, and then the resulting carboxylic acid was substituted for 37 in Example 14, step 3, using 1.1 equivalent of NH$_2$OH.HCl and triethylamine each, to afford the title compound 112 in 35% yield. $^1$H NMR: (300 MHz, CDCl$_3$) δ 7.62 (m, 2H), 7.20-7.00 (m, 3H), 2.82 (m, 2H), 2.00 (m, 2H), 1.62 (m, 2H), 1.22 (m, 4H).

Example 65

N-Hydroxy-6-[(2-benzo[b]thiophene)carbonyl]hexanamide (113)

Following the procedure described in Example 18, step 1, 2, 3, but substituting respectively ethyl-6-iodohexanoate for ethyl-7-iodoheptanoate and 2-benzo[b]thiophene-carbonyl chloride for benzoyl chloride, and then the resulting carboxylic acid was substituted for 37 in Example 14, step 3, using 1.1 equivalent of NH$_2$OH.HCl and triethylamine each, to afford the title compound 113 in 79% yield. $^1$H NMR: (300 MHz, CDCl$_3$) δ 7.60 (m, 2H), 7.20-7.00 (m, 3H), 2.80 (m, 2H), 2.00 (m, 2H), 1.60 (m, 2H), 1.20 (m, 4H).

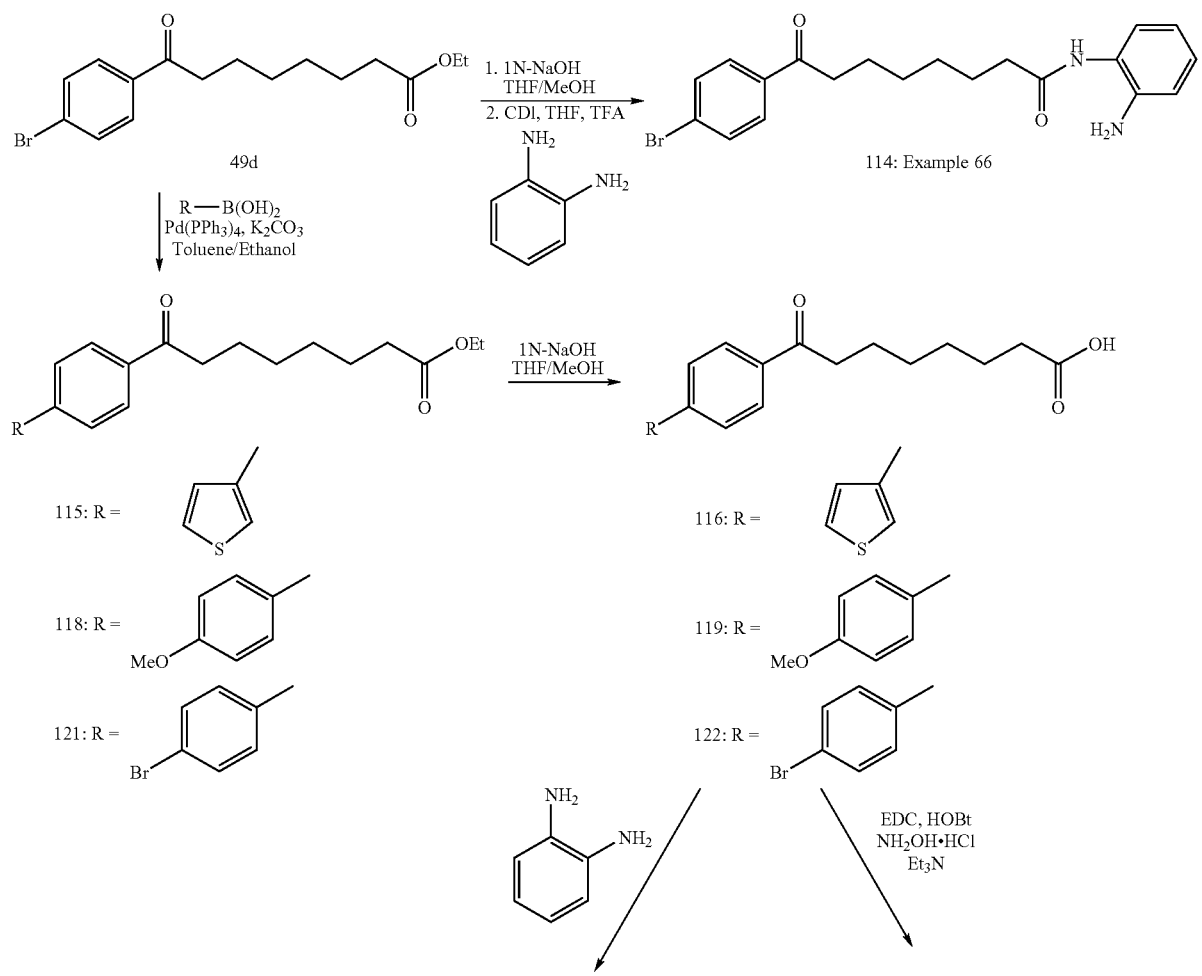

-continued

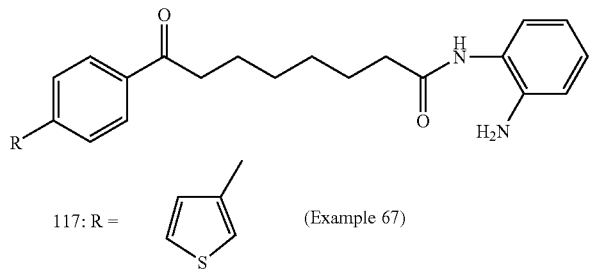

117: R = [3-methylthiophene] (Example 67)

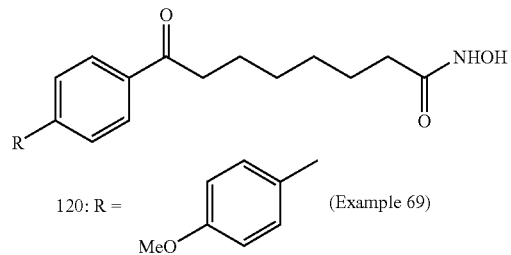

120: R = [4-methoxyphenyl] (Example 69)

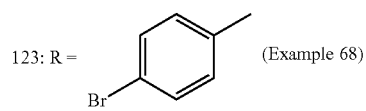

123: R = [4-bromophenyl] (Example 68)

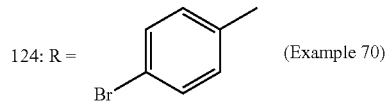

124: R = [4-bromophenyl] (Example 70)

Example 66

N-(2-Aminophenyl)-7-(4-bromobenzoyl)heptanamide (114)

Following the procedure described in Example 6, but substituting the carboxylic acid 50d for the carboxylic acid 50g, the title compound 114 was obtained in 30% yield. $^1$H NMR (300 MHz, 20% CD$_3$OD in CDCl$_3$): δ 7.81 (d, J=8.1 Hz, 2H), 7.59 (d, J=8.1 Hz, 2H), 7.45 (br s, 1H), 7.16-6.73 (m, 3H), 2.92 (t, J=7.2 Hz, 2H), 2.36 (t, J=7.2 Hz, 2H), 1.73 (m, 4H), 1.41 (m, 4H). $^{13}$C NMR (75 MHz, 20% CD$_3$OD in CDCl$_3$): δ 23.85, 25.49, 28.79, 28.89, 36.68, 38.29, 118.07, 119.36, 124.29, 125.23, 127.06, 128.05, 129.53, 131.82, 135.60, 140.80, 171.86, 199.37.

Example 67

N-(2-Aminophenyl)-7-[4-(3-thiophenyl)benzoyl]heptanamide (117)

Step 1: Ethyl-7-[4-(3-thiophenyl)benzoyl]heptanoate (115)

To a mixture of 3-thiophene boronic acid (383 mg, 3 mmol) and bromoester 49d (1.03 g, 3 mmol) were added anhydrous toluene (30 mL) and ethanol (1.5 mL) (20:1, c=1.0M) followed by 2M K$_2$CO$_3$ aqueous solution (3 mL, 6 mmol). The reaction mixture was stirred under nitrogen for 30 minutes and then Pd(PPh$_3$)$_4$ (191 mg, 5 mol %, 0.16 mmol) was quickly added. After 24 hours of reflux, the mixture was cooled to room temperature, filtered through a pad of Celite and rinsed with ethyl acetate (50 mL). The organic solution was washed with brine (30 mL), dried (MgSO$_4$), and concentrated. Purification by flash silica gel chromatography (10% methanol in dichloromethane) followed by crystallization from ethyl acetate afforded the corresponding ester 115 (210 mg, 20% yield) as a white solid.

Step 2: 7-[4-(3-Thiophenyl)benzoyl]heptanoic acid (116)

Following the procedure described in Example 18, step 3, but substituting ester 115 for ester 49a, the title compound 116 was obtained in 57% yield. $^1$H NMR (300 MHz, CDCl$_3$:CD$_3$OD 5:1): δ 7.87 (d, J=8.2 Hz, 2H), 7.59 (d, J=8.2 Hz, 2H), 7.50 (m, 1H), 7.34 (m, 2H), 2.88 (t, J=7.7 Hz, 2H), 2.21 (m, 2H), 1.64 (m, 2H), 1.53 (m, 2H), 1.30 (m, 4H).

Step 3: N-(2-Aminophenyl)-7-[4-(3-thiophenyl)benzoyl]heptanamide (117)

Following the procedure described in Example 22, but substituting carboxylic acid 116 for carboxylic acid 50g, the title compound 117 was obtained in 55% yield. $^1$H NMR (300 MHz, CDCl$_3$:CD$_3$OD 5:1): δ 7.88 (d, J=8.7 Hz, 2H), 7.59 (d, J=8.7 Hz, 2H), 7.50 (m, 2H), 7.34 (m, 2H), 7.08 (m, 3H), 2.90 (m, 2H), 2.37 (t, J=7.5 Hz, 2H), 1.65 (m, 4H), 1.35 (m, 4H).

Example 68

N-(2-Aminophenyl)-7-[4-(4-bromophenyl)benzoyl]heptanamide hydrochloride (123)

Step 1: Ethyl-7-[4-(4-bromophenyl)benzoyl]heptanoate (121)

Following the procedure described in Example 67, step 1, but substituting 4-bromophenyl boronic acid for 3-thiophene boronic acid, the title compound 121 was obtained in 52% yield. $^1$H NMR (300 MHz, 20% CD$_3$OD in CDCl$_3$): δ 8.02 (d, J=8.7 Hz, 2H), 7.75-7.40 (m, 6H), 4.13 (q, J=6.9 Hz, 2H), 3.01 (t, J=6.9 Hz, 2H), 2.32 (t, J=7.2 Hz, 2H), 1.75 (m, 2H), 1.66 (m, 2H), 1.41 (m, 4H), 1.26 (t, J=6.9 Hz, 3H).

Step 2: 7-[4-(4-bromophenyl)benzoyl]heptanoic acid (122)

Following the procedure described in Example 18, step 3, but substituting ester 121 for ester 49a, the title compound 122 was obtained in 88% yield. $^1$H NMR (300 MHz, 20% CD$_3$OD in CDCl$_3$): δ 7.91 (d, J=8.7 Hz, 2H), 7.54 (d, J=8.7 Hz, 2H), 7.50-7.37 (m, 4H), 2.89 (t, J=7.2 Hz, 2H), 2.20 (t, J=7.5 Hz, 2H), 1.65 (m, 2H), 1.53 (m, 2H), 1.31 (m, 4H). $^{13}$C NMR (75 MHz, 20% CD$_3$OD in CD$_3$OD) δ 24.00, 24.50, 28.70(2), 33.77, 38.37, 122.38, 126.83, 128.58(2), 131.85, 135.64, 138.53, 144.27, 176.33, 200.65.

Step 3: N-(2-Aminophenyl)-7-[4-(4-bromophenyl)benzoyl]heptanamide hydrochloride (123)

Following the procedure described in Example 6, but substituting the carboxylic acid 122 for the carboxylic acid 16, the resulting amide was washed with 1N HCl and then precipitated out affording the title compound 123 in 67% yield. $^1$H NMR (300 MHz, 20% CD$_3$OD in CDCl$_3$): δ 7.97 (d, J=8.7 Hz, 2H), 7.62-7.25 (m, 10H), 2.97 (t, J=7.5 Hz, 2H), 2.49 (t, J=7.5 Hz, 2H), 1.72 (m, 4H), 1.40 (m, 4H).

119 was obtained in 94% yield. $^1$H NMR (CDCl$_3$:CD$_3$OD 5:1): δ 7.88 (d, J=8.6 Hz, 2H), 7.53 (d, J=8.6 Hz, 2H), (d, J=8.8 Hz, 2H), 6.89 (d, J=8.8 Hz, 2H), 2.89 (d, J=7.5 Hz, 2H), 3.50 (s, 3H), 2.19 (d, J=7.5 Hz, 2H), 1.64 (m, 2H), 1.55 (m, 2H), 1.31 (m, 4H).

Step 3: N-Hydroxy-7-[4-(4-methoxyphenyl)benzoyl]heptanamide (120)

Following the procedure described in Example 14, step 3, but substituting carboxylic acid 119 for 37, and using 1.1 equivalent of NH$_2$OH.HCl and triethylamine each, the title compound 120 was obtained in 9% yield. MS (ESI)=356 (MH$^+$).

Example 70

N-Hydroxy-7-[4-(4-bromophenyl)benzoyl]heptanamide (124)

Following the procedure described in Example 14, step 3, but substituting carboxylic acid 122 for 37 and using 1.1 equivalent of NH$_2$OH.HCl and triethylamine each, the title compound 124 was obtained in 41% yield. $^1$H NMR (300 MHz, DMSO-d6): δ 10.33 (s, 1H), 8.66 (s, 1H), 8.04-7.70 (m, 8H), 3.04 (m, 2H), 1.94 (m, 2H), 1.62 (m, 2H), 1.49 (m, 2H), 1.30 (m, 4H).

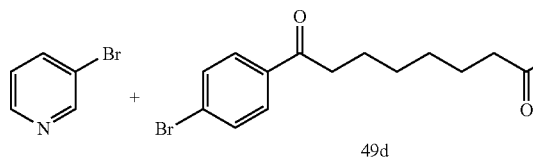

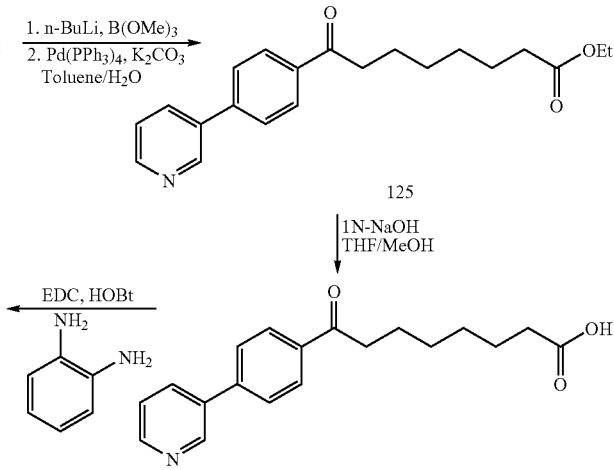

127: Example 71

Example 69

N-Hydroxy-7-[4-(4-methoxyphenyl)benzoyl]heptanamide (120)
Step 1:
Ethyl-7-[4-(4-methoxyphenyl)benzoyl]heptanoate (118)

Following the procedure described in Example 67, step 1, but substituting 2-methoxyphenyl boronic acid for 3-thiophene boronic acid, the title compound 118 was obtained in 26% yield.

Step 2: 7-[4-(4methoxyphenyl)benzoyl]heptanoic acid (119)

Following the procedure described in Example 18, step 3, but substituting ester 118 for ester 49a, the title compound

Example 71

N-(2-Aminophenyl)-7-[4-(3-pyridyl)benzoyl]heptanamide (127)

Step 1: Ethyl-7-[4-(3-pyridyl)benzoyl]heptanoate (125)

To a solution of 3-bromopyridine (728 mg, 4.6 mmol) in dry diethyl ether (9 mL) at −78° C. was added n-BuLi (2.5M solution in hexane, 1.8 mL, 4.5 mmol). The reaction mixture was stirred for 20 minutes at 0° C. After a dropwise addition of trimethyl borate (0.5 mL, 4.5 mmol) the mixture was stirred for 1 hour at 0° C. and then a solution of bromoester 49d (1.02 g, 3 mmol) in THF (9 mL) and water (2.3 mL)

containing Pd(PPh$_3$)$_4$ (278 mg, 8 mol %, 0.27 mmol) was added. The reaction mixture was refluxed at 70° C. for 24 hours, cooled to room temperature, filtered through a pad of Celite and rinsed with ethyl acetate. The solution was extracted with ethyl acetate (2×30 mL), washed with brine (10 mL), dried (MgSO$_4$) and concentrated. Purification by flash silica gel chromatography (1% methanol in dichloromethane) afforded the corresponding ester 125 (259 mg, 25% yield) as a white solid. MS (ESI)=340 (MH$^+$).

Step 2: 7-[(3-pyridyl)-4-benzoyl]heptanoic acid (126)

Following the procedure described in Example 18, step 3, but substituting ester 125 for ester 49a, the title compound 126 was obtained in 75% yield.

Step 3: N-(2-Aminophenyl)-7-[4-(3-pyridyl)benzoyl]heptanamide (127)

Following the procedure described in Example 22, but substituting carboxylic acid 126 for carboxylic acid 50g, the title compound 127 was obtained in 6% yield. $^1$H NMR (CDCl$_3$:CD$_3$OD 5:1): δ 8.73 (d, J=2.0 Hz, 1H), 8.48 (m, 1H), 7.96 (m, 3H), 7.59 (d, J=8.6 Hz, 2H), 7.42 (m, 1H), 7.10 (m, 2H), 6.92 (m, 2H), 2.94 (t, J=7.3 Hz, 2H), 2.35 (t, J=7.5 Hz, 2H), 1.67 (m, 4H), 1.36 (m, 4H).

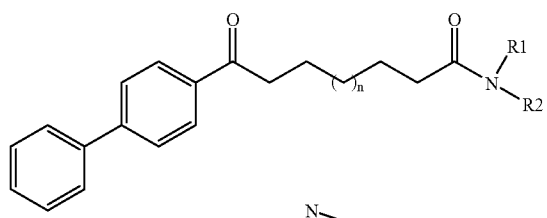

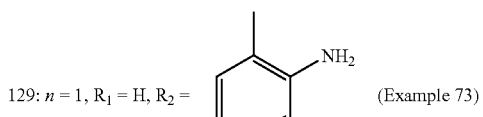

128: n = 1, R$_1$ = H, R$_2$ = (Example 72)

129: n = 1, R$_1$ = H, R$_2$ = (Example 73)

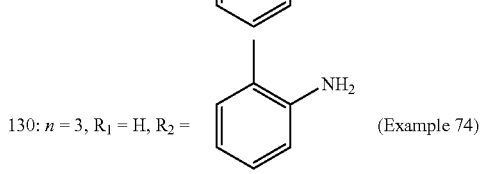

130: n = 3, R$_1$ = H, R$_2$ = (Example 74)

Example 72

N-(4,5-Dihydro-5-thioxo-1,3,4-thiadiazol-2-yl)-6-[(4-biphenyl)carbonyl]hexanamide (128)

Following the procedure described in Example 18, step 1, 2, but substituting respectively ethyl-6-iodohexanoate for ethyl-7-iodoheptanoate and 4-bromobenzoyl chloride for benzoyl chloride, the resulting ester was substituted for 49d in Example 67, step 1. Then, following the procedure described in Example 18, step 3, but substituting the final ester for ester 49a, the resulting acid was substituted for 50g in Example 22, to afford the title compound 128 in 33% yield. $^1$H NMR (300 MHz, 20% CD$_3$OD in CDCl$_3$): δ 7.97 (d, J=8.7 Hz, 2H), 7.65-7.31 (m, 7H), 2.98 (t, J=7.2 Hz, 2H), 2.39 (t, J=7.2 Hz, 2H), 1.73 (m, 4H), 1.40 (m, 2H).

Example 73

N-(2-Aminophenyl)-6-[(biphenyl)carbonyl]hexanamide (129)

Following the procedure described in Example 18, step 1, 2, but substituting respectively ethyl-6-iodohexanoate for ethyl-7-iodoheptanoate and 4-bromobenzoyl chloride for benzoyl chloride, the resulting ester was substituted for 49d in Example 67, step 1. Then, following the procedure described in Example 18, step 3, but substituting the final ester for ester 49a, the resulting acid was substituted for 50g in Example 22, to afford the title compound 129 in 29% yield. $^1$H NMR (300 MHz, 20% CD$_3$OD in CDCl$_3$): δ 8.01 (d, J=8.1 Hz, 2H), 7.68 (d, J=8.1 Hz, 2H), 7.65-7.35 (m, 5H), 7.20-6.74 (m, 4H), 3.05 (t, J=7.5 Hz, 2H), 2.44 (t, J=7.5 Hz, 2H), 1.78 (m, 4H), 1.50 (m, 2H).

Example 74

N-(2-Aminophenyl)-8[(4-biphenyl)carbonyl]octanamide (130)

Following the procedure described in Example 18, step 1, 2, but substituting respectively ethyl-8-iodooctanoate for ethyl-7-iodoheptanoate and 4-bromobenzoyl chloride for benzoyl chloride, the resulting ester was substituted for 49d in Example 67, step 1. Then, following the procedure described in Example 18, step 3, but substituting the final ester for ester 49a, the resulting acid was substituted for 50g in Example 22, to afford the title compound 130 in 45% yield. $^1$H NMR (300 MHz, CDCl$_3$): δ 7.87 (d, J=7.5 Hz, 2H), 7.55 (d, J=7.5 Hz, 2H), 7.51-7.20 (m, 5H), 7.05-6.58 (m, 4H), 2.86 (t, J=7.5 Hz, 2H), 2.24 (t, J=7.5 Hz, 2H), 1.58-1.26 (m, 10H).

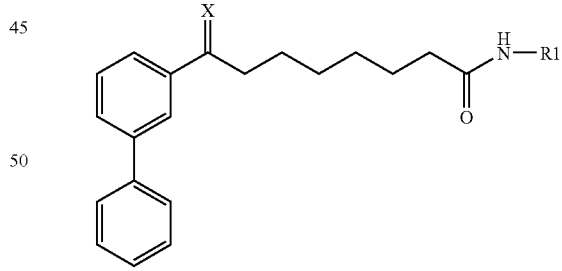

131: X = O, R$_1$ = OH (Example 75)

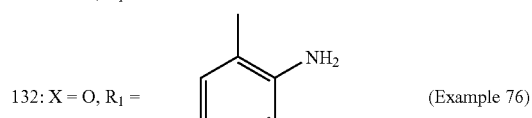

132: X = O, R$_1$ = (Example 76)

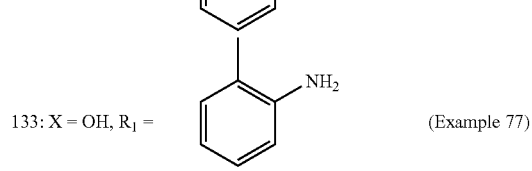

133: X = OH, R$_1$ = (Example 77)

134: X = NOH, R₁ = 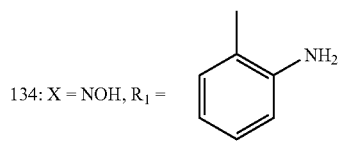 (Example 78)

135: X = NOCH₃, R₁ = 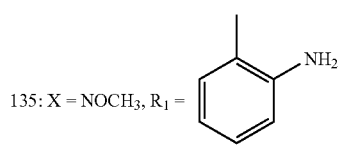 (Example 79)

Example 75

N-Hydroxy-7-[(3-biphenyl)carbonyl]heptanamide (131)

Following the procedure described in Example 18, step 1, 2, but substituting respectively 3-bromobenzoyl chloride for benzoyl chloride, the resulting ester was substituted for 49d in Example 67, step 1. Then, following the procedure described in Example 18, step 3, but substituting the final ester for ester 49a, the resulting acid was substituted in Example 14, step 3, using 1.1 equivalent of NH₂OH.HCl and triethylamine each, to afford the title compound 131 in 35% yield. ¹H NMR (300 MHz, CDCl₃): δ 8.13 (s, 1H), 7.88-7.30 (m, 8H), 2.96 (br t, 2H), 2.17 (m, 2H), 1.77-1.58 (m, 4H), 1.35 (m, 4H). ¹³C NMR (75 MHz, CDCl₃) δ623.93, 25.12, 28.71(2), 32.73, 38.48, 126.61, 126.88, 127.08, 127.72, 128.85, 128.99, 131.58, 137.30, 140.06, 141.57, 171.82, 200.75.

Example 76

N-(2-Aminophenyl)-7-[(3-biphenyl)carbonyl]heptanamide (132)

Following the procedure described in Example 18, step 1, 2, but substituting respectively 3-bromobenzoyl chloride for benzoyl chloride, the resulting ester was substituted for 49d in Example 67, step 1. Then, following the procedure described in Example 18, step 3, but substituting the final ester for ester 49a, the resulting acid was substituted for 50g in Example 22, to afford the title compound 132 in 58% yield. ¹H NMR (300 MHz, CDCl₃): δ 8.15 (s, 1H), 8.08 (s, 1H), 7.88-7.30 (m, 8H), 7.20-6.62 (m, 4H), 2.99 (t, J=7.2 Hz, 2H), 2.28 (t, J=7.5 Hz, 2H), 1.77-1.58 (m, 4H), 1.36 (m, 4H). ¹³C NMR (75 MHz, CDCl₃) δ23.85, 25.39, 28.71, 28.79, 36.30, 38.33, 117.49, 118.72, 124.00, 125.38, 126.38, 126.67, 126.74, 126.89, 127.56, 128.70, 128.84, 131.35, 137.21, 139.87, 140.90, 141.38, 172.14, 200.35.

Example 77

N-(2-Aminophenyl)-8-(3-biphenyl)-8-hydroxy-octanamide (133)

To a suspension of NaBH₄ (28.4 mg, 0.75 mmol) in THF (4 mL) at −20° C. was added a solution of ketone 132 (300 mg, 0.75 mmol) in THF (1 mL), followed by addition of methanol (1 mL). After being stirred at 0° C. for 2 hours, the reaction was quenched by adding water (1 mL). The solvent was removed under reduced pressure, and the resulting residue was then partitioned between ethyl acetate and water. After drying the combined organic phase (MgSO₄) and concentration, the crude was purified by flash chromatography using ethyl acetate as an eluent to give the title compound 133 (260 mg, 86% yield). ¹H NMR (300 MHz, CDCl₃): δ 7.62 (s, 1H), 7.62-7.30 (m, 8H), 7.20-6.66 (m, 4H), 4.70 (br t, 1H), 2.35 (t, J=7.2 Hz, 2H), 2.00-1.3 (m, 10H).

Example 78

N-(2-Aminophenyl)-8-(E)-oximino-8-(3-biphenyl) octanamide (E-134)

A mixture of 132 (100 mg, 0.25mmol) and NH₂OH.HCl (70 mg, 1.0 mmol) in pyridine (0.4 mL) was heated at 50° C. for 16 hours. The pyridine was then removed under reduced pressure and the resulting residue was partitioned between ethyl acetate and water. After drying the combined organic phase (MgSO₄) and concentration, the crude was purified by flash chromatography using ethyl acetate as an eluent to give the title compound 134 (81 mg, 78% yield) as a mixture of E and Z isomer in a ca 5:1 ratio. ¹H NMR for a major E isomer (300 MHz, CDCl₃): δ 9.25 (br s, 1H), 7.80 (m, 1H), 7.62-7.35 (m, 8H), 7.20-6.62 (m, 4H), 3.82 (br s, 2H), 2.85 (t, J=7.5 Hz, 2H), 2.30 (t, J=7.5 Hz, 2H), 1.68 (m, 2H), 1.59 (m, 2H), 1.39 (m, 4H).

Example 79

N-(2-Aminophenyl)-8-(E)-O-methyl-oximino-8-(3-biphenyl)octanamide (E-135)

Following the procedure described in Example 78, but substituting N-methoxylamine.HCl for N-hydroxylamine.HCl, the title compound 135 was obtained in 57% yield as a mixture of E and Z isomer in a ca 3:1 ratio. ¹H NMR for a major E isomer (300 MHz, CDCl₃): δ 7.84 (m, 1H), 7.62-7.31 (m, 8H), 7.22-6.75 (m, 4H), 3.99 (s, 3H), 3.80 (br s, 2H), 2.78 (t, J=7.5 Hz, 2H), 2.35 (t, J=7.5 Hz, 2H), 1.72 (m, 2H), 1.57 (m, 2H), 1.39 (m, 4H).

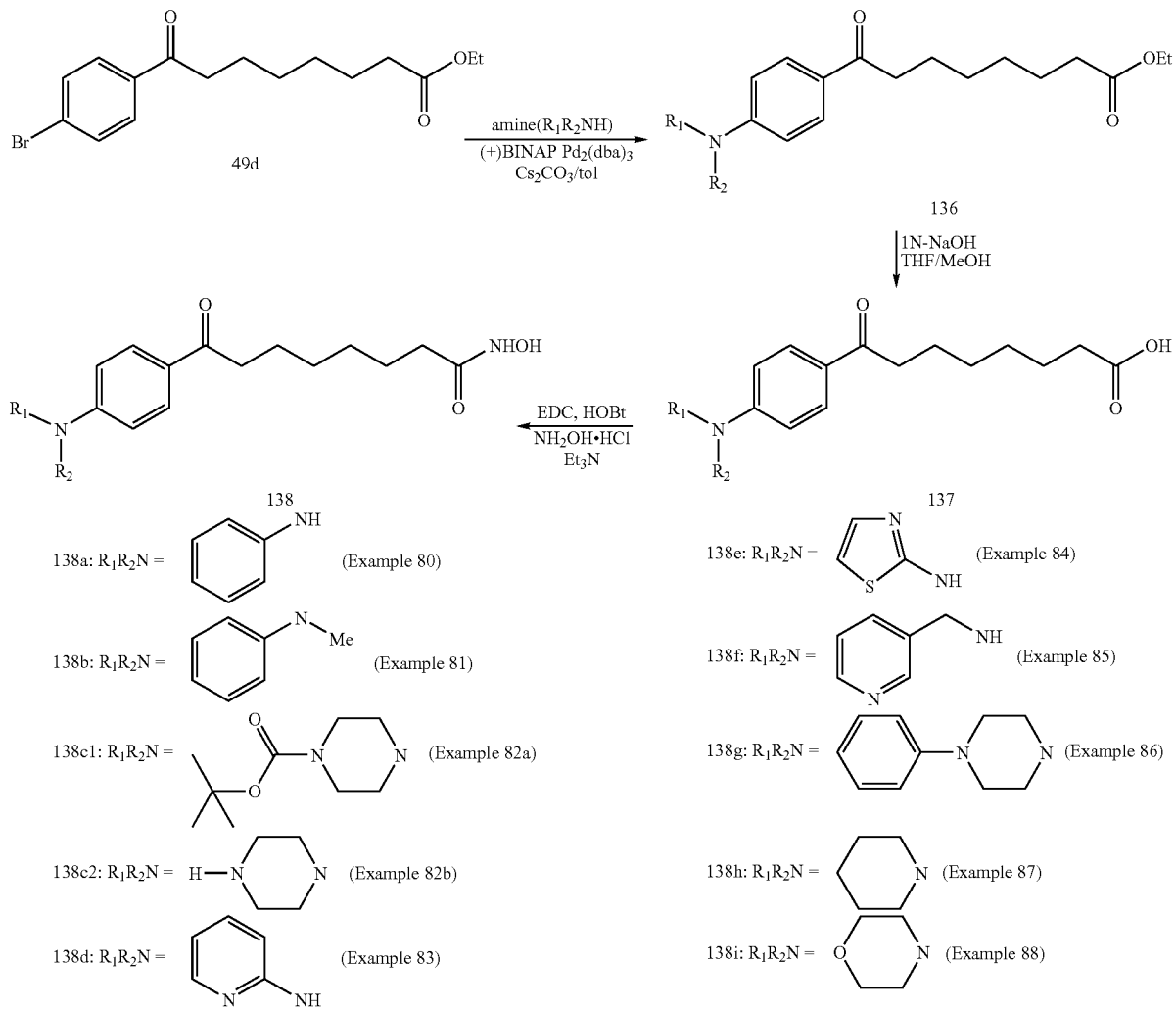

Example 80

N-Hydroxy-7-[4-(N-phenyl)benzoyl]heptanamide (138a)

Step 1: Ethyl-7-[4-(N-phenyl)benzoyl]heptanoate (136a)

To a mixture of bromoester 49d (171 mg, 0.5 mmol), $Pd_2(dba)_3$ (9.2 mg, 0.01 mmol), BINAP (12.4 mg, 0.032 mmol), and $Cs_2CO_3$ (228 mg, 0.7 mmol) dissolved in dry toluene (2 mL), was added aniline (56 mg, 0.6 mmol). The reaction mixture was degassed for 10 minutes by bubbling with nitrogen stream and then heated at 100° C. until TLC showed no starting material 49d (ca 20-30 hours). After cooling to room temperature, the reaction mixture was partitioned between ethyl acetate and water and then the combined organic layers were dried ($MgSO_4$), and concentrated.

Purification by flash chromatography using ethyl acetate and hexane as eluents gave the title compound 136a in 45% yield. $^1$H NMR (300 MHz, $CDCl_3$): δ 7.86 (d, J=9.0 Hz, 2H), 7.36-6.98 (m, 7H), 6.30 (s, 1H), 4.11 (q, J=7.2 Hz, 2H), 2.87 (t, J=7.5 Hz, 2H), 2.29 (t, J=7.5 Hz, 2H), 1.72 (m, 2H), 1.63 (m, 2H), 1.37 (m, 4H), 1.25 (t, J=7.2 Hz, 3H). $^{13}$C NMR (75 MHz, $CDCl_3$) δ 14.18, 24.53, 24.77, 28.92, 19.01, 34.24, 37.88, 60.12, 114.40, 120.48, 123.1, 128.65, 129.4 1, 130.26, 140.67, 148.20, 174.77, 198.63.

Step 2: 7-[4-(N-phenyl)benzoyl]heptanoic acid (137a)

Following the procedure described in Example 18, step 3, but substituting ester 136a for ester 49a, the title compound 137a was obtained in 95% yield. $^1$H NMR (300 MHz, $CDCl_3$): δ 7.85 (d, J=9.0 Hz, 2H), 7.36-7.17 (m, 4H), 7.05 (m, 1H), 7.00 (d, J=9.0 Hz, 2H), 3.95 (br s, 1H), 2.88 (t, J=7.5 Hz, 2H), 2.30 (t, J=7.5 Hz, 2H), 1.72-1.58 (m, 4H), 1.38 (m, 4H). $^{13}$C NMR (75 MHz, $CDCl_3$) δ 24.56, 24.58, 28.77, 28.90, 33.82, 33.80, 114.14, 120.29, 122.87, 128.01, 129.27, 130.30, 140.63, 148.52, 176.68, 199.47.

Step 3: N-(Hydroxy)-7-[4-(N-phenyl)benzoyl]heptanamide (138a)

Following the procedure described in Example 14, step 3, but substituting carboxylic acid 137a for 37, and using 1.1 equivalent of $NH_2OH\cdot HCl$ and triethylamine each, the title compound 138a was obtained in 43% yield. ¹H NMR (300 MHz, 20% CD₃OD in CDCl₃): δ 7.85 (d, J=8.7 Hz, 2H), 7.36-7.00 (m, 7H), 2.89 (t, J=7.2 Hz, 2H), 2.10 (t, J=7.5 Hz, 2H), 1.72-1.58 (m, 4H), 1.37 (m, 4H). ¹³C NMR (75 MHz, 20% CD₃OD in CDCl₃) δ 24.48, 25.03, 28.55, 28.62, 32.50, 37.62, 113.94, 120.22, 122.73, 127.54, 129.15, 130.28, 140.63, 148.86, 171.12, 199.83.

Example 81

N-Hydroxy-7-[4-(N-methyl-N-phenyl)benzoyl]heptanamide (138b)

Step 1:
Ethyl-7-[4-(N-methyl-N-phenyl)benzoyl]heptanoate (136b)

Following the procedure described in Example 80, step 1, but substituting N-methylaniline for aniline, the title compound 136b was obtained in 11% yield. ¹H NMR (300 MHz, CDCl₃): δ 7.81 (d, J=9.3 Hz, 2H), 7.39 (m, 2H), 7.21 (m, 3H), 6.74 (d, J=9.3 Hz, 2H), 4.11 (q, J=7.2 Hz, 2H), 3.36 (s, 3H), 2.85 (t, J=7.5 Hz, 2H), 2.28 (t, J=7.5 Hz, 2H), 1.74-1.56 (m, 4H), 1.36 (m, 4H), 1.24 (t, J=7.2 Hz, 3H). ¹³C NMR (75 MHz, CDCl₃) δ14.20, 24.63, 24.76, 28.92, 29.02, 34.23, 37.79, 40.11, 60.07, 113.50, 125.45, 125.94, 126.88, 129.75, 129.83, 147.23, 152.46, 173.70, 198.61.

Step 2: 7-[4-(-(N-methyl-N-phenyl)benzoyl]heptanoic acid (137b)

Following the procedure described in Example 18, step 3, but substituting ester 136b for ester 49a, the title compound 137b was obtained in 95% yield. ¹H NMR (300 MHz, CDCl₃): δ 7.81 (d, J=9.3 Hz, 2H), 7.40 (m, 2H), 7.21 (m, 3H), 6.75 (d, J=9.3 Hz, 2H), 3.37 (s, 3H), 2.86 (t, J=7.5 Hz, 2H), 2.34 (t, J=7.5 Hz, 2H), 1.78-1.56 (m, 4H), 1.38 (m, 4H). ¹³C NMR (75 MHz, CDCl₃) δ 24.47, 24.67, 28.83, 28.98, 33.92, 37.79, 40.13, 113.48, 125.51, 125.99, 126.77, 129.77, 129.92, 147.21, 152.53, 179.51, 198.92.

Step 3: N-Hydroxy-7-[4-(N-methyl-N-phenyl)benzoyl]heptanamide (138b)

Following the procedure described in Example 14, step 3, but substituting carboxylic acid 137b for 37, and using 1.1 equivalent of NH₂OH.HCl and triethylamine each, the title compound 138b was obtained in 37% yield. ¹H NMR (300 MHz, 20% CD₃OD in CDCl₃): δ 7.74 (d, J=9.0 Hz, 2H), 7.36 (m, 2H), 7.17 (m, 3H), 6.68 (d, J=9.0 Hz, 2H), 3.31 (s, 3H), 2.80 (t, J=7.2 Hz, 2H), 2.03 (t, J=7.2 Hz, 2H), 170-1.50 (m, 4H), 1.30 (m, 4H). ¹³C NMR (75 MHz, 20% CD₃OD in CDCl₃) δ 24.53, 25.01, 28.53, 28.60, 32.47, 37.57, 38.87, 113.10, 125.55, 125.96, 126.03, 129.62, 129.87, 146.85, 152.67, 171.14, 199.83.

Example 82a

N-Hydroxy-7-[4-(1-(4-tert-butyloxycarbonylpiperazinyl))benzoyl]heptanamide (138c1)

Step 1: Ethyl-7-[4-(1-(4-tert-butyloxycarbonylpiperazinyl))benzoyl]heptanoate (136c1)

Following the procedure described in Example 80, step 1, but substituting 1-butyloxycarbonylpiperazine for aniline, the title compound 136c1 was obtained in 14% yield. ¹H NMR (300 MHz, CDCl₃): δ 7.88 (d, J=9.0 Hz, 2H), 6.86 (d, J=9.0 Hz, 2H), 4.12 (q, J=7.2 Hz, 2H), 3.58(m, 4H), 3.32(m, 4H), 2.87(t, J=7.5 Hz, 2H), 2.28(t, J=7.5 Hz, 2H), 1.72 (m, 2H), 1.63 (m, 2H), 1.49 (s, 9H), 1.38 (m, 4H), 1.25 (t, J=7.2 Hz, 3H). ¹³C NMR (75 MHz, CDCl₃) δ 14.15, 24.48, 24.73, 28.31, 28.89, 28.97, 34.20, 37.85, 42.30, 47.30, 60.06, 80.03, 113.71, 127.74, 130.02, 153.77, 154.54, 173.68, 198.66.

Step 2: 7-[4-(1-(4-tert-butyloxycarbonylpiperazinyl))benzoyl]heptanoic acid (137c1)

Following the procedure described in Example 18, step 3, but substituting ester 136c1 for ester 49a, the title compound 137c1 was obtained in 93% yield. ¹H NMR (300 MHz, CDCl₃): δ 7.88 (d, J=9.0 Hz, 2H), 6.88 (d, J=9.0 Hz, 2H), 3.58 (m, 4H), 3.33 (m, 4H), 2.88 (t, J=7.5 Hz, 2H), 2.34 (t, J=7.5 Hz, 2H), 1.74-1.58 (m, 4H), 1.49 (s, 9H), 1.39 (m, 4H). ¹³C NMR (75 MHz, CDCl₃) δ 24.47, 28.30(2), 28.79, 28.92, 33.87, 37.81, 42.40, 47.24, 80.16, 113.69, 127.63, 130.06, 153.75, 154.61, 179.01, 198.86.

Step 3: N-Hydroxy-7-[4-(1-(4-tert-butyloxycarbonylpiperazinyl))benzoyl]-heptanamide (138c1)

Following the procedure described in Example 14, step 3, but substituting carboxylic acid 137c1 for 37, and using 1.1 equivalent of NH₂OH.HCl and triethylamine each, the title compound 138c1 was obtained in 46% yield. ¹H NMR (300 MHz, 20% CD₃OD in CDCl₃): δ 7.76 (d, J=9.0 Hz, 21H), 6.76 (d, J=9.0 Hz, 2H), 3.48 (m, 4H), 3.24 (m, 4H), 2.77 (t, J=6.9 Hz, 2H), 1.98 (t, J=7.2 Hz, 2H), 1.70-1.48 (m, 4H), 1.37 (s, 9H), 1.25 (m, 4H). ¹³C NMR (75 MHz, 20% CD₃OD in CDCl₃) δ 24.39, 25.03, 28.04, 28.56, 28.61, 32.50, 37.67, 42.93, 46.96, 80.35, 113.51, 127.11, 130.07, 153.81, 154.73, 171.06, 198.87.

Example 82b

N-Hydroxy-7-[4-(1-(piperazinyl1)benzoyl]heptanamide (138c2)

To a stirred solution of 138c1 (56 mg, 0.129 mmol) in dichloromethane(0.5 mL) at room temperature was added trifluoroacetic acid (0.2 mL, 2.6 mmol). After being stirred at room temperature for 30 minutes, the reaction mixture was concentrated under reduced pressure. The residue obtained was dissolved in water (2 mL), neutralized with saturated aqueous sodium bicarbonate solution (2 mL), extracted with ethyl acetate and then with 10% methanol in chloroform. The combined organic layers were dried and concentrated under reduced pressure to give the title compound 138c2 (20 mg, 46% yield). ¹H NMR (300 MHz, 20% CD₃OD in CDCl₃): 7.75 (d, J=8.4 Hz, 2H), 6.77 (d, J=8.4 Hz, 2H), 3.24 (m, 4H), 2.91 (m, 4H), 2.77 (t, J=7.2 Hz, 2H), 2.28 (t, J=6.6 Hz, 2H), 1.58 (m, 4H), 1.25 (m, 4H).

Example 83

N-Hydroxy-7-[4-(N-2-aminopyridyl)benzoyl]heptanamide (138d)

Step 1: Ethyl-7-[4-(N-2-aminopyridyl)benzoyl]heptanoate (136d)

Following the procedure described in Example 80, step 1, but substituting 2-aminopyridine for aniline, the title compound 136d was obtained in 40% yield. $^1$H NMR (300 MHz, CDCl$_3$): δ 8.28 (dd, J=8.1, 1.2 Hz, 1H), 7.93 (d, J=8.7 Hz, 2H), 7.57 (m, 1H), 7.48 (d, J=8.7 Hz, 2H), 7.17 (s, 1H), 6.93 (m, 1H), 6.84 (m, 1H), 5.39 (t, J5.7 Hz, 1H), 4.12 (q, J=7.2 Hz, 2H), 2.90 (t, J=7.5 Hz, 2H), 2.30 (t, J=7.5 Hz, 2H), 1.78-1.56 (m, 4H), 1.38 (m, 4H), 1.25 (t, J=7.2 Hz, 3H). $^{13}$C NMR (75 MHz, CDCl$_3$) δ14.21, 24.43, 24.78, 28.94, 29.00, 34.26, 38.04, 60.15, 110.40, 116.32, 117.19, 129.86, 130.27, 137.77, 145.24, 148.23, 154.45, 173.78, 198.92.

Step 2: 7-[4-(N-2-aminopyridyl)benzoyl]heptanoic acid (137d)

Following the procedure described in Example 18, step 3, but substituting ester 136d for ester 49a, the title compound 137d was obtained in 95% yield. $^1$H NMR (300 MHz, CDCl$_3$): δ 7.85 (d, J=9.0 Hz, 2H), 7.36-7.17 (m, 4H), 7.05 (m, 1H), 7.00 (d, J=9.0 Hz, 2H), 3.95 (br s, 1H), 2.88 (t, J=7.5 Hz, 2H), 2.30 (t, J=7.5 Hz, 2H), 1.72-1.58 (m, 4H), 1.38 (m, 4H). $^{13}$C NMR (75 MHz, CDCl$_3$) δ 24.56, 24.58, 28.77, 28.90, 33.82, 33.80, 114.14, 120.29, 122.87, 128.01, 129.27, 130.30, 140.63, 148.52, 176.68, 199.47.

Step 3: N-Hydroxy-7-[4-(N-2-aminopyridyl)benzoyl]heptanamide (138d)

Following the procedure described in Example 14, step 3, but substituting carboxylic acid 137d for 37, and using 1.1 equivalent of NH$_2$OH.HCl and triethylamine each, the title compound 138d was obtained in 11% yield. $^1$H NMR (300 MHz, DMSO-d$_6$): δ 8.61 (br s, 1H), 8.20 (m, 1H), 7.95-6.80 (m, 6H), 2.88 (t, J=7.5 Hz, 2H), 1.91 (t, J=7.5 Hz, 2H), 1.68-1.40 (m, 4H), 1.26 (m, 4H). $^{13}$C NMR (75 MHz, CDCl$_3$) 24.27, 25.16, 28.59(2), 32.37, 37.41, 111.96, 115.80, 116.62, 128.70, 129.54, 137.81, 146.344, 147.43, 155.16, 169.43, 198.48.

Example 84

N-Hydroxy-7-[4-(N-2-aminothiazolyl)benzoyl]heptanamide (138e)

Step 1: Ethyl-7-[4-(N-2-aminothiazolyl)benzoyl]heptanoate (136e)

Following the procedure described in Example 80, step 1, but substituting 2-aminothiazole for aniline, the title compound 136e was obtained in 76% yield. $^1$H NMR (300 MHz, CDCl$_3$): δ 10.05 (br s, 1H), 7.97 (d, J=8.7 Hz, 2H), 7.48 (d, J=8.7 Hz, 2H), 7.39 (d, J=3.6 Hz, 1H), 6.75 (d, J=3.6 Hz, 1H), 4.13 (q, J=7.2 Hz, 2H), 2.92 (t, J=7.5 Hz, 2H), 2.30 (t, J=7.5 Hz, 2H), 1.78-1.56 (m, 4H), 1.38 (m, 4H), 1.26 (t, J=7.2 Hz, 3H). $^{13}$C NMR (75 MHz, CDCl$_3$) δ 14.07, 24.24, 24.64, 28.79, 28.84, 34.12, 37.95, 60.08, 108.66, 115.90, 129.90, 130.35, 138.23, 144.74, 163,98, 173.75, 198.88.

Step 2: 7-[4-(N-2-aminothiazolyl)benzoyl]heptanoic acid (137e)

Following the procedure described in Example 18, step 3, but substituting ester 136e for ester 49a, the title compound 137e was obtained in 98% yield. $^1$H NMR (300 MHz, 20% CD$_3$OD in CDCl$_3$): δ 7.44 (d, J=9.0 Hz, 2H), 7.62 (d, J=9.0 Hz, 2H), 7.30 (d, J=3.6 Hz, 1H), 6.83 (d, J=3.6 Hz, 1H), 2.96 (t, J=7.5 Hz, 2H), 2.30 (t, 2H, 7.5 Hz, 2H), 1.73 (m, 2H), 1.64 (m, 2H), 1.41 (m, 4H). $^{13}$C NMR (75 MHz, 20% CD$_3$OD in CDCl$_3$): δ 23.86, 24.02, 28.21(2), 33.18, 37.23, 108.65, 115.35, 129.20(2), 137.81, 145.08, 163.90, 175.84, 199.74.

Step 3: N-Hydroxy-7-[4-(N-2-aminothiazolyl)benzoyl]heptanamide (138e)

Following the procedure described in Example 14, step 3, but substituting carboxylic acid 137e for 37, and using 1.1 equivalent of NH$_2$OH.HCl and triethylamine each, the title compound 138e was obtained in 28% yield. $^1$H NMR (300 MHz, 20% CD$_3$OD in CD$_3$OD): δ 7.88 (d, J=8.7 Hz, 2H), 7.63 (d, J=8.7 Hz, 2H), 7.25 (d, J=3.3 Hz, 1H), 6.71 (d, J=3.3 Hz, 1H), 2.87 (t, J=6.9 Hz, 2H), 2.04 (t, J=7.5 Hz, 2H), 1.72-1.50 (m, 4H), 1.31 (m, 4H). $^{13}$C NMR (75 MHz, 20% CD$_3$OD in CDCl$_3$) δ 24.24, 25.03, 28.58(2), 33.52, 37.83, 108.94, 115.92, 129.83, 138.21, 145.08, 171.10, 199.97.

Example 85

N-Hydroxy-7-[4(N-3-aminomethylpyridyl)benzoyl]heptanamide (138f)

Step 1: Ethyl-7-[4-(N-3-aminomethylpyridyl)benzoyl]heptanoate (136f)

Following the procedure described in Example 80, step 1, but substituting 3-aminomethylpyridine for aniline, the title compound 136f was obtained in 61% yield. $^1$H NMR (300 MHz, CDCl$_3$): δ 8.58 (br s, 1H), 8.50 (d, J=3.9 Hz, 1H), 7.00 (d, J=8.7 Hz, 2H), 7.65 (m, 1H), 7.24 (dd, J=7.5, 1.5 Hz, 1H), 6.58 (d, J=8.7 Hz, 2H), 5.39 (t, J=5.7 Hz, 1H), 4.42 (d, J=5.7 Hz, 2H), 4.12 (q, J=7.2 Hz, 2H), 2.82 (t, J=7.5 Hz, 2H), 2.28 (t, J=7.5 Hz, 2H), 1.74-1.56 (m, 4H), 1.35 (m, 4H), 1.24 (t, J=7.2 Hz, 3H). $^{13}$C NMR (75 MHz, CDCl$_3$) δ 14.01, 24.44, 24.58, 28.73, 28.83, 34.03, 37.54, 44.69, 59.92, 111.47, 123.37, 126.53, 130.24, 133.90, 134.74, 148.51, 148.68, 151.46, 173.56, 198.44.

Step 2: 7-[4-(N-3aminomethylpyridyl)benzoyl]heptanoic acid (137f)

Following the procedure described in Example 18, step 3, but substituting ester 136f for ester 49a, the title compound 137f was obtained in 83% yield. $^1$H NMR (300 MHz, 20% CD$_3$OD in CDCl$_3$): δ 8.52 (br s, 1H), 8.54 (d, J=3.9 Hz, 1H), 7.79 (d, J=9.0 Hz, 2H), 7.70-7.24 (m, 3H), 6.59 (d, J=9.0 Hz, 2H), 4.40 (s, 2H), 2.84 (t, J=7.5 Hz, 2H), 2.28 (t, J=7.5 Hz, 2H), 1.74-1.54 (m, 2H), 1.37 (m, 4H).

Step 3: N-Hydroxy-7-[4-(N-3-aminomethylpyridyl)benzoyl]heptanamide (138f)

Following the procedure described in Example 14, step 3, but substituting carboxylic acid 137f for 37, and using 1.1 equivalent of NH$_2$OH.HCl and triethylamine each, the title compound 138f was obtained in 46% yield. $^1$H NMR (300 MHz, 20% CD$_3$OD in CDCl$_3$): δ 8.46 (m, 1H), 8.38 (m, 1H), 7.71 (d, J=8.7 Hz, 2H), 6.66 (m, 1H), 7.25 (m, 1H), 6.51 (d, J=8.7 Hz, 2H), 4.38 (m, 2H), 2.76 (t, J=7.2 Hz, 2H), 2.00 (t, J=7.2 Hz, 2H), 1.66-1.44 (m, 4H), 1.26 (m, 4H). $^{13}$C NMR (75 MHz, 20% CD$_3$OD in CDCl$_3$) δ 24.55, 25.01, 28.52, 28.59, 32.48, 37.49, 44.33, 111.44, 123.78, 126.00, 130.47, 134.64, 135.49, 147.76, 147.90, 151.85, 171.07, 199.83.

Example 86

N-Hydroxy-7-[4-(1-(4-phenylpiperazinyl))benzoyl]heptanamide (138g)

Step 1: Ethyl-7-[4-(1-(4-phenylpiperazinyl))benzoyl]heptanoate (136g)

Following the procedure described in Example 80, step 1, but substituting 1-phenylpiperazine for aniline, the title compound 136g was obtained in 32% yield. $^1$H NMR (300 MHz, CDCl$_3$): δ 7.90 (d, J=9.0 Hz, 2H), 7.33-7.26 (m, 3H), 6.97 (m, 2H), 6.92 (d, J=9.0 Hz, 2H), 4.12 (q, J=7.2 Hz, 2H), 3.51 (m, 4H), 3.34 (m, 4H), 2.88 (t, J=7.5 Hz, 2H), 2.29 (t, J=7.5 Hz, 2H), 1.72 (m, 2H), 1.63 (m, 2H), 1.49 (s, 9), 1.38 (m, 4H), 1.25 (t, J=7.2 Hz, 3H). $^{13}$C NMR (75 MHz, CDCl$_3$) δ 14.23, 24.59, 24.82, 28.98, 29.07, 34.29, 37.93, 47.48, 49.06, 60.15, 113.62, 116.31, 120.27, 127.68, 129.22, 130.10, 150. 93, 153.89, 173.78, 198.78.

Step 2: 7-[4-(1-(4-phenylpiperazinyl))benzoyl]heptanoic acid (137g)

Following the procedure described in Example 18, step 3, but substituting ester 136g for ester 49a, the title compound 137g was obtained in 96% yield. $^1$H NMR (300 MHz, CDCl$_3$): δ 7.79 (d, J=9.0 Hz, 2H), 7.25-7.17 (m, 3H), 6.89-6.78 (m, 5H), 6.92 (d, J=9.0 Hz, 2H), 3.41 (m, 4H), 3.24 (m, 4H), 2.89 (t, J=7.5 Hz, 2H), 2.35 (t, J=7.5 Hz, 2H), 1.73 (m, 2H), 1.65 (m, 2H), 1.28 (m, 4H), $^{13}$C NMR (75 MHz, CDCl$_3$) δ 24.52, 24.57, 28.88, 29.02, 33.84, 37.90, 47.46, 49.10, 113.64, 116.37, 120.34, 127.64, 129.23, 130.14, 150.91, 153.91, 179.02, 198.88.

Step 3: N-Hydroxy-7-[4-(1-(4-phenylpiperazinyl))benzoyl]heptanamide (138g)

Following the procedure described in Example 14, step 3, but substituting carboxylic acid 137g for 37, and using 1.1 equivalent of NH$_2$OH.HCl and triethylamine each, the title compound 138g was obtained in 38% yield. $^1$H NMR (300 MHz, 20% CD$_3$OD in CDCl$_3$): δ 7.79 (d, J=8.7 Hz, 2H), 7.19 (m, 2H), 6.89-6.78 (m, 5H), 3.41 (m, 4H), 3.24 (m, 4H), 2.78 (t, J=7.5 Hz, 2H), 2.00 (t, J=7.5 Hz, 2H), 1.66-1.46 (m, 4H), 1.26 (m, 4H), $^{13}$C NMR (75 MHz, 20% CD$_3$OD in CDCl$_3$) δ 24.40, 25.03, 28.61(2), 32.48, 37.65, 47.06, 48.96, 113.35, 116.24, 120.22, 126.89, 128.98, 130.06, 150.65, 153.89, 171.11, 199.86.

Example 87

N-Hydroxy-7-[4-(1-piperidinyl)benzoyl]heptanamide (138h)

Step 1: Ethyl-7-[4-(1-piperidinyl)benzoyl]heptanoate (136h)

Following the procedure described in Example 80, step 1, but substituting 1-piperidine for aniline, the title compound 136h was obtained in 40% yield. $^1$H NMR (300 MHz, CDCl$_3$): δ 7.81 (d, J=9.0 Hz, 2H), 6.80 (d, J=9.0 Hz, 2H), 4.07 (q, J=7.2 Hz, 2H), 3.30 (m, 4H), 2.81 (t, J=7.5 Hz, 2H), 2.24 (t, J=7.5 Hz, 2H), 1.74-1.56 (m, 10H), 1.20 (m, 4H), 1.24 (t, J=7.2 Hz, 3H). $^{13}$C NMR (75 MHz, CDCl$_3$) δ 14.23, 24.3 24.28, 24.81, 25.32, 28.97, 29.07, 34.28, 37.79, 48.58, 60.11, 113.26, 126.40, 130.13, 154.29, 173.77, 198.63.

Step 2: 7-[4-(1-piperidinyl)benzoyl]heptanoic acid (137h)

Following the procedure described in Example 18, step 3, but substituting ester 136h for ester 49a, the title compound 137h was obtained in 98% yield. $^1$H NMR (300 MHz, CDCl$_3$): δ 7.84 (d, J=9.0 Hz, 2H), 6.84 (d, J=9.0 Hz, 2H), 3.35 (m, 4H), 2.86 (t, J=7.5 Hz, 2H), 2.35 (t, J=7.5 Hz, 2H), 1.74-1.56 (m, 10H), 1.20 (m, 4H). $^{13}$C NMR (75 MHz, CDCl$_3$) δ 24.25, 24.46, 24.65, 25.24, 28.81, 28.97, 33.92, 37.71, 48.53, 113.24, 126.25, 130.17, 154.27, 179.53, 198.87.

Step 3: N-Hydroxy-7-[4-(1-piperidinyl)benzoyl]heptanamide (138h)

Following the procedure described in Example 14, step 3, but substituting carboxylic acid 137h for 37, and using 1.1 equivalent of NH$_2$OH.HCl and triethylamine each, the title compound 138h was obtained in 45% yield. $^1$H NMR (300 MHz, 20% CD$_3$OD in CDCl$_3$): δ 7.71 (d, J=8.7 Hz, 2H), 6.73 (d, J=8.7 Hz, 2H), 3.23 (m, 4H), 2.74 (t, J=7.2 Hz, 2H), 1.98 (t, J=6.6 Hz, 2H), 1.54 (m, 10H), 1.24 (m, 4H). $^{13}$C NMR (75 MHz, 20% CD$_3$OD in CDCl$_3$) δ 24.00, 24.50 24.99(2), 28.49, 28.58, 32.43, 37.49, 48.23, 112.96, 125.55, 130.11, 154.25, 171.15, 199.72.

Example 88

N-Hydroxy-7-[4-(N-morpholinyl)benzoyl]heptanamide (138i)

Step 1: Ethyl-7-[4-(N-morpholinyl)benzoyl]heptanoate (136i)

Following the procedure described in Example 80, step 1, but substituting morpholine for aniline, the title compound 136i was obtained in 43% yield. $^1$H NMR (300 MHz, CDCl$_3$): δ 7.90 (d, J=9.0 Hz, 2H), 6.87 (d, J=9.0 Hz, 2H), 4.12 (q, J=7.2 Hz, 2H), 3.87 (m, 4H), 3.30 (m, 4H), 2.88 (t, J=7.5 Hz, 2H), 2.29 (t, J=7.5 Hz, 2H), 1.72 (m, 2H), 1.63 (m, 2H), 1.38 (m, 4H), 1.25 (t, J=7.2 Hz, 3H). $^{13}$C NMR (75 MHz, CDCl$_3$) δ 14.21, 24.52, 24.78, 28.94, 29.03, 34.25, 37.90, 47.53, 60.12, 113.29, 127.90, 130.01, 154.06, 173.74, 198.75.

Step 2: 7-[4-(N-morpholinyl)benzoyl]heptanoic acid (137i)

Following the procedure described in Example 18, step 3, but substituting ester 136i for ester 49a, the title compound 137i was obtained in 93% yield. $^1$H NMR (300 MHz, CDCl$_3$): δ 7.89 (d, J=9.0 Hz, 2H), 6.86 (d, J=9.0 Hz, 2H), 3.85 (m, 4H), 3.29 (m, 4H), 2.87 (t, J=7.5 Hz, 2H), 2.33 (t, J=7.5 Hz, 2H), 1.76-1.58 (m, 4H), 1.38 (m, 4H). $^{13}$C NMR (75 MHz, CDCl$_3$) δ 24.48, 24.51, 28.85, 28.98, 33.90, 37.88, 47.51, 66.51, 113.32, 127.86, 130.06, 154.09, 179.41, 198.92.

Step 3: N-Hydroxy-7-[4-(N-morpholinyl)benzoyl]heptanamide (138i)

Following the procedure described in Example 14, step 3, but substituting carboxylic acid 137i for 37, and using 1.1 equivalent of NH$_2$OH.HCl and triethylamine each, the title compound 138i was obtained in 34% yield. $^1$H NMR (300 MHz, 20% CD$_3$OD in CDCl$_3$): δ 7.89 (d, J=9.0 Hz, 2H), 6.86 (d, J=9.0 Hz, 2H), 3.87 (m, 4H), 3.33 (m, 4H), 2.90 (t, J=7.2 Hz, 2H), 2.11 (t, J=7.2 Hz, 2H), 1.76-1.58 (m, 4H), 1.37 (m, 4H). $^{13}$C NMR (75 MHz, 20% CD$_3$OD in CDCl$_3$) δ 24.34, 25.00, 28.53, 28.58, 32.46, 37.64, 47.15, 66.28, 113.08, 127.20, 129.97, 154.07, 171.13, 199.87.

To a stirred solution of 3-bromopyridine (1.58 g, 10 mmol) in anhydrous ethyl ether (100 mL) at −78° C. was added n-butyl lithium (1.6M in hexane, 7.5 mL) via a syringe, and the resulting solution was stirred at −78° C. for 10 minutes. Trimethyltin chloride (2.39 g, 12 mmol) was then added, and the mixture was stirred at −78° C. for 20 minutes, and then warmed to room temperature over 1 hour. The reaction mixture was diluted with hexanes (30 mL) and washed with water. The organic phase was dried and concentrated to give the crude product which was purified by vacuum distillation (125° C. at 15-20 mmHg) to give 3-trimethylstannyl pyridine (1.93 g, 80% yield).

ii) Stille Coupling

A mixture of 3-trimethylstannyl pyridine (from i) (1.89 g, 7.81 mmol) and methyl 8-chloro-8-oxooctanoate in benzene (20 mL) was heated overnight at reflux in the presence of PdCl$_2$(PPh$_3$)$_2$ (274 mg, 0.39 mmol). After cooling to room temperature, the reaction mixture was partitioned between ethyl acetate and water. The combined organic layers were dried, and concentrated. Purification by flash chromatography (ethyl acetate/hexane=1/1) gave the desired product 139a1 (1.15 g, 59% yield) as a light yellow solid. $^1$H NMR (300 MHz, CD$_3$OD): δ 9.16 (d, J=1.8 Hz, 1H), 8.77 (dd, J=4.8, 1.8 Hz, 1H), 8.23 (m, 1H), 7.43 (dd, J=7.8, 4.8 Hz, 1H), 3.67 (s, 3H), 2.99 (t, J=7.5 Hz, 2H), 2.32 (t, J=7.5 Hz, 2H), 1.77 (m, 2H), 1.65 (m, 2H), 1.41 (m, 4H). $^{13}$C NMR (75

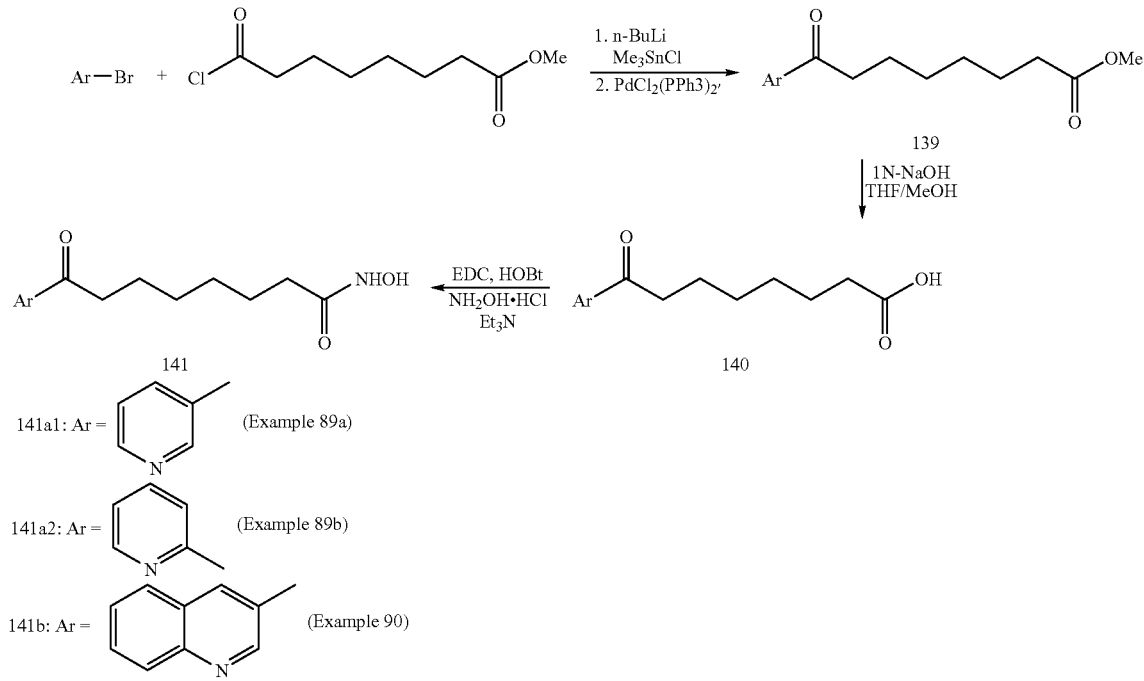

Example 89

N-Hydroxy-7-[(3-pyridyl)carbonyl]heptanamide (141a1)

Step 1: Methyl-7-[3-(pyridyl)carbonyl]heptanoate (139a1)

i) Preparation of Tin Compound

MHz, CDCl$_3$) δ 23.66, 24.66, 28.78, 28.84, 33.89, 38.67, 51.41, 123.58, 132.11, 135.27, 149.54, 153.31, 174.06, 198.96.

Step 2: 7-[3-(pyridyl)carbonyl]heptanoic acid (140a1)

Following the procedure described in Example 18, step 3, but substituting ester 139a1 for ester 49a, the title compound 140a1 was obtained in 98% yield. $^1$H NMR (300 MHz, 20%

CD$_3$OD in CD$_3$OD): δ 9.12 (d, J=1.8 Hz, 1H), 8.74 (dd, J=4.8, 1.8 Hz, 1H), 8.30 (m, 1H), 7.50 (dd, J=7.8, 4.8 Hz, 1H), 3.02 (t, J=7.5 Hz, 2H), 2.32 (t, J=7.5 Hz, 2H), 1.77 (m, 2H), 1.65 (m, 2H), 1.41 (m, 4H). $^{13}$C NMR (75 MHz, 20% CD$_3$OD in CD$_3$OD) δ 23.00, 24.01, 28.12, 28.18, 33.30, 38.09, 123.42, 131.81, 135.37, 148.39, 152.13, 175.80, 198.76.

Step 3:
N-Hydroxy-7-[3-(pyridyl)carbonyl]heptanamide (141a1)

Following the procedure described in Example 14, step 3, but substituting carboxylic acid 140a1 for 37, and using 1.1 equivalent of NH$_2$OH.HCl and triethylamine each, the title compound 141a1 was obtained in 26% yield. $^1$H NMR (300 MHz, 20% CD$_3$OD in CD$_3$OD): δ 9.12 (d, J=1.5 Hz, 1H), 8.74 (dd, J=4.8, 1.5 Hz, 1H), 8.30 (m, 1H), 7.50 (dd, J=7.8, 4.8 Hz, 1H), 3.02 (t, J=7.5 Hz, 2H), 2.12 (t, J=7.5 Hz, 2H), 1.75 (m, 2H), 1.65 (m, 2H), 1.40 (m, 4H). $^{13}$C NMR (75 MHz, 20% CD$_3$OD in CD$_3$OD) δ 23.39, 25.00, 28.44, 28.53, 32.48, 38.46, 123.86, 132.17, 135.80, 148.83, 152.61, 171.06, 199.31.

Example 89b

N-Hydroxy-7-[(2-pyridyl)carbonyl]heptanamide (141a2)

Step 3:
N-Hydroxy-7-[2-(pyridyl)carbonyl]heptanamide (141a2)

Following the procedure described in Example 90, step 1, but substituting 2-bromopyridine for 3-bromopyridine and without addition of palladium (0) catalyst, followed by Example 18, step 3, but substituting ester 139a2 for ester 49a, and then the resulting carboxylic acid was substituted for 37 in Example 14, step 3, using 1.1 equivalent of NH$_2$OH.HCl and triethylamine each, to afford the title compound 141a2 was obtained in 5% yield. $^1$H NMR (300 MHz, 20% CD$_3$OD in CDCl$_3$): δ 8.67 (m, 1H), 8.03 (dt, J=7.8, 1.2 Hz, 1H), 7.90 (m, 1H), 7.53 (m, 1H), 3.21 (t, J=7.5 Hz, 2H), 2.10 (t, J=7.2 Hz, 2H), 1.73 (m, 2H), 1.65 (m, 2H), 1.40 (m, 4H). $^{13}$C NMR (75 MHz, 20% CD$_3$OD in CDCl$_3$) δ 23.45, 25.07, 28.53, 28.58, 32.55, 37.40, 121.77, 127.12, 137.05, 148.65, 152.97, 171.19, 202.24.

Example 90

N-Hydroxy-7-[(3-quinolinyl)carbonyl]heptanamide (141b)

Step 1:
Methyl-7-[3-(quinolinyl)carbonyl]heptanoate (139b)

Following the procedure described in Example 90, step 1, but substituting 3-bromoquinoline for 3-bromopyridine, the title compound 140b was obtained in 90% yield $^1$H NMR (300 MHz CDCl$_3$): δ 9.43 (d, J=2.1 Hz, 1H), 8.71 (d, J=2.1 Hz, 1H), 8.16 (m, 1H), 7.97 (m, 1H), 8.84 (m, 1H), 7.63 (m, 1H), 4.13 (q, J=7.2 Hz, 2H), 3.10 (t, J=7.5 Hz, 2H), 2.31 (t, 7.5 Hz, 2H), 1.81 (m, 2H), 1.66 (m, 2H), 1.43 (m, 4H), 1.25 (t, J=7.2 Hz, 3H). $^{13}$C NMR (75 MHz, CDCl$_3$): δ 14.15, 23.77, 24.66, 28.82(2), 34.13, 38.68, 60.09, 126.78, 127.44, 129.03, 129.25, 131.82, 136.87, 148.97, 149.55, 173.59, 198.90.

Step 2: 7-[3-(quinolinyl)carbonyl]heptanoic acid (140b)

Following the procedure described in Example 18, step 3, but substituting ester 139b for ester 49a, the title compound 140b was obtained in 93% yield. $^1$H NMR (300 MHz, 20% CD$_3$OD in CDCl$_3$): δ 9.25 (d, J=2.1 Hz, 1H), 8.67 (d, J=1.8 Hz, 2H), 8.01 (d, J=8.1 Hz, 1H), 7.89 (m, 1H), 7.76 (m, 1H), 7.56 (m, 1H), 3.01 (t, J=7.5 Hz, 2H), 2.20 (t, J=7.2 Hz, 2H), 1.70 (m, 2H), 1.54 (m, 2H), 1.33 (m, 4H). $^{13}$C NMR (75 MHz, 20% CD$_3$OD in CDCl$_3$) δ 23.60, 24.46, 28.62(2), 33.74, 38.55, 126.82, 127.65, 128.36, 128.99, 129.29, 132.19, 137.47, 148.58, 148.91, 176.22, 199.23.

Step 3:
N-Hydroxy-7-[3-(quinolinyl)carbonyl]heptanamide (141b)

Following the procedure described in Example 14, step 3, but substituting carboxylic acid 140b for 37, and using 1.1 equivalent of NH$_2$OH.HCl and triethylamine each, the title compound 141b was obtained in 43% yield. $^1$H NMR (300 MHz, DMSO-d$_6$): δ 9.32 (d, J=2.1 Hz, 1H), 9.06 (d, J=1.8 Hz, 1H), 8.20 (d, J=7.2 Hz, 1H), 8.09 (d, J=8.7 Hz, 1H), 7.91 (m, 1H), 7.72 (m, 1H), 3.19 (t, J=7.2 Hz, 2H), 1.95 (t, J=7.5 Hz, 2H), 1.67 (m, 2H), 1.50 (m, 2H), 1.33 (m, 4H).

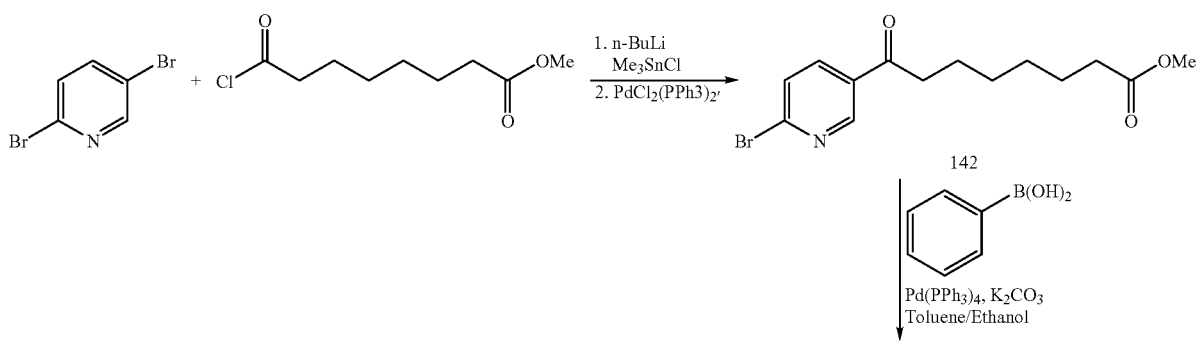

-continued

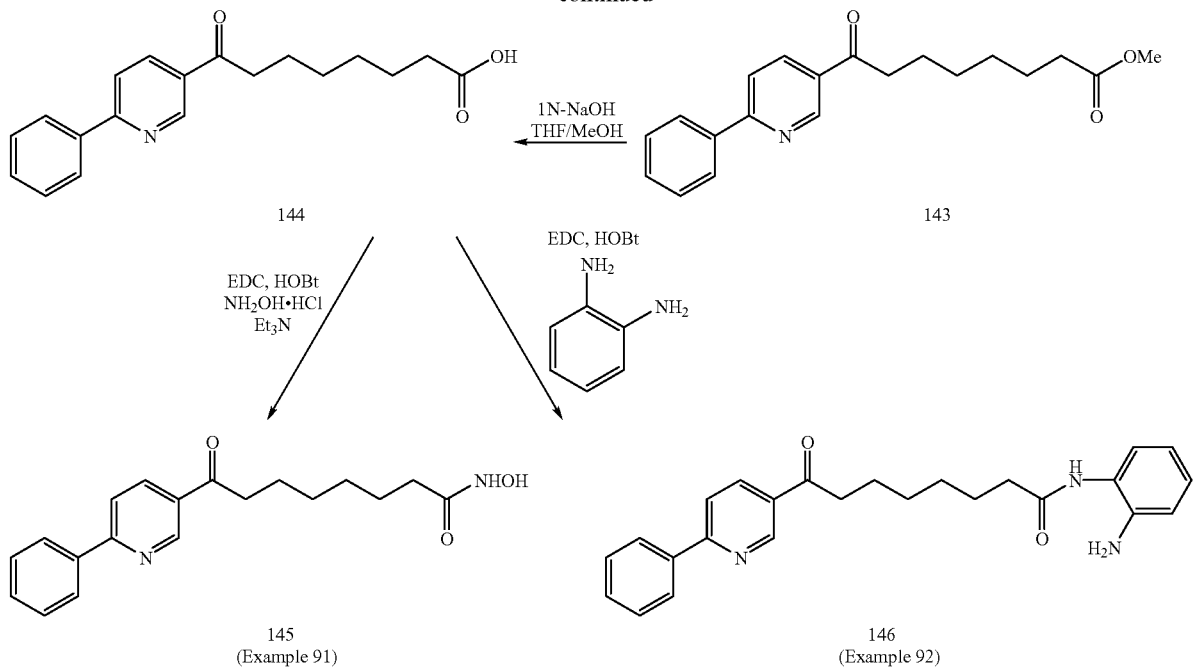

144

145
(Example 91)

143

146
(Example 92)

Example 91

N-Hydroxy-7-[(5-(2-phenyl)pyridyl)carbonyl]heptanamide (145)

Step 1: Methyl-7-[(5-(2-bromo)pyridyl)carbonyl]heptanoate (142)

Following the procedure described in Example 89, step 1, but substituting 2,3-dibromopyridine for 3-bromopyridine, the title compound 142 was obtained in 39% yield. $^1$H NMR (300 MHz, CDCl$_3$): δ 8.85 (d, J=1.8 Hz, 1H), 8.77 (dd, J=8.1, 2.4 Hz, 1H), 7.43 (d, J=8.1 Hz, 1H), 3.63 (s, 3H), 2.91 (t, J=7.5 Hz, 2H), 2.28 (t, J=7.5 Hz, 2H), 1.71 (m, 2H), 1.60 (m, 4H), 1.35 (m, 4H).

Step 2: Methyl-7-[(5-(2-phenyl)pyridyl)carbonyl]heptanoate (143)

Following the procedure described in Example 67, step 1, but substituting respectively 142 for 49d and phenyl boronic acid for 3-thiophene boronic acid, the title compound 143 was obtained in 88% yield. $^1$H NMR (300 MHz, CDCl$_3$): δ 9.23 (dd, J=2.4, 0.9 Hz, 1H), 8.30 (dd, J=8.7, 2.4 Hz, 1H), 8.09-8.05 (m, 2H), 7.84 (dd, J=8.7, 0.9 Hz, 1H), 7.56-7.40 (m, 3H), 3.67 (s, 3H), 3.00 (t, J=7.5 Hz, 2H), 2.32 (t, J=7.5 Hz, 2H), 1.78 (m, 2H), 1.65 (m, 2H), 1.41 (m, 4H). $^{13}$C NMR (75 MHz, CDCl$_3$): δ 23.89, 24.73, 28.89, 28.93, 33.97, 38.74, 51.47, 120.24, 127.35, 128.93, 130.08, 130.45, 136.42, 138.01, 149.61, 160.66, 174.13, 198.72.

Step 3: 7-[(5-(2-Phenyl)pyridyl)carbonyl]heptanoic acid (144)

Following the procedure described in Example 18, step 3, but substituting ester 143 for ester 49a, the title compound 144 was obtained in 90% yield. $^1$H NMR (300 MHz, 20% CD$_3$OD in CDCl$_3$): δ 9.08 (d, J=1.8 Hz, 1H), 8.20 (dd, J=8.7, 1.8 Hz, 1H), 7.90 (m, 2H), 7.74(d, J=8.7 Hz, 1H), 7.42-7.36 (m, 3H), 2.92 (t, J=7.2 Hz, 2H), 2.17 (t, J=7.5 Hz, 2H), 1.67 (m, 2H), 1.54 (m, 2H), 1.31 (m, 4H). $^{13}$C NMR (75 MHz, 20% CD$_3$OD in CDCl$_3$) δ 23.66, 24.68, 28.65, 28.72, 34.31, 38.54, 120.54, 127.17, 128.73, 129.91, 130.31, 136.45, 137.79, 149.32, 160.82, 177.18, 199.18.

Step 4: N-Hydroxy-7-[(5-(2-phenyl)pyridyl)carbonyl]heptanamide (145)

Following the procedure described in Example 14, step 3, but substituting carboxylic acid 144 for 37, and using 1.1 equivalent of NH$_2$OH.HCl and triethylamine each, the title compound 145 was obtained in 33% yield. $^1$H NMR (300 MHz, 20% CD$_3$OD in CDCl$_3$): δ 9.08 (d, J=1.5 Hz, 1H), 8.20 (d, J=8.4, 1.5 Hz, 1H), 7.91-6.87 (m, 2H), 7.75 (d, J=8.4 Hz, 1H), 7.46-7.35 (m, 3H), 2.91 (t, J=7.5 Hz, 2H), 2.00 (br t, 2H), 1.66 (m, 2H), 1.54 (m, 2H), 1.30 (m, 4H). $^{13}$C NMR (75 MHz, 20% CD$_3$OD in CDCl$_3$): δ 23.60, 25.02, 28.50, 28.56, 32.51, 38.47, 120.55, 127.16, 128.74, 129.93, 130.27, 136.45, 137.76, 149.31, 160.85, 171.05, 199.27.

Example 92

N-(2-Aminophenyl)-7-[(5-(2-phenyl)pyridyl)carbonyl]heptanamide (146)

Following the procedure described in Example 22, but substituting carboxylic acid 144 for 50g, the title compound 146 was obtained in 42% yield. $^1$H NMR (300 MHz, 20% CD$_3$OD in CDCl$_3$): δ 9.08 (dd, J=2.1, 0.6 Hz, 1H), 8.21 (dd, J=8.1, 2.1 Hz, 1H), 7.92-7.87 (m, 2H), 7.75 (dd, J=8.1, 0.6 Hz, 1H), 7.46-7.35 (m, 3H), 7.03-6.91 (m, 2H), 6.72-6.64 (m, 2H), 2.94 (t, J=7.5 Hz, 2H), 2.31 (t, J=7.5 Hz, 2H), 1.74-1.58 (m, 4H), 1.36 (m, 4H). $^{13}$C NMR (75 MHz, 20%

CD$_3$OD in CDCl$_3$): δ 23.63, 25.40, 28.61, 28.74, 36.14, 38.51, 117.84, 119.27, 120.55, 124.14, 125.35, 126.96, 127.18, 128.75, 129.93, 130.30, 136.46, 137.80, 140.58, 149.33, 160.87, 172.81, 199.30.

Hz, 1H), 7.77 (dd, J=8.4, 5.4 Hz, 1H), 7.60 (d, J=2.1 Hz, 1H), 7.53 (dd, J=8.4, 0.9 Hz, 1H), 7.73 (dd, J=8.4, 2.1 Hz, 1H), 6.89 (d, J=8.4 Hz, 1H), 3.95 (s, 3H), 3.90 (s, 3H). $^{13}$C

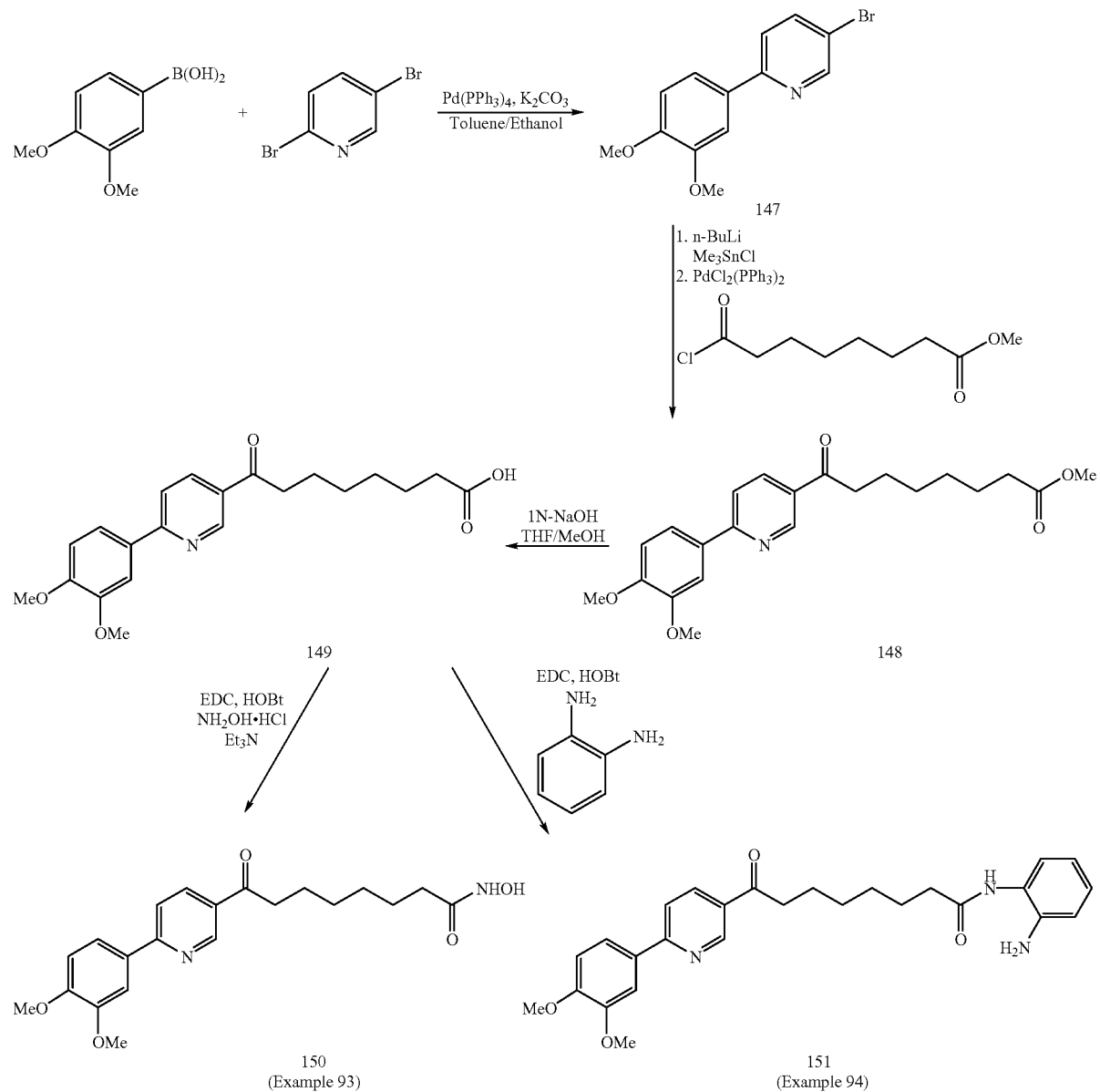

150
(Example 93)

151
(Example 94)

Example 93

N-Hydroxy-7-[5-(2-(3,4-dimethoxyphenyl)pyridyl)carbonyl]heptanamide (150)

Step 1: 2-(3,4-dimethoxyphenyl)-5-bromopyridine (147)

Following the procedure described in Example 67, step 1, but substituting respectively 2,5-dibromopyridine for 49d and 3,4-dimethoxyphenyl boronic acid for 3-thiophene boronic acid, the title compound 147 was obtained in 78% Yield. $^1$H NMR (300 MHz, CDCl$_3$): δ 8.65 (dd, J=2.4, 0.9

NMR (75 MHz, CDCl$_3$): δ 55.92, 55.93, 109.64, 111.01, 118.46, 119.25, 120.92, 131.05, 139.09, 149.28, 150.21, 150.3 6, 155.40.

Step 2: Methyl-7-[5-(2-(3,4-dimethoxyphenyl)pyridyl)carbonyl]heptanoate (148)

Following the procedure described in Example 89, step 1, but substituting 2-(3,4-dimethoxyphenyl)-5-bromopyridine for 3-bromopyridine, the title compound 148 was obtained in 78% yield. $^1$H NMR (300 MHz, CDCl$_3$): δ 9.12 (δ, J=2.1 Hz, H), 8.17 (dd, J=8.4, 2.1 Hz, 1H), 7.74 (d, J=8.4 Hz, 1H), 7.69 (d, J=1.8 Hz, 1H), 7.54 (dd, J=8.4, 1.8 Hz, 1H), 6.91 (d, J=8.4 Hz, 1H), 3.95 (s, 3H), 3.89 (s, 3H), 3.61 (s, 3H), 2.93 (t, J=7.2 Hz, 2H), 2.27 (t, J=7.5 Hz, 2H), 1.71 (m, 2H), 1.60 (m, 2H), 1.35 (m, 4H). $^{13}$C NMR (75 MHz, CDCl$_3$): δ 23.90, 24.68, 28.86, 28.88, 33.91, 38.61, 51.42, 55.92, 55.93, 110.03, 110.96, 119.30, 120.08, 129.78, 130.91, 136.08, 149.30, 149.61, 150.83, 160.16, 174.08, 198.70.

Step 3: 7-[5-(2-(3,4-dimethoxyphenyl)pyridyl)carbonyl]heptanoic acid (149)

Following the procedure described in Example 18, step 3, but substituting ester 148 for ester 49a, the title compound 149 was obtained in 89% yield. $^1$H NMR (300 MHz, CDCl$_3$): δ 9.20 (d, J=1.8 Hz, 1H), 8.25 (dd, J=8.1, 1.8 Hz, 1H), 7.78 (d, J=8.1 Hz, 1H), 7.71 (d, J=1.8 Hz, 1H), 7.57 (dd, J=8.1, 1.8 Hz, 1H), 6.96 (d, J=8.1 Hz, 1H), 4.00 (s, 3H), 3.95 (s, 3H), 2.99 (t, J=7.2 Hz, 2H), 2.36 (t, J=7.5 Hz, 2H), 1.77 (m, 2H), 1.66 (m, 2H), 1.41 (m, 4H). $^{13}$C NMR (75 MHz, CDCl$_3$): δ 23.84, 24.46, 28.80, 28.81, 33.89, 38.60, 55.95, 55.96, 110.19, 110.04, 119.65, 120.24, 129.91, 130.72, 136.33, 149.34, 149.47, 150.91, 160.19, 179.04, 198.64.

Step 4: N-Hydroxy-7-[5-(2-(3,4-dimethoxyphenyl)pyridyl)carbonyl]heptanamide (150)

Following the procedure described in Example 14, step 3, but substituting carboxylic acid 149 for 37, and using 1.1 equivalent of NH$_2$OH.HCl and triethylamine each, the title compound 150 was obtained in 32% yield. $^1$H NMR (300 MHz, 20% CD$_3$OD in CDCl$_3$): δ 9.20 (br s, 1H), 8.25 (d, J=8.1 Hz, 1H), 7.81 (d, J=8.1 Hz, 1H), 7.63 (br s, 1H), 7.54 (d, J=8.1 Hz, 1H), 6.98 (d, J=8.1 Hz, 1H), 3.95 (s, 3H), 3.91 (s, 3H), 2.98 (t, J=7.2 Hz, 2H), 2.06 (t, J=7.2 Hz, 2H), 1.72 (m, 2H), 1.61 (m, 2H), 1.37 (m, 4H).

Example 94

N-(2-Aminophenyl)-7-[5-(2-(3,4-dimethoxyphenyl)pyridyl)carbonyl]heptanamide (151)

Following the procedure described in Example 22, but substituting carboxylic acid 149 for 50g, the title compound 151 was obtained in 32% Yield. $^1$H NMR (300 MHz, CDCl$_3$): δ 9.18(d, J=1.8 Hz, 1H), 8.23 (dd, J=8.4, 2.1 Hz, 1H), 7.77 (d, J=8.4, 0.9 Hz, 1H), 7.73 (d, J=2.1 Hz, 1H), 7.59 (dd, J=8.4, 2.1 Hz, 1H), 7.35 (br s, 1H), 7.15 (m, 1H), 7.04 (m, 1H), 6.96 (d, J=8.4 Hz, 1H), 6.78 (m, 2H), 4.00 (s, 3H), 3.95 (s, 3H), 2.99 (t, J=7.2 Hz, 2H), 2.39 (t, J=7.5 Hz, 2H), 1.72 (m, 4H), 1.44 (m, 4H). $^{13}$C NMR (75 MHz, CDCl$_3$): δ 23.71, 25.38, 28.69, 28.81, 36.39, 38.42, 55.78, 55.79, 109.94, 110.88, 117.68, 118.92, 119.16, 120.01, 124.08, 125.27, 126.83, 129.58, 130.70, 135.96, 140.86, 149.13, 149.43, 150.69, 159.98, 171.95, 198.75.

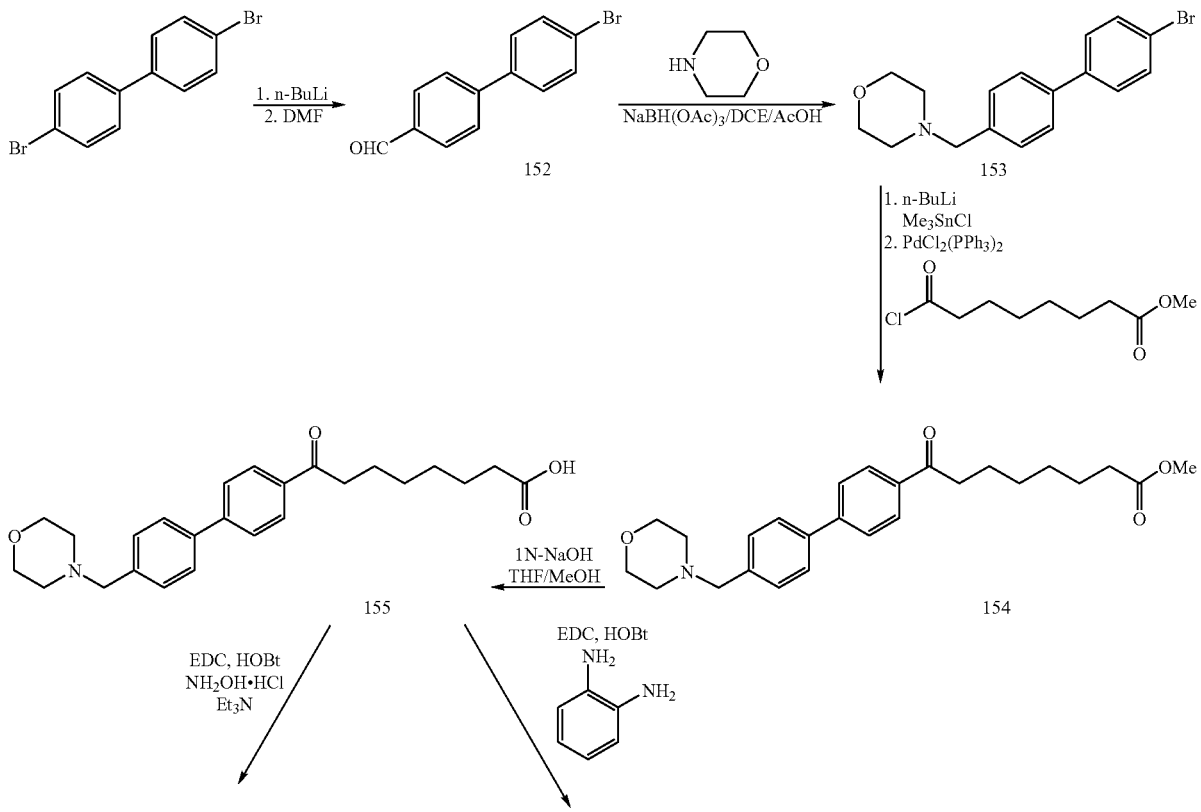

-continued

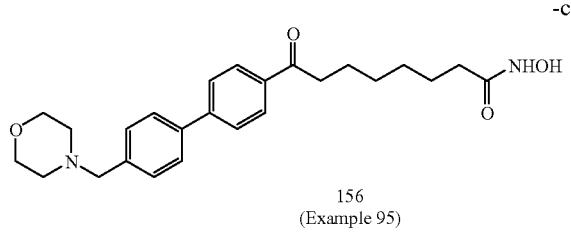

156
(Example 95)

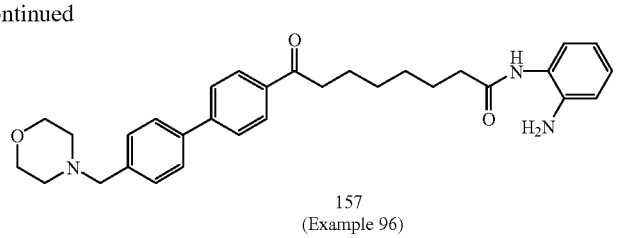

157
(Example 96)

Example 95

N-Hydroxy-7-[4-(4-(N-methylmorpholinyl)phenyl)benzoyl]heptanamide (156)

Step 1: 4-(4-bromophenyl)benzaldehyde (152)

To a solution of 4',4-dibromobiphenyl (3.12 g, 10 mmol) in dry THF (50 mL) at −78° C. was added dropwise a solution of n-BuLi (1.6M in hexane, 10 mmol). After addition, the mixture was stirred for 30 minutes at −78° C. Anhydrous DMF (50 mL) was then added and the mixture was allowed to stir at room temperature for 2 hours. The solvent was removed under high vacuum and the residue was taken in water and extracted with dichloromethane (2×50 mL). The combined organic layer were dried (MgSO$_4$) and concentrated. Purification by flash chromatography (ethyl acetate/hexane: 2/8) gave the title compound 152 55% yield. MS (ESI)=261 (MH$^+$).

Step 2: (4-(N-methylmorpholinyl)phenyl)-4-bromophenyl (153)

To a solution of aldehyde 152 (2.6 g, 10 mmol) in 1,2-dichloroethane (20 mL), morpholine (0.737 g, 10.1 mmol) was added followed by sodium triacetoxyborohydride (2.2 g, 10.4 mmol) and then few drops of acetic acid. The mixture was stirred at room temperature for 4 hours and then quenched by addition of a saturated solution of sodium bicarbonate. The mixture was extracted with ethyl acetate, dried (MgSO$_4$) and concentrated. Purification by flash chromatography (ethyl acetate/hexane: 2/8) gave the title compound 153 (1.75 g, 55% yield). MS (ESI)=333 (MH$^+$)

Step 3: Ethyl-7-[4-(4-(N-methylmorpholinyl)phenyl)benzoyl]heptanoate (154)

Following the procedure described in Example 89, step 1, but substituting 153 for 3-bromopyridine, the title compound 154 was obtained in 40% yield.
MS (ESI)=424 (MH$^+$)

Step 4: 7-[4-(4-(N-methylmorpholinyl)phenyl)benzoyl]heptanoic acid (155)

Following the procedure described in Example 18, step 3, but substituting ester 154 for ester 49a, the title compound 155 was obtained in 95% yield.
MS (ESI)=410 (MH$^+$)

Step 5: N-Hydroxy-7-[4-(4-(N-methylmorpholinyl)phenyl)benzoyl]heptanamide (156)

Following the procedure described in Example 14, step 3, but substituting carboxylic acid 155 for 37, and using 1.1 equivalent of NH$_2$OH.HCl and triethylamine each, the title compound 156 was obtained in 20% yield. $^1$H NMR: (300 MHz, CDCl$_3$) δ 8.00 (m, 2H), 7.40-7.60 (m, 10H), 3.80 (m, 4H), 3.60 (s, 2H), 3.00 (m, 2H), 2.70 (m, 4H), 2.35 (m, 2H), 1.60 (m, 4H), 1.20 (m, 4H).

Example 96

N-(2-Aminophenyl)-7-[4-(4-(N-methylmorpholinyl)phenyl)benzoyl]heptanamide (157)

Following the procedure described in Example 22, but substituting carboxylic acid 155 for 50g, the title compound 157 was obtained in 35% yield. $^1$H NMR: (300 MHz, CDCl$_3$) δ 8.00 (m, 2H), 7.40-7.60 (m, 6H), 3.80 (m, 4H), 3.60 (s, 2H), 3.00 (m, 2H), 2.70 (m, 4H), 2.35 (m, 2H), 1.60 (m, 4H), 1.20 (m, 4H).

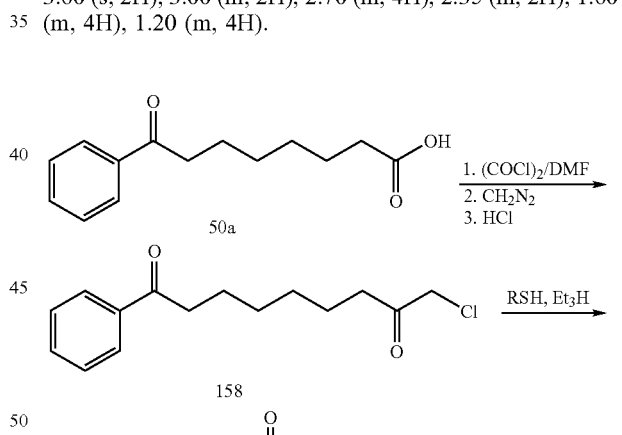

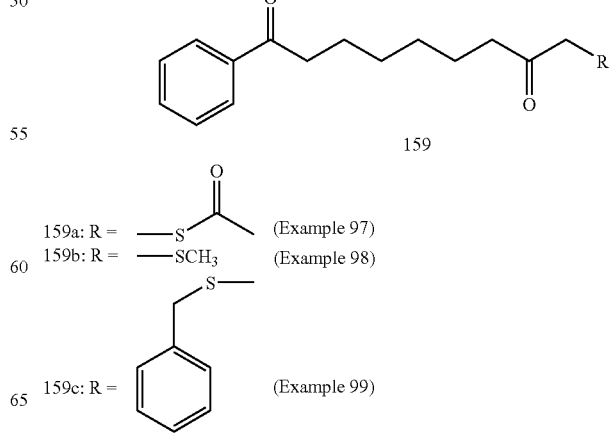

-continued

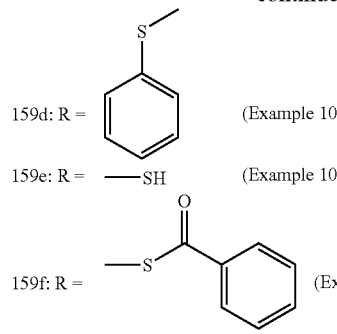

159d: R = [S-methyl-phenyl] (Example 100)

159e: R = —SH (Example 101)

159f: R = [S-C(=O)-phenyl] (Example 102)

Example 97

1-Acetylthio-2,9-dioxo-9-phenyl-nonane (159a)

Step 1: 1-chloro-2,9-dioxo-9-phenyl-nonane (158a)

To a solution of the carboxylic acid 50a (5 g, 0.02 mmol) in anhydrous dichloromethane (20 mL) under nitrogen was added dropwise, an excess of oxalyl chloride (5 mL, 0.06 mmol) neat followed by few drops of anhydrous DMF. The mixture was stirred at room temperature overnight. The solvent was evaporated and the residue was dried under high vacuum. The acid chloride was then taken in dry ether (20 mL) and to which was added a freshly prepared solution of diazomethane in ether. After addition the mixture was stirred at room temperature for four hours. The solvent was evaporated and the residue was treated with a solution of 4N HCl in dioxane (50 mL) at room temperature. After 4 hours the dioxane was evaporated and the residue was taken in water and extracted with dichloromethane to give a residue which was chromatographed on silica gel to obtain the desired product 158a (4 g, 75% yield). MS (ESI)=267 (MH$^+$)

Step 2: 1-Acetylthio-2,9-dioxo-9-phenyl-nonane (159a)

To a solution of the chloro ketone 158a (300 mg, 1 mmol) in anhydrous dichloromethane (25 mL) was added at 0-5° C. a solution of the thiolacetic acid (92 mg, 1.2 mmol) in dichloromethane. The mixture was allowed to stir at room temperature for 18 hours. The mixture was then extracted from dichloromethane to give a residue, which was chromatographed on silica gel to obtain the desired product 159a (103 mg, 50% yield). $^1$H NMR: (300 MHz, CDCl$_3$) δ 8.00 (m, 2H), 7.60-7.40 (m, 3H), 3.80 (s, 2H), 3.00 (m, 2H), 2.60 (m, 2H), 2.40 (s, 3H), 1.60 (m, 4H), 1.20 (m, 4H).

Example 98

1-Methylthio-2,9-dioxo-9-phenyl-nonane (159b)

Following the procedure described in Example 97, step 1, 2, but substituting methanethiol for thiolacetic acid, the title compound 159b was obtained in 60% yield. $^1$H NMR: (300 MHz, CDCl$_3$) δ 8.00 (m, 2H), 7.40-7.60 (m, 3H), 3.20 (s, 2H), 300 (m, 2H), 2.60 (m, 2H), 2.10 (s, 3H), 1.60 (m, 4H), 1.20 (m, 4H).

Example 99

1-Benzylthio-2,9-dioxo-9-phenyl-nonane (159c)

Following the procedure described in Example 97, step 1, 2, but substituting benzylthiol for thiolacetic acid, the title compound 159c was obtained in 35% yield. $^1$H NMR: (300 MHz, CDCl$_3$) δ 8.00 (m, 2H), 7.40-7.60 (m, 3H), 3.60 (s, 2H), 3.10 (s, 2H), 3.00 (m, 2H), 2.60 (m, 2H), 1.60 (m, 4H), 1.20 (m, 4H).

Example 100

1-Phenylthio-2,9-dioxo-9-phenyl-nonane (159d)

Following the procedure described in Example 97, step 1, 2, but substituting phenylthiol for thiolacetic acid, the title compound 159d was obtained in 50% yield. $^1$H NMR: (300 MHz, CDCl$_3$) δ 8.00 (m, 2H), 7.20-7.60 (m, 8H), 3.60 (s, 2H), 3.00 (m, 2H), 2.60 (m, 2H), 1.60 (m, 4H), 1.20 (m, 4H).

Example 101

1-Mercapto-2,9-dioxo-9-phenyl-nonane (159e)

Following the procedure described in Example 97, step 1, 2, but substituting hydrogen sulfide for thiolacetic acid, the title compound 159e was obtained in 30% yield. $^1$H NMR: (300 MHz, CDCl$_3$) δ 8.00 (m, 2H), 7.40-7.60 (m, 3H), 3.20 (d, J=7.5 Hz, 2H), 3.00 (m, 2H), 2.60 (m, 2H), 1.80 (t, J=7.5Hz), 1.60 (m, 4H), 1.20 (m, 4H).

Example 102

1-Benzoylthio-2,9-dioxo-9-phenyl-nonane (159f)

Following the procedure described in Example 97, step 1, 2, but substituting benzoylthiol for thiolacetic acid, the title compound 159f was obtained in 52% yield. $^1$H NMR: (300 MHz, CDCl$_3$) δ 8.00 (m, 4H), 7.60-7.40 (m, 6H), 4.00 (s, 2H), 3.00 (m, 2H), 2.60 (m, 2H), 1.60 (m, 4H), 1.20 (m, 4H).

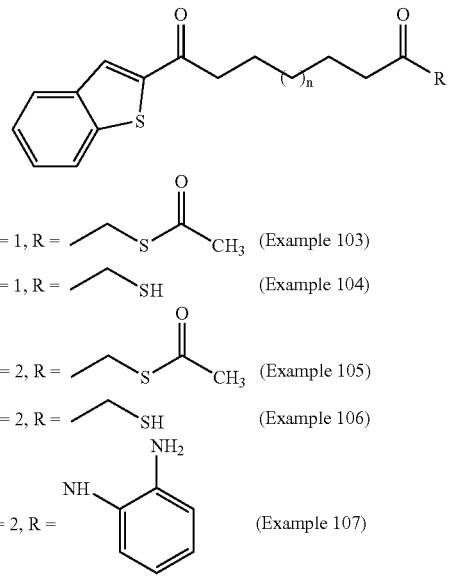

160: n = 1, R = —CH$_2$—S—C(=O)—CH$_3$ (Example 103)

161: n = 1, R = —CH$_2$—SH (Example 104)

162: n = 2, R = —CH$_2$—S—C(=O)—CH$_3$ (Example 105)

163: n = 2, R = —CH$_2$—SH (Example 106)

164: n = 2, R = —NH—(2-aminophenyl) (Example 107)

Example 103

1-Acetylthio-2,8dioxo-8-(2-benzo[b]thiophene)-octane (160)

Following the procedure described in Example 18, step 1, 2, 3, but substituting respectively ethyl-6-iodohexanoate for ethyl-7-iodoheptanoate and 2-benzo[b]thiophene-carbonyl chloride for benzoyl chloride, and then the resulting carboxylic acid was substituted for 50a in Example 97, step 1, 2, to afford the title compound 160 obtained in 450% yield. $^1$H NMR: (300 MHz, CDCl$_3$) δ 8.00 (m, 2H), 7.40-7.60 (m, 3H), 3.80 (s, 2H), 3.00 (m, 2H), 2.60 (m, 2H), 2.40 (s, 3H), 1.60 (m, 2H), 1.20 (m, 4H).

Example 104

1-Mercapto-2,8-dioxo-8-(2-benzo[b]thiophene)-octane (161)

Following the procedure described in Example 18, step 1, 2, 3, but substituting respectively ethyl-6-iodohexanoate for ethyl-7-iodoheptanoate and 2-benzo[b]thiophene-carbonyl chloride for benzoyl chloride, and then the resulting carboxylic acid was substituted for 50a in Example 97, step 1, 2, and hydrogen sulfide for thiolacetic acid, to afford the title compound 161 obtained in 20% yield. $^1$H NMR: (300 MHz, CDCl$_3$) δ 8.00 (m, 2H), 7.40-7.60 (m, 3H), 3.20 (d, J=7.5 Hz, 2H), 3.00 (m, 2H), 2.60 (m, 2H), 1.80 (t, J=7.5 Hz, 1H), 1.60 (m, 2H), 1.20 (m, 4H).

Example 105

1-Acetylthio-2,9-dioxo-9-(2-benzo[b]thiophene)-nonane (162)

Following the procedure described in Example 97, step 1, 2, but substituting carboxylic acid 50m for 50a, the title compound 162 was obtained in 50% yield. $^1$H NMR: (300 MHz, CDCl$_3$) δ 8.00 (m, 2H), 7.60-7.40 (m, 3H), 3.80 (s, 2H), 3.00 (m, 2H), 2.60 (m, 2H), 2.40 (s, 3H), 1.60 (m, 4H), 1.20 (m, 4H).

Example 106

1-Mercapto-2,9-dioxo-9-(2-benzo[b]thiophene)-nonane (163)

Following the procedure described in Example 97, step 1, 2, but substituting respectively carboxylic acid 50m for 50a and hydrogen sulfide for thiolacetic acid, the title compound 163 was obtained in 30% yield. $^1$H NMR: (300 MHz, CDCl$_3$) δ 8.00 (m, 2H), 7.60-7.40 (m, 3H), 3.20 (d, J=7.5 Hz, 2H), 3.00 (m, 2H), 2.60 (m, 2H), 180 (t, J=7.5 Hz, 1H), 1.60 (m, 4H), 1.20 (m, 4H).

Example 107

N-(2-Aminophenyl)-7-[(2-benzo[b]thiophene)carbonyl]heptanamide (164)

Following the procedure described in Example 22, but substituting carboxylic acid 50m for carboxylic acid 50a, the title compound 164 was obtained in 79% yield. $^1$H NMR: (300 MHz, CDCl$_3$) δ 8.00-7.60 (m, 6H), 7-7.20 (m, 3H), 2.80 (m, 2H), 2.00 (m, 2H), 1.60 (m, 4H), 1.20 (m, 4H).

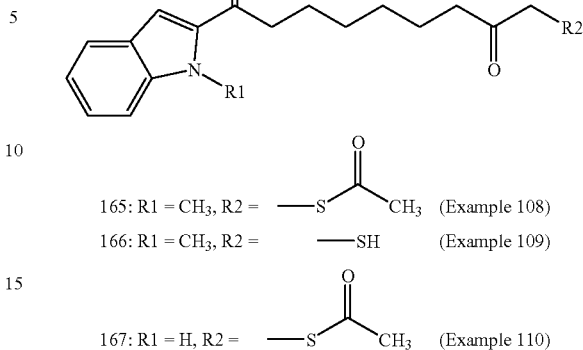

Example 108

1-Acetylthio-2,9-dioxo-9-(2-(N-methyl)indolyl)-nonane (165)

Following the procedure described in Example 1, step 4, but substituting 1-methyl indole-2-carboxylic acid for 5, followed by Example 18, step 2, 3, but substituting N-methyl indole-2-carbonyl chloride for benzoyl chloride, and then the resulting carboxylic acid was substituted for 50a in Example 97, step 1, 2, to afford the title compound 165 in 40% yield. $^1$H NMR: (300 MHz, CDCl$_3$) δ 8.00 (m, 5H), 7.60-7.40 (m, 5H), 4.10 (s, 3H), 3.80 (s, 2H), 3.00 (m, 2H), 2.60 (m, 2H), 2.40 (s, 3H), 160 (m, 2H), 1.20 (m, 4H).

Example 109

1-Mercapto-2,9-dioxo-9-(2-N-methylindolyl)-nonane (166)

Following the procedure described in Example 1, step 4, but substituting 1-methyl indole-2-carboxylic acid for 5, followed by Example 18, step 2, 3, but substituting N-methyl indole-2-carbonyl chloride for benzoyl chloride, and then the resulting carboxylic acid was substituted for 50a in Example 97, step 1, 2, and hydrogen sulfide for thiolacetic acid, to afford the title compound 166 in 25% yield. $^1$H NMR: (300 MHz, CDCl$_3$) δ 8.00 (m, 2H), 7.60-7.40 (m, 3H), 4.10(s, 3H), 3.20 (d, J=7.5 Hz, 2H), 3.00 (m, 2H), 2.60 (m, 2H), 1.80 (t, J=7.5 Hz, 1H), 1.60 (m, 4H), 1.20 (m, 4H).

Example 110

1-Acetylthio-2,9-dioxo-9-(2-indolyl)-nonane (167)

Following the procedure described in Example 1, step 4, but substituting indole-2-carboxylic acid for 5, followed by Example 18, step 2, 3, but substituting indole-2-carbonyl chloride for benzoyl chloride, and then the resulting carboxylic acid was substituted for 50a in Example 97, step 1, 2, to afford the title compound 167 in 60% yield. $^1$H NMR: (300 MHz, CDCl$_3$) δ 8.00 (m, 2H), 7.40-7.60 (m, 3H), 3.80 (s, 2H), 3.00 (m, 2H), 2.60 (m, 2H), 2.40 (s, 3H), 1.60 (m, 2H), 1.20 (m, 4H).

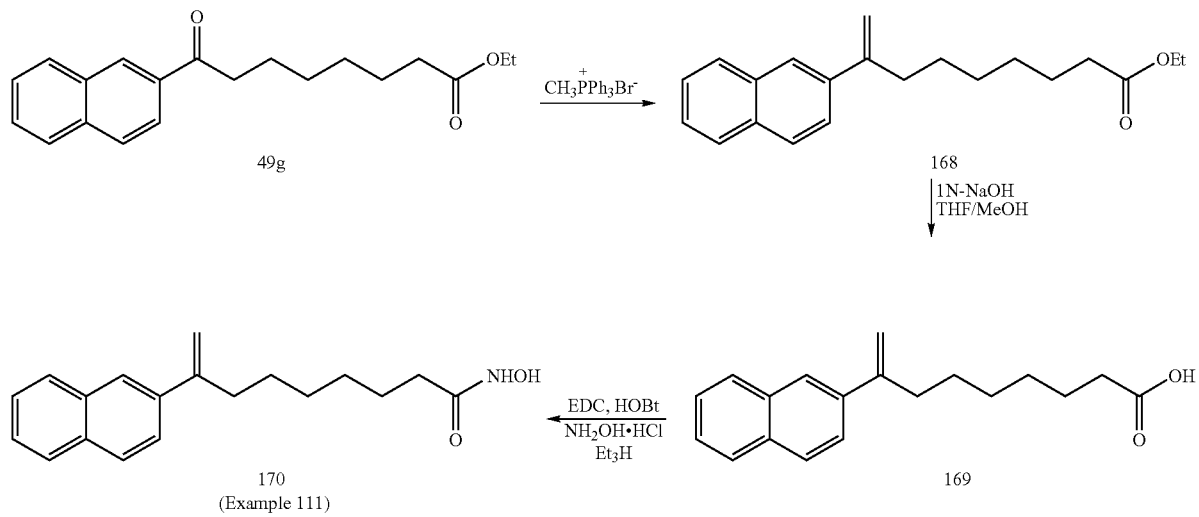

Example 111

N-Hydroxy-8-(2-naphthyl)non-8-enamide (170)

Step 1: Ethyl 8-(2-naphthyl)non-8-enoate (168)

To a solution of methyltriphenylphosphonium bromide (469 mg, 1.31 mmol) in THF (6 mL) pre-cooled to 0° C. under nitrogen atmosphere was added dropwise n-butyl-lithium (1.42M solution in hexanes, 905 µL, 1.28 mmol) and stirred over 20 minutes. To this a THF (4mL) solution of 49g (82 mg, 0.262 mmol) was transferred via cannula. The yellow mixture was stirred over 30 minutes and quenched with a saturated aqueous solution of ammonium chloride, as the yellow color immediately disappeared. The solvent was removed by evaporation in vacuo and the aqueous residue was partitioned between water and ethyl acetate. The aqueous layer was then extracted with ethyl acetate and the combined organic layers were washed with brine, dried (MgSO$_4$) and concentrated. The crude residue was purified by flash chromatography (5% to 8% diethyl ether in hexane) to afford the title compound 168 (43 mg) in 52% yield. $^1$H NMR: (CDCl$_3$) δ: 7.85-7.78 (m, 4H), 7.58 (dd, J=8.8, 1.9 Hz, 1H), 7.48-7.44 (m, 2H), 5.42 (d, J=1.1 Hz, 1H), 5.16 (d, J=1.4 Hz, 1H), 4.12 (q, J=7.1 Hz, 2H), 2.62 (t, J=6.9 Hz, 2H), 2.28 (d, J=7.4 Hz, 2H), 1.64-1.49 (m, 4H), 1.39-1.33 (m, 4H), 1.25 (t, J=7.1 Hz, 3H). MS (ESI)=311 (MH$^+$).

Step 2: 8-(2-Naphthyl)non-8-enoic acid (169)

Following a procedure analogous to that described in Example 18, step 3, but substituting ester 169 for ester 49a, the title compound was obtained in 99%. $^1$H NMR: (CDCl$_3$) δ: 7.83-7.77 (m, 4H), 7.57 (d, J=8.8 Hz, 1H), 7.47-7.44 (m, 2H), 5.40 (s, 1H), 5.14 (s, 1H), 2.61 (t, J=7.1 Hz, 2H), 2.33 (t, J=7.4 Hz, 2H), 1.64-1.21 (m, 8H). MS (ESI)=283 (MH$^+$).

Step 3: N-Hydroxy-8-(2-naphthyl)non-8-enamide (170)

Following the procedure described in Example 14, step 3, but substituting carboxylic acid 169 for 37, and using 1.1 equivalent of NH$_2$OH·HCl and triethylamine each, the title compound 170 was obtained in 33% yield. $^1$H NMR: (CDCl$_3$) δ: 8.22 (br s, 1H), 7.80-7.77 (m, 4H), 7.56 (d, J=8.5 Hz, 1H), 7.46-7.44 (m, 2H), 5.39 (s, 1H), 5.13 (s, 1H), 2.59 (t, J=6.6 Hz, 2H), 2.05 (br s, 2H), 1.56-1.11 (m, 8H). HRMS: (calc.) 297.1729 (M+), (found) 297.1744.

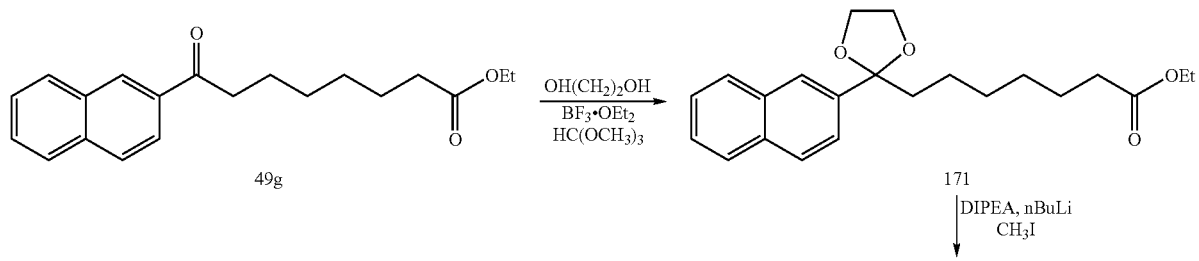

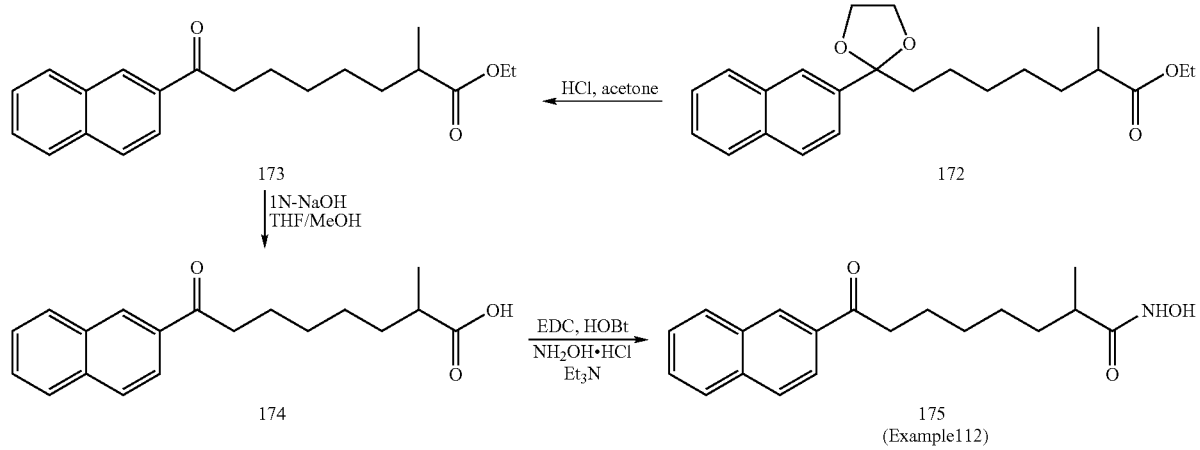

Example 112

N-Hydroxy-2-methyl-7-(2-naphthoyl)heptanamide (175)

Step 1: Ethyl-8-(2-naphthyl)-8-[2-(1,3-dioxolyl)]octanoate (171)

To a solution of 49g (4.52 g, 14.47 mmol) in dichloromethane (140 mL) was added ethylene glycol (8.07 mL, 144.7 mmol) followed by boron trifluoride etherate (3.67 mL, 28.94 mmol). The mixture was stirred for 1 hour at room temperature. Then trimethyl orthoformate (2.73 mL, 21.71 mmol) was added and the mixture was stirred overnight. The reaction was quenched with a saturated aqueous solution of sodium bicarbonate and the layers were separated. The aqueous layer was extracted with dichloromethane and the combined organic layers were washed with brine, dried (MgSO$_4$) and concentrated. The crude residue was purified by flash chromatography (15% to 20% ethyl acetate/hexane), to afford the title compound 171 in 44% yield. $^1$H NMR: (300 MHz, CDCl$_3$) δ: 7.91 (s, 1H), 7.87-7.81 (m, 3H), 7.54 (dd, J=8.5, 1.4 Hz, 1H), 7.49-7.46 (m, 2H), 4.12-4.03 (m, 4H), 3.82-3.78 (m, 2H), 2.23 (t, J=7.4 Hz, 2H), 1.99-1.94 (m, 2H), 1.59-1.54 (m, 2H). MS (ESI)=357(MH$^+$).

Step 2: Ethyl-2-methyl-8-(2-naphthyl)-8-[2-(1,3-dioxolyl)]octanoate (172)

To a solution of freshly distilled (over sodium hydride) diisopropylamine (550 µL, 3.93 mmol) in THF (40 mL) pre-cooled to 0° C. under nitrogen atmosphere was added dropwise n-butyllithium (1.2M solution in hexanes, 3.12 mL, 3.65 mmol). The mixture was stirred at 0° C. for 20 minutes and cooled down to −78° C. Then a pre-cooled (−78° C.) solution of 171 (1.0 g, 2.81 mmol) in THF (15 mL) was transferred via cannula. The mixture was stirred for 1 hour at −78° C. Then a pre-cooled (−78° C.) solution of iodomethane (349 µL, 5.61 mmol) in THF (15 mL) was transferred via cannula. The resulting mixture was stirred at −78° C. for 30 minutes, quenched with a saturated aqueous solution of ammonium chloride, and then warmed to room temperature. Water was added and the mixture was stirred for 4 hours, after which the THF layer had turned yellow. The mixture was concentrated in vacuo and the aqueous residue was partitioned between diethyl ether and water. The organic layer was washed with brine, dried (MgSO$_4$) and concentrated. The crude residue was purified by flash chromatography (10% ethyl acetate in hexane) to afford the title compound 172 (950 mg) in 91% yield. $^1$H NMR: (300 MHz, CDCl$_3$) δ: 7.91 (s, 1H), 7.87-7.81 (m, 3H), 7.54 (dd, J=8.8, 1.9 Hz, 1H), 7.51-7.45 (m, 2H), 4.12-4.03 (m, 4H), 3.86-3.78 (m, 2H), 2.35 (sext, J=7.1 Hz, 1H), 1.99-1.94 (m, 2H), 1.60-1.54 (m, 2H), 1.35-1.19 (m, 9H), 1.09 (d, J=6.9 Hz, 3H). MS (ESI)=371 (MH$^+$).

Step 3: Ethyl-2-methyl-7-(2-naphthoyl)heptanoate (173)

To a solution of 172 (950 mg, 2.56 mmol) in acetone (75 mL) was added an aqueous 1N solution of hydrochloric acid (15 mL) until a precipitate persisted, and then more acetone was added until a solution is obtained. The mixture was stirred at room temperature for 1 hour and then at 50° C. for 1 hour. The mixture was concentrated in vacuo to a 10 mL volume. The white precipitate formed was filtered, rinsed with water to give 173. $^1$H NMR: (300 MHz, CDCl$_3$) δ: 8.47 (s, 1H), 8.04-7.96 (m, 2H), 7.91-7.86 (m, 2H), 5.57 (quint d, J=7.7, 1.9 Hz, 2H), 4.12 (q, J=7.1 Hz, 2H), 3.09 (t, J=7.4 Hz, 2H), 2.46-2.39 (m, 1H), 1.82-1.51 (m, 4H), 2.45-2.34 (m, 4H), 1.24 (t, J=7.1 Hz, 3H), 1.14 (d, J=6.9 Hz, 3H). MS (ESI)=327 (MH$^+$).

Step 4: 2-Methyl-7-(2-naphthoyl)heptanoic acid (174)

Following a procedure analogous to that described in Example 18, step 3, but substituting ester 173 for ester 49a, the title compound 174 was obtained in 73%. $^1$H NMR: (300 MHz, CDCl$_3$) δ: 8.47 (s, 1H), 8.03 (dd, J=8.5, 1.6 Hz, 1H), 7.97 (d, J 8.0 Hz, 1H), 7.89 (d, J=8.5 Hz, 1H), 7.87 (d, J=8.0 Hz, 1H), 7.57 (quint d, J=7.7, 1.9 Hz, 2H), 3.10 (t, J=7.1 Hz, 2H), 2.52-2.46 (m, 1H), 1.83-1.72 (m, 4H), 1.52-1.42 (m, 4H), 1.19 (d, J=6.9 Hz, 3H). MS (ESI)=299 (MH$^+$).

Step 5: N-Hydroxy-2-methyl-7-(2-naphthoyl)heptanamide (175)

Following a procedure analogous to that described in Example 14, step 3, but substituting carboxylic acid 174 for 37, and using 1.1 equivalent of NH$_2$OH.HCl and triethylamine each, the title compound 175 was obtained in 65%. $^1$H NMR: (300 MHz, CDCl$_3$) δ: 8.47 (s, 1H), 8.02 (d, J=8.8 Hz, 1H), 7.97 (d, J=8.8 Hz, 1H), 7.91-7.86 (m, 2H), 7.63-7.55 (m, 2H), 3.18-3.02 (m, 2H), 2.31-2.17 (m, 1H), 1.73-1.694 (m, 2H), 1.50-1.28 (m, 4H), 1.11-1.07 (m, 3H). HRMS: (calc.) 313.1678, (found) 313.1685.

ammonium chloride. Most of the THF was removed by evaporation in vacuo and the aqueous residue was partitioned between diethyl ether and water. The aqueous layer was extracted with diethyl ether and the combined organic layers were successively washed with water, brine, dried over magnesium sulfate and concentrated. The crude residue was purified by flash chromatography (6% to 8% ethyl

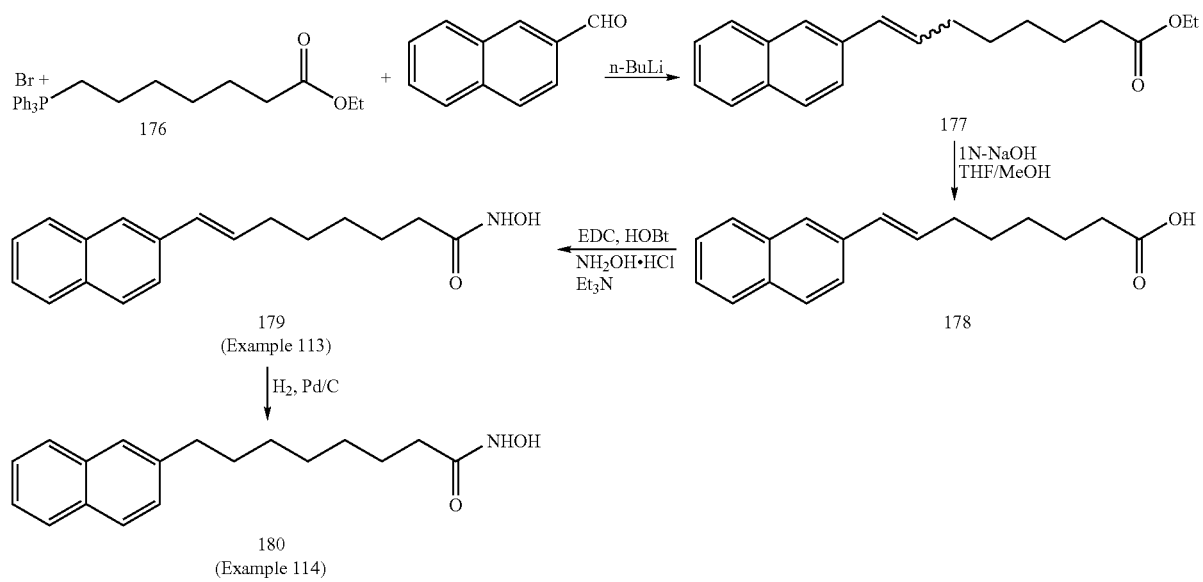

acetate in hexane) affording the title compound 177 in 34% yield as a mixture of E and Z isomers. $^1$H NMR: (CDCl$_3$) δ: 7.83-7.75 (m, 3H), 7.71 (s, 0.5H), 7.67 (s, 0.5H), 7.57 (dd, J=8.5, 1.9 Hz, 0.5H), 7.49-7.38 (m, 2.5H), 6.57 (d, J=11.5 Hz, 0.5H), 6.54 (d, J=15.9 Hz, 0.5H), 6.34 (dt, J=15.7, 7.1 Hz, 0.5H), 5.73 (dt, J=11.8, 7.1 Hz, 0.5H), 4.17-4.10 (m, 2H), 2.42 (qd, J=7.4, 1.9 Hz, 1H), 2.34-2.24 (m, 3H), 1.73-1.31 (m, 6H), 1.28-1.22 (m, 3H). MS (ESI)=297 (MH$^+$).

Example 113

(E)-N-Hydroxy-8-(2-naphthyl)-7-octenamide (179)

Step1: (Carbethoxyhexyl)triphenylphosphonium bromide (176)

To a solution of ethyl 7-bromoheptanoate (10.0 g, 42.17 mmol) in toluene (280 mL) was added solid triphenylphosphine (11.06 g, 42.17 mmol). The solution was refluxed over 24 hours under nitrogen atmosphere and then cooled to room temperature. The supernatant was transferred into a different flask and an excess of triphenylphosphine (5.53 g, 21.09 mmol) was added. The solution was refluxed over 3 days and cooled to room temperature without stirring to favor sedimentation. The supernatant again removed by decantation and the resulting colorless oil was dried over high vacuum affording the title compound 176 (18.24 g) in 87% yield. $^1$H NMR: (300 MHz, CDCl$_3$) δ: 7.96-7.62 (m, 9H), 7.37-7.08 (m, 6H), 4.11-4.00 (m, 2H), 3.86-3.70 (m, 2H), 2.37-2.32 (m, 4H), 2.28-2.19 (m, 2H), 1.72-1.46 (m, 6H), 1.31-1.25 (m, 2H), 1.22-1.15 (m, 3H). MS (ESI)=419 (Phosphonium Ion).

Step2: (E/Z)-Ethyl 8-(2-naphthyl)-7-octenoate (177)

To a suspension of phosphonium salt 176 (18.14 g, 36.32 mmol) in THF (300 mL) pre-cooled to 0° C. was added dropwise n-butyllithium (1.13M solution in hexanes, 35.4 mL, 39.95 mmol). The resulting light yellow solution was stirred at 0° C. over 30 minutes and a solution of a 2-naphthaldehyde (5.67 g, 36.32 mmol) in THF (60 mL) was transferred dropwise via cannula. The mixture was stirred overnight, allowing to warm to room temperature. The reaction was quenched with a saturated aqueous solution of Step3: (E)-8-(2-Naphthyl)-7-octenoic acid (178)

Following a procedure analogous to that described in Example 18, step 3, but substituting ester 177 for ester 49a, the title compound 178 was obtained in 60%. $^1$H NMR: (CDCl$_3$) δ: 7.79-7.75 (m, 3H), 7.67 (s, 1H), 7.57 (dd, J=8.5, 1.7 Hz, 1H), 7.47-7.38 (m, 2H), 6.54 (d, J=15.7 Hz, 1H), 6.34 (dt, J=9.0, 6.6 Hz, 1H), 2.38 (t, J=7.4 Hz, 2H), 2.28 (q, J=6.6 Hz, 1H), 1.74-1.64 (m, 2H), 1.57-1.40 (m, 4H). MS (ESI)=269 (MH$^+$).

Step 4: (E)-N-Hydroxy-8-(2-naphthyl)-7-octenamide (179)

Following a procedure analogous to that described in Example 14, step 3, but substituting carboxylic acid 178 for 37, and using 1.1 equivalent of NH$_2$OH.HCl and triethylamine each, the title compound 179 was obtained in 37% yield. $^1$H NMR: (CD$_3$OD) δ: 7.79-7.74 (m, 3H), 7.67 (s, 1H), 7.60 (d, J=8.8 Hz, 1H), 7.45-7.36 (m, 2H), 6.56 (d, J=15.7 Hz, 1H), 6.38 (dt, J=15.7, 6.9 Hz, 1H), 2.28 (q, J=6.3 Hz, 2H), 2.11 (t, J=7.4 Hz, 2H), 1.72-1.62 (m, 2H), 1.58-1.50 (m, 2H), 1.46-1.40 (m, 2H). HRMS (calc.): 283.1572, (found): 283.1567.

Example 114

N-Hydroxy-8-(2-naphthyl)octanamide (180)

To a solution of compound 179 (30 mg, 0.106 mmol) in methanol (2 mL) was added a catalytic amount of 10% palladium on charcoal. The mixture was degassed and applied under hydrogen atmosphere and stirred for 15 minutes. Hydrogen was evacuated by vacuum and the mixture was filtered through Celite and rinsed with methanol. The filtrate was concentrated in vacuo, affording the title compound 180 (29.1 mg) in 97% yield. $^1$H NMR: (300 MHz, CD$_3$OD) δ: 7.80-7.74 (m, 3H), 7.60 (s, 1H), 7.44-7.37 (m, 2H), 7.33 (dd, J=8.2, 1.6 Hz, 1H), 2.77 (t, J=7.4 Hz, 2H), 2.07 (t, J=7.1 Hz, 2H), 1.71-1.64 (m, 2H), 1.62-1.57 (m, 2H), 1.37-1.28 (m, 6H). HRMS (calc.): 285.1729, (found): 285.1727.

Example 115

N-Hydroxy-8-hydroxy-8-(2-naphthyl)-2-octenamide (187)

Step1: 1-(2-Naphthyl)-6-heptenol (181)

A flame-dried round-bottomed flask was charged with magnesium turnings (1.23 g, 50.75 mmol) and stirred under vacuum for 15 minutes and then applied under nitrogen atmosphere. THF (70 mL) was added followed by 1,2-dibromoethane (381 mg, 2.03 mmol), and the mixture was brought to the boiling point for 1 minute, then and cooled down to room temperature. A solution of 6-bromohexene (8.28 g, 50.75 mmol) in THF (30 mL) was transferred via cannula to the magnesium flask and the mixture was refluxed overnight and cooled to −78° C. A solution of

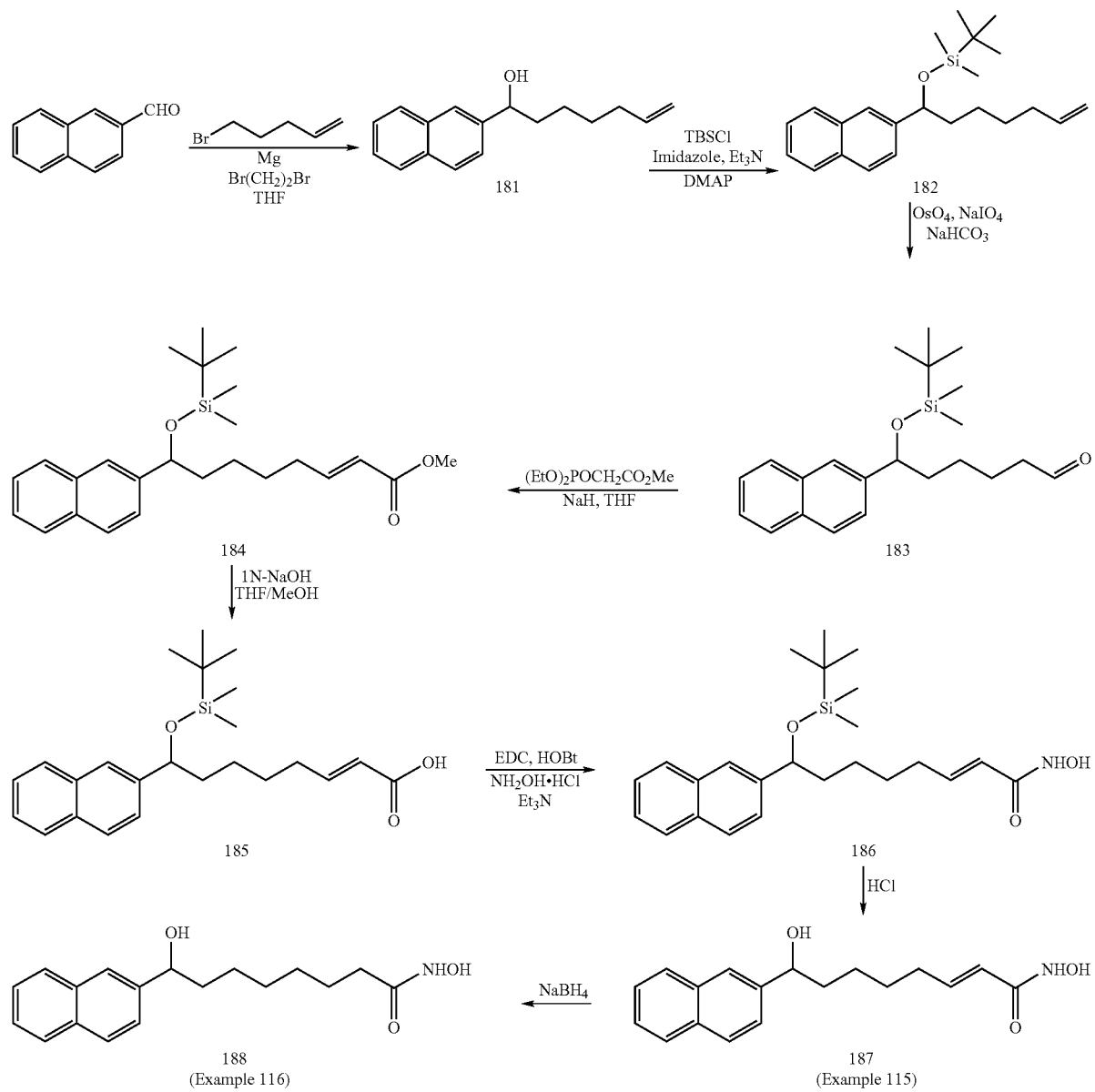

2-naphthaldehyde (6.10 g, 39.04 mmol) in THF (30 mL) was transferred via cannula to the Grignard reagent and the mixture was slowly warmed to 0° C. over 3 hours and kept at that temperature for 2 hours. The reaction was quenched with a saturated aqueous ammonium chloride solution and THF was evaporated in vacuo. The aqueous residue was poured into a separating funnel containing water and the compound was extracted with diethyl ether (2×100 mL). The combined organic layers were washed with brine, dried over magnesium sulfate and concentrated. The residue was purified by flash chromatography (10% to 15% ethyl acetate in hexane), affording the title compound 181 in 89% yield (8.33g). $^1$H NMR: (300 MHz, CDCl$_3$) δ: 7.85-7.78 (m, 4H), 7.51-7.44 (m, 3H), 5.85-5.72 (m, 1H), 5.02-4.91 (m, 2H), 4.87-4.82 (m, 2H), 2.08-2.01 (m, 2H), 1.94-1.80 (m, 2H), 1.53-1.23(m, 4H). MS (ESI)=223 (MH$^+$—H$_2$O).

Step2: O-(t-Butyldimethylsilyl)-1-(2-naphthyl)-6-heptenol (182)

To a solution of alcohol 181 (1.0 g, 4.16 mmol) in dichloromethane (40 mL) at room temperature under nitrogen atmosphere were successively added solid t-butyldimethylsilyl chloride (815 mg, 5.41 mmol), imidazole (340 mg, 4.99 mmol), and a catalytic amount of 2,6-dimethylaminopyridine. The mixture was stirred over 1 hour and triethylamine (696 μL, 4.99 mmol) was added. The mixture was stirred for 2 days. The reaction was quenched with water and the layers separated. The aqueous layer was extracted with dichloromethane and the combined organic layers were washed successively with a 1N HCl (2×10 mL), a saturated solution of sodium bicarbonate and brine, dried (MgSO$_4$) and concentrated in vacuo. The crude residue was purified by flash chromatography using hexane as the eluent, and affording the title compound 182 in 84% yield (1.24 g). $^1$H NMR: (300 MHz, CDCl$_3$) δ: 7.83-7.79 (m, 3H), 7.70 (s, 1H), 7.47-7.40 (m, 3H), 5.78 (ddt, J=17.0, 10.4, 6.6 Hz, 1H), 5.85-5.71 (m, 2H), 4.79 (dd, J=6.9, 4.9 Hz, 1H), 2.04-1.98 (m, 2H), 1.80-1.54 (m, 2H), 0.90 (s, 9H), 0.04 (s, 3H), −0.14 (s, 3H). MS (ESI)=223 (MH$^+$-TBSO).

Step3:
6-t-Butyldimethylsilyloxy-6-(2-naphthyl)hexanal (183)

To a solution of alkene 182 (1.05 g, 3.23 mmol) in t-butyl alcohol (50 mL) were successively added water (10 mL), solid sodium bicarbonate (2.71 g, 32.3 mmol), sodium periodate (4.15 g, 19.38 mmol), and osmium tetroxide (8 mg, 0.032 mmol). The mixture turned light brown and a precipitate formed in large amount, making magnetic stirring impossible so the mixture was shaken by hand every 10 minutes for 3.5 hours and the brownish color almost disappeared. The reaction was quenched with a 10% aqueous solution of sodium thiosulfate. After 30 minutes, the white precipitate was filtered off and rinsed with diethyl ether. The filtrate was concentrated in vacuo. The residue was partitioned between diethyl ether and water. The aqueous layer was extracted (2×50 mL) with diethyl ether. The combined organic layers were washed successively with a 10% aqueous solution of sodium thiosulfate, water and brine, dried (MgSO$_4$), and concentrated in vacuo, yielding the title compound 183 as a crude oil in 91% yield (1.05 g). $^1$H NMR: (300 MHz, CDCl$_3$) δ: 9.73 (t, J=1.9 Hz, 1H), 7.83-7.78 (m, 3H), 7.69 (s, 1H), 7.49-7.43 (m, 3H), 4.80 (t, J=6.9 Hz, 1H), 2.39 (td, J=7.1, 1.6 Hz, 2H), 1.81-1.55 (m, 4H), 1.43-1.25 (m, 2H) 0.90 (s, 9H), 0.04 (s, 3H), −0.15 (s, 3H). MS (ESI) 225 (M+1-TBSO).

Step 4: Methyl 8-t-butyldimethylsilyloxy-8-(2-naphthyl)-2-octenoate (184)

To a suspension of sodium hydride (60% in mineral oil, 177 mg, 4.42 mmol) in THF (25 mL) at room temperature under nitrogen atmosphere was added dropwise neat methyl diethylphosphonoacetate (811 μL, 4.42 mmol). The resulting solution was stirred for 10 minutes while cooling down to 0° C. A solution of crude aldehyde 183 (1.05 g, 2.94 mmol) in THF (10 mL) was transferred via cannula. The resulting solution was stirred for 15 minutes at 0° C. and quenched with a saturated aqueous solution of ammonium chloride. The THF was evaporated in vacuo and the aqueous residue was partitioned between diethyl ether and water. The aqueous layer was extracted with diethyl ether and the combined organic layers were washed with brine, dried (MgSO$_4$) and concentrated in vacuo. The crude residue was purified by flash chromatography (5% ethyl acetate/hexane), affording the title compound 184 in 63% yield (1.30 g). $^1$H NMR: (300 MHz, CDCl$_3$) δ: 7.83-7.78 (m, 3H), 7.69 (s, 1H), 7.49-7.41 (m, 3H), 6.94 (dt, J=15.4, 7.1 Hz, 1H), 5.79 (dt, J=15.7, 1.1 Hz, 1H), 4.79 (dd, J=7.1, 5.2 Hz, 1H), 3.71 (s, 3H), 2.16 (q, J=7.4 Hz, 2H), 1.81-1.62 (m, 2H), 1.48-1.29 (m, 4H), 0.90 (s, 9H), 0.04 (s, 3H), −0.15 (s, 3H). MS (ESI)=413 (MH$^+$).

Step 5: 8-t-Butyldimethylsilyloxy-8-(2-naphthyl)-2-octenoic acid (185)

Following a procedure analogous to that described in Example 18, step 3, but substituting ester 184 for ester 49a, the title compound 185 was obtained in 100%. $^1$H NMR: (CDCl$_3$) δ: 7.83-7.78 (m, 3H), 7.72 (s, 1H), 7.48-7.40 (m, 3H), 6.74 (dt, J=15.4 7.1 Hz, 1H), 5.78 (d, J=15.4 Hz, 1H), 4.88-4.84 (m, 1H), 2.17-2.11 (m, 2H), 1.82-1.69 (m, 2H), 1.47-1.28 (m, 4H), 0.89 (s, 9H), 0.06 (s, 3H), =0.16 (s, 3H). MS (ESI)=421 (M$^+$+Na).

Step 6: N-Hydroxy-8-t-butyldimethylsilyloxy-8-(2-naphthyl)-2-octenamide (186)

Following a procedure analogous to that described in Example 14, step 3, but substituting carboxylic acid 185 for 37, and using 1.1 equivalent of NH$_2$OH.HCl and triethylamine each, the title compound 186 was obtained in 44% yield. $^1$H NMR: (CD$_3$OD) δ: 7.83-7.72 (m, 4H), 7.48-7.40 (m, 3H), 6.77 (dt, J=15.1, 7.1 Hz, 1H), 5.75 (d, J=15.4 Hz, 1H), 4.91-4.79 (m, 1H), 2.18-2.14 (m, 2H), 1.79-1.68 (m, 2H), 1.48-1.39 (m, 2H), 1.28-1.21 (m, 2H), 0.89 (s, 9H), 0.06 (s, 3H), −0.16 (s, 3H). MS (ESI)=436 (M$^+$+Na).

Step 7: N-Hydroxy-8-hydroxy-8-(2-naphthyl)-2-octenamide (187)

To a solution of the silyl ether 186 (300 mg, 0.725 mmol) in THF (3 mL) at room temperature was added 1N aqueous solution of hydrochloric acid (3 mL). The mixture was stirred for 3 hours at 30° C. and then added a large volume of ethyl acetate and water. The water layer was washed with ethyl acetate and the combined organic layers were washed with brine, dried (MgSO$_4$) and concentrated in vacuo. The crude residue was purified by flash chromatography (75% to 100% ethyl acetate/hexane) affording unsatisfactory purity. So the compound was purified again using 8% methanol in dichloromethane affording the title compound 187 in 33% yield (77 mg). $^1$H NMR: (300 MHz, CD$_3$OD) δ: 7.87-7.71 (m, 4H), 7.52-7.40 (m, 3H), 6.77 (dt, J=15.1, 6.9 Hz, 1H), 5.75 (d, J=15.1 Hz, 1H), 4.76 (t, J=6.9 Hz, 1H), 2.17-2.10 (m, 2H), 1.84-1.77 (m, 2H), 1.49-1.27 (m, 4H) 1.88-1.75 (m, 4). MS (ESI)=282 (M$^+$–OH), 322 (M$^+$+Na).

Example 116

N-Hydroxy-8-hydroxy-8-(2-naphthyl)octanamide (188)

To a solution of 187 (20 mg, 0.067 mmol) in methanol (670 μL) was added solid sodium borohydride (2.5 mg, 0.067 mmol). The mixture was stirred for 15 minutes and the solvent was evaporated in vacuo. The residue was partitioned between ethyl acetate and water. The organic layer was dried (MgSO$_4$) and concentrated. Purification by flash silica gel chromatography (6% methanol in dichloromethane) afforded the title compound 188 in 46% yield (9.1 mg). $^1$H NMR: (300 MHz, CD$_3$OD) δ: 7.84-7.76 (m, 4H), 7.50-7.40 (m, 3H), 4.75 (t, J=6.6 Hz, 1H), 2.05 (t, J=7.4 Hz, 2H), 1.86-1.76 (m, 2H), 1.62-1.55 (m, 2H), 1.43-1.23 (m, 6H). HRMS: (calc.) 283.1572 (M–H$_2$O), (found) 283.1581.

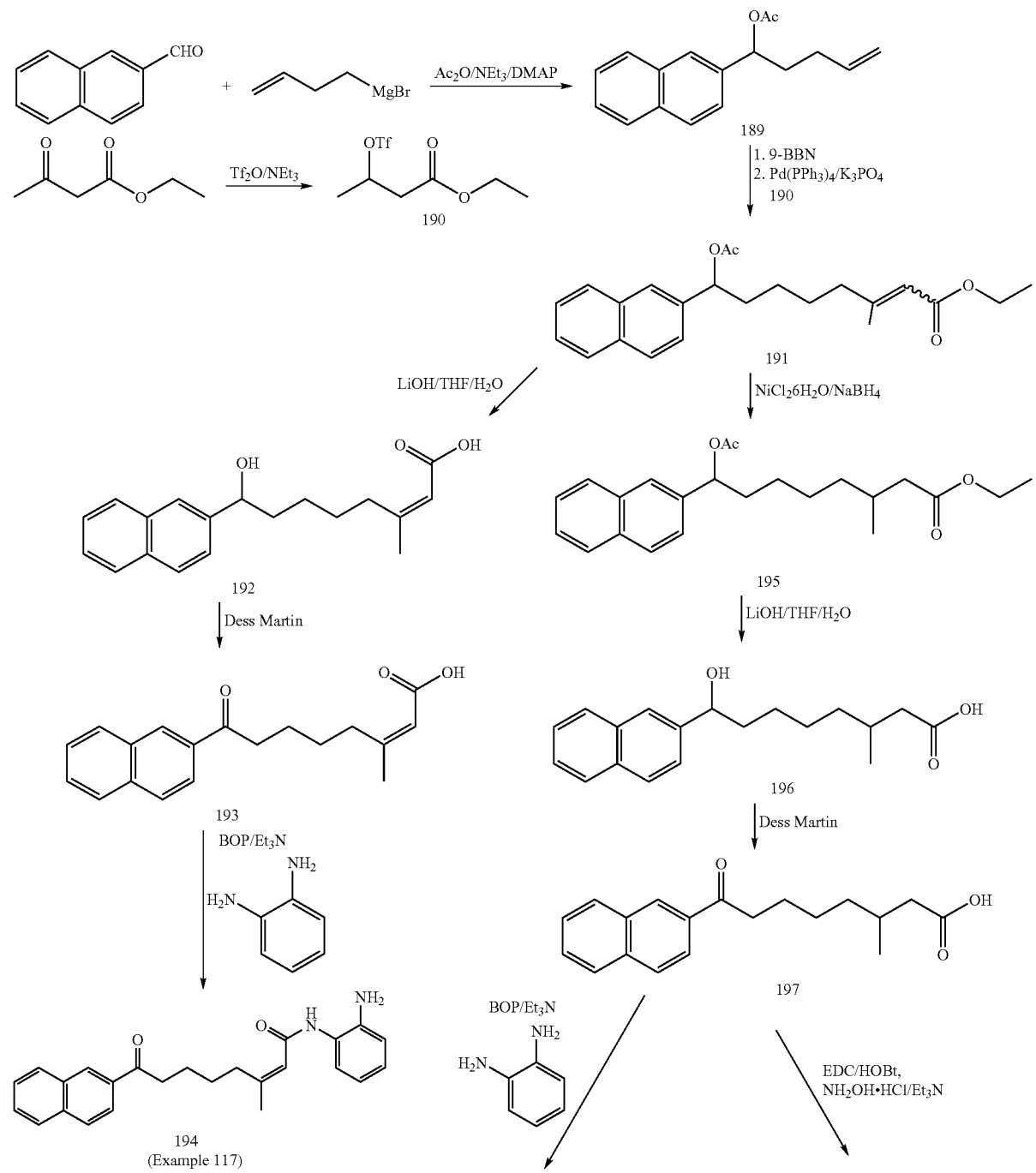

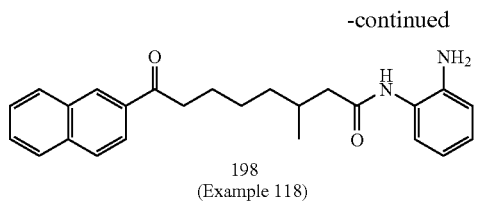

198
(Example 118)

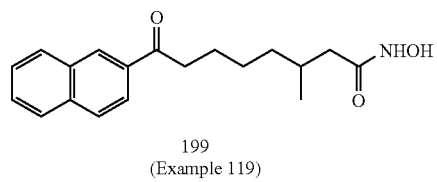

199
(Example 119)

Example 117

(Z)-N-(2-Aminophenyl)-3-methyl-7-(2-naphthoyl)-2-heptenamide (194)

Step 1: 1-O-Acetyl-2-naphthyl-4pentenol (189)

Following a procedure analogous to that described in Example 115, step 1, but substituting 4-bromobutene for 6-bromohexene, the resulting alcohol (2.16 g, 10.16 mmol) was dissolved in dichloromethane (80 ml) and was added Et$_3$N (5.7 ml, 40.6 mmol), acetic anhydride (2.9 ml, 30.5 mmol) and DMAP (62 mg, 5%) at 0° C. The solution was warmed up at room temperature and stirred for 5 hours. The resulting solution was washed with a saturated solution of NaHCO$_3$ (2×50 mL), brine and then dried over Na$_2$SO$_4$ and concentrated to give the product 189 (2.6 g, 99%). $^{13}$C NMR: (75 MHz, CDCl$_3$) δ: 21.2, 29.6, 35.2, 75.5, 115.2, 124.2, 125.7, 125.9, 126.1, 127.6, 127.9, 128.2, 133.0, 133.0, 137.3, 137.7, 170.2. MS (ESI)=277 (M$^+$+Na).

Step 2: (E/Z)-Ethyl-3-trifluoromethanesulfonyloxy-2-butenoate (190)

To a solution of ethyl acetoacetate (545 μl, 5 mmol) in dichloromethane at −78° C. was added Et$_3$N (2.1 ml, 15 mmol). After for 2 hours Tf$_2$O (1.1 ml, 3.9 mmol) was added and the solution was stirred at −78° C. for 5 hours. The solution was warmed up at room temperature and was diluted with anhydrous methanol. The oil was filtered through a pad of silica gel eluting with ether and concentrated to give yellow oil. Purification by column chromatography over silica gel gave the following compounds 190: E-isomer (575 mg, 46%), Z-isomer (409 mg, 33%). $^{13}$C NMR: (75 MHz, CD$_3$OD) δ: 25.2, 25.3, 28.7, 33.7, 39.1, 117.4, 124.7, 127.8, 128.7, 129.0, 129.5, 130.6, 131.0, 137.8, 161.9, 170.1. MS (ESI)=297 (MH$^+$).

Step 3: (E/Z)-Ethyl-3-methyl-8-acetoxy-8-(2-naphthyl)-2-octenoate (191)

An oven-dried flask equipped with a reflux condenser and a septum inlet was flushed with nitrogen and charged with a solution of 9-BBN (0.5M, 0.66 mmol) and then alkene 189 (168 mg, 0.66 mmol) at 0° C. The mixture was warmed up slowly to room temperature and stirred for 6 hours. To this solution were added dioxane (4 ml), powder K$_3$PO$_4$ (191 mg, 0.90 mmol), Pd(PPh$_3$)$_4$ (18 mg, 0.015 mmol), and triflate 190 (solution in dioxane 0.18M, 3.42 ml, 0.60 mmol). The mixture was heated at 85° C. for 17 hours. Then the mixture was diluted with hexane at room temperature, and the residual borane was oxidized with 3 M NaOH (1 ml) and 30% H$_2$O$_2$ (1 ml) for 1 hour. The product was extracted, washed with brine, dried over Na$_2$SO$_4$, and finally isolated by chromatography over silica gel (hexanes:Et$_2$O: 10:1 to 1:1) to give 70% as mixture of E and Z-isomers 191 in a 1:1.1 ratio. The 20% of Z-isomer was isolated from the mixture: $^{13}$C NMR: (75 MHz, CDCl$_3$) δ: 21.1, 24.9, 25.5, 27.6, 32.9, 35.8, 50.6, 75.9, 115.6, 124.1, 125.5, 125.8, 126.0, 127.5, 127.8, 128.1, 132.8, 132.9, 137.9, 160.4, 166.5, 170.2. MS (ESI)=375 (M$^+$+Na).

Step 4: (Z)-8-Hydroxy-3-methyl-8-(2-naphthyl)-2-octenoic acid (192)

Following a procedure described in Example 1, step 4, but substituting ester 191 for ester 3, the compound 192 was obtained in 99% yield. $^{13}$C NMR: (75 MHz, CDCl$_3$) δ 25.3, 26.9, 29.1, 34.0, 39.7, 75.1, 117.1, 125.3, 125.6, 126.5, 126.9, 128.5, 128.8, 128.9, 134.3, 134.7, 143.9, 162.2, 169.7. MS (ESI)=281 (MH$^+$–H$_2$O)

Step 5: (Z)-3-Methyl-7-(2-naphthoyl)-2-heptenoic acid (193)

To a solution of 192 (98 mg, 0.33 mmol) in dry dichloromethane (6 mL) was added a solution of Dess-Martin reagent (162 mg, 0.38 mmol) in dry dichloromethane (1 mL) via cannula. The mixture was stirred at room temperature for 24 hours. The mixture was diluted with ether and NaHSO$_3$ (221 mg) in aqueous solution was added with stirring until the phases are homogeneous. The product was extracted, washed with 5% KHSO$_4$, brine, dried over Na$_2$SO$_4$, and finally isolated by chromatography over silica gel (hexanes:Et$_2$O: 4:1 to 1:1) to give 193 in 94% yield. $^{13}$CNMR: (75 MHz, CD$_3$OD) δ: 25.2, 25.3, 28.7, 33.7, 39.1, 117.4, 124.7, 127.8, 128.7, 129.0, 129.5, 130.6, 131.0, 137.8, 161.9, 170.1. MS (ESI)=297 (MH$^+$).

Step 6: (Z)-N-(2-Aminophenyl)-3-methyl-7-naphthoyl-2-heptenamide (194)

Following a procedure described in Example 35, but substituting respectively acid 193 for acid 80 and 1,2-phenylenediamine for aniline, the compound 194 was obtained in 99% yield. $^1$H NMR: (300 MHz, CD$_3$OD): 8.01 (d, 2H, J=8.0 Hz), 7.92 (d, 2H, J=8.8 Hz), 7.65-7.54 (m, 3H), 7.09 (d, J=8.0 Hz, 1H), 6.68 (dd, J=7.7, 7.4 Hz, 1H), 5.97 (s, 1H), 3.22 (t, J=7.1 Hz, 2H), 2.82 (dd, J=7.4, 7.7 Hz, 2H), 1.91-1.80 (m, 2H), 1.77-1.63 (m, 2H). $^{13}$C NMR: (75 MHz, CH$_3$OD): 25.1, 25.2, 28.7, 33.4, 39.1, 118.6, 119.6, 124.7, 125.4, 126.9, 127.8, 127.9, 128.7, 129.4, 129.5, 130.7, 131.1, 133.9, 135.5, 136.9, 140.8, 143.0, 157.6, 167.5, 202.6

Example 118

(Z)-N-(2-Aminophenyl)-3-methyl-7-(2-naphthoyl)heptanamide (198)

Step 1: Ethyl-3-methyl-8-O-acetoxy-8-(2-naphthyl)-2-octenoate (195)

To a cold (ice bath) solution of 191 (126 mg, 0.36 mmol) in dry CH$_3$OH (4 ml) were added 3 ml of a 4% CH$_3$OH solution of NiCl$_2$.6H$_2$O (0.6 mmol). The solution was stirred for 30 min at 0° C. and then treated portionwise with NaBH$_4$ (46 mg, 1.22 mmol). The resulting black solution was stirred for additional 1 hour at 0° C., and then the ice bath was removed. After 18 hours at room temperature the mixture was treated with NaHCO$_3$, filtered through Celite, and concentrated. The residue was partitioned between saturated NaHCO$_3$ solution and dichloromethane. The combined organic layers were dried Na$_2$SO$_4$ and concentrated to give crude 195. Flash chromatography on silica gel of the residue afforded 67% of 195 (86 mg). $^{13}$C NMR: (75 MHz, CDCl$_3$) δ: 19.5, 25.5, 26.5, 30.1, 36.0, 36.4, 41.1, 41.4, 51.3, 76.1, 124.2, 125.6, 125.9, 127.6, 127.9, 128.2, 132.9, 133.0, 137.9, 170.3, 173.6. MS (ESI)=379 (M$^+$+Na).

Step 2: 8-Hydroxy-3-methyl-8-(2-naphthyl)-octanoic acid (196)

Following a procedure described in Example 1, step 4, but substituting ester 195 for ester 3, the compound 196 was obtained in 99% yield. $^{13}$C NMR: (75 MHz, CDCl$_3$) δ: 20.0, 27.0, 27.9, 31.4, 37.6, 39.9, 42.6, 75.2, 125.3, 125.6, 126.5, 126.9, 128.6, 128.8, 128.9, 134.3, 134.7, 143.9, 177.2. MS (ESI)=323 (M$^+$+Na$^+$).

Step 3: 3-Methyl-7-naphthoyl-heptanoic acid (197)

Following a procedure described in Example 117, step 5, but substituting 196 for 192, the compound 197 was obtained in 94% yield. $^{1}$H NMR: (300 MHz, CDCl$_3$) δ 8.06-7.55 (m, 7H), 3.32 (br s, 1H), 3.16 (t, J=6.9 Hz, 1H), 2.32 (dd, J=6.0, 14.0 Hz, 1H), 2.14-2.06 (m, 1H), 1.96-1.95 (m, 1H), 1.78-1.73 (m, 2H), 1.47-1.29 (m, 3H), 0.97 (d, J=6.04 Hz, 3H). MS (ESI)=299 (MH$^+$).

Step 4: N-(2-Aminophenyl)-3-Methyl-7-naphthoyl-heptanamide (198)

Following a procedure described in Example 35, but substituting acid 193 for acid 80 1,2-phenylenediamine for aniline, the compound 198 was obtained in 87% yield. $^{1}$H NMR: (300 MHz, CD$_3$OD): 8.05-7.91 (m, 4H), 7.67-7.53 (m, 2H), 7.10-6.68 (m, 5H), 3.33-3.31 (m, 2H), 3.19 (dd, J=6.9, 7.4 Hz, 2H), 2.47-1.29 (m, 7H), 1.05 (d, J=6.6 Hz, 3H), $^{13}$C NMR (75 MHz, CD$_3$OD): 20.1, 25.8, 27.7, 32.1, 37.7, 39.4, 44.87, 118.6, 119.5, 124.7, 127.1, 127.8, 128.3, 128.8, 129.5, 129.6, 130.7, 131.1, 134.1, 137.1, 174.6, 202.7.

Example 119

N-Hydroxy-3-methyl-7-(2-naphthoyl)heptanamide (199)

Following a procedure analogous to that described in Example 14, step 3, but substituting carboxylic acid 197 for 37, and using 1.1 equivalent of NH$_2$OH.HCl and triethylamine each, the title compound 199 was obtained in 63% yield. $^{1}$H NMR: (300 MHz, CD$_3$OD): 8.07-7.58 (m, 7H), 3.32 (t, J=1.7 Hz, 2H), 3.18 (dd, J=7.4, 6.7 Hz, 2H), 2.13-1.30 (m, 7H), 0.95 (d, J=6.3 Hz, 3H). $^{13}$C NMR (75 MHz, CD$_3$OD): 19.7, 25.7, 27.6, 31.7, 37.6, 39.4, 41.4, 124.7, 127.9, 128.7, 129.4, 129.6, 130.7, 131.1, 134.1, 135.6, 137.1, 172.4, 202.8.

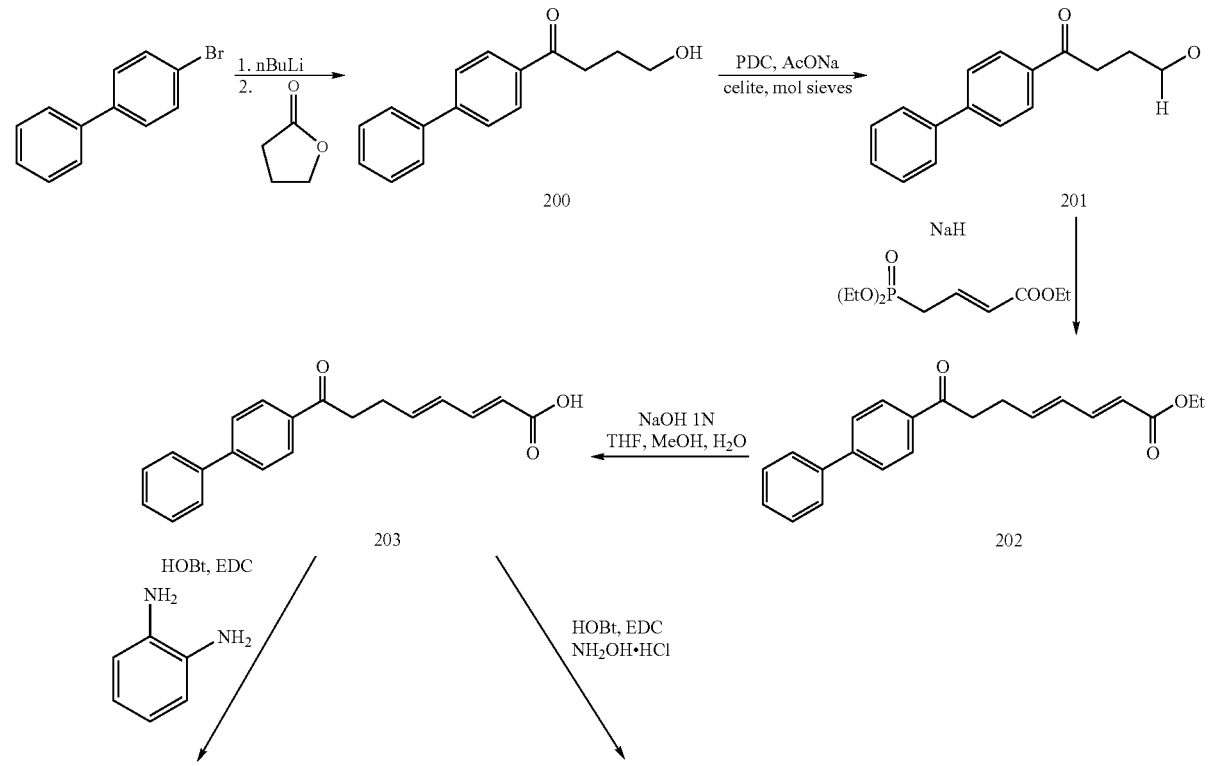

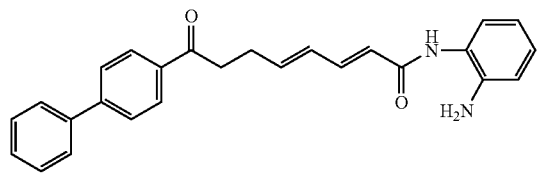

204: Example 120

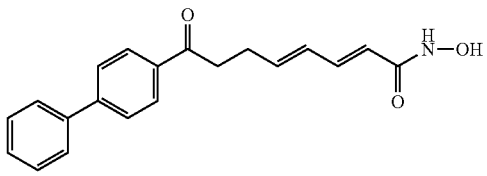

205: Example 121

Example 120

(E,E)-N-(2-Aminophenyl)-7-[(4-biphenyl)carbonyl]-2,4-heptadienamide (204)

Step 1: 1-(4-Biphenyl)-4-hydroxybutanone (200)

To a solution of bromobiphenyl (1 g, 4.3 mmol) in THF (20 mL) stirred at −78° C. under nitrogen was dropwise added n-BuLi (2.5M in hexane, 1.89 mL, 4.72 mmol). The mixture was stirred for 2 hours at −78° C., then warmed up to 0° C. and transferred via cannula over a solution of γ-butyrolactone (362 μL, 4.72 mmol) in THF (10 mL) cooled at −78° C. The reaction mixture was stirred for 2 hours at −78° C., quenched by a slow addition of water (10 mL), and then extracted with ethyl acetate (3×50 mL). The combined organic layers were dried (MgSO$_4$) and concentrated. Purification by flash silica gel chromatography (40% ethyl acetate in hexane) afforded the corresponding alcohol 200 (430 mg, 42% yield). MS (ESI)=241 (MH$^+$).

Step 2: 3-[(4-Biphenyl)carbonyl]propionaldehyde (201)

To a suspension of pyridinium chlorochromate (448 mg, 2.08 mmol), sodium acetate (170 mg, 2.08 mmol), Celite (200 mg) and molecular sieves 4 Å (10 mg) in anhydrous dichloromethane (10 mL) at room temperature under nitrogen was slowly added a solution of alcohol 200 in dichloromethane (5 mL). The reaction mixture was stirred at room temperature for 30 minutes and then filtered through a short pad of Celite. The organic layer was dried (MgSO$_4$), concentrated, and the crude was purified by flash silica gel chromatography (40% ethyl acetate in hexane) affording the aldehyde 201 (160 mg, 73% yield). MS (ESI)=239 (MH$^+$).

Step 3: (E,E)-Ethyl-7-[(4-biphenyl)carbonyl]-2,4heptadienoate (202)

To a solution of aldehyde 201 (180 mg, 0.75 mmol) in THF (10 mL), stirred at 0° C. under nitrogen, was added triethyl-4-phosphonocrotonate (220 μL, 0.98 mmol) followed by sodium hydride (40 mg, 0.98 mmol). The mixture was allowed to warm up to room temperature in 2 hours and then quenched by adding water, and extracted with ethyl acetate. The combined organic layers were washed with brine, dried (MgSO$_4$) and concentrated. Purification by flash silica gel chromatography (30% ethyl acetate in hexane) afforded the corresponding diene 202 (100 mg, 40% yield). MS (ESI)=335 (MH$^+$).

Step 4: (E,E)-7-[(4-Biphenyl)carbonyl]-2,4-heptadienoic acid (203)

Following the procedure described in Example 18, step 3, but substituting ester 202 for ester 49a, the title compound 203 was obtained in 80% yield. $^1$H NMR: (300 MHz, CDCl$_3$:CD$_3$OD 5:1) δ: 7.89-7.95 (2 m, 2 H), 7.49-7.65 (m, 4 H), 7.28-7.40 (m, 3 H), 7.15 (dd, J=15.3, 9.9 Hz, 1 H), 6.05-6.24 (m, 2 H), 5.69 (d, J=15.6 Hz, 1 H), 3.1 (t, J=7.2 Hz, 2 H), 2.50-2.60 (m, 2 H).

Step 5: (E,E)-N-(2-Aminophenyl)-7-[(4-biphenyl)carbonyl]-2,4-heptadienamide (204)

Following the procedure described in Example 22, but substituting carboxylic acid 203 for 50g, the title compound 204 was obtained in 47% yield. MS (ESI)=397 (MH$^-$).

Example 121

(E,E)-N-Hydroxy-7-[(4-biphenyl)carbonyl]-2,4-heptadienamide (205)

Following the procedure described in Example 14, step 3, but substituting carboxylic acid 203 for 37, and using 1.1 equivalent of NH$_2$OH.HCl and triethylamine each, the title compound 205 was obtained in 35% yield. MS (ESI)=322 (MH$^+$).

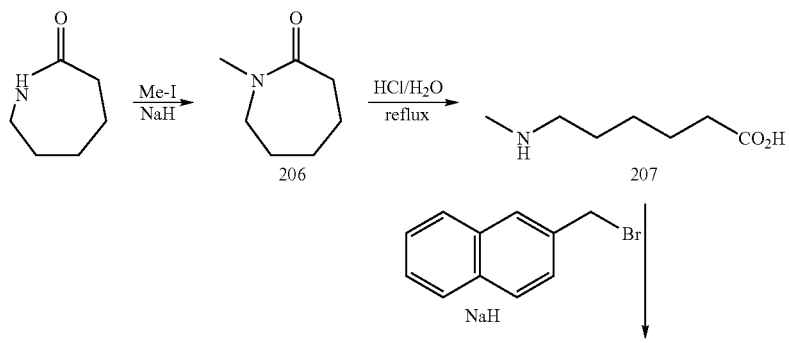

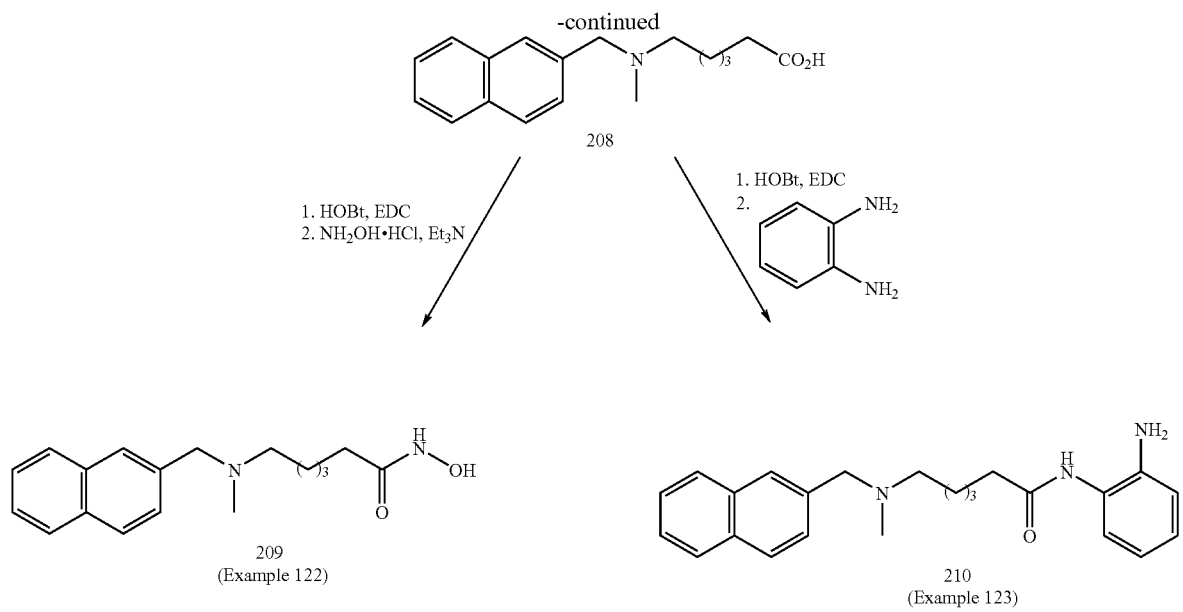

Example 122

N-Hydroxy-N-(2-naphthylmethyl-methylamino)hexanamide (209)

Step 1: N-Methyl-ε-caprolactam (206)

To a solution of ε-caprolactam (2.0 g, 17.6 mmol) in anhydrous THF (15 mL) at 0° C. was added NaH, 60% dispersion in oil (1.06 g, 26.0 mmol), and the mixture was stirred at 0° C. for 30 minutes. The cold bath was removed and the mixture was stirred at room temperature for 1 hour and then cooled again to 0° C. Methyl iodide (1.65 mL, 26.0 mmol) was added dropwise over 10 minutes, then the cold bath was removed and the mixture was stirred at room temperature for 18 hours. The excess NaH was quenched with methanol, THF was removed in vacuo and the crude was partitioned between ethyl acetate and water. The aqueous phase was washed with ethyl acetate (2×30 mL), adding solid NaCl to break the emulsion. Organic washings were combined and dried over $Na_2SO_4$. Ethyl acetate was removed in vacuo and the crude product 206 (1.54 g, 68%) was used without further purification. MS (ESI)=128 (MH$^+$).

Step 2: 6-N-Methylamino hexanoic acid (207)

A mixture of N-methyl ε-caprolactam 206 (1.1 g, 8.6 mmol) and 8N HCl (8 mL) and $H_2O$ (4 mL) was refluxed for 18 hours. The resulting solution was cooled to room temperature, diluted with $H_2O$ (20 mL) and the mixture was evaporated to dryness. Additional $H_2O$ (10 mL) was added and again removed in vacuo. The crude residue was triturated with acetone (2×5 mL), removing acetone each time. The resulting solid was dried in vacuo to yield the desired product 207 (1.21 g, 96%). MS (ESI)=146 (MH$^+$).

Step 3: 6-N-(2-naphthylmethyl-methylamino)hexanoic acid (208)

Following the procedure described in Example 122, step 1, but substituting respectively the amino acid 207 for the azepan-2-one, 2-bromomethyl-naphthalene for methyl iodide, and DMF for THF, the title compound 208 was obtained in 45% yield after purification by column chromatography (33% to 90% methanol in dichloromethane).

Step 4: N-Hydroxy-6-N-(2-naphthylmethyl-methylamino)hexanamide (209)

Following the procedure described in Example 14, step 3, but substituting carboxylic acid 208 for 37, and using 1.1 equivalent of NH$_2$OH.HCl and triethylamine each, the title compound 209 was obtained in 20% yield. $^1$H NMR: (300 MHz, DMSO-d$_6$) δ 10.3 (br s, 1H), 8.65 (br d, J=0.8 Hz, 1H), 7.86 (m, 3H), 7.80 (s, 1H), 7.47 (m, 3H), 3.58 (s, 2H), 2.33 (t, J=7.2 Hz, 2H), 2.12 (s, 3H), 1.93 (t, J=7.3 Hz, 2H), 1.48 (m, 4H), 1.26 (m, 2H).

Example 123

N-(2-Aminophenyl)-N-(2-naphthylmethyl-methylamino)hexanamide (210)

Following the procedure described in Example 22, but substituting carboxylic acid 208 for 50g, the title compound 210 was obtained in 20% yield. $^1$H NMR: (300 MHz, DMSO-d$_6$) δ 9.1 (br s, 1H), 7.86 (m, 3H), 7.86 (m, 3H), 7.78 (br s, 1H), 7.47 (m, 3H), 7.14 (dd, J=8.0, 1.4 Hz, 1H), 6.87 (dt, J=8.0, 1.4 Hz, 1H), 6.70 (dd, J=8.0, 1.4 Hz, 1H), 6.51 (dt, J=7.4, 1.4 Hz, 1H), 4.81 (br, 2H), 3.63 (br, 2H), 2.39 (br, 2H), 2.30 (t, J=7.3 Hz, 2H), 2.16 (br s, 3H), 1.56 (m, 4H), 1.35 (m, 2H).

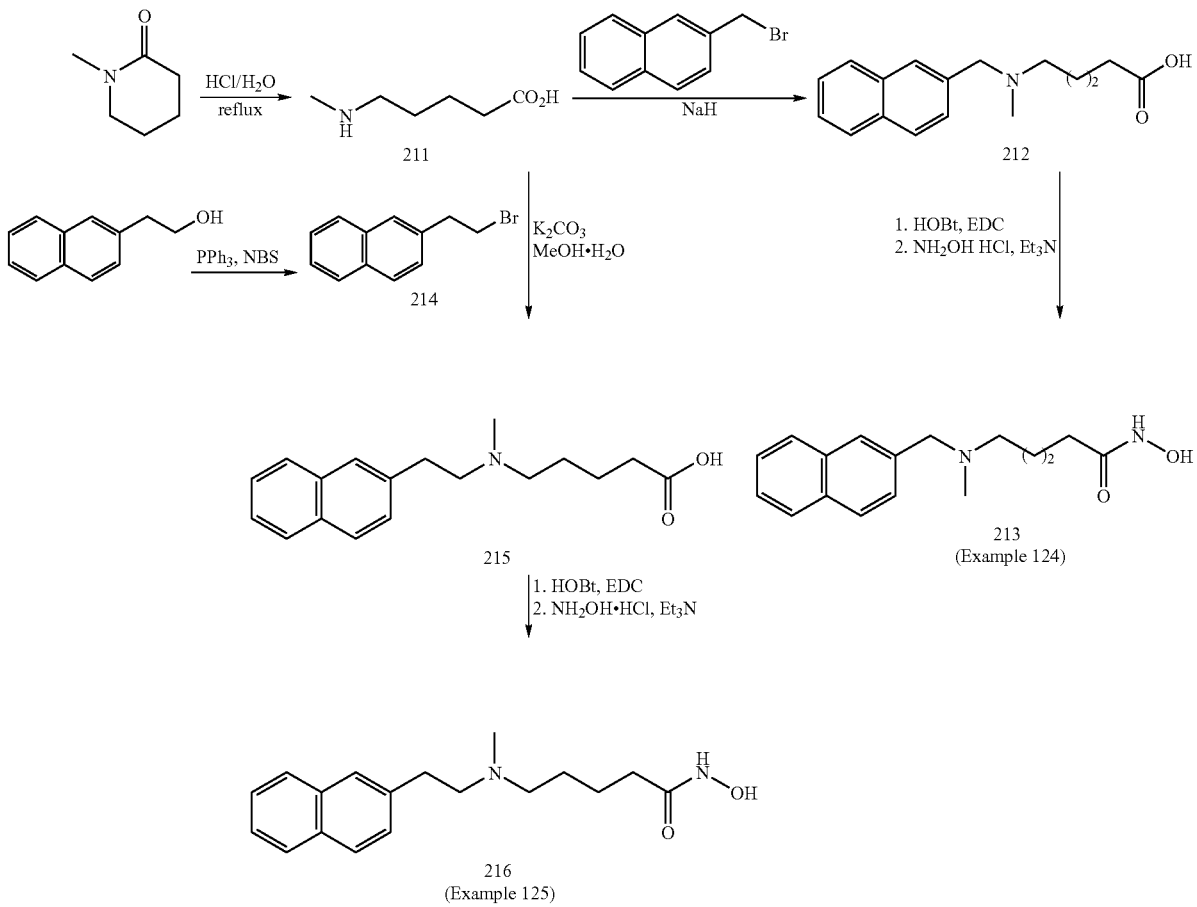

Example 124

N-Hydroxy-5-N-(2-naphthylmethyl-methylamino)pentanamide (213)

Step 1: 5-Methylamino-pentanoic acid (211)

Following the procedure described in Example 122, step 2, but substituting 1-methyl-2-piperidone for 206, the title compound 211 was obtained in 95% yield. MS (ESI)=132 (MH$^+$).

Step 2: 5-N-(2-naphthylmethyl-methylamino)pentanoic acid (212)

Following the procedure described in Example 122, step 3, but substituting amino acid 211 for 207, the title compound 212 was obtained in 58% yield. MS (ESI)=272 (MH$^+$).

Step 3: N-Hydroxy-5-N-(2-naphthylmethyl-methylamino)pentanamide (213)

Following the procedure described in Example 14, step 3, but substituting carboxylic acid 212 for 37, and using 1.1 equivalent of NH$_2$OH.HCl and triethylamine each, the title compound 213 was obtained in 33% yield. $^1$H NMR: (300 MHz, DMSO-d$_6$) δ 10.30 (br s, 1H), 8.61 (br s, 1H), 7.85 (m, 3H), 7.75 (s, 1H), 7.46 (m, 3H), 3.57 (s, 2H), 2.34 (t, J=6.9 Hz, 2H), 2.1 (s, 3H), 1.93 (t, J=6.9 Hz, 2H), 1.47 (m, 4H).

Example 125

N-Hydroxy-5-N-[2-(2-naphthylethyl)-methylamino]pentanamide (216)

Step 1: 2-(2-Bromoethyl)naphthalene (214)

A solution of triphenylphosphine (0.57 g, 2.2 mmol) and N-bromosuccinimide (0.39 g, 2.2 mmol) in anhydrous dichloromethane (4 mL) was stirred for 10 minutes. 2-Naphthalenethanol (0.25 g, 1.45 mmol) was added, followed inmmediately by imidazole (0.25 g, 1.45 mmol) and the mixture was stirred at room temperature for 18 hours. The reaction mixture was partitioned between H$_2$O and dichloromethane. The aqueous layer was extracted with diethyl ether (2×20 mL) and the combined organic extracts were dried over MgSO$_4$ and evaporated to dryness. The crude residue was purified by column chromatography through a plug of silica gel eluting with 10% ethyl acetate in hexanes to afford a colorless solid 214 (0.29 g, 86%).

Step 2: 5-N-[2-(2-Naphthylethyl)-methylamino]pentanoic acid (215)

A mixture of amino acid 211 (60 mg, 0.45 mmol), 2-(2-bromoethyl)naphthalene (0.15 g, 0.64 mmol) and potassium carbonate (0.24 g, 1.7 mmol) in methanol-$H_2O$ (2: 1.5 mL) was heated at reflux for 7 hours and then at room temperature for 18 hours. Methanol was removed in vacuo, the remaining aqueous residue was partitioned between ethyl acetate and $H_2O$ and extracted with ethyl acetate (2×20 mL). The aqueous layer was evaporated to dryness, triturated with methanol and filtered to remove inorganic solids. The filtrate was evaporated to dryness and then purified by column chromatography using a gradient of 25 to 75% methanol in dichloromethane to afford a colorless solid 215 (85 mg, 69%). MS (ESI)=286 (M+1).

Step 3: N-Hydroxy-5-N-[2-(2-naphthylethyl)-methylamino]pentanamide (216)

Following the procedure described in Example 14, step 3, but substituting carboxylic acid 215 for 37, and using 1.1 equivalent of $NH_2OH \cdot HCl$ and triethylamine each, the title compound 216 was obtained in 15% yield. $^1H$ NMR: (300 MHz, DMSO-$d_6$) δ 7.83 (m, 3H), 7.71 (s, 1H), 7.44 (m, 3H), 2.86 (dd, J=8.5, 6.9 Hz, 2H), 2.60 (m, 2H), 2.34 (t, J=7.0 Hz, 2H), 2.2 (s, 3H), 1.93 (t, J=7.15 Hz, 2H), 1.43 (m, 4H).

Example 126

N-Hydroxy-6-N-(Benzyloxycarbonyl-2-naphthylmethylamino)hexanamide (220a)

Step 1: N-2-Naphthylmethyl-ε-caprolactam (217)

Following the procedure described in Example 122, step 1, but substituting respectively 2-bromomethylnaphthalene for methyl iodide, and DMF for THF, the title compound 217 was obtained in 97% yield. MS (ESI)=254 (MH$^+$).

Step 2: 6-N-(2-Naphthylmethylaminohexanoic acid (218)

Following the procedure described in Example 122, step 2, but substituting 217 for 206, the title compound 218 was obtained in 69% yield. MS (ESI)=272 (MH$^+$).

Step 3: 6-N-(Benzyloxycarbonyl-2-naphthylmethylamino)hexanoic acid (219)

To an emulsion of compound 218 (70 mg, 0.26 mmol) in dioxane-$H_2O$ (1.5:2.5 mL) stirring at room temperature was added NaOH (0.1 g, 2.5 mmol) dissolved in 1 mL $H_2O$ followed by benzyloxycarbonyl chloride (0.044 mL, 0.31 mmol). The mixture was stirred vigorously for 18 hours. Dioxane was removed in vacuo and the resulting aqueous

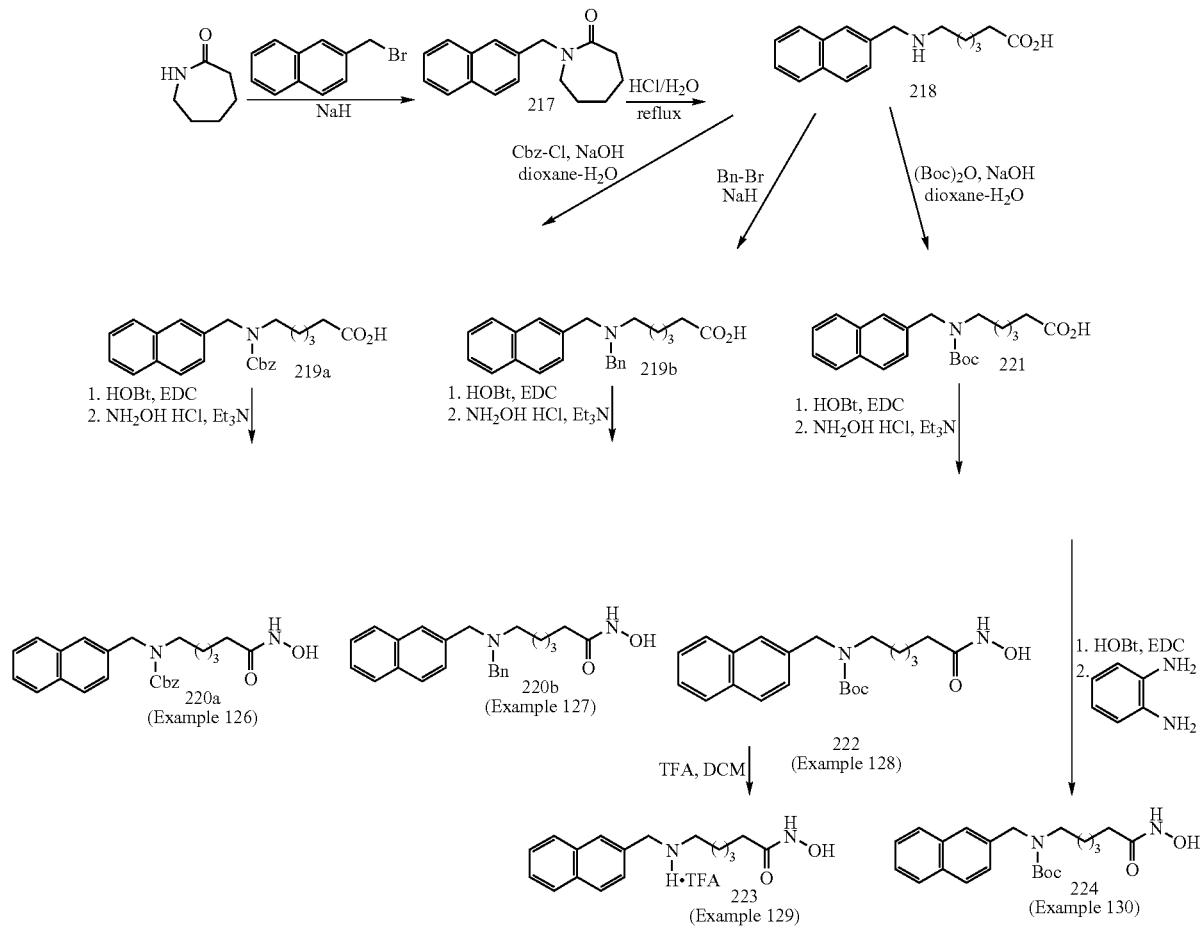

layer was diluted with H$_2$O and extracted with diethyl ether (2×20 mL). Subsequently, the aqueous layer was neutralized to pH 7 using a KHSO$_4$ solution (0.37 M) and then extracted with ethyl acetate (2×30 mL). The combined organic extracts were dried over Na$_2$SO$_4$ and then evaporated to dryness to afford a crude oil 219a (75 mg, 72%) that was used without further purification. MS (ESI)=428 (MH$^+$).

Step 4: N-Hydroxy-6-N-(Benzyloxycarbonyl-2-naphthylmethylamino)hexanamide (220a)

Following the procedure described in Example 14, step 3, but substituting carboxylic acid 219a for 37, and using 1.1 equivalent of NH$_2$OH.HCl and triethylamine each, the title compound 220a was obtained in 66% yield. $^1$H NMR: (300 MHz, DMSO-d$_6$) δ 10.30 (br s, 1H), 8.65 (br s, 1H), 7.87 (m, 3H), 7.7 (br d, J=10.7 Hz, 1H), 7.49 (t, J=3.7 Hz, 2H), 7.38 (m, 4H), 7.25 (m, 2H), 5.13 (br d, J=6.6 Hz, 2H), 4.61 (s, 2H), 3.22 (m, 2H), 2.1 (m, 1H), 1.88 (m, 2H), 1.47 (m, 4H), 1.20 (m, 2H).

Example 127

N-Hydroxy-6-N-(Benzyl-2-naphthylmethylamino)hexanamide (220b)

Step 1:
6-N-(Benzyl-2-naphthylmethylamino)hexanoic acid (219b)

Following the procedure described in Example 122, step 1, but substituting respectively the amino acid 218 for the ε-caprolactam, benzyl bromide for methyl iodide, and DMF for THF, the title compound 219b was obtained in 56% yield. MS (ESI)=362 (MH$^+$).

Step 2: N-Hydroxy-6-N-(benzyl-2-naphthylmethylamino)hexanamide (220b)

Following the procedure described in Example 14, step 3, but substituting carboxylic acid 219b for 37, and using 1.1 equivalent of NH$_2$OH.HCl and triethylamine each, the title compound 220b was obtained in 27% yield. $^1$H NMR: (300 MHz, DMSO-d$_6$) δ 10.29 (br s, 1H), 8.65 (br s, 1H), 7.84 (m, 4H), 7.48 (m, 3H), 7.33 (m, 4H), 7.21 (m, 1H), 3.66 (s, 2H), 3.54 (s, 2H), 3.35 (t, J=7.1 Hz, 2H), 1.87 (t, J=7.3 Hz, 2H), 1.46 (m, 2H), 1.40 (m, 2H), 1.19 (m, 2H).

Example 128

N-Hydroxy-6-N-(tert-butoxycarbonyl-2-naphthylmethylamino)hexanamide (222)

Step 1: 6-N-(tert-Butoxycarbonyl-2-naphthylmethylamino)hexanoic acid (221)

Following the procedure described in Example 126, step 3, but substituting di-tert-butyl dicarbonate for benzyloxy carbonyl chloride, the title compound 221 was obtained in 88% yield. MS (ESI)=394 (MH$^+$).

Step 2: N-Hydroxy-6-N-(tert-butoxycarbonyl-2-naphthylmethylamino)hexanamide (222)

Following the procedure described in Example 14, step 3, but substituting carboxylic acid 221 for 37, and using 1.1 equivalent of NH$_2$OH.HCl and triethylamine each, the title compound 222 was obtained in 60% yield. $^1$H NMR: (300 MHz, DMSO-d$_6$) δ 10.31 (br s, 1H), 8.65 (br s, 1H), 7.87 (m, 3H), 7.7 (br s, 1H), 7.5 (m, 2H), 7.37 (m, 1H), 4.52 (br s, 2H), 3.15 (m, 2H), 1.90 (t, J=7.3 Hz, 2H), 1.41 (m, 13H), 1.17 (m, 2H).

Example 129

N-Hydroxy-6-N-(2-naphthylmethylamino)hexanamide trifluoroacetate (223)

To a stirring solution of compound 222 (65.0 mg, 0.17 mmol) in anhydrous dichloromethane (3 mL) at room temperature was added trifluoroacetic acid (3.5 mL) dropwise. The solution was stirred for 18 hours. dichloromethane and trifluoroacetic acid were removed in vacuo, the residue was dissolved in H$_2$O and then extracted with ethyl acetate (2×20 mL). The aqueous layer was lyophilized to yield the final product 223 as a colorless oil (30.0 mg, 45%). $^1$H NMR: (300 MHz, DMSO-d$_6$) δ 10.35 (s, 1H), 8.79 (br s, 2H), 8.67 (s, 1H), 7.96 (m, 4H), 7.58 (m, 3H), 4.3 (br s, 2H), 2.94 (br s, 2H), 1.93 (t, J=7.4 Hz, 2H), 1.61 (m, 2H), 1.49 (m, 2H), 1.27 (m, 2H).

Example 130

N-(2-Aminophenyl)-6-N-(tert-butoxycarbonyl-2-naphthylmethylamino)-hexanamide (224)

Following the procedure described in Example 22, but substituting carboxylic acid 221 for 50g, the title compound 224 was obtained in 53% yield. $^1$H NMR: (300 MHz, DMSO-d$_6$) δ 9.06 (br s, 1H), 7.87 (m, 3H), 7.71(br s, 1H), 7.49 (m, 2H), 7.38 (d, J=8.5 Hz, 1H), 7.13 (d, J=6.6 Hz, 1H), 6.88 (m, 1H), 6.70 (dd, J=1.1, 8.0 Hz, 1H), 6.52 (dt, J=1.4, 8.2 Hz, 1H), 4.8 (m, 2H), 4.54 (br s, 2H), 3.17 (m, 2H), 2.28 (t, J=7.3 Hz, 2H), 1.44 (m, 15H).

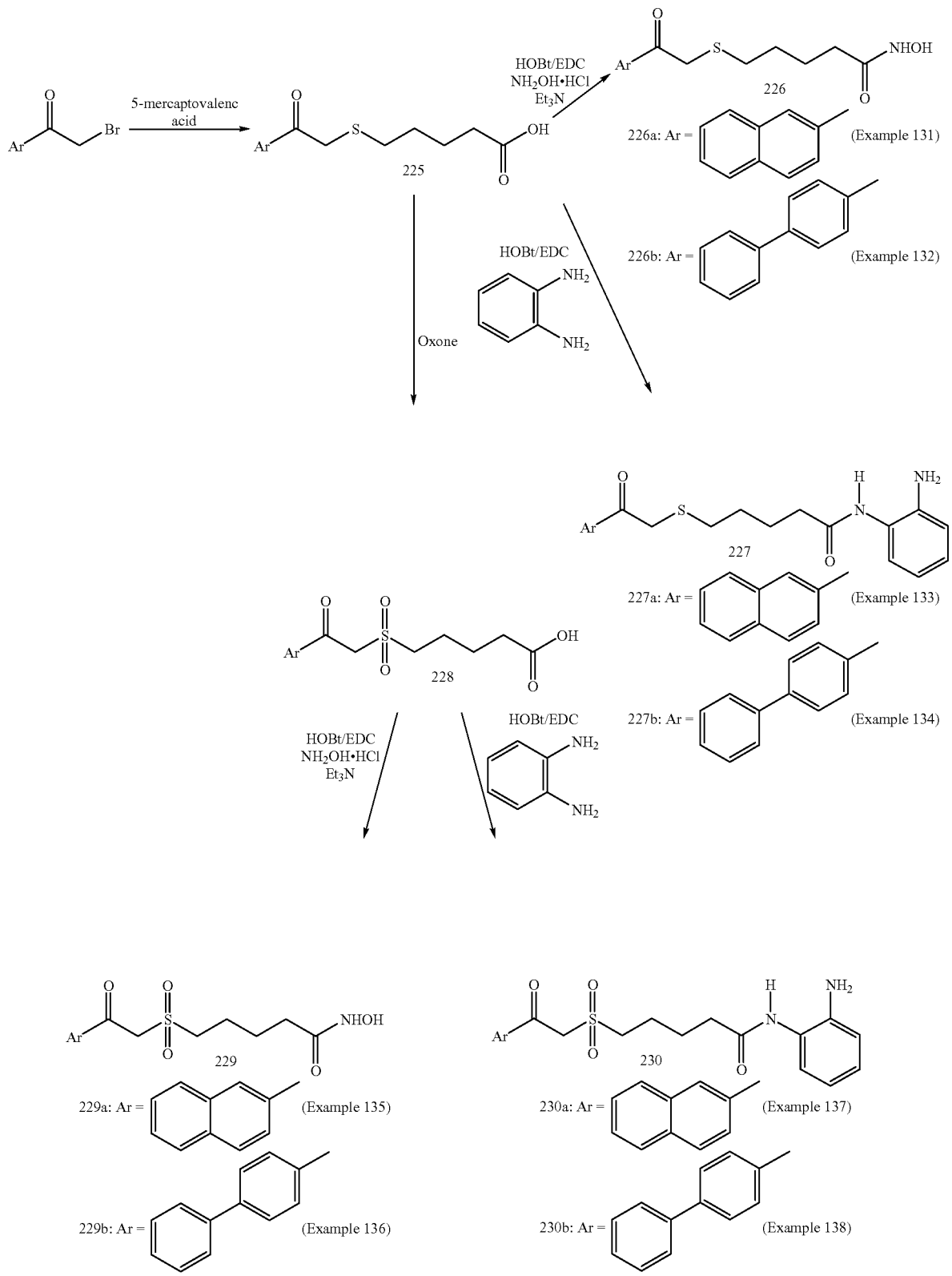

Example 131

N-Hydroxy-5-(2-naphthoylmethylsulfanyl)pentanamide (226a)

Step 1: 5-(2-Naphthoylmethylsulfanyl)pentanoic acid (225a)

To a solution of bromomethyl-2-naphthyl ketone (2 g, 8.00 mmol) in anhydrous THF (50 mL) was added 5-mercaptovaleric acid (1.07 g, 8.00 mmol), followed by potassium carbonate (5.71 g, 41 mmol). The suspension was refluxed for 1 hour, cooled to the room temperature and filtered. The solid was collected, dissolved in a 1:1 mixture water-THF and acidified with HCl (pH 1-2). The acidic solution was extracted with ether, dried (MgSO$_4$), filtered and evaporated to produce the title compound 225a (1.21 g, 50% yield). $^1$H NMR: (300 MHz, DMSO-d$_6$) δ 11.98 (br s, 1H), 8.69 (s, 1H), 8.10 (d, J=7.5 Hz, 1H), 8.00-7.98 (m, 3H), 7.67-7.61 (m, 2H), 4.09 (s, 2H), 2.52 (t, J=6.6 Hz, 2H), 2.19 (t, J=6.6 Hz, 2H), 1.56-1.53 (m, 4H).

Step 2: N-Hydroxy 5-(2-naphthoylmethylsulfanyl)pentanamide (226a)

Following the procedure described in Example 14, step 3, but substituting carboxylic acid 225a for 37, and using 1.1 equivalent of NH$_2$OH.HCl and triethylamine each, the title compound 226a was obtained in 24% yield. 1H NMR: (300 MHz, DMSO-d$_6$) δ 10.33 (s, 1H), 8.70 (s, 1H), 8.66 (s, 1H), 8.10 (d, J=7.7 Hz, 1H), 8.00-7.97 (m, 3H), 7.70-7.59 (m, 2H), 2.51 (t, J 6.9 Hz, 2H), 4.10 (s, 2H), 1.94-1.91 (m, 2H), 1.53-1.51 (m, 4H).

Example 132

N-Hydroxy-5-(4-biphenylcarbonylmethanesulfanyl) pentanamide (226b)

Step 1: 5-(4-Biphenylcarbonylmethanesulfanyl)pentanoic acid (225b)

Following the procedure described in Example 131, step 1, but substituting bromomethyl-4-biphenyl ketone for bromomethyl-2-naphthyl ketone, the title compound 225b was obtained in 81% yield. $^1$H NMR: (300 MHz, CDCl$_3$) δ 8.05 (d, J=8.0 Hz, 2H), 7.71-7.62 (m, 4H), 7.50-7.40 (m, 3H), 3.81 (s, 2H), 2.60 (t, J=6.3 Hz, 2H), 2.38 (t, J=6.9 Hz, 2H),1.72-1.68 (m, 4H).

Step 2: N-Hydroxy-5-(4-biphenylcarbonylmethanesulfanyl)pentanamide (226b)

Following the procedure described in Example 14, step 3, but substituting carboxylic acid 225b for 37, and using 1.1 equivalent of NH$_2$OH.HCl and triethylamine each, the title compound 226b was obtained in 30% yield. $^1$H NMR: (300 MHz, DMSO-d$_6$) δ 10.31 (s, 1H), 8.65 (s, 1H), 8.05 (d, J=8.2 Hz, 2H), 7.73 (d, J=8.0 Hz, 2H), 7.80 (d, J=8.5 Hz, 2H), 7.51-7.41 (m, 3H), 3.98 (s, 2H), 1.92 (br s, 4H), 1.51 (br. s, 4H),

Example 133

N-(2-Aminophenyl)-5-(2-naphthoylmethylsulfanyl) pentanamide (227a)

Following the procedure described in Example 22, but substituting carboxylic acid 225a for 50g, the title compound 227a was obtained in 20% yield. $^1$H NMR: (300 MHz, DMSO-d$_6$) δ 9.07 (s, 1H), 8.69 (s, 1H), 8.10-7.97 (m, 4H), 7.68-7.58 (m, 2H), 7.11 (d, J=7.1 Hz, 1H), 6.86 (t, J=7.1 Hz, 1H), 6.80 (d, J=7.7 Hz, 1H), 6.50 (t, J=7.4 Hz, 1H), 4.78 (s, 2H), 4.10 (s, 2H), 2.56 (t, J=6.6 Hz, 2H), 2.30 (t, J=6.6 Hz, 2H), 1.61 (br s, 4H).

Example 134

N-(2-Aminophenyl)-5-(4-biphenylcarbonylmethanesulfanyl)pentanamide (227b)

Following the procedure described in Example 22, but substituting carboxylic acid 225b for 50g, the title compound 227b was obtained in 34% yield. $^1$H NMR: (300 MHz, DMSO-d$_6$) δ 9.07 (s, 1H), 8.05 (d, J=8.2 Hz, 2H), 7.80 (d, J=8.0 Hz, 2H), 7.73 (d, J=7.7 Hz, 2H), 7.51-7.41 (m, 3H), 7.12 (d, J=7.5 Hz, 1H), 6.86 (t, J=7.5 Hz, 1H), 6.69 (d, J=7.8 Hz, 1H), 6.51 (t, J=7.5 Hz, 1H), 4.79 (s, 2H), 4.00 (s, 2H), 2.53 (t, J=6.6 Hz, 2H), 2.30 (t, J=7.2 Hz, 2H), 1.61 (br s, 4H).

Example 135

N-Hydroxy-5-(2-naphthoylmethylsulfonyl)pentanamide (229a)

Step 1: 5-(2-Naphthoylmethylsulfonyl)pentanoic acid (228a)

To a solution of 225a (755 mg, 2.50 mmol) in methanol (30 mL) at 0° C. was added a solution of oxone (2.3 g, 3.75 mmol) in water (30 mL). The mixture stirred at the same conditions for 6 hours, methanol was removed in vacuum and the water phase was extracted with chloroform. The extract was dried over MgSO$_4$, filtered and evaporated to afford the title compound 228a (520 mg, 62% yield). MS (ESI)=335 (MH$^+$).

Step 2: N-Hydroxy-5-(2-naphthoylmethylsulfonyl)pentanamide (229a)

Following the procedure described in Example 14, step 3, but substituting carboxylic acid 228a for 37, and using 1.1 equivalent of NH$_2$OH.HCl and triethylamine each, the title compound 229a was obtained in 30% yield. $^1$H NMR: (300 MHz, DMSO-d$_6$) δ 10.38 (br s, 1H), 8.83 (s, 1H), 8.71 (s, 1H), 8.13 (d, J=7.7 Hz, 1H), 8.06-7.99 (m, 3H), 7.74-7.63 (m, 2H), 5.19 (s, 1H), 3.34 (t, J=7.4 Hz, 2H), 2.00 (t, J=6.7 Hz, 2H), 1.78-1.60 (m, 4H).

Example 136

N-Hydroxy-5-(4-biphenylcarbonylmethylsulfonyl) pentanamide (229b)

Step 1: 5-(4-Biphenylcarbonylmethanesulfonyl)pentanoic acid (228b)

Following the procedure described in Example 135, step 1, but substituting 228b for 228a, the title compound 228b was obtained in 91% yield.

Step 2: N-Hydroxy-5-(4-biphenylcarbonylmethyl-sulfonyl)pentanamide (229b)

Following the procedure described in Example 14, step 3, but substituting carboxylic acid 228b for 37, and using 1.1 equivalent of NH$_2$OH.HCl and triethylamine each, the title compound 228b was obtained in 52% yield. $^1$H NMR: (300 MHz, DMSO-d$_6$) δ 10.37 (s, 1H), 8.70 (s, 1H), 8.11 (d, J=8.5 Hz, 2H), 7.86 (d, J=8.5 Hz, 2H), 7.77 (dd, J=1.4 Hz, J=8.5 Hz, 2H), 7.53-7.43 (m, 3H), 5.08 (s, 2H), 3.38-3.25 (t, 2H), 1.99 (t, J=6.6 Hz, 2H), 1.72-1.61 (m, 4H).

Example 137

N-(2-Aminophenyl)-5-(2-naphthoylmethylsulfonyl)pentanamide (230a)

Following the procedure described in Example 22, but substituting carboxylic acid 228a for 50g, the title compound 230a was obtained in 30% yield. $^1$H NMR: (300 MHz, DMSO-d$_6$) δ 9.12 (s, 1H), 8.83 (s, 1H), 8.12 (d, J=7.4 Hz, 1H), 8.06-7.99 (m, 3H), 7.74-7.63 (m, 2H), 7.15 (dd, J=1.4 Hz, J=8.0 Hz, 1H), 6.88 (dd, J=1.4 Hz, 8.0 Hz, 1H), 6.70 (dd, J=1.4 Hz, 8.0 Hz, 1H), 6.52 (dd, J=1.2 Hz, 8.8 Hz, 1H), 5.21 (s, 1H), 4.892 (br s, 2H), 3.38 (t, J=7.1 Hz, 2H), 2.38 (t, J=7.1 Hz, 2H), 1.84-1.72 (m, 4H).

Example 138

N-(2-Aminophenyl)-5-(4-biphenylcarbonylmethyl-sulfonyl)pentanamide (229b)

Following the procedure described in Example 22, but substituting carboxylic acid 228b for 50g, the title compound 230b was obtained in 52% yield. $^1$H NMR: (300 MHz, DMSO-d$_6$) δ 9.12 (s, 1H), 8.13 (d, J=8.2 Hz, 2H), 7.87 (d, J=8.2 Hz, 2H), 7.77 (d, J=6.7 Hz, 2H), 7.53-7.44 (m, 3H), 7.15 (d, J=8.0 Hz, 1H), 6.88 (t, J=8.0 Hz, 1H), 6.70 (d J=8.0 Hz, 1H), 6.52 (t, J=7.7 Hz, 1H), 5.11 (s, 2H), 4.82 (s, 2H), 3.36 (t, J=6.9 Hz, 2H), 2.37 (t, J=7.1 Hz, 2H), 1.78-1.71 (m, 4H).

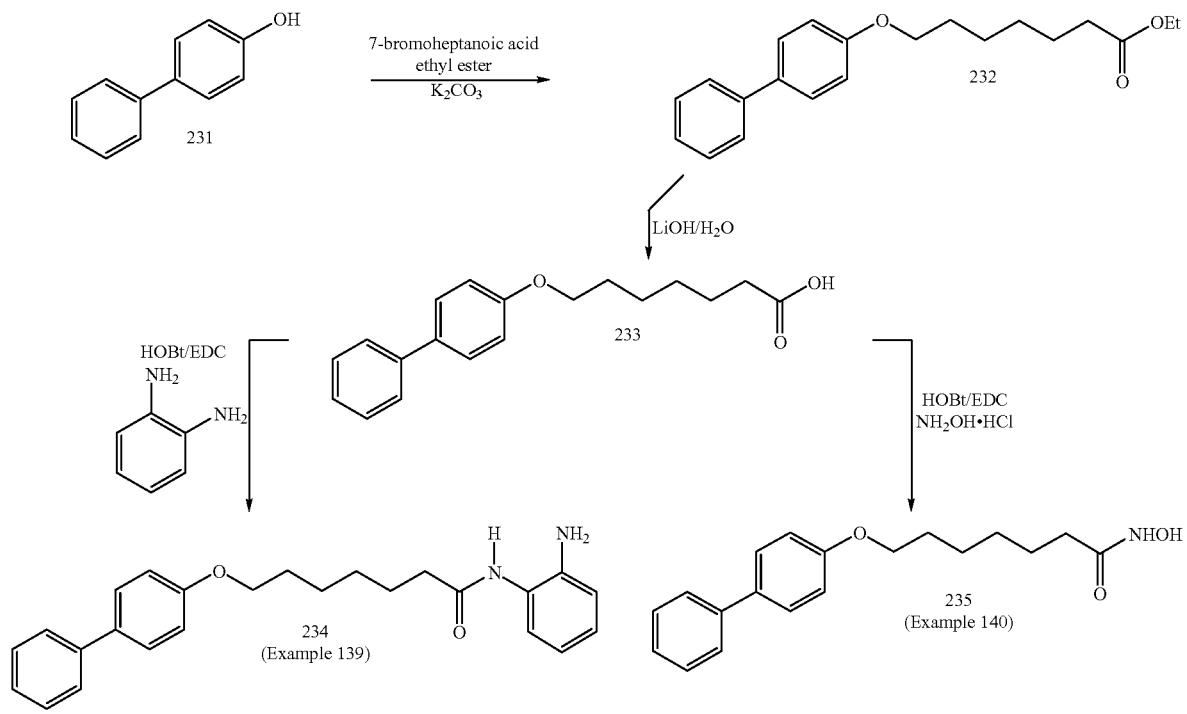

Example 139

N-(2-Aminophenyl)-7-(4biphenyloxy)heptanamide (234)

Step 1: Ethyl-7-(4-biphenyloxyheptanoate (232)

To a solution of 4-phenylphenol (231) (1.00 g, 5.88 mmol) in acetone (100 mL) was added potassium carbonate (3.25 g, 23.52 mmol) and potassium iodide (200 mg, 1.57 mmol), followed by the addition of ethyl-7-bromoheptanoate (1.81 g, 7.65 mmol). The suspension was refluxed for 36 hours, cooled to room temperature and filtered. Filtrate was evaporated and the remained solid was recrystallized from hexane to produce the title compound 232 (1.73 g, 90% yield). MS (ESI)=327 (MH$^+$).

Step 2: 7-(4-Biphenyloxy)heptanoic acid (233)

To a solution of the ester 232 (1.70 g, 5.21 mmol) in THF (50 mL) was added a solution of lithium hydroxide hydrate (1.30 g, 30.95 mmol) in water (50 mL). The reaction mixture was stirred 18 hours at room temperature, THF was evaporated and the aqueous phase was acidified with conc. HCl (pH 1-2). A precipitate formed which was collected by filtration and dried to afford the title compound 233 (1.54 g, 99%). MS (ESI)=321 (M$^+$+Na).

Step 3: N-(2-Aminophenyl)-7-(4-biphenyloxy)heptanamide (234)

Following the procedure described in Example 22, but substituting carboxylic acid 233 for 50g, the title compound 234 was obtained in 44% yield. $^1$H NMR: (300 MHz, DMSO-$d_6$) δ 9.08 (s, 1H), 7.60-7.55 (m, 4H), 7.41 (t, J=7.7 Hz, 2H), 7.29 (t, J=7.1 Hz, 1H), 7.14 (dd, J=8.0, 1.4 Hz, 1H), 7.00 (d, J=8.8 Hz, 2H), 6.87 (t, J=8.0 Hz, 1H) 6.70 (dd, J=8.0, 1.4 Hz, 1H), 6.52 (dd, J=8.5, 1.1 Hz, 1H), 4.81 (br s, 2H), 4.00 (t, J=6.3 Hz, 2H), 2.32 (t, J=7.4 Hz, 2H), 1.76-1.69 (m, 2H), 1.67-1.57 (m, 2H), 1.47-1.38 (m, 4H).

Example 140

N-Hydroxy-7-(4-biphenyloxy)heptanamide (235)

Following the procedure described in Example 14, step 3, but substituting carboxylic acid 233 for 37, and using 1.1 equivalent of NH$_2$OH.HCl and triethylamine each, the title compound 235 was obtained in 52% yield. $^1$H NMR: (300 MHz, DMSO-$d_6$) δ 10.33 (s, 1H), 8.65 (s, 1H), 7.60-7.54 (m, 4H), 7.40 (t, J=7.5 Hz, 2H), 7.28 (t, J=7.2 Hz, 1H), 6.98 (d, J=8.7 Hz, 2H), 3.97 (t, J=6.3 Hz, 2H), 1.93 (t, J=7.1 Hz, 2H), 1.70 (t, J=7.4 Hz, 2H), 1.52-1.28 (m, 6H).

evaporated in vacuum to form an oily residue. This material was refluxed for 7 hours in formic acid (70 ml), cooled to room temperature and evaporated. The solid was dissolved in dichloromethane, decolorized with the activated charcoal, filtered and evaporated to give an oily material which upon crystallization in methanol (−10° C.) afforded the title compound 237a (2.38 g, 46% yield). MS (ESI)=261 (MH$^+$).

Step 2: N-Hydroxy-6-[3-(4-oxo-4H-quinazolinyl]hexanamide (238a)

Following the procedure described in Example 14, step 3, but substituting carboxylic acid 1H-benzo[d][1,3]oxazine-2,4-dione 237a for 37, and using 1.1 equivalent of NH$_2$OH.HCl and triethylamine each, the title compound 238a was obtained in 23% yield. $^1$H NMR: (400 MHz, DMSO-$d_6$) δ 10.32 (s, 1H), 8.66 (s, 1H), 8.38 (s, 1H), 8.14 (br d, J=7.1 Hz, 1H), 7.81 (dd, J=8.2, 1.3 Hz, 1H), 7.66 (br d, J=8.1 1H), 7.53 (br t, J=7.7 Hz, 1H), 3.95 (t, J=7.1 Hz, 2H), 1.93 (t, J=7.2 Hz, 2H), 1.72-1.62 (m, 2H), 1.56-1.46 (m, 2H), 1.30-1.23 (m, 2H).

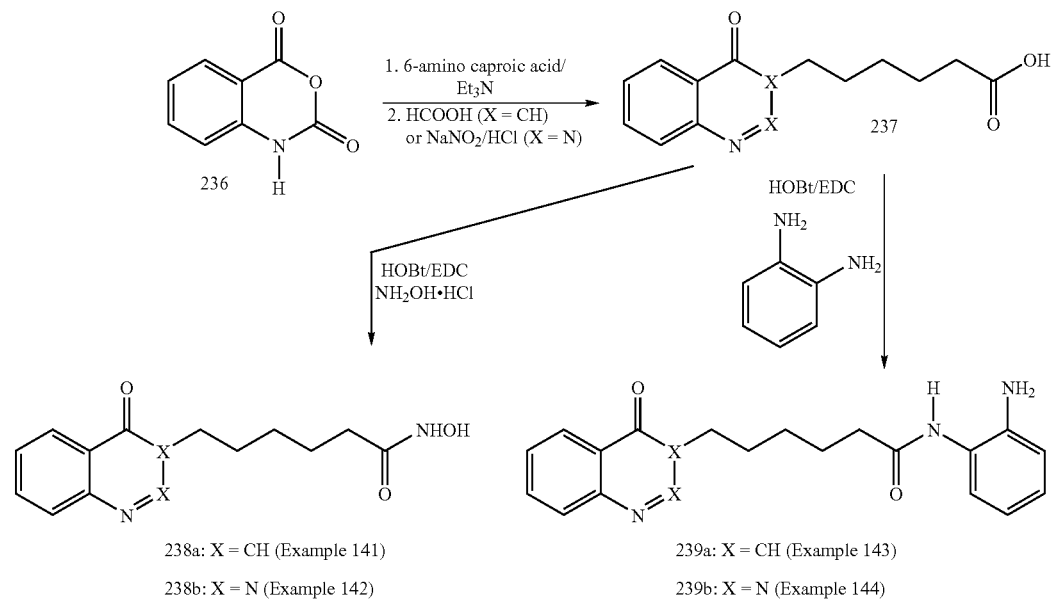

238a: X = CH (Example 141)
238b: X = N (Example 142)

239a: X = CH (Example 143)
239b: X = N (Example 144)

Example 141

N-Hydroxy-6-[3-(4-Oxo-4H-quinazolinyl)]hexanamide (238a)

Step 1: 6-[3-(4-Oxo-4H-quinazolinyl)]hexanoic acid (237a)

To a solution of 6-aminohexanoic acid (2.88 g, 20.00 mmol) in water (50 mL) was added triethylamine (3.06 ml, 22.00 mmol) followed by a portionwise addition of 1H-benzo[d][1,3]oxazine-2,4-dione (isatoic anhydride, 236) (3.26 g, 20.00 mmol). The reaction mixture was stirred for 2 hours at 30-40° C., cooled to room temperature and

Example 142

N-Hydroxy-6-[3-(4-oxo-4H-benzo[d][1,2,3]triazinyl)]hexanamide (238b)

Step 1: 6-[3-(4Oxo-4H-benzo[d][1,2,3]triazinyl)]hexanoic acid (237b)

To a solution of 6-aminohexanoic acid (2.88 g, 20.00 mmol) in water (50 mL) was added triethylamine (3.06 ml, 22.00 mmol) followed by a portionwise addition of 1H-benzo[d][1,3]oxazine-2,4-dione (isatoic anhydride, 236) (3.26 g, 20.00 mmol). The reaction mixture was stirred for 2 hours at 30-40° C., cooled to 0° C., acidified with 20 mL 20% HCl and treated with a solution of sodium nitrite (1.70 g, 25 mmol) in 10 mL water (over a 10 min period of time). The whole mixture was stirring at ambient temperature for 18 hours to form a solid which was collected by filtration, dried, dissolved in dichloromethane and decolorized with the activated charcoal, filtered and evaporated. The residual material was crystallized in a dichloromethane-hexane mixture at −10° C. to afford the title compound 237b in 75% yield. MS (ESI)=262 (MH$^+$).

Step 2: N-Hydroxy-6-[3-(4-oxo-4H-benzo[d][1,2,3]triazinyl]hexanamide (238b)

Following the procedure described in Example 14, step 3, but substituting carboxylic acid 237b for 37, and using 1.1 equivalent of NH$_2$OH.HCl and triethylamine each, the title compound 238b was obtained in 32%. $^1$H NMR: (400 MHz, DMSO-d$_6$) δ 10.32 (s, 1H), 8.66 (s, 1H), 8.25 (dd, J=7.9, 1.0 Hz, 1H), 8.19 (br d, J=7.7 Hz, 1H), 8.08 (dd, J=7.2, 1.4 Hz, 1H), 7.94 (dd, J=7.2, 1.4 Hz, 1H), 4.37 (t, J=7.1 Hz, 2H), 1.94 (t, J=7.2 Hz, 2H), 1.85-1.75 (m, 2H), 1.58-1.48 (m, 2H), 1.35-1.27 (m, 2H).

Example 143

N-(2-Aminophenyl)-6-[3-(4-oxo-4H-quinazolinyl)]hexanamide (239a)

Following the procedure described in Example 22, but substituting carboxylic acid 237a for 50g, the title compound 239a was obtained in 25% yield. $^1$H NMR: (400 MHz, DMSO-d$_6$) δ 9.08 (s, 1H), 8.41 (s, 1H), 8.17 (dd, J=8.0, 1.1 Hz, 1H), 7.83 (dd, J=8.4, 1.5 Hz, 1H), 7.68 (br d, J=8.1 Hz, 1H), 7.55 (dd, J=8.0, 1.0 Hz, 1H), 7.12 (dd, J=7.8, 1.1 Hz, 1H), 6.88 (dd, J=8.0, 1.3 Hz, 1H), 6.70 (dd, J=7.9, 1.1 Hz, 1H), 6.51 (dd, J=7.7, 1.3 Hz, 1H), 4.80 (s, 2H), 3.99 (t, J=7.3 Hz, 2H), 2.32 (t, J=7.3 Hz, 2H), 1.77-1.70 (m, 2H), 1.67-1.60 (m, 2H), 1.39-1.33 (m, 2H).

Example 144

N-(2-Aminophenyl)-6-[3-(4-oxo-4H-benzo[d][1,2,3]triazinyl]hexanamide (239b)

Following the procedure described in Example 22, but substituting carboxylic acid 237b for 50g, the title compound 239b was obtained in 45% yield. $^1$H NMR: (400 MHz, DMSO-d$_6$) δ 9.07 (s, 1H), 8.25 (dd, J=7.9, 0.9 Hz, 1H), 8.19 (br d, J=8.1 Hz, 1H), 8.08 (dd, J=7.2, 1.4 Hz, 1H), 7.92 (dd, J=8.2, 1.2 Hz, 1H), 7.09 (dd, J=7.8, 1.2 Hz, 1H), 6.87 (dd, J=8.5, 1.4 Hz, 1H), 6.69 (dd, J=8.0, 1.3 Hz, 1H), 6.49 (dd, J=7.8, 1.4 Hz, 1H), 4.78 (s, 2H), 4.39 (t, J=7.1 Hz, 2H), 2.28 (t, J=7.4 Hz, 2H), 1.90-1.82 (m, 2H), 1.69-1.58 (m, 2H), 1.43-1.34 (m, 2H).

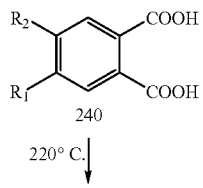

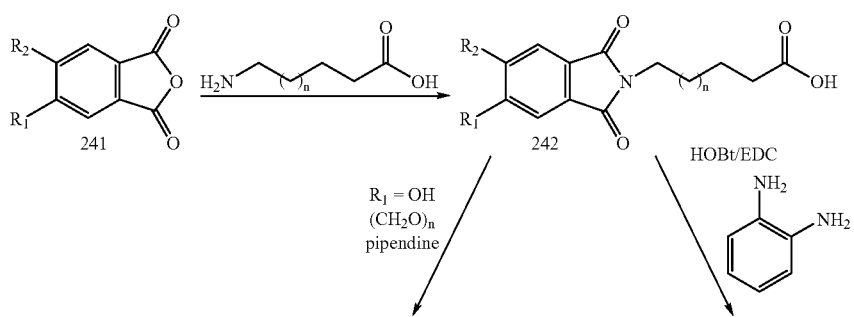

-continued

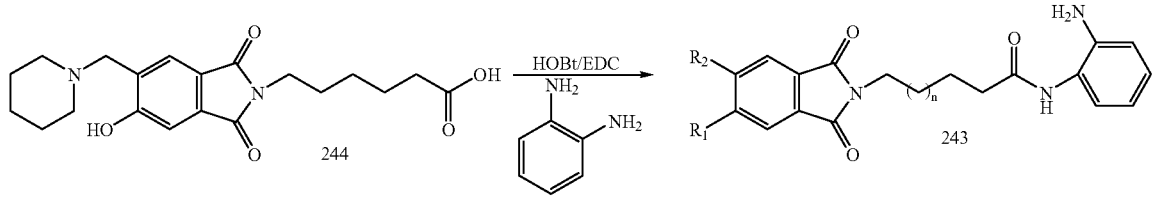

243a: n = 2, R₁ = R₂ = H (Example 145)
243b: n = 1, R₁ = R₂ = H (Example 146)
243c: n = 3, R₁ = R₂ = H (Example 147)
243d: n = 2, R₁ = CH₃, R₂ = H (Example 148)
243e: n = 2, R₁ = NO₂, R₂ = H (Example 149)
243f: n = 2, R₁ = R₂ = Cl (Example 150)
243g: n = 2, R₁ = OH, R₂ = H (Example 151)
243h: n = 2, R₁ = OH, R₂ = 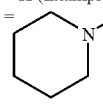 (Example 152)

Example 145

N-(2-Aminophenyl)-6-(N-phthaloyl)hexanamide (243a)

Step 1: 6-N-Phthaloylhexanoic acid (242a)

To a solution of phthalic anhydride 241a (1.48 g, 10.00 mmol) in anhydrous ethyl alcohol (20 mL) was added 6-aminocaproic acid (1.97 g, 15.00 mmol). The reaction mixture was refluxed for 16 hours, cooled to room temperature, evaporated to dryness to produce a solid material, which was triturated with water to form a suspension. The suspension was filtered, the solid was collected and dried to afford the title compound 242a (1.18 g, 45% yield). $^1$H NMR: (400 MHz, DMSO-d6) δ 7.87-7.80 (m, 4H), 3.54 (t, J=7.1 Hz, 2H), 2.17 (t, J=7.3 Hz, 2H), 1.62-1.44 (m, 4H), 1.30-1.23 (m, 2H).

Step 2: N-(2-Aminophenyl)-6-(N-phthaloyl)hexanamide (243a)

Following the procedure described in Example 22, but substituting carboxylic acid 242a for 50g, the title compound 243a was obtained in 31% yield. $^1$H NMR: (400 MHz, DMSO-d₆) δ 9.05 (s, 1H), 7.88-7.80 (m, 4H), 7.09 (dd, J=7.8, 1.4 Hz, 1H), 6.86 (dd, J=8.0, 1.5 Hz, 1H), 6.68 (dd, J=8.0, 1.4 Hz, 1H), 6.49 (dd, J=7.8, 1.5 Hz, 1H), 4.80 (s, 2H), 3.57 (t, J=7.0 Hz, 2H), 2.28 (t, J=7.3 Hz, 2H), 1.64-1.57 (m, 4H), 1.37-1.27 (m, 2H),

Example 146

N-(2-Aminophenyl)-5-(N-phthaloyl)pentanamide (243b)

Step 1: 5-(N-Phthaloyl)pentanoic acid (242b)

Following a procedure analogous to that described in Example 145, step 1, but substituting 5-amino-valeric acid for 6-amino-caproic acid, the title compound 242b was obtained in 46% yield. MS (ESI)=270 (M+Na⁺).

Step 2: N-(2-Aminophenyl)-5-(N-phthaloyl)-pentanamide (243b)

Following the procedure described in Example 22, but substituting carboxylic acid 242b for 50g, the title compound 243b was obtained in 28% yield. $^1$H NMR: (300 MHz, DMSO-d6) δ 9.06 (s, 1H), 7.87-7.80 (m, 4H), 7.11 (d, J=7.7 Hz, 1H), 6.86 (t, J=7.4 Hz, 1H), 6.68 (dd, J=8.0, 1.4 Hz, 1H), 6.50 (dd, J=8.8, 1.1 Hz, 1H), 4.78 (br s, 2H), 3.59 (t, J=5.8 Hz, 2H), 2.33 (t, J=6.6 Hz, 2H), 1.60 (m, 4H).

Example 147

N-(2-Aminophenyl)-7-(N-phthaloyl)heptanamide (243c)

Step 1: 7-(N-Phthaloyl)heptanoic acid (242c)

Following a procedure analogous to that described in Example 145, step 1, but substituting 7-aminoheptanoic acid for 6-amino-caproic acid, the title compound 242c was obtained in 46% yield. MS (ESI)=298 (MH⁺).

Step 2: N-(2-Aminophenyl)-7-(N-phthaloyl)-heptanamide (243c)

Following the procedure described in Example 22, but substituting carboxylic acid 242c for 50g, the title compound 243c was obtained in 28% yield. $^1$H NMR: (300 MHz, DMSO-d₆) δ 9.05 (s, 1H), 7.87-7.79 (m, 4H), 7.11 (d, J=7.7 Hz, 1H), 6.86 (t, J=7.4 Hz, 1H), 6.68 (d, J=8.0 Hz, 1H), 6.50 (t, J=7.7 Hz, 1H), 4.77 (s, 2H), 3.55 (t, J=7.1 Hz, 2H), 2.27 (t, J=7.4 Hz, 2H), 1.61-1.53 (m, 4H), 1.31-1.28 (m, 4H).

Example 148

N-(2-Aminophenyl)-6-(5-methyl-N-phthaloyl)hexanamide (243d)

Step 1: 6-(5-Methyl-N-phthaloyl)hexanoic acid (242d)

Following a procedure analogous to that described in Example 145, step 1, but substituting 5-methyl-N-phthaloyl for N-phthaloyl, the title compound 242d was obtained in 85% yield. MS (ESI)=276 (MH$^+$).

Step 2: N-(2-Aminophenyl)-6-(5-methyl-N-phthaloyl)hexanamide (243d)

Following the procedure described in Example 22, but substituting carboxylic acid 242d for 50g, the title compound 243d was obtained in 43% yield. $^1$H NMR: (300 MHz, DMSO-d$_6$) δ 9.04 (s, 1H), 7.73-7.60 (m, 3H), 7.07 (d, J=7.7 Hz, 1H), 6.85 (t, J=8.0 Hz, 1H), 6.67 (dd, J=8.0, 1.1 Hz, 1H), 6.50 (t, J=7.7 Hz, 1H), 4.77 (s, 2H), 3.52 (t, J=7.1 Hz, 2H), 2.46 (s, 3H, CH3), 2.27 (t, J=7.1 Hz, 2H), 1.58 (br s, 4H), 1.32-1.22 (m, 2H).

Example 149

N-(2-Aminophenyl)-6-(5-nitro-N-phthaloyl)hexanamide (243e)

Step 1: 6-(5-Nitro-N-phthaloyl)hexanoic acid (242e)

Following a procedure analogous to that described in Example 145, step 1, but substituting 5-nitro-N-phthaloyl for N-phthaloyl, the title compound 242e was obtained in 26% yield. MS (ESI)=305 (MH$^+$).

Step 2: N-(2-Aminophenyl)-6-(5-nitro-N-phthaloyl)hexanamide (243e)

Following the procedure described in Example 22, but substituting carboxylic acid 242e for 50g, the title compound 243e was obtained in 14% yield. $^1$H NMR: (400 MHz, DMSO-d$_6$) δ 9.05 (s, 1H), 8.60 (dd, J=8.2 Hz, 1.9 Hz, 1H), 8.47 (d, J=1.5 Hz, 1H), 8.10 (d, J=8.2 Hz, 1H), 7.10 (dd, J=7.9, 1.3 Hz, 1H), 6.86 (dd, J=8.0, 1.5 Hz, 1H), 6.67 (dd, J=1.3, J=8.0 Hz, 1H), 6.49 (dd, J=7.7, 1.4 Hz, 1H), 4.76 (s, 2H, 3.62 (t, J=7.0 Hz, 2H), 2.29 (t, J=7.3 Hz, 2H), 1.71-1.55 (m, 4H), 1.38-1.30 (m, 2H).

Example 150

N-(2-Aminophenyl)-6-(5,6-dichloro-N-phthaloyl)hexanamide (243f)

Step 1: 6-(5,6-Dichloro-N-phthaloyl)hexanoic acid (242f)

Following a procedure analogous to that described in Example 145, step 1, but substituting 5,6-dichloro-N-phthaloyl for N-phthaloyl, the title compound 242f was obtained in 64% yield. MS (ESI)=328 (MH$^+$).

Step 2: N-(2-Aminophenyl)-6-(5,6-dichloro-N-phthaloyl)hexanamide (243f)

Following the procedure described in Example 22, but substituting carboxylic acid 242f for 50g, the title compound 243f was obtained in 52% yield. $^1$H NMR: (300 MHz, DMSO-d6) δ 9.04 (s, 1H), 8.15 (s, 2H), 7.07 (d, J=7.4 Hz, 1H), 6.85 (t, J=7.8 Hz, 1H), 6.67 (d, J=8.0 Hz, 1H), 6.48 (t, J=7.7 Hz, 1H), 4.76 (s, 2H), 3.56 (t, J=6.9 Hz, 2H), 2.27 (t, J=7.1 Hz, 2H), 1.63-1.56 (m, 4H), 1.34-1.27 (m, 2H).

Example 151

N-(2-Aminophenyl)-6-(5-hydroxy-N-phthaloyl)hexanamide (243g)

Step 1: 6-(5-Hydroxy-N-phthaloyl)hexanoic acid (242g)

4-Hydroxy-phthalic acid 240 (2.30 g, 12.64 mmol) was heated for two hours at 220° C. under vacuum, cooled to room temperature and dissolved in 50 mL anhydrous ethyl alcohol. To this solution 6-amino caproic acid (2.48 g, 18.93 mmol) was added and the mixture was refluxed for 28 hours, cooled and evaporated to produce an oily residue. This material was triturated with water to form a precipitate which was collected and dried to afford the title compound 242g (2.24 g, 64% yield). MS (ESI)=276 (MH$^+$).

Step 2: N-(2-Aminophenyl)-6-(5-hydroxy-N-phthaloyl)hexanamide (243g)

Following the procedure described in Example 22, but substituting carboxylic acid 242g for 50g, the title compound 243g was obtained in 11% yield. $^1$H NMR: (300 MHz, DMSO-d6) δ 10.88 (br s, 1H), 9.04 (s, 1H), 7.71 (d, J=8.0 Hz, 4H), 7.11-7.07 (m, 3H), 6.86 (d, J=6.3 Hz, 1H), 6.68 (d, J=6.3 Hz, 1H), 6.49 (t, J=7.4 Hz, 1H), 4.77 (s, 2H), 3.51 (t, J=7.1 Hz, 2H), 2.27 (t, J=7.4 Hz, 2H), 1.62-1.54 (m, 4H), 1.37-1.25 (m, 2H).

Example 152

N-(2-Aminophenyl)-6-(5-hydroxy-6-(1-methylpiperidinyl)-N-phthaloyl)-hexanamide (243h)

Step 1: 6-(5-Hydroxy-6-(1-methylpiperidinyl)-N-phthaloyl)hexanoic acid (244)

To a stirring suspension of the phthalimido acid 242g (500 mg, 1.81 mmol) in a mixture of anhydrous dioxane (7 mL) and anhydrous DMF (3.5 mL) at room temperature was added paraformaldehyde (73 mg, 2.4 mmol) followed by addition of piperidine (0.22 mL, 2.2 mmol). The reaction mixture was stirred at 80° C. for 8 hours, solvents were removed in vacuum and the crude residue was purified by column chromatography using a gradient of 100% dichloromethane to 5% methanol in dichloromethane. The resulting yellow solid was crystallized from methanol-diethyl ether to afford the title compound 244 (0.25 g, 37%). MS (ESI)=375 (MH$^+$).

Step 2: N-(2-Aminophenyl)-6-(5-hydroxy-6-(1-methylpiperidinyl)-N-phthaloyl)hexanamide (243h)

Following the procedure described in Example 22, but substituting carboxylic acid 244 for 50g, the title compound 243h was obtained in 44% yield. 1HNMR: (300 MHz, DMSO-d6) δ 9.04 (s, 1H), 7.58 (s, 1H), 7.07 (d, J=7.97 Hz, 1H), 7.02 (s, 1H), 6.85 (t, J=7.69 Hz, 1H), 6.67 (d, J=7.97 Hz, 1H), 6.48 (t, J=7.69 Hz, 1H), 4.76 (br s 2H), 3.75 (s, 2H), 3.50 (t, J=6.87 Hz, 2H), 2.26 (t, J=7.28 Hz, 2H), 1.54 (m, 8H), 1.44 (m, 2H), 1.27 (m, 2H).

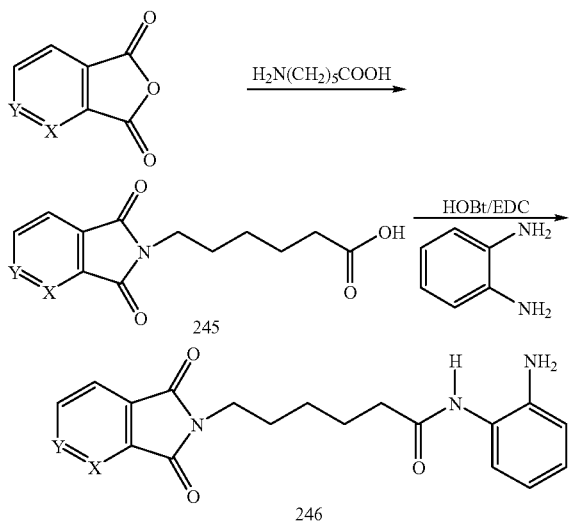

246a: X = N, Y = CH (Example 153)
246b: X = CH, Y = N (Example 154)

Example 153

N-(2-Aminophenyl)-6(5,7-dioxo-5,7-dihydro-pyrrolo[3,4-b]pyridinyl)]hexanamide (246a)

Step 1: 5-[6-(5,7-Dioxo-5,7-dihydro-pyrrolo[3,4-b]pyridinyl)]hexanoic acid (245a)

Following a procedure analogous to that described in Example 145, step 1, but substituting 2,3-pyridinedicarboxylic anhydride for N-phthalic anhydride, the title compound 245a was obtained in 22% yield. MS (ESI)=363 (MH$^+$).

Step 2: N-(2-Aminophenyl)-6-[6-(5,7-dioxo-5,7-dihydro-pyrrolo[3,4-b]pyridinyl]hexanamide (246a)

Following the procedure described in Example 22, but substituting carboxylic acid 245a for 50g, the title compound 246a was obtained in 40% yield. $^1$H NMR: (300 MHz, DMSO-d6) δ 9.06 (s, 1H), 8.94 (dd, J=4.9, 1.4 Hz, 1H), 8.27 (dd, J=7.7, 1.4 Hz, 1H), 7.75 (dd, J=7.7, 4.9 Hz, 1H), 7.08 (d, J=8.0 Hz, 1H), 6.85 (t, J=8.2 H, 1H), 6.67 (d, J=8.2 Hz, 1H), 6.49 (t, J=7.7 Hz, 1H), 4.76 (s, 2H), 3.60 (t, J=7.1 H, 2H), 2.28 (t, J=6.9 Hz, 2H), 1.63-1.57 (m, 4H), 1.35-0.28 (m, 2H).

Example 154

N-(2-Aminophenyl)-6-(5,7-dioxo-5,7-dihydro-pyrrolo[3,4-c]pyridinyl)]hexanamide (246b)

Step 1: 5-[6-(5,7-Dioxo-5,7-dihydro-pyrrolo[3,4-c]pyridinyl)]hexanoic acid (245b)

Following a procedure analogous to that described in Example 145, step 1, but substituting 3,4-pyridinedicarboxylic anhydride for N-phthalic anhydride, the title compound 245b was obtained in 8% yield. MS (ESI)=363 (MH$^+$).

Step 2: N-(2-Aminophenyl)-6-[6-(5,7-Dioxo-5,7-dihydro-pyrrolo[3,4-c]pyridin]hexanamide (246b)

Following the procedure described in Example 22, but substituting carboxylic acid 245b for 50g, the title compound 246b was obtained in 61% yield. $^1$H NMR: (300 MHz, DMSO-d6) δ 9.05-9.09 (m, 3H), 7.87 (d, J=4.7Hz, 1H), 7.08 (d, J=7.4 Hz, 1H), 6.86 (t, J=7.1 Hz, 1H), 6.67 (d, J=6.9 Hz, 1H), 6.49 (t, J=6.3 Hz, 1H), 4.77 (s, 2H), 3.58 (t, J=6.9 Hz, 2H), 2.28 (t, J=7.1 Hz, 2H), 2.00-1.90 (m, 2H), 1.64-1.54 (m, 4H), 1.33-1.29 (m, 2H).

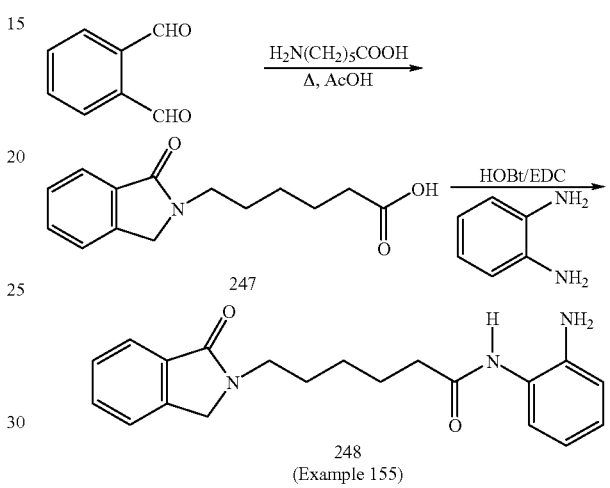

248
(Example 155)

Example 155

N-(2-Aminophenyl)-6-[2-(1-oxo-1,3-dihydro-isoindolyl)]hexanamide (248)

Step 1: 6-[2-(1-Oxo-1,3-dihydro-isoindolyl)]hexanoic acid (247)

To a solution of benzene-1,2-carbaldehyde (670 mg, 5.00 mmol) in acetic acid (6 mL) was added 6-amino-hexanoic acid (655 mg, 5.00 mmol). The reaction mixture was refluxed for 15 minutes, cooled to room temperature and evaporated. The residue was chromatographed on a silica gel column (5% to 10% methanol in dichloromethane) to produce the title compound 247 (1.20 g, 97% yield). MS (ESI)=248 (MH$^+$).

Step 2: N-(2-Aminophenyl)-6-[2-(1-oxo-1,3-dihydro-isoindolyl)]hexanamide (248)

Following the procedure described in Example 22, but substituting carboxylic acid 247 for 50g, the title compound 248 was obtained in 27% yield. $^1$H NMR: (300 MHz, DMSO-d6) δ 9.06 (s, 1H), 7.66-7.46 (m, 4H), 7.09 (d, J=8.0 Hz, 1H), 6.86 (t, J=7.7 Hz, 1H), 6.68 (d, J=7.7 Hz, 1H), 6.49 (t, J=7.7 Hz, 1H), 4.78 (s, 2H), 4.45 (s, 2H), 3.51 (t, J=6.9 Hz, 2H), 2.29 (t, J=7.1 Hz, 2H), 1.63-1.60 (m, 4H), 1.33-1.27 (m, 2H).

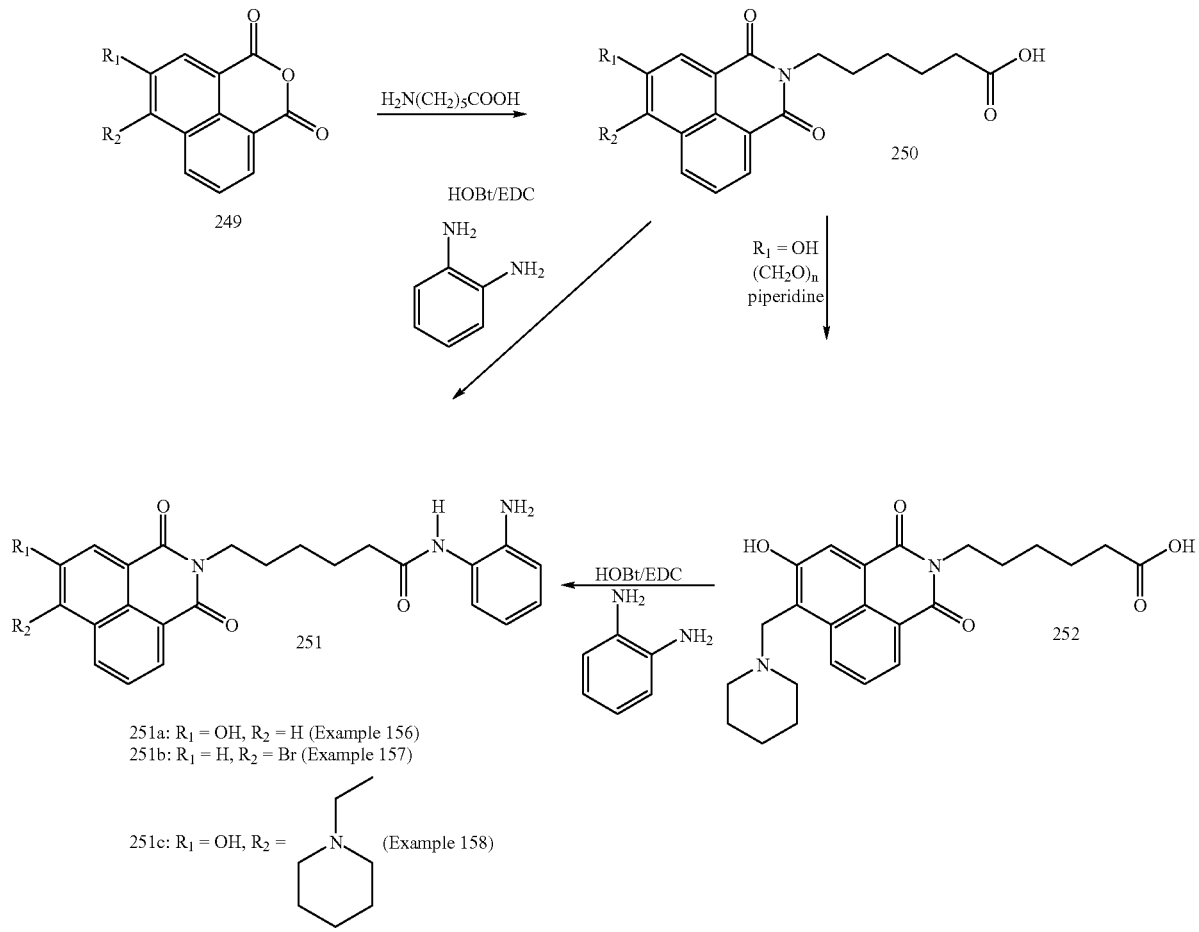

Example 156

N-(2-Aminophenyl)-6-[2-(5-hydroxy-1,3-dioxo-1H,3H-benzo[de]isoquinolinyl)]hexanamide (251a)

Step 1: 6-[2-(5-Hydroxy-1,3-dioxo-1H,3H-benzo[de]isoquinolinyl)]-hexanoic acid (250a)

Following a procedure analogous to that described in Example 145, step 1, but substituting 3-hydroxy-1,8-naphthalic anhydride for N-phthalic anhydride, the title compound 250a was obtained in 98% yield. MS (ESI)=328 (MH$^+$).

Step 2: N-(2-Aminophenyl)-6-[2-(5-hydroxy-1,3-dioxo-1H,3H-benzo[de]isoquinolinyl)]-hexanamide (251a)

Following the procedure described in Example 22, but substituting carboxylic acid 250a for 50g, the title compound 251a was obtained in 18% yield. $^1$H NMR: (400 MHz, DMSO-d$_6$) δ 10.52 (s, 1H), 9.07 (s, 1H), 8.22 (t, J=6.5 Hz, 2H), 8.00 (d, J=2.4 Hz, 1H), 7.72 (t, J=7.4 Hz, 1H), 7.63 (d, J=2.4 Hz, 1H), 7.09 (dd, J=7.8 Hz, 1.3 Hz, 1H), 6.87 (dd, J=8.0 Hz, 1.4 Hz, 1H), 6.69 (dd, J=8.0 Hz, 1.3 Hz, 1H), 6.49 (dd, J=7.7 Hz, 1.4 Hz, 1H), 4.81 (s, 2H), 4.02 (t, J=7.3 Hz, 2H), 2.31 (t, J=7.3 Hz, 2H), 1.67-1.58 (m, 4H), 1.42-1.35 (m, 2H).

Example 157

N-(2-Aminophenyl)-6-[2-(6-bromo-1,3-dioxo-1H,3H-benzo[de]isoquinolinyl)]-hexanamide (251b)

Step 1: 6-[2-(6-Bromo-1,3-dioxo-1H,3H-benzo[de]isoquinolinyl)]hexanoic acid (250b)

Following a procedure analogous to that described in Example 145, step 1, but substituting 4-bromo-1,8-naphthalic anhydride for N-phthalic anhydride, the title compound 250a was obtained in 96% yield. MS (ESI)=390 (MH$^+$).

Step 2: N-(2-Aminophenyl)-6-[2-(6-bromo-1,3-dioxo-1H,3H-benzo[de]isoquinolinyl)]-hexanamide (251b)

Following the procedure described in Example 22, but substituting carboxylic acid 250b for 50g, the title compound 251b was obtained in 26% yield. $^1$H NMR: (300

MHz, DMSO-d6) δ 9.05 (s, 1H, NH), 8.52 (t, J=8.2 Hz, 2H), 8.30 (d, J=7.7 Hz, 1H), 8.18 (d, J=7.7 Hz, 1H), 7.96 (t, J=7.7 Hz, 1H), 7.06 (d, J=8.0 Hz, 1H), 6.85 (t, J=8.0 Hz, 1H), 6.67 (d, J=8.0 Hz, 1H), 6.47 (t, J=7.7 Hz, 1H), 4.78 (br s, 2H), 4.02 (t, J=7.1 Hz, 2H), 2.30 (t, J=7.1 Hz, 2H), 1.66-1.58 (m, 4H), 1.41-1.34 (m, 2H).

Example 158

N-(2-Aminophenyl)-6-[2-(5-hydroxy-1,3-dioxo-6-(1-methylpiperidynyl)-1H,3H-benzo[de]isoquinolinyl)]-hexanamide (251c)

Step 1: 6-[2-(5-Hydroxy-1,3-dioxo-6piperidyn-1-ylmethyl-1H,3H-benzo[de]isoquinolinyl)]hexanoic acid (252)

To a stirring suspension of the acid 250a (390 mg, 1.19 mmol) in a mixture of anhydrous dioxane (5 mL) and anhydrous DMF (2 mL) at room temperature was added paraformaldehyde (70 mg, 2.33 mmol) followed by addition of piperidine (0.14 mL, 1.42 mmol). The reaction mixture was stirred for 18 hours at ambient temperature, solvents were removed in vacuum and the crude residue was triturated with 0.5 mL methanol followed by addition of 25 mL ether. The formed suspension was filtered to afford the title compound 252 as yellow crystals (424 mg, 84%). MS (ESI)=425 (MH+).

Step 2: N-(2-Aminophenyl)-6-[2-(5-hydroxy -1,3-dioxo-6-(1-methylpiperidynyl)-1H,3H-benzo[de]isoquinolinyl)]hexanamide (251c)

Following the procedure described in Example 22, but substituting carboxylic acid 252 for 50g, the title compound 251c was obtained in 39% yield. $^1$H NMR: (300 MHz, DMSO-d6) δ 9.05 (s, 1H), 8.43 (d, J=8.2 Hz, 1H), 8.27 (d, J=7.1 Hz, 1H), 7.96 (s, 1H), 7.75 (t, J=8.2 Hz, 1H), 7.08 (d, J=8.0 Hz, 1H), 6.85 (t, J=6.7 Hz, 1H), 6.68 (d, J=8.0 Hz, 1H), 6.47 (t, J=7.1 Hz, 1H), 4.77 (s, 2H), 4.15 (s, 2H), 4.02 (t, J=6.9 Hz, 2H), 2.54 (br s, 4H), 2.30 (t, J=7.1 Hz, 2H), 1.65-1.36 (m, 12H).

Example 159

Inhibition of Histone Deacetylase Enzymatic Activity

HDAC inhibitors were screened against histone deacetylase enzyme in nuclear extracts prepared from the human small cell lung cancer cell line H446 (ATTC HTB-171) and against a cloned recombinant human HDAC-1 enzyme expressed and purified from a Baculovirus insect cell expression system.

For deacetylase assays, 20,000 cpm of the [$^3$H]-metabolically labeled acetylated histone substrate (M. Yoshida et al., *J. Biol. Chem.* 265(28): 17174-17179 (1990)) was incubated with 30 μg of H446 nuclear extract or an equivalent amount of the cloned recombinant hHDAC-1 for 10 minutes at 37° C. The reaction was stopped by adding acetic acid (0.04 M, final concentration) and HCl (250 mM, final concentration). The mixture was extracted with ethyl acetate and the released [$^3$H]-acetic acid was quantified by scintillation counting. For inhibition studies, the enzyme was preincubated with compounds at 4° C. for 30 minutes prior to initiation of the enzymatic assay. IC$_{50}$ values for HDAC enzyme inhibitors were determined by performing dose response curves with individual compounds and determining the concentration of inhibitor producing fifty percent of the maximal inhibition.

Representative data are presented in Table 2. In the first column are reported IC$_{50}$ values determined against histone deacetylase in nuclear extracts from H446 cells (pooled HDACs). In the second column are reported IC$_{50}$ values determined against recombinant human HDAC-1 enzyme (rHDAC-1).

TABLE 2

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 1 | 6 | *structure with OMe, MeO substituents and NHOH group* | 3 | 0.25 |
| Ex. 2 | 12 | *structure with OMe substituent and NHOH group* | 9.4 | ND |
| Ex. 3 | 17 | *structure with OMe, Me$_2$N substituents and NHOH group* | 4 | 0.25 |

TABLE 2-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 4 | 18 | 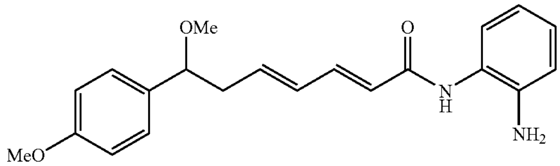 | >100 | 1 |
| Ex. 5 | 19 | 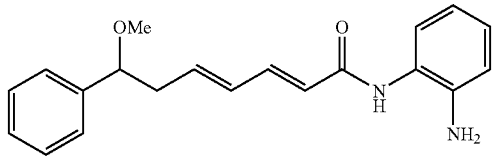 | >100 | <20 |
| Ex. 6 | 20 | 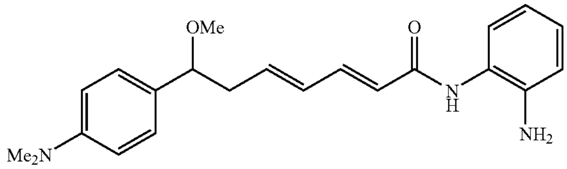 | >20 | 3 |
| Ex. 7 | 21 | 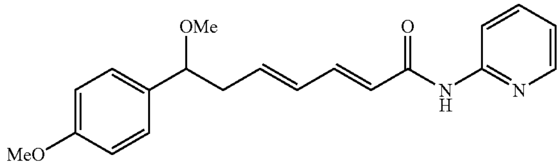 | >100 | ND |
| Ex. 8 | 26 | 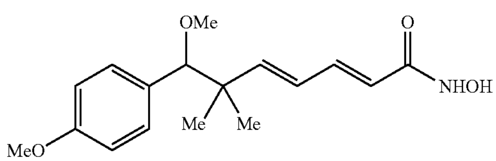 | 5 | 1 |
| Ex. 9 | 27 | 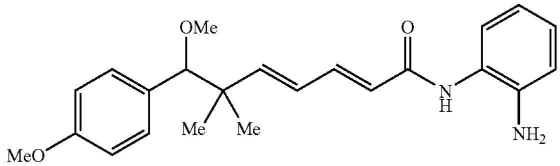 | >100 | ND |
| Ex. 10 | 28 | 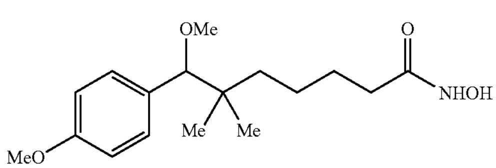 | 4 | 0.1 |
| Ex. 11 | 33 | 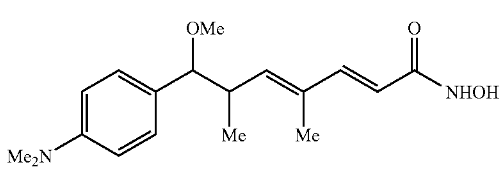 | >10 | ND |

TABLE 2-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 12 | 34 | [structure: 4-(Me$_2$N)C$_6$H$_4$-CH(OMe)-CH(Me)-CH=C(Me)-CH=CH-C(O)NH-C$_6$H$_4$-2-NH$_2$] | >100 | 7 |
| Ex. 13 | 35 | [structure: 4-(Me$_2$N)C$_6$H$_4$-C(O)-CH(Me)-CH=C(Me)-CH=CH-C(O)NH-C$_6$H$_4$-2-NH$_2$] | >100 | 2 |
| Ex. 14 | 38 | [structure: 4-(Me$_2$N)C$_6$H$_4$-CH$_2$-CH(Me)-CH=C(Me)-CH=CH-C(O)NHOH] | >20 | ND |
| Ex. 15 | 39 | [structure: 4-(Me$_2$N)C$_6$H$_4$-CH$_2$-CH(Me)-CH=C(Me)-CH=CH-C(O)NH-C$_6$H$_4$-2-NH$_2$] | >20 | 7 |
| Ex. 16 | 42 | [structure: PhSO$_2$NH-(CH$_2$)$_4$-C(O)NHOH] | 6 | 1 |
| Ex. 17 | 47 | [structure: PhSO$_2$NH-(CH$_2$)$_4$-C(O)-CH$_2$-C(O)NHOH] | 4.5 | 0.5 |
| Ex. 18 | 52c | [structure: 4-(F$_3$C)C$_6$H$_4$-C(O)-(CH$_2$)$_5$-C(O)NHOH] | 0.55 | 0.06 |
| Ex. 18 | 52g | [structure: 2-naphthyl-C(O)-(CH$_2$)$_5$-C(O)NHOH] | 0.03 | 0.005 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 18 | (Z)-51h | [biphenyl-C(=NOH)-(CH$_2$)$_5$-C(=O)NHOH] | 75% | |
| Ex. 18 | 52i | [furan-2-yl-C(=O)-(CH$_2$)$_5$-C(=O)NHOH] | 3 | 0.1 |
| Ex. 18 | 52k | [thiophen-2-yl-C(=O)-(CH$_2$)$_5$-C(=O)NHOH] | 0.9 | 0.18 |
| Ex. 18 | 52l | [benzofuran-2-yl-C(=O)-(CH$_2$)$_5$-C(=O)NHOH] | 0.3 | 0.03 |
| Ex. 18 | 51a | [phenyl-C(=NOH)-(CH$_2$)$_5$-C(=O)NHOH] | 0.35 | 0.1 |
| Ex. 18 | 52e | [2-hydroxyphenyl-C(=O)-(CH$_2$)$_5$-C(=O)NHOH] | 0.55 | 0.06 |
| Ex. 18 | 52d | [4-bromophenyl-C(=O)-(CH$_2$)$_5$-C(=O)NHOH] | 0.05 | 0.055 |
| Ex. 18 | 52f | [naphthalen-1-yl-C(=O)-(CH$_2$)$_5$-C(=O)NHOH] | 0.55 | 0.01 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 18 | (E)-51h | | 99% | |
| Ex. 18 | 51i | | 0.9 | 0.1 |
| Ex. 18 | 52j | | 3 | 0.45 |
| Ex. 18 | 52m | | 0.1 | 0.01 |
| Ex. 19 | 53a | | | 0.6 |
| Ex. 19 | 53b | | 0% | 1 |
| Ex. 19 | 53f | | 3% | 2 |
| Ex. 20 | 58 | 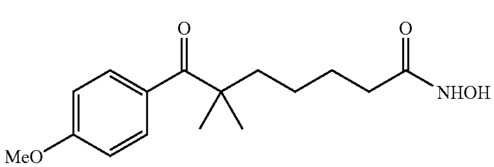 | 3 | 0.25 |

TABLE 2-continued

Inhibition of Histone Deacetylase

| Example | Cpd. | Structure | pooled HDACs IC$_{50}$ (μM) | rHDAC-1 IC$_{50}$ (μM) |
|---------|------|-----------|------------------------------|-------------------------|
| Ex. 21 | 62 | 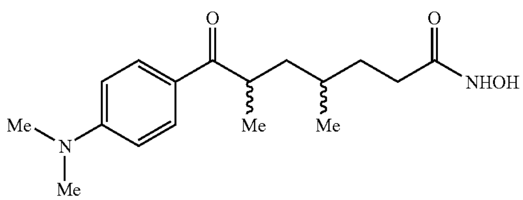 | 1.1 | |
| Ex. 22 | 63 | 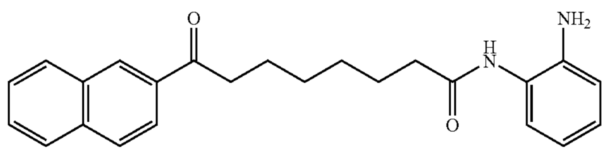 | >20 | 2.2 |
| Ex. 25 | 66 | 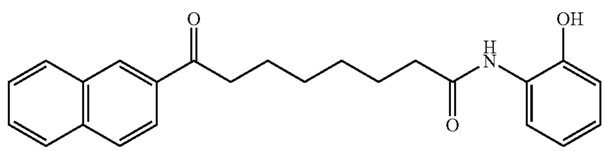 | 0% | 2.3 |
| Ex. 29 | 74 | 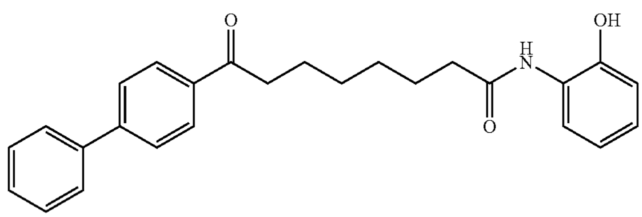 | 0% | 7.8 |
| Ex. 30 | 75 | 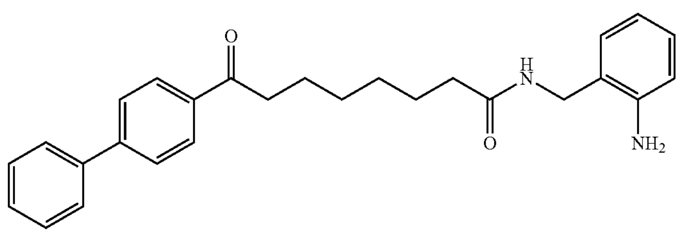 | 0% | 8.4 |
| Ex. 31 | 76 | 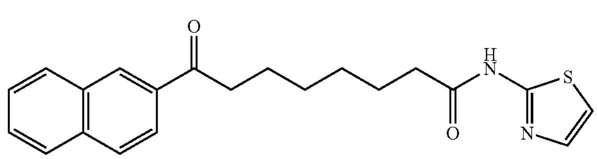 | | 23 |
| Ex. 32 | 77 | 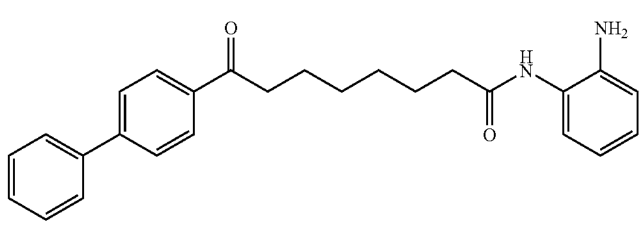 | 11% | 1.9 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 33 | 78 | 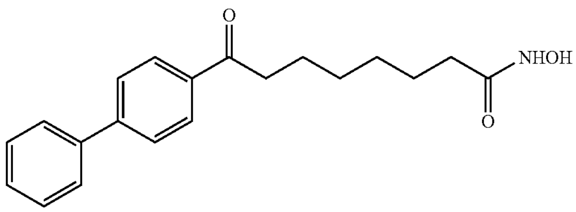 | 0.04 | 0.004 |
| Ex. 34 | 79 | 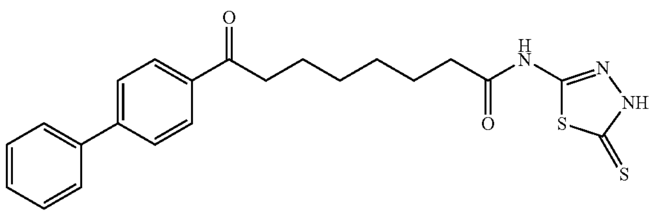 | | 9 |
| Ex. 36 | 81 | 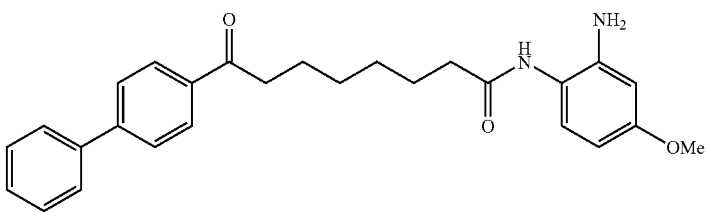 | 27% | 25 |
| Ex. 37 | 82 | 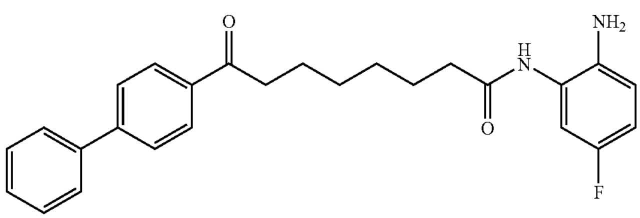 | | 20 |
| Ex. 38 | 83 | 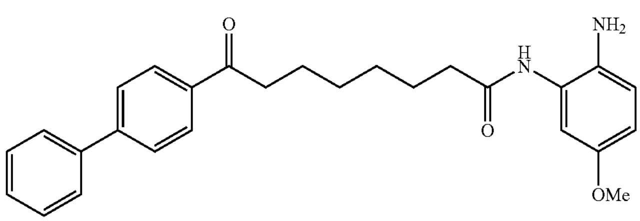 | | 25 |
| Ex. 40 | 85 | 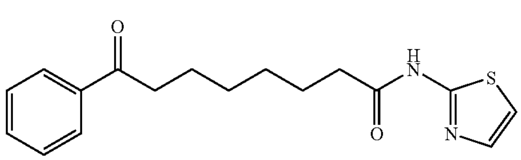 | | 20 |
| Ex. 41 | 86 | 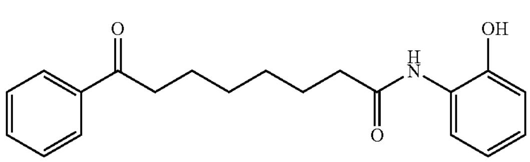 | | 5 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 43 | 89 | 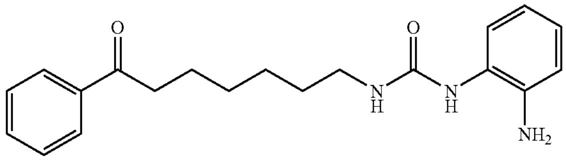 | 0% | 16.3 |
| Ex. 44 | 92 | 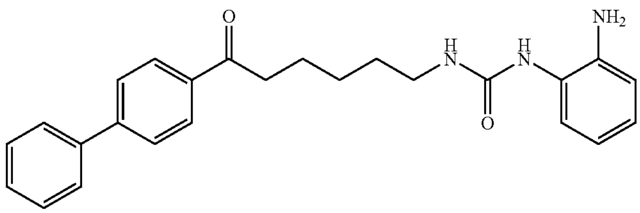 | 0% | 15.9 |
| Ex. 45 | 93 | 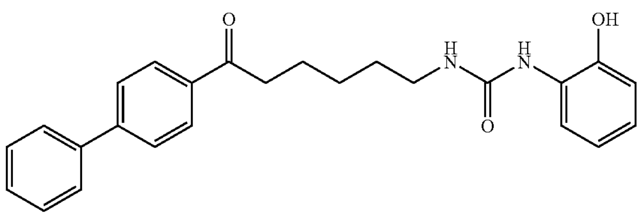 | 0% | 6.4 |
| Ex. 48 | 96 | (E):(Z) = 9•1 | 0.1 | 0.035 |
| Ex. 49 | 97 | 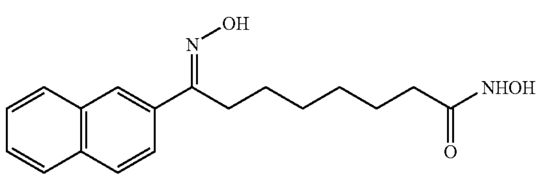 | 0.03 | 0.01 |
| Ex. 50 | 98 | 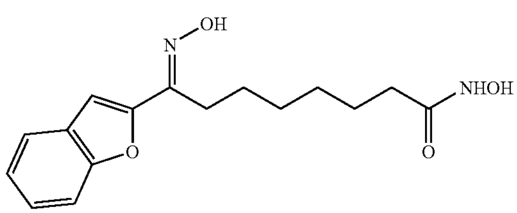 | 0.04 | 0.03 |
| Ex. 51 | 99 | 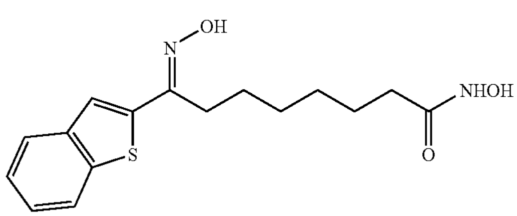 | 0.035 | 0.008 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 52 | 100 | indol-2-yl-C(O)-(CH2)5-C(O)-NHOH | | 4 |
| Ex. 54 | 102 | cyclohexyl-C(O)-(CH2)5-C(O)-NHOH | | |
| Ex. 55 | 103 | (N-methylindol-2-yl)-C(O)-(CH2)5-C(O)-NHOH | 0.1 | 0.05 |
| Ex. 56 | 104 | (4-phenoxyphenyl)-C(O)-(CH2)5-C(O)-NHOH | 61% @ 1 μM | 0.16 |
| Ex. 57a | 105a | (6-methoxynaphth-2-yl)-C(O)-(CH2)5-C(O)-NHOH | 83% @ 1 μM | 0.01 |
| Ex. 57b | 105b | (2-methylthiopyridin-3-yl)-C(O)-(CH2)5-C(O)-NHOH | 40% @ 1 μM | 0.02 |
| Ex. 58 | 106 | naphth-2-yl-C(=NOH)-(CH2)5-C(O)-NH-(2-aminophenyl) | >20 | 4 |
| Ex. 63 | 111 | naphth-2-yl-C(O)-(CH2)5-C(O)-NHOH | 0.35 | 0.2 |
| Ex. 64 | 112 | indol-2-yl-C(O)-(CH2)4-C(O)-NHOH | 0.25 | 0.039 |

TABLE 2-continued

Inhibition of Histone Deacetylase

| Example | Cpd. | Structure | pooled HDACs IC$_{50}$ (μM) | rHDAC-1 IC$_{50}$ (μM) |
|---------|------|-----------|-----------------------------|------------------------|
| Ex. 65 | 113 | benzothiophene-C(O)-(CH$_2$)$_4$-C(O)NHOH | 33% @ 1 μM | 0.13 |
| Ex. 66 | 114 | 4-Br-C$_6$H$_4$-C(O)-(CH$_2$)$_5$-C(O)NH-(2-aminophenyl) | >20 | 6.3 |
| Ex. 67 | 117 | 4-(thiophen-3-yl)-C$_6$H$_4$-C(O)-(CH$_2$)$_5$-C(O)NH-(2-aminophenyl) | 0% | 9 |
| Ex. 68 | 123 | 4-biphenyl-C(O)-(CH$_2$)$_5$-C(O)NH-(2-aminophenyl) | | 4 |
| Ex. 69 | 120 | 4'-MeO-biphenyl-4-C(O)-(CH$_2$)$_5$-C(O)NHOH | 83% | 0.002 |
| Ex. 70 | 124 | 4'-Br-biphenyl-4-C(O)-(CH$_2$)$_5$-C(O)NHOH | | 0.001 |
| Ex. 71 | 127 | 4-(pyridin-3-yl)-C$_6$H$_4$-C(O)-(CH$_2$)$_5$-C(O)NH-(2-aminophenyl) | 0% | 10.3 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 72 | 128 | 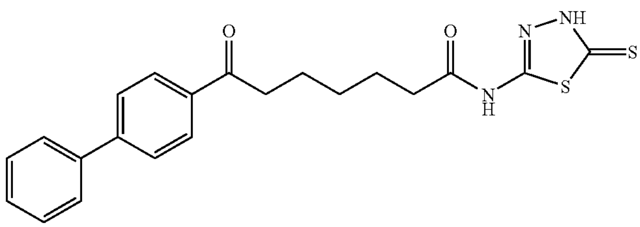 | | 19 |
| Ex. 73 | 129 | 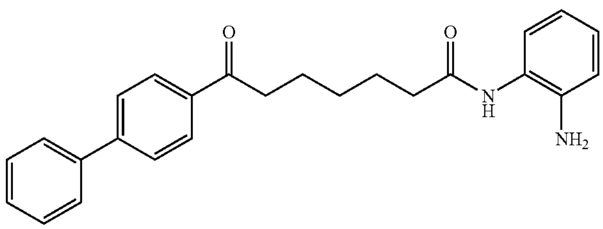 | | 1 |
| Ex. 74 | 130 | 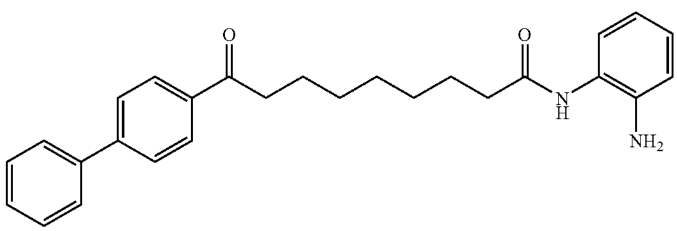 | | 3 |
| Ex. 75 | 131 | 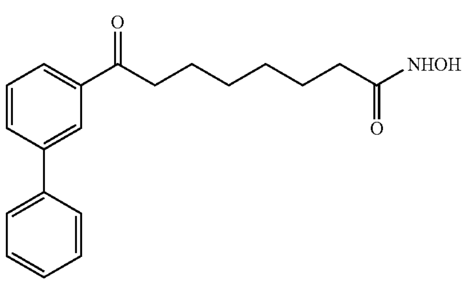 | | 0.008 |
| Ex. 76 | 132 | 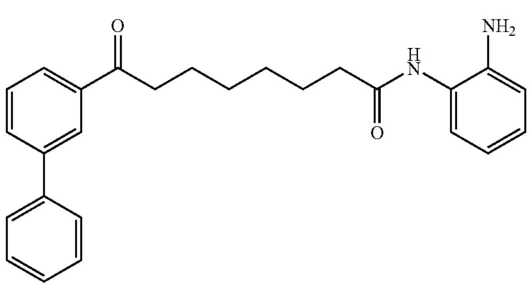 | | 0.8 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 77 | 133 | 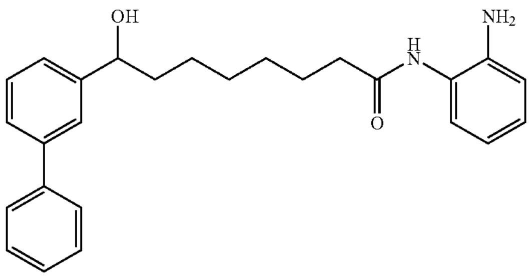 | | 1 |
| Ex. 78 | 134 | 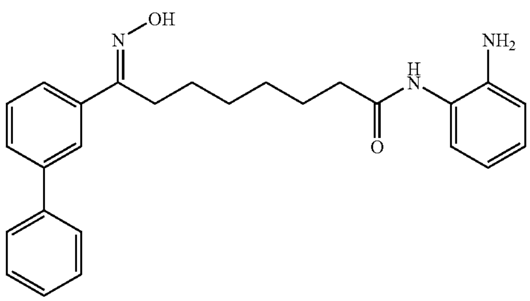 | | 1 |
| Ex. 79 | 135 | 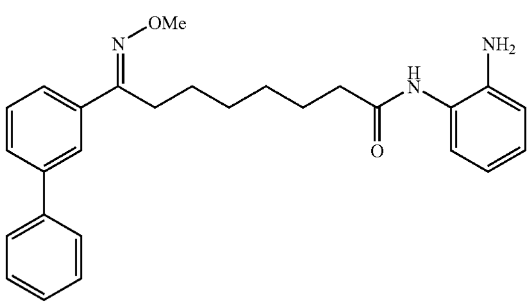 | | 2 |
| Ex. 80 | 138a | 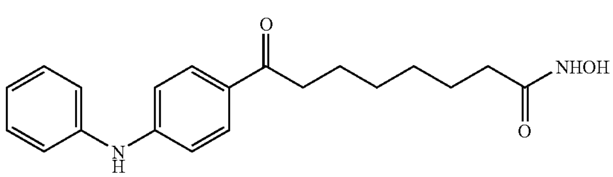 | 83% @ 1 μM | 0.004 |
| Ex. 81 | 138b | 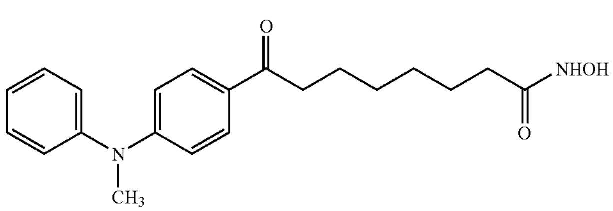 | 0.049 | 0.008 |

TABLE 2-continued
Inhibition of Histone Deacetylase
| Example | Cpd. | Structure | pooled HDACs IC$_{50}$ (μM) | rHDAC-1 IC$_{50}$ (μM) |
|---|---|---|---|---|
| Ex. 82a | 138c1 | 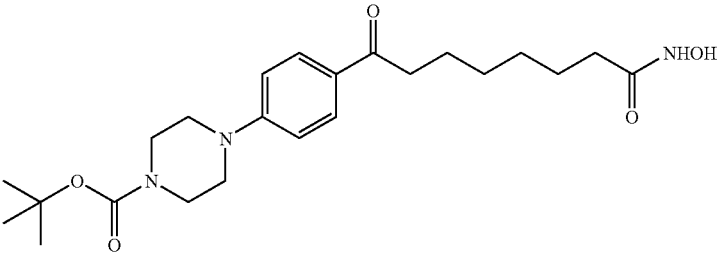 | | 0.03 |
| Ex. 82b | 138c2 | 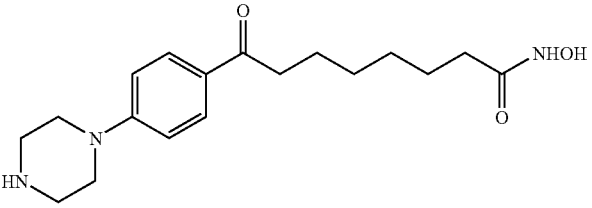 | | 0.03 |
| Ex. 83 | 138d | 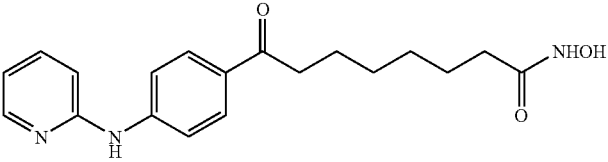 | 0.02 | 0.004 |
| Ex. 84 | 138e | 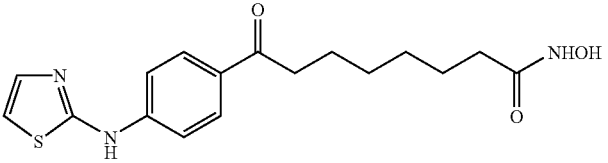 | 0.02 | 0.004 |
| Ex. 85 | 138f | 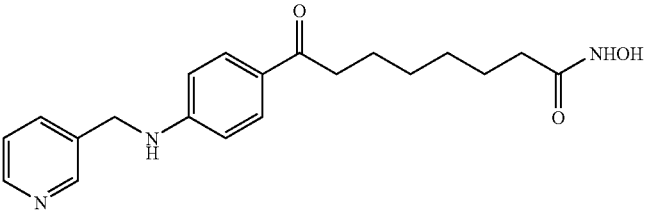 | | 0.02 |
| Ex. 86 | 138g | 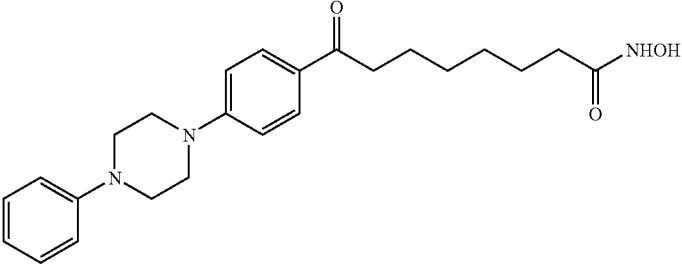 | 0.051 | 0.006 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 87 | 138h | 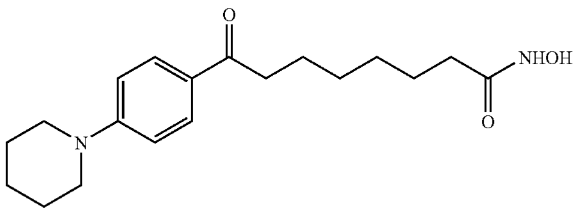 | 0.048 | 0.009 |
| Ex. 88 | 138i | 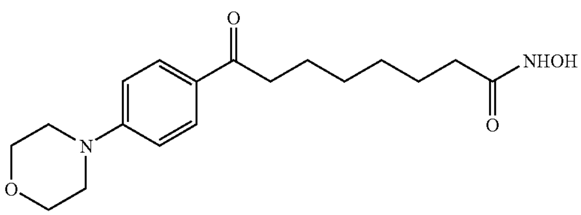 | 0.1 | 0.033 |
| Ex. 89a | 141a1 | 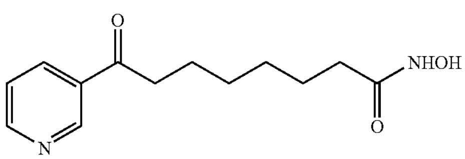 | 22% @ 1 μM | 0.06 |
| Ex. 89b | 141a2 | 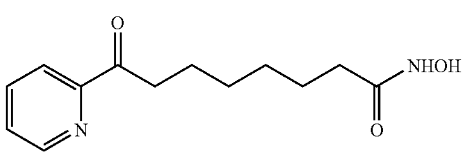 | 12% @ 1 μM | |
| Ex. 90 | 141b | 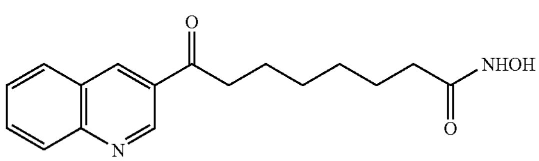 | 71% @ 1 μM | 0.035 |
| Ex. 91 | 145 | 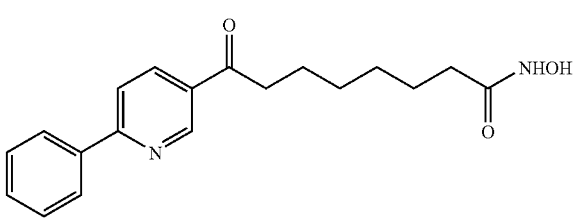 | | 0.008 |
| Ex. 92 | 146 | 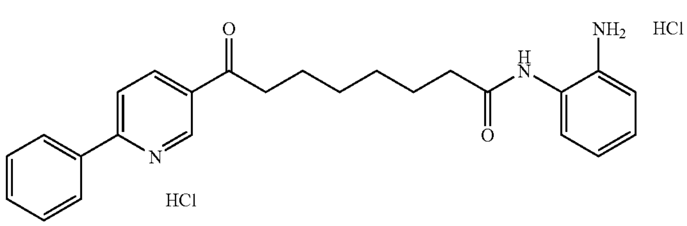 | | 2 |

TABLE 2-continued

Inhibition of Histone Deacetylase

| Example | Cpd. | Structure | pooled HDACs IC$_{50}$ (μM) | rHDAC-1 IC$_{50}$ (μM) |
|---------|------|-----------|------------------------------|-------------------------|
| Ex. 93  | 150  | 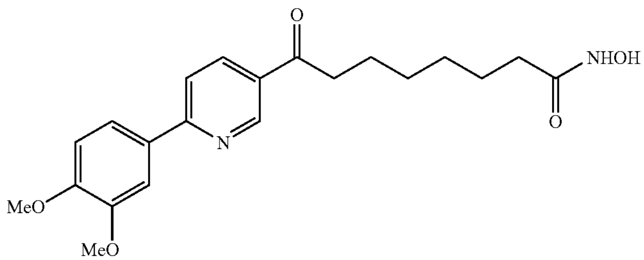          |                              | 0.05                    |
| Ex. 94  | 151  | 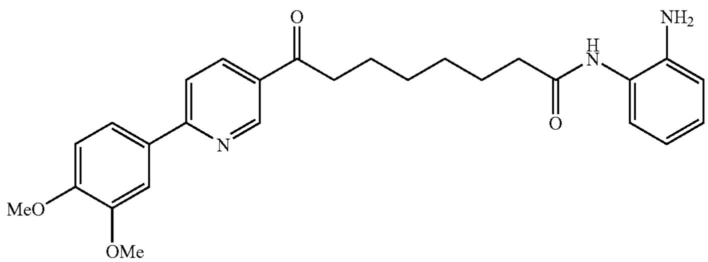          |                              | 4                       |
| Ex. 95  | 156  | 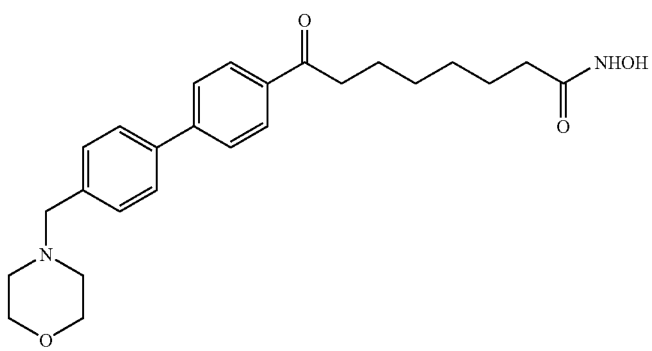          |                              | 20                      |
| Ex. 96  | 157  | 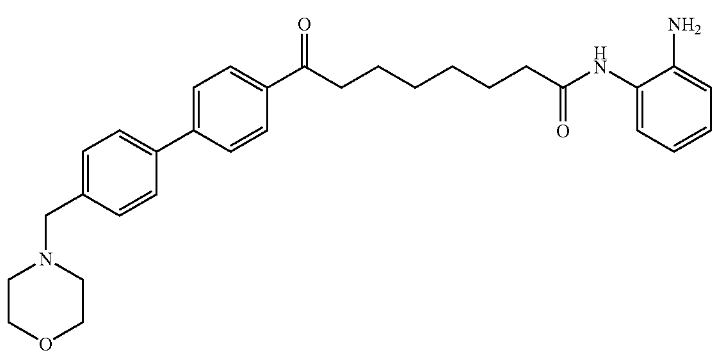          |                              | 4                       |
| Ex. 97  | 159a | 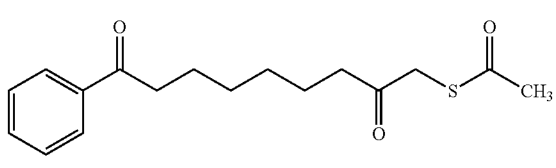          | 0.05                         | 0.1                     |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 98 | 159b | 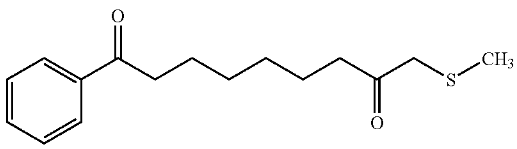 | 14% @ 5 μM | 0.5 |
| Ex. 99 | 159c | 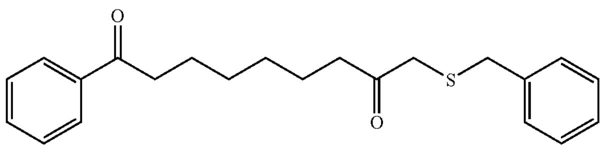 | 0% @ 5 μM | 5 |
| Ex. 100 | 159d | 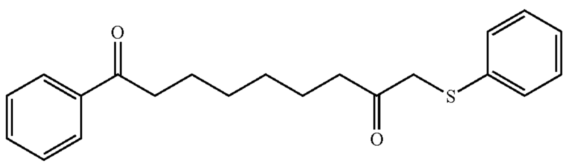 | 50 | 5 |
| Ex. 101 | 159e | 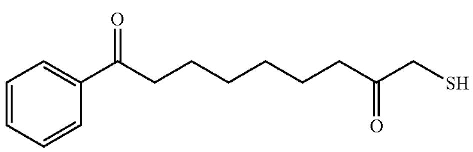 | 0.05 | 0.05 |
| Ex. 102 | 159f | 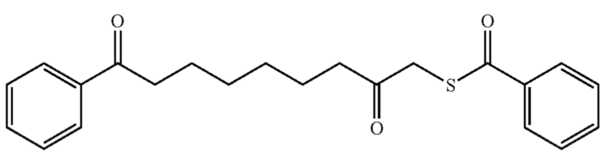 | 0.35 | 0.7 |
| Ex. 103 | 160 | 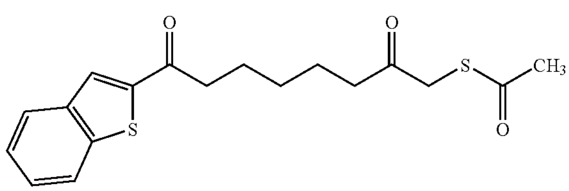 | 0.08 | 0.13 |
| Ex. 104 | 161 | 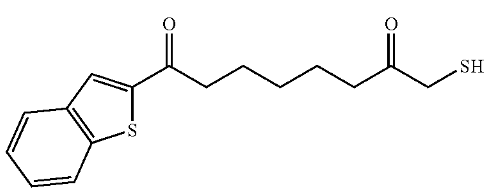 | 0.094 | 0.071 |
| Ex. 105 | 162 | 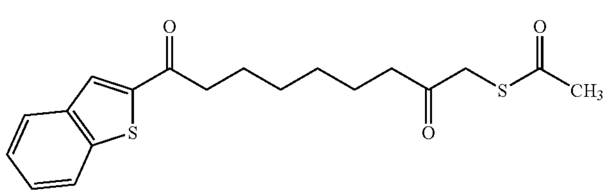 | 0.04 | 0.035 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 106 | 163 | benzothiophene-C(O)-(CH$_2$)$_5$-C(O)-CH$_2$-SH | 0.04 | 0.01 |
| Ex. 107 | 164 | benzothiophene-C(O)-(CH$_2$)$_6$-C(O)-NH-(2-aminophenyl) | 18% | 2.3 |
| Ex. 108 | 165 | 1-methylindole-2-C(O)-(CH$_2$)$_5$-C(O)-CH$_2$-S-C(O)CH$_3$ | 0.04 | 0.09 |
| Ex. 109 | 166 | 1-methylindole-2-C(O)-(CH$_2$)$_5$-C(O)-CH$_2$-SH | 0.05 | 0.42 |
| Ex. 110 | 167 | indole-2-C(O)-(CH$_2$)$_5$-C(O)-CH$_2$-S-C(O)CH$_3$ | 0.3 | 0.4 |
| Ex. 111 | 170 | 2-naphthyl-C(=CH$_2$)-(CH$_2$)$_5$-C(O)-NHOH | | 0.01 |
| Ex. 112 | 175 | 2-naphthyl-C(O)-(CH$_2$)$_4$-CH(CH$_3$)-C(O)-NHOH | 2.5 | 0.5 |
| Ex. 115 | 187 | 2-naphthyl-CH(OH)-(CH$_2$)$_3$-CH=CH-C(O)-NHOH | | 0.04 |

TABLE 2-continued
Inhibition of Histone Deacetylase
| Example | Cpd. | Structure | pooled HDACs IC$_{50}$ (μM) | rHDAC-1 IC$_{50}$ (μM) |
|---|---|---|---|---|
| Ex. 116 | 188 | 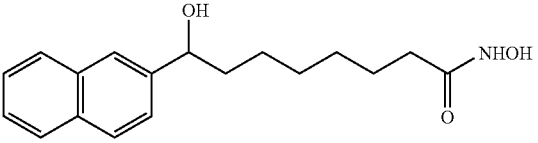 | | 0.02 |
| Ex. 117 | 194 | 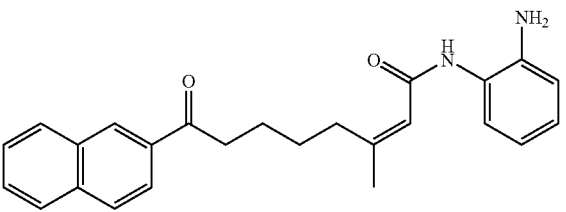 | | 24 |
| Ex. 118 | 198 | 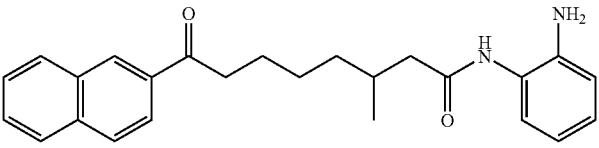 | | 16 |
| Ex. 119 | 199 | 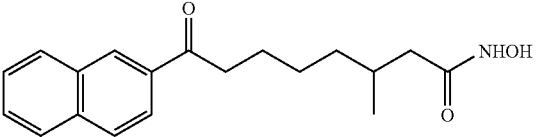 | 0.08 | 0.03 |
| Ex. 120 | 204 | 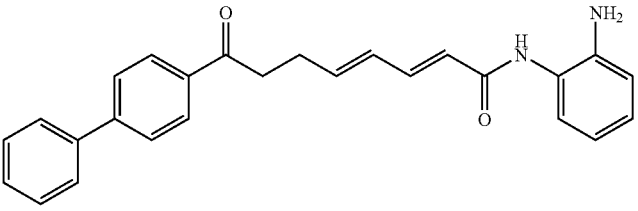 | | 5 |
| Ex. 121 | 205 | 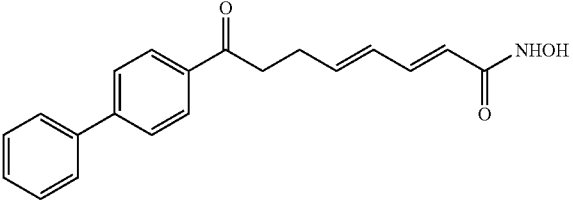 | | 0.04 |
| Ex. 122 | 209 | 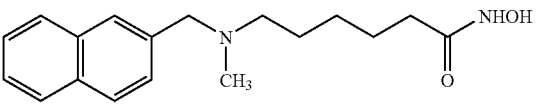 | | 0.05 |
| Ex. 123 | 210 | 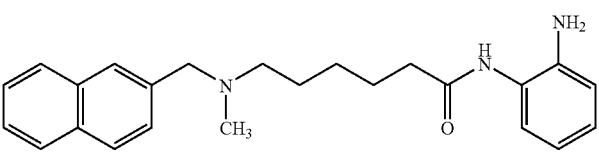 | | 10 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 124 | 213 | 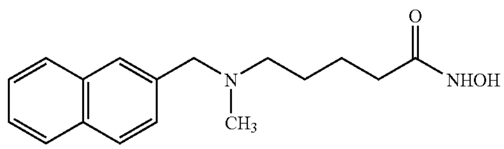 | | 3 |
| Ex. 125 | 216 | 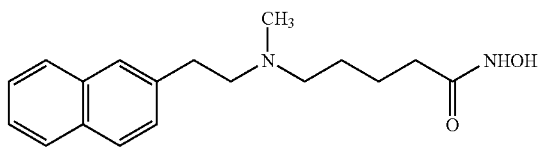 | | 0.3 |
| Ex. 126 | 220a | 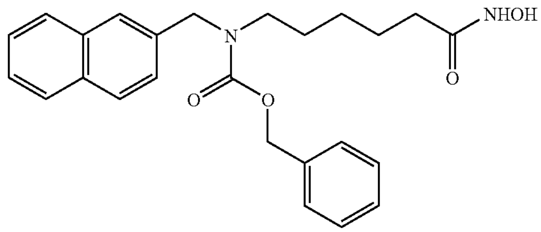 | | 0.02 |
| Ex. 127 | 220b | 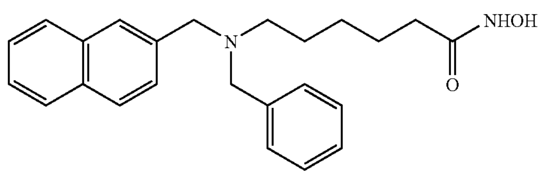 | | 0.1 |
| Ex. 128 | 222 | 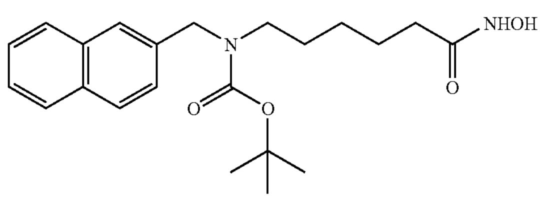 | | 0.1 |
| Ex. 129 | 223 | 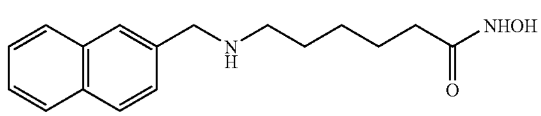 | | 2 |
| Ex. 130 | 224 | 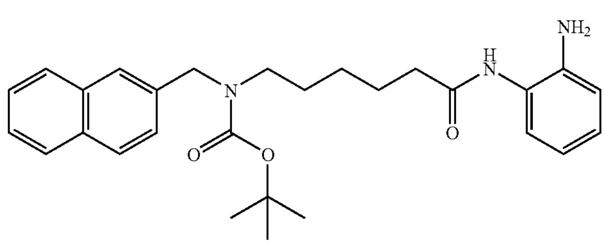 | | 3 |
| Ex. 131 | 226a | 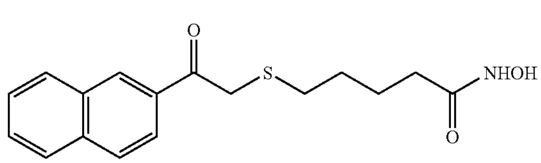 | | 0.007 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 132 | 226b | biphenyl-C(O)-CH$_2$-S-(CH$_2$)$_3$-C(O)-NHOH | | 0.006 |
| Ex. 133 | 227a | naphthyl-C(O)-CH$_2$-S-(CH$_2$)$_3$-C(O)-NH-(2-aminophenyl) | | 3 |
| Ex. 134 | 227b | biphenyl-C(O)-CH$_2$-S-(CH$_2$)$_3$-C(O)-NH-(2-aminophenyl) | | 3 |
| Ex. 135 | 229a | naphthyl-C(O)-CH$_2$-SO$_2$-(CH$_2$)$_3$-C(O)-NHOH | | 1 |
| Ex. 136 | 229b | biphenyl-C(O)-CH$_2$-SO$_2$-(CH$_2$)$_3$-C(O)-NHOH | | 0.04 |
| Ex. 137 | 230a | naphthyl-C(O)-CH$_2$-SO$_2$-(CH$_2$)$_3$-C(O)-NH-(2-aminophenyl) | | 5 |
| Ex. 138 | 230b | biphenyl-C(O)-CH$_2$-SO$_2$-(CH$_2$)$_3$-C(O)-NH-(2-aminophenyl) | | 12 |

TABLE 2-continued

Inhibition of Histone Deacetylase

| Example | Cpd. | Structure | pooled HDACs IC$_{50}$ (μM) | rHDAC-1 IC$_{50}$ (μM) |
|---|---|---|---|---|
| Ex. 139 | 234 | (biphenyl-O-(CH$_2$)$_5$-C(O)-NH-(2-aminophenyl)) | | 1 |
| Ex. 140 | 235 | (biphenyl-O-(CH$_2$)$_5$-C(O)-NHOH) | | 0.004 |
| Ex. 141 | 238a | (quinazolin-4(3H)-one-N-(CH$_2$)$_4$-C(O)-NHOH) | 0% @ 1 μM | 0.05 |
| Ex. 142 | 238b | (benzo[1,2,3]triazin-4(3H)-one-N-(CH$_2$)$_4$-C(O)-NHOH) | 20% @ 1 μM | 0.76 |
| Ex. 143 | 239a | (quinazolin-4(3H)-one-N-(CH$_2$)$_4$-C(O)-NH-(2-aminophenyl)) | 0% | 11.6 |
| Ex. 144 | 239b | (benzo[1,2,3]triazin-4(3H)-one-N-(CH$_2$)$_4$-C(O)-NH-(2-aminophenyl)) | 14% | 8.1 |
| Ex. 145 | 243a | (phthalimido-N-(CH$_2$)$_4$-C(O)-NH-(2-aminophenyl)) | 6% | 1.6 |
| Ex. 146 | 243b | (phthalimido-N-(CH$_2$)$_3$-C(O)-NH-(2-aminophenyl)) | | 99 |

TABLE 2-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 147 | 243c | phthalimide-(CH$_2$)$_5$-C(O)NH-(2-aminophenyl) | | 4 |
| Ex. 148 | 243d | 4-methylphthalimide-(CH$_2$)$_5$-C(O)NH-(2-aminophenyl) | | 3 |
| Ex. 149 | 243e | 4-nitrophthalimide-(CH$_2$)$_5$-C(O)NH-(2-aminophenyl) | | 12 |
| Ex. 150 | 243f | 4,5-dichlorophthalimide-(CH$_2$)$_5$-C(O)NH-(2-aminophenyl) | | 3 |
| Ex. 151 | 243g | 4-hydroxyphthalimide-(CH$_2$)$_5$-C(O)NH-(2-aminophenyl) | | 3 |
| Ex. 152 | 243h | 5-(piperidinylmethyl)-6-hydroxyphthalimide-(CH$_2$)$_5$-C(O)NH-(2-aminophenyl) | | 3 |
| Ex. 153 | 246a | pyrido[2,3]-dicarboximide-(CH$_2$)$_5$-C(O)NH-(2-aminophenyl) | | 5 |
| Ex. 154 | 246b | pyrido[3,4]-dicarboximide-(CH$_2$)$_5$-C(O)NH-(2-aminophenyl) | | 14 |

TABLE 2-continued

Inhibition of Histone Deacetylase

| Example | Cpd. | Structure | pooled HDACs IC$_{50}$ (µM) | rHDAC-1 IC$_{50}$ (µM) |
|---|---|---|---|---|
| Ex. 155 | 248 | 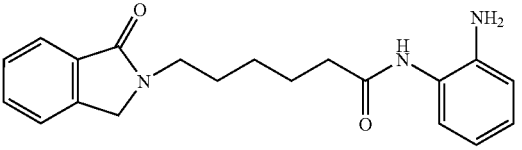 | | 4 |
| Ex. 156 | 251a | 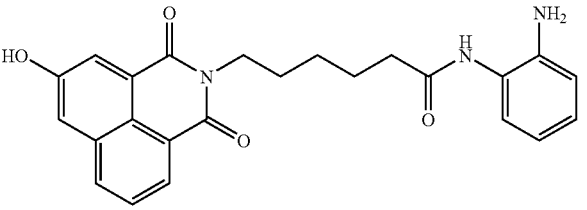 | 0% | 0.7 |
| Ex. 157 | 251b | 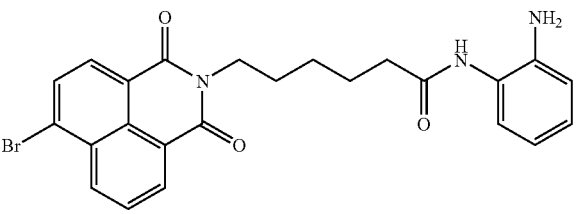 | | 1 |
| Ex. 158 | 251c | 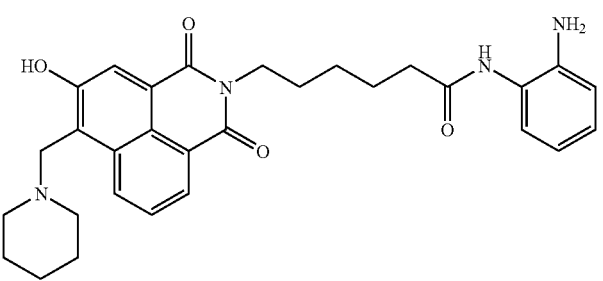 | | 2 |
| | 252 | 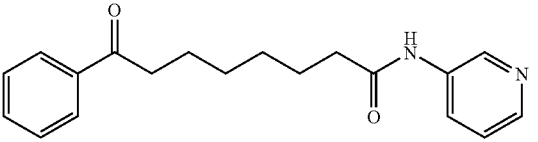 | 0% | >20 |
| | 253 | 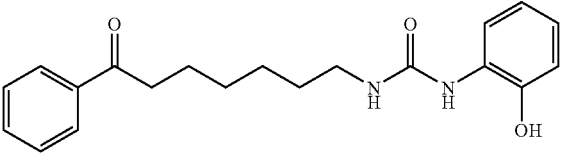 | 0% | >20 |

[a]Unless otherwise indicated, inhibition values expressed in percent refer to the percent inhibition at 20 µM.

Example 160

Inhibition of Histone Deacetylase in Whole Cells

1. Histone H4 Acetylation in Whole Cells by Immunoblots

T24 human bladder cancer cells growing in culture were incubated with HDAC inhibitors for 16 hours. Histones were extracted from the cells after the culture period as described by M. Yoshida et al. (*J. Biol. Chem.* 265(28): 17174-17179 (1990)). 20 µg of total histone protein was loaded onto SDS/PAGE and transferred to nitrocellulose membranes. Membranes were probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection was performed using Kodak films (Eastman Kodak). Acetylated H-4 signal was quantified by densitometry.

Data for selected compounds are presented in Table 3. Data are presented as the concentration effective for reducing the acetylated H-4 signal by 50% ($EC_{50}$).

TABLE 3

Inhibition of Histone Acetylation in Cells

| Example | Cpd. | Structure | $EC_{50}$ (μM) |
|---|---|---|---|
| Ex. 4 | 18 | 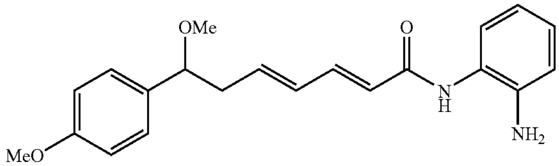 | 10 |
| Ex. 6 | 20 | 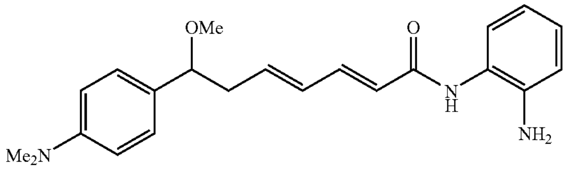 | 5 |
| Ex. 12 | 34 | 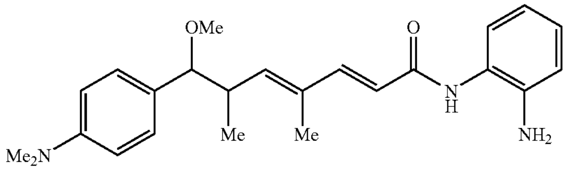 | 5 |
| Ex. 13 | 35 | 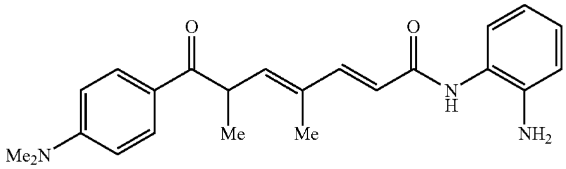 | 5 |
| Ex. 15 | 39 | 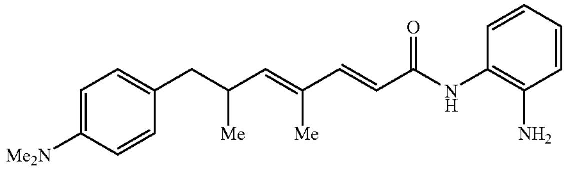 | 10 |
| Ex. 32 | 77 | 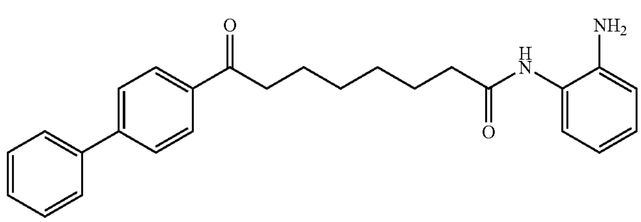 | 10 |
| Ex. 33 | 78 | 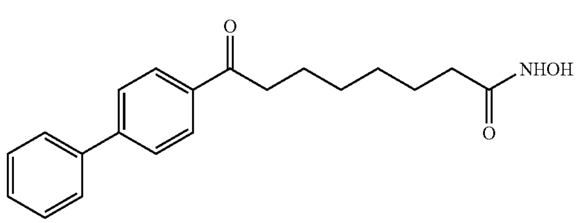 | 10 |

TABLE 3-continued

Inhibition of Histone Acetylation in Cells

| Example | Cpd. | Structure | EC$_{50}$ (µM) |
|---|---|---|---|
| Ex. 69 | 120 | MeO-C$_6$H$_4$-C$_6$H$_4$-CO-(CH$_2$)$_5$-CO-NHOH | 10 |
| Ex. 70 | 124 | Br-C$_6$H$_4$-C$_6$H$_4$-CO-(CH$_2$)$_5$-CO-NHOH | 3 |
| Ex. 78 | 134 | Ph-C$_6$H$_4$-C(=NOH)-(CH$_2$)$_5$-CO-NH-C$_6$H$_4$-NH$_2$ | 10 |
| Ex. 86 | 138g | Ph-N(piperazine)N-C$_6$H$_4$-CO-(CH$_2$)$_5$-CO-NHOH | 5 |
| Ex. 91 | 145 | Ph-(2-pyridyl-5)-CO-(CH$_2$)$_5$-CO-NHOH | 10 |
| Ex. 92 | 146 | Ph-(2-pyridyl-5)-CO-(CH$_2$)$_5$-CO-NH-C$_6$H$_4$-NH$_2$·HCl | 5 |

TABLE 3-continued

Inhibition of Histone Acetylation in Cells

| Example | Cpd. | Structure | EC$_{50}$ (µM) |
|---------|------|-----------|----------------|
| Ex. 94 | 151 | 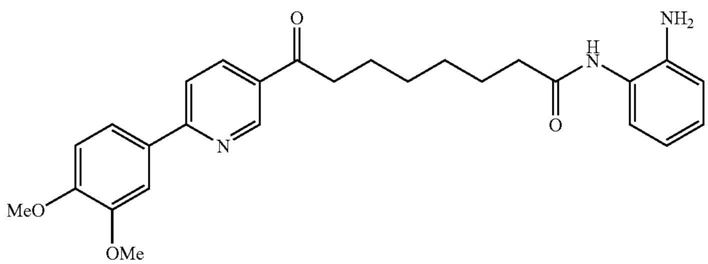 | 3 |
| Ex. 120 | 204 | 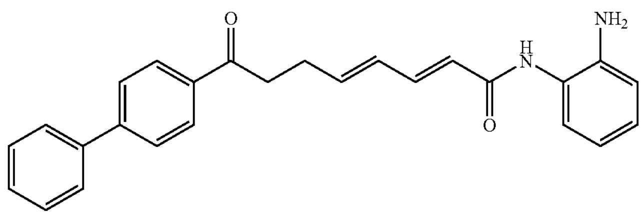 | 15 |
| Ex. 121 | 205 | 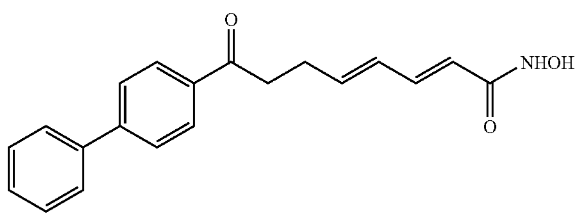 | 3 |
| Ex. 140 | 235 | 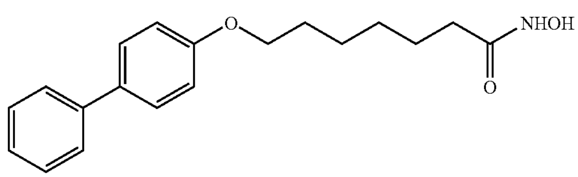 | 5 |
| Ex. 143 | 239a | 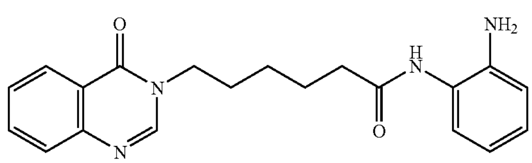 | 5 |
| Ex. 148 | 243d | 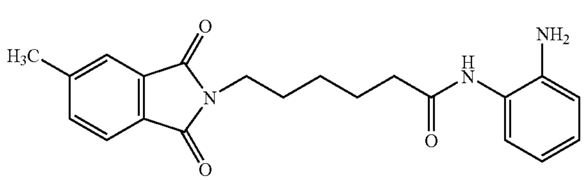 | 3 |
| Ex. 156 | 251a | 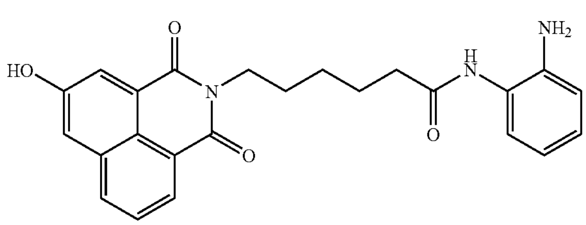 | 5 |

TABLE 3-continued

Inhibition of Histone Acetylation in Cells

| Example | Cpd. | Structure | EC$_{50}$ (μM) |
|---|---|---|---|
| Ex. 158 | 251c | 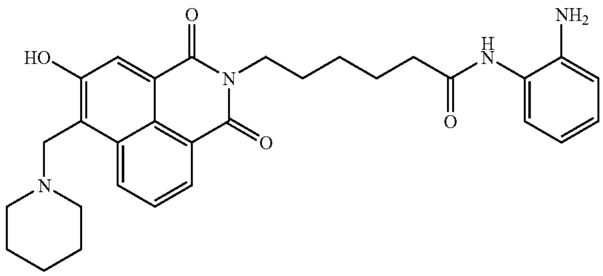 | 1 |

2. Acid Urea Triton (AUT) Gel Analysis of Histone Acetylation

Human cancer cells (T24, 293T or Jurkat cells) growing in culture are incubated with HDAC inhibitors for 24 h Histones are extracted from the cells as described by M. Yoshida et al. (J. Biol. Chem. 265(28): 17174-17179 (1990)). Acid urea triton (AUT) gel electrophoresis is used for detection of acetylated histone m olecules. Histones (150 μg of total protein) are electrophoresed at 80 V for 16 h at room temperature as described by M. Yoshida et al., supra. Gels are stained with Coomassie brilliant blue to visualize histones, dried and scanned by densitometry to quantified acetylation of histones.

Example 161

Antineoplastic Effect of Histone Deacetylase Inhibitors on Tumor Cells In Vivo

Eight to ten week old female BALB/c nude mice (Taconic Labs, Great Barrington, N.Y.) were injected subcutaneously in the flank area with 2×10$^6$ preconditioned A549 human lung carcinoma cells. Preconditioning of these cells was accomplished by a minimum of three consecutive tumor transplantations in the same strain of nude mice. Subsequently, tumor fragments of approximately 30 mgs were excised and implanted subcutaneously in mice, in the left flank area, under isoflurane anesthesia (Abbott Labs, Geneva, Switzerland). When the tumors reached a mean volume of 100 mm$^3$, the mice were treated intravenously, subcutaneously or intraperitoneally, by daily injection of a solution of the inhibitor in an appropriate vehicle such as PBS, DMSO/water, or Tween 80/water, at a dose from about 10 mg/kg to about 50 mg/kg, for 21 days. Tumor volume was calculated every second day post infusion according to standard methods (e.g., Meyer et al., Int. J. Cancer 43: 851-856 (1989)). Treatment with compound 34 caused a significant reduction in tumor weight and volume relative to controls treated with saline only (i.e., no HDAC inhibitor). In addition, the activity of histone deacetylase, when measured, is expected to be significantly reduced relative to saline treated controls.

Example 162

Synergistic Antineoplastic Effect of Histone Deacetylase Inhibitors and Histone Deacetylase Antisense Oligonucleotides on Tumor Cells In Vivo The purpose of this example is to illustrate the ability of the histone deacetylase inhibitor of the invention and a histone deacetylase antisense oligonucleotide to synergistically inhibit tumor growth in a mammal. Preferably, the antisense oligonucleotide and the HDAC inhibitor inhibit the expression and activity of the same histone deacetylase.

As described in Example 161, mice bearing implanted A549 tumors (mean volume 100 mm$^3$) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitor according to the invention causes a significant reduction in tumor weight and volume relative to controls.

What is claimed is:

1. An inhibitor of histone deacetylase represented by formula (1):

$$Cy—X—Y^1—W \qquad (1)$$

wherein

Cy is a heterocyclic moiety selected from the group consisting of furan, benzofuran, thiophene and benzothiophene, any of which may be optionally substituted;

X is selected from the group consisting of C=O, C=CH$_2$, CH(OH), CH(OR$^1$), C=N(OH), and C=N (OR$^1$), where R$^1$ is alkyl, aryl, aralkyl, or acyl;

Y$^1$ is a C$_3$-C$_7$ alkylene, wherein said alkylene may be optionally substituted, and wherein one or two carbon atoms in the alkylene chain connecting X and W may be replaced with O, NR$^3$, or S(O)$_n$, where R$^3$ is hydrogen, alkyl, aryl, aralkyl, acyl, alkoxycarbonyl, or carbamoyl, and n is 0, 1, or 2, provided that the atoms in Y₁ that are attached to X and W are carbon atoms, and further provided that $Y^1$ does not comprise an ester or amide linkage in the alkylene chain connecting X and W; and W is selected from the group consisting of —C(O)—CH₂—SR², —C(O)—NH—OM, —NH—C(O)—NH-Z, and —C(O)—NH-Z, where $R^2$ is alkyl, aryl, aralkyl, or acyl, wherein the aryl portion of any such groups may be optionally substituted;

M is hydrogen or a pharmaceutically acceptable cation;

and Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy.

2. The inhibitor of claim 1, wherein the heterocyclic moiety is substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, ($C_6$-$C_{10}$)ar($C_1$-$C_6$)alkyl, halo, nitro, hydroxy, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino.

3. The inhibitor of claim 1, where X is selected from the group consisting of CH(OR¹), C=N(OH), and C=N(OR¹), where $R^1$ is $C_1$-$C_6$ alkyl, $C_6$-$C_{10}$ aryl, or ($C_6$-$C_{10}$)ar($C_1$-$C_6$) alkyl.

4. The inhibitor of claim 1, wherein one to three carbon atoms of the alkylene are independently substituted with halo, oxo, oximino, nitro, haloalkyl, alkyl, aralkyl, alkoxy, aryloxy, alkoxycarbonyl, carboxy, hydroxyalkyl, acyl, acyloxy, or cyano.

5. The inhibitor of claim 1, wherein $Y^1$ is an all carbon alkylene chain connecting X and W.

6. The inhibitor of claim 5, wherein the alkylene chain connecting X and W is a dienyl moiety, wherein the dienyl moiety is attached to W.

7. The inhibitor of claim 6, wherein $Y^1$ is selected from the group consisting of

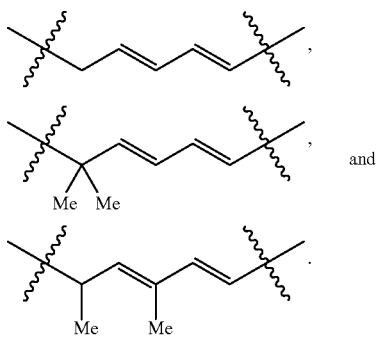

and

8. The inhibitor of claim 5, wherein $Y^1$ is —(CH₂)ₘ, where m is 5, 6, or 7.

9. The inhibitor of claim 1, wherein one carbon atom in the linear chain connecting X and W is replaced with O, NR³, or S(O)ₙ.

10. The inhibitor of claim 9, wherein $Y^1$ is —(CH₂)—S(O)ₙ—(CH₂)ₚ, where n is 0, 1, or 2, and p is 3, 4, or 5.

11. The inhibitor of claim 1, wherein W is —C(O)—NH—OM, M being selected from the group consisting of hydrogen, sodium, potassium, magnesium, and calcium.

12. The inhibitor of claim 1, wherein W is —C(O)—NH-Z or NH—C(O)NH-Z, Z being unsubstituted 2-anilinyl or unsubstituted 2-pyridyl.

13. The inhibitor of claim 1, wherein W is —C(O)—CH₂—SR², R² being selected from the group consisting of $C_1$-$C_6$ alkyl, $C_6$-$C_{10}$ aryl, ($C_6$-$C_{10}$)ar($C_1$-$C_6$)alkyl, ($C_1$-$C_6$ alkyl)Carbonyl, ($C_6$-$C_{10}$ aryl)carbonyl, and (($C_6$-$C_{10}$)ar($C_1$-$C_6$)alkyl)carbonyl, wherein the aryl portion of any such groups may be optionally substituted.

14. The inhibitor of claim 13, wherein R² is selected from the group consisting of methyl, phenyl, benzyl, benzoyl, and acetyl.

15. An inhibitor of histone deacetylase represented by formula (2):

wherein

Cy is a heterocyclic moiety selected from the group consisting of furan and thiophene, any of which may be optionally substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, ($C_6$-$C_{10}$)ar($C_1$-$C_6$)alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino;

$Y^2$ is $C_5$-$C_7$ wherein alkylene maybe optionally substituted, and wherein one or two carbon atoms in the alkylene chain connecting CY and W may be replaced with NR³, or S(O)ₙ, where R³ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and W is selected from the group consisting of —C(O)—CH₂—SR², —NH—C(O)—NH-Z, and —C(O)—NH-Z, where $R^2$ is alkyl, aryl, aralkyl, or acyl, wherein the aryl portion of any such groups may be optionally substituted; and Z is selected from the group consisting of anilinyl, pyridyl, thiazolyl, hydroxyphenyl, thiadiazolyl, anilinymethyl, or pyridylmethyl, any of which groups optionally may be substituted with halo, hydroxyl, amino, nitro, $C_1$-$C_4$ alkyl, or $C_1$-$C_4$ alkoxy.

16. The inhibitor of claim 15, wherein one to four carbon atoms of the alkylene are independently substituted with halo, oxo, oximino, nitro, haloalkyl, alkyl, aralkyl, alkoxy, aryloxy, alkoxycarbonyl, carboxy, hydroxyalkyl, acyl, acyloxy, or cyano.

17. The inhibitor of claim 15, wherein one carbon atom in the alkylene chain connecting Cy and W is replaced with O, NR³, or S(O)ₙ.

18. The inhibitor of claim 15, wherein one carbon atom in the alkylene chain connecting Cy and W is replaced with NR³, where R³ is selected from the group consisting of $C_1$-$C_6$ alkyl, $C_6$-$C_{10}$ aryl, ($C_6$-$C_{10}$)ar($C_1$-$C_6$)alkyl, ($C_1$-$C_6$alkyl) oxycarbonyl, ($C_6$-$C_{10}$ aryl)oxycarbonyl, (($C_6$-$C_{10}$)ar($C_1$-$C_6$)alkyl)oxycarbonyl, ($C_1$-$C_6$ alkyl)carbonyl, ($C_6$-$C_{10}$ aryl)carbonyl, and (($C_6$-$C_{10}$)ar($C_1$-$C_6$)alkyl)carbonyl.

19. The inhibitor of claim 15, wherein one or two carbon atoms in the alkylene chain connecting Cy and W are replaced by O.

20. The inhibitor of claim 15, wherein W is —C(O)—NH-Z or NH—C(O)—NH-Z, Z being unsubstituted 2-anilinyl or unsubstituted 2-pyridyl.

21. The inhibitor of claim 15, wherein W is —C(O)—CH₂—SR², R² being selected from the group consisting of $C_1$-$C_6$ alkyl, $C_6$-$C_{10}$ aryl, $(C_6$-$C_{10})$ar$(C_1$-$C_6)$alkyl, $(C_1$-$C_6$ alkyl)carbonyl, $(C_6$-$C_{10}$ aryl)carbonyl, and $((C_6$-$C_{10})$ar$(C_1$-$C_6)$alkyl)carbonyl, wherein the aryl portion of any such groups may be optionally substituted.

22. The inhibitor of claim 21, wherein $R^2$ is selected from the group consisting of methyl, phenyl, benzyl, benzoyl, and acetyl.

23. An inhibitor of histone deacetylase represented by formula (3):

   (3)

wherein

Cy is a heterocyclic moiety selected from the group consisting of furan, benzofuran, thiophene and benzothiophene, any of which may be optionally substituted;

$Y^3$ is $C_2$-$C_6$ alkylene, wherein said alkylene may be optionally substituted with one or more substituents independently selected from the group consisting of halo, hydroxyl, oxo, nitro, haloalkyl, alkyl, aralkyl, alkoxy, aryloxy, carboxy, hydroxyalkyl, acyl, acyloxy, and cyano; and W is selected from the group consisting of —C(O)—CH$_2$—SR$^2$, —C(O)—NH—OM, —NH—C(O)—NH-Z, and —C(O)—NH-Z, where $R^2$ is alkyl, aryl, aralkyl, or acyl, wherein the aryl portion of any such groups may be optionally substituted;

M is hydrogen; or a pharmaceutically acceptable cation;

Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$, alkyl, or $C_1$-$C_4$ alkoxy;

or a pharmaceutically acceptable salt thereof.

24. The inhibitor of claim 23, wherein the aryl or heterocyclic moiety is substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, $(C_6$-$C_{10})$ar$(C_1$-$C_6)$alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino.

25. The inhibitor of claim 23, wherein $Y^3$ is a $C_2$-$C_6$ alkylene optionally substituted with one or two non-hydrogen substituents independently selected from the group consisting of halo, hydroxyl, oxo, nitro, (halo)$_{1-5}$($C_1$-$C_3$) alkyl, $C_1$-$C_6$ alkyl, $(C_6$-$C_{10})$ar$(C_1$-$C_6)$alkyl, $C_1$-$C_6$ alkoxy, $C_6$-$C_{10}$ aryloxy, carboxy, hydroxy $(C_1$-$C_6)$alkyl, $C_1$-$C_6$ alkylcarbonyl, $C_6$-$C_{10}$ arylcarbonyl, $C_1$-$C_6$ alkylcarbonyloxy, $C_6$-$C_{10}$ arylcarbonyloxy, and cyano.

26. The inhibitor of claim 23, wherein $Y^3$ is an optionally substituted saturated $C_4$-$C_5$ alkylene.

27. The inhibitor of claim 23, wherein W is —C(O)—NH—OM, M being selected from the group consisting of hydrogen, sodium, potassium, magnesium, and calcium.

28. The inhibitor of claim 23, wherein W is —C(O)—NH-Z or NH—C(O)—NH-Z, Z being unsubstituted 2-anilinyl or unsubstituted 2-pyridyl.

29. The inhibitor of claim 23, where W is —C(O)—CH$_2$—SR$^2$, $R^2$ being selected from the group consisting of $C_1$-$C_6$ alkyl, $C_6$-$C_{10}$ aryl, $(C_6$-$C_{10})$ar$(C_1$-$C_6)$alkyl, $(C_1$-$C_6$ alkyl)carbonyl, $(C_6$-$C_{10}$ aryl)carbonyl, and $((C_6$-$C_{10})$ar$(C_1$-$C_6)$alkyl)carbonyl, wherein the aryl portion of any such groups may be optionally substituted.

30. A pharmaceutical composition comprising an inhibitor of histone deacetylase represented by formula (1):

   (1)

wherein

Cy is a heterocyclic moiety selected from the group consisting of furan, benzofuran, thiophene and benzothiophene, any of which may be optionally substituted;

X is selected from the group consisting of C=O, C=CH$_2$, CH(OH), CH(OR$^1$), C=N(OH), and C=N(OR$^1$), where $R^1$ is alkyl, aryl, aralkyl, or acyl;

$Y^1$ is a $C_3$-$C_7$ alkylene, wherein said alkylene may be optionally substituted, and wherein one or two carbon atoms in the alkylene chain connecting X and W may be replaced with O, NR$^3$, or S(O)$_n$, where $R^3$ is hydrogen, alkyl, aryl, aralkyl, acyl, alkoxycarbonyl, or carbamoyl, and n is 0, 1, or 2, provided that the atoms in $Y^1$ that are attached to X and to W are carbon atoms, and further provided that $Y^1$ does not comprise an ester or amide linkage in the alkylene chain connecting X and W; and W is selected from the group consisting of —C(O)—CH$_2$—SR$^2$, —C(O)—NH—OM, —NH—C(O)—NH-Z, and —C(O)—NH-Z, where $R^2$ is alkyl, aryl, aralkyl, or acyl, wherein the aryl portion of any such groups may be optionally substituted;

M is hydrogen or a pharmaceutically acceptable cation;

Z is selected from the group consisting of anilinyl, pyridyl, thiazolyl, hydroxyphenyl, thiadiazolyl, anilinylmethyl, or pyridylmethyl, any of which group optionally may be substituted with halo, hydroxyl, amino, nitro, $C_1$-$C_4$ alkyl, or $C_1$-$C_4$ alkoxy; and a pharmaceutically acceptable carrier, excipient, or diluent.

31. A pharmaceutical composition comprising an inhibitor of histone deacetylase represented by formula (2):

   (2)

wherein

Cy is a heterocyclic moiety selected from the group consisting of furan and thiophene, any of which may be optionally substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, $(C_6$-$C_{10})$ar$(C_1$-$C_6)$alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino;

$Y^2$ is $C_5$-$C_7$ wherein alkylene may be optionally substituted, and wherein one or two carbon atoms in the alkylene chain connecting Cy and W may be replaced with O, NR$^3$, or S(O)$_n$, where $R^3$ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and W is selected from the group consisting of —C(O)—CH$_2$—SR$^2$, —NH—C(O)—NH-Z, and —C(O)—NH-Z, where $R^2$ is alkyl, aryl, aralkyl, or acyl, wherein the aryl portion of any such groups may be optionally substituted; and Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy; and a pharmaceutically acceptable carrier, excipient, or diluent.

32. A pharmaceutical composition comprising an inhibitor of histone deacetylase represented by formula (3):

$$Cy\text{-}S(O)_2\text{—}NH\text{—}Y^3\text{—}W \qquad (3)$$

wherein
Cy is a heterocyclic moiety selected from the group consisting of furan, benzofuran, thiophene and benzothiophene, any of which may be optionally substituted;
$Y^3$ is $C_2$-$C_6$ alkylene, wherein said alkylene may be optionally substituted with one or more substituents independently selected from the group consisting of halo, hydroxyl, oxo, nitro, haloalkyl, alkyl, aralkyl, alkoxy, aryloxy, carboxy, hydroxyalkyl, acyl, acyloxy, and cyano; and
W is selected from the group consisting of —C(O)—CH$_2$—SR$^2$, —C(O)—NH—OM, —NH—C(O)—NH-Z, and —C(O)—NH-Z, where
R$^2$ is alkyl, aryl, aralkyl, or acyl, wherein the aryl portion of any such groups may be optionally substituted;
M is hydrogen or a pharmaceutically acceptable cation; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy; and
a pharmaceutically acceptable carrier, excipient, or diluent.

33. A method for treating small cell lung cancer comprising administering a therapeutically effective amount of an inhibitor of histone deacetylase represented by formula (1):

$$Cy\text{-}X\text{—}Y^1\text{—}W \qquad (1)$$

wherein
Cy is a heterocyclic moiety selected from the group consisting of furan, benzofuran, thiophene and benzothiophene, any of which may be optionally substituted;
X is selected from the group consisting of C=O, C—CH$_2$, CH(OH), CH(OR$^1$), C=N(OH), and C=N(OR$^1$), where R$^1$ is alkyl, aryl, aralkyl, or acyl;
$Y^1$ is a $C_3$-$C_7$ alkylene, wherein said alkylene may be optionally substituted, and wherein one or two carbon atoms in the alkylene chain connecting X and W may be replaced with O, NR$^3$, or S(O)$_n$, where R$^3$ is hydrogen, alkyl, aryl, aralkyl, acyl, alkoxycarbonyl, or carbamoyl, and n is 0, 1, or 2, provided that the atoms in $Y^1$ that are attached to X and W are carbon atoms, and further provided that $Y^1$ does not comprise an ester or amide linkage in the alkylene chain connecting X and W; and
W is selected from the group consisting of —C(O)—CH$_2$—SR$^2$—C(O)—NH—OM, —NH—C(O)—NH-Z, and —C(O)—NH-Z, where
R$^2$ is alkyl, aryl, aralkyl, or acyl, wherein the aryl portion of any such groups may be optionally substituted;
M is hydrogen or a pharmaceutically acceptable cation; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy.

34. A method for treating small cell lung cancer comprising administering a therapeutically effective amount of an inhibitor of histone deacetylase represented by formula (2):

$$Cy\text{-}Y^2\text{—}W \qquad (2)$$

wherein
Cy is a heterocyclic moiety selected from the group consisting of furan and thiophene, any of which may be optionally substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, $(C_6$-$C_{10})$ar$(C_1$-$C_6)$alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino;
$Y^2$ is $C_5$-$C_7$ wherein alkylene may be optionally substituted, and wherein one or two carbon atoms in the alkylene chain connecting Cy and W may be replaced with O, NR$^3$, or S(O)$_n$, where R$^3$ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and
W is selected from the group consisting of —C(O)—CH$_2$SR$^2$, —NH—C(O)—NH-Z, and —C(O)—NH-Z, where
R$^2$ is alkyl, aryl, aralkyl, or acyl, wherein the aryl portion of any such groups may be optionally substituted; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C^1$-$C^4$ alkyl, or $C_1$-$C_4$ alkoxy.

35. A method for treating small cell lung cancer comprising administering a therapeutically effective amount of an inhibitor of histone deacetylase represented by formula (3):

$$Cy\text{-}S(O)_2\text{—}NH\text{—}Y^3\text{—}W \qquad (3)$$

wherein
Cy is a heterocyclic moiety selected from the group consisting of furan, benzofuran, thiophene and benzothiophene, any of which may be optionally substituted;
$Y^3$ is $C_2$-$C_6$ alkylene, wherein said alkylene may be optionally substituted with one or more substituents independently selected from the group consisting of halo, hydroxyl, oxo, nitro, haloalkyl, alkyl, aralkyl, alkoxy, aryloxy, carboxy, hydroxyalkyl, acyl, acyloxy, and cyano; and
W is selected from the group consisting of —C(O)—CH$_2$—SR$^2$, —C(O)—NH—OM, —NH—C(O)—NH-Z, and C(O)—NH-Z, where
R$^2$ is alkyl, aryl, aralkyl, or acyl, wherein the aryl portion of any such groups may be optionally substituted;
M is hydrogen or a pharmaceutically acceptable cation; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy.

36. The inhibitor according to claim 1, wherein the cation is a monovalent or divalent cation.

37. The inhibitor according to claim 23, wherein the cation is a monovalent or divalent cation.

38. The pharmaceutical composition according to claim 30, wherein the cation is a monovalent or divalent cation.

39. The pharmaceutical composition according to claim 32, wherein the cation is a monovalent or divalent cation.

40. The method according to claim 33, wherein the cation is a monovalent or divalent cation.

41. The method according to claim 35, wherein the cation is a monovalent or divalent cation.

42. An inhibitor of histone deacetylase represented by formula (2):

$$\text{Cy-Y}^2\text{—W} \qquad (2)$$

wherein
Cy is a heterocyclic moiety selected from the group consisting of benzofuran, and benzothiophene, any of which may be optionally substituted;
$Y^2$ is $C_5$-$C_7$ alkylene, wherein said alkylene maybe optionally substituted, and wherein one or two carbon atoms in the alkylene chain connecting CY and W may be replaced with O, $NR^3$, or $S(O)_n$, where $R^3$ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and
W is selected from the group consisting of —C(O)—CH$_2$—SR$^2$, —NH—C(O)—NH-Z, and —C(O)—NH-Z, where
$R^2$ is alkyl, aryl, aralkyl, or acyl, wherein the aryl portion of any such groups may be optionally substituted; and
Z is selected from the group consisting of anilinyl, pyridyl, thiazolyl, hydroxyphenyl, thiadiazolyl, anilinymethyl, or pyridylmethyl, any of which groups optionally may be substituted with halo, hydroxyl, amino, nitro, $C_1$-$C_4$ alkyl, or $C_1$-$C_4$ alkoxy.

43. The inhibitor of claim 42, wherein the heterocyclic moiety is substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, ($C_6$-$C_{10}$)ar($C_1$-$C_6$)alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino.

44. The inhibitor of claim 42, wherein one to four carbon atoms of the alkylene are independently substituted with halo, oxo, oximino, nitro, haloalkyl, alkyl, aralkyl, alkoxy, aryloxy, alkoxycarbonyl, carboxy, hydroxyalkyl, acyl, acyloxy, or cyano.

45. The inhibitor of claim 42, wherein one carbon atom in the alkylene chain connecting Cy and W is replaced with O, $NR^3$, or $S(O)_n$.

46. The inhibitor of claim 42, wherein one carbon atom in the alkylene chain connecting Cy and W is replaced with $NR^3$, where $R^3$ is selected from the group consisting of $C_1$-$C_6$ alkyl, $C_6$-$C_{10}$ aryl, ($C_6$-$C_{10}$)ar($C_1$-$C_6$)alkyl, ($C_1$-$C_6$alkyl) oxycarbonyl, ($C_6$-$C_{10}$ aryl)oxycarbonyl, (($C_6$-$C_{10}$)ar($C_1$-$C_6$)alkyl)oxycarbonyl, ($C_1$-$C_6$ alkyl)carbonyl, ($C_6$-$C_{10}$ aryl)carbonyl, and (($C_6$-$C_{10}$)ar($C_1$-$C_6$)alkyl)carbonyl.

47. The inhibitor of claim 42, wherein one or two carbon atoms in the alkylene chain connecting Cy and W are replaced by O.

48. The inhibitor of claim 42, wherein W is —C(O)—NH-Z or NH—C(O)—NH-Z, Z being unsubstituted 2-anilinyl or unsubstituted 2-pyridyl.

49. The inhibitor of claim 42, wherein W is —C(O)—CH$_2$—SR$^2$, $R^2$ being selected from the group consisting of $C_1$-$C_6$ alkyl, $C_6$-$C_{10}$ aryl, ($C_6$-$C_{10}$)ar($C_1$-$C_6$)alkyl, ($C_1$-$C_6$ alkyl)carbonyl, ($C_6$-$C_{10}$ aryl)carbonyl, and (($C_6$-$C_{10}$)ar($C_1$-$C_6$)alkyl)carbonyl, wherein the aryl portion of any such groups may be optionally substituted.

50. The inhibitor of claim 49, wherein $R^2$ is selected from the group consisting of methyl, phenyl, benzyl, benzoyl, and acetyl.

51. A pharmaceutical composition comprising an inhibitor of histone deacetylase represented by formula (2):

$$\text{Cy-Y}^2\text{—W} \qquad (2)$$

wherein
Cy is a heterocyclic moiety selected from the group consisting of benzofuran and benzothiophene, any of which may be optionally substituted;
$Y^2$ is $C_5$-$C_7$ alkylene, wherein said alkylene may be optionally substituted, and wherein one or two carbon atoms in the alkylene chain connecting Cy and W may be replaced with O, $NR^3$, or $S(O)_n$, where $R^3$ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and
W is selected from the group consisting of —C(O)—CH$_2$—SR$^2$, —NH—C(O)—NH-Z, and —C(O)—NH-Z, where $R^2$ is alkyl, aryl, aralkyl, or acyl, wherein the aryl portion of any such groups may be optionally substituted; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C_1$-$C_4$ alkyl, or $C_1$-$C_4$ alkoxy; and a pharmaceutically acceptable carrier, excipient, or diluent.

52. The composition according to claim 51, wherein the heterocyclic moiety is substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, ($C_6$-$C_{10}$)ar($C_1$-$C_6$)alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino.

53. A method for treating small cell lung cancer comprising administering a therapeutically effective amount of an inhibitor of histone deacetylase represented by formula (2):

$$\text{Cy-Y}^2\text{—W} \qquad (2)$$

wherein
Cy is a heterocyclic moiety selected from the group consisting of benzofuran and benzothiophene, any of which may be optionally substituted;
$Y^2$ is $C_5$-$C_7$ alkylene, wherein said alkylene may be optionally substituted, and wherein one or two carbon atoms in the alkylene chain connecting Cy and W may be replaced with O, $NR^3$, or $S(O)_n$, where $R^3$ is hydrogen, alkyl, aryl, aralkyl, acyl, alkoxycarbonyl, or carbamoyl, and n is 0, 1, or 2, provided that $Y^2$ does not comprise an ester or amide linkage in the alkylene chain connecting Cy and W; and
W is selected from the group consisting of —C(O)—CH$_2$SR$^2$, —NH—C(O)—NH-Z, and —C(O)—NH-Z, where
$R^2$ is alkyl, aryl, aralkyl, or acyl, wherein the aryl portion of any such groups may be optionally substituted; and
Z is selected from the group consisting of anilinyl, pyridyl, thiazolyl, hydroxyphenyl, thiadiazolyl, anilinylmethyl, or pyridylmethyl, any of which groups optionally may be substituted with halo, hydroxyl, amino, nitro, $C^1$-$C^4$ alkyl, or $C_1$-$C_4$ alkoxy.

54. The method according to claim 53, wherein the heterocyclic moiety is substituted by one or two substituents independently selected from the group consisting of $C_1$-$C_4$ alkyl, $C_1$-$C_4$ haloalkyl, $C_6$-$C_{10}$ aryl, heteroaryl, heterocyclyl, $(C_6$-$C_{10})$ar$(C_1$-$C_6)$alkyl, halo, nitro, hydroxyl, $C_1$-$C_6$ alkoxy, $C_6$-$C_{10}$ aryloxy, heteroaryloxy, $C_1$-$C_6$ alkoxycarbonyl, $C_6$-$C_{10}$ aryloxycarbonyl, heteroaryloxycarbonyl, carboxy, and amino.

* * * * *

UNITED STATES PATENT AND TRADEMARK OFFICE
CERTIFICATE OF CORRECTION

PATENT NO. : 7,288,567 B2  Page 1 of 1
APPLICATION NO. : 09/817374
DATED : October 30, 2007
INVENTOR(S) : Daniel Delorme et al.

It is certified that error appears in the above-identified patent and that said Letters Patent is hereby corrected as shown below:

In claim 15, Column 236, line 27, please cancel the text "$Y^2$ is $C_5$-$C_7$ wherein alkylene maybe optionally substi-" and insert the following text: --$Y^2$ is $C_5$-$C_7$ alkylene, wherein said alkylene may be optionally substi- --

In claim 33, Column 239, line 44, please cancel the text "C-$CH_2$, CH(OH), CH($OR^1$), C=N(OH), and C=N" and insert the following text: --C=$CH_2$, CH(OH), CH($OR^1$), C=N(OH), and C=N--

In claim 33, Column 239, lines 57-59, please cancel the text "W is seleced from the group consisting of —C(O)-$CH_2$-$SR_2$-C(O)-NH-OM, -NH-C(O)-NH-Z, and -C(O)-NH-Z, where" and insert the following text: --W is selected from the group consisting of —C(O)-$CH_2$-$SR_2$, -C(O)-NH-OM, -NH-C(O)-NH-Z, and -C(O)-NH-Z, where--

In claim 34, Column 240, line 16, please cancel the text "$Y^2$ is $C_5$-$C_7$ wherein alkylene may be optionally substi-" and insert the following text: --$Y^2$ is $C_5$-$C_7$ alkylene, wherein said alkylene may be optionally substi- --

Signed and Sealed this

Twenty-third Day of March, 2010

David J. Kappos
*Director of the United States Patent and Trademark Office*